US006930104B2

(12) United States Patent
Kakihana et al.

(10) Patent No.: US 6,930,104 B2
(45) Date of Patent: Aug. 16, 2005

(54) HETEROCYCLIC DERIVATIVES

(75) Inventors: Mitsuru Kakihana, Kobe (JP); Kaneyoshi Kato, Kawanishi (JP); Masaaki Mori, Tsukuba (JP); Toshiro Yamashita, Tsukuba (JP)

(73) Assignee: Takeda Chemical Industries, Ltd., Osaka (JP)

( * ) Notice: Subject to any disclaimer, the term of this patent is extended or adjusted under 35 U.S.C. 154(b) by 0 days.

(21) Appl. No.: 10/474,963

(22) PCT Filed: Apr. 25, 2002

(86) PCT No.: PCT/JP02/04148

§ 371 (c)(1),
(2), (4) Date: Oct. 16, 2003

(87) PCT Pub. No.: WO02/088087

PCT Pub. Date: Nov. 7, 2002

(65) Prior Publication Data

US 2004/0157850 A1 Aug. 12, 2004

(30) Foreign Application Priority Data

Apr. 26, 2001 (JP) ....................................... 2001-128677
Feb. 20, 2002 (JP) ....................................... 2002-043523

(51) Int. Cl.[7] ....................... C07D 401/02; A61K 31/47

(52) U.S. Cl. ....................... 514/217; 514/248; 514/290; 514/311; 514/314; 540/567; 544/344; 544/349; 546/79; 546/168

(58) Field of Search ................................ 514/248, 290, 514/311, 314, 217; 544/344, 349; 546/79, 168; 540/567

(56) References Cited

FOREIGN PATENT DOCUMENTS

| | | |
|---|---|---|
| WO | WO 98/38156 | 9/1998 |
| WO | WO 01/76629 | 10/2001 |

OTHER PUBLICATIONS

Shmyreve, Zh. v. et al., "Benzoylation of a 2, 2, 4–trimethyl–1, 2–dihydroquinoline dimmer, Izv. Vyssh. Uchebn. Zaved., Khim, Khim. Technol.", 30(10):25–28(1987) (no translation).

Chemical Abstracts, vol. 62, 3907c–d(1965) [Zh. Obshch. Khim. 34(10), 3392–5(1964)].

Chemical Abstracts, vol. 69, 27206h(1968) [=Tr. Probl. Lab. Khim. Vysokomol. Soedin, Voronezh. Gos. Univ. (1996), No. 4, 5–16].

Funabashi, et al. "Configuration and Conformation of So–called Bis(alkylidenearylamines)" Bulletin of the Chemical Society of Japan 10(42): 2885–2894 (1969).

*Primary Examiner*—Zinna Northington Davis
(74) *Attorney, Agent, or Firm*—Elaine M. Ramesh; Mark Chao

(57) ABSTRACT

The object of the present invention is to provide soluble β-amyloid precursor protein secretory stimulators, which are effective in treating neurodegenerative diseases as well as cerebrovascular disorder-induced neuronopathy. More specifically, the present invention provides a novel compound of the following Formula (I) or a salt or prodrug thereof:

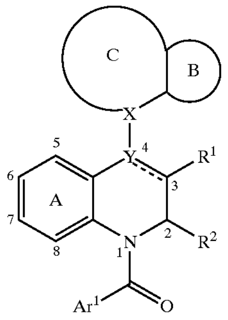

[wherein $R^1$ and $R^2$ each represent a hydrogen atom or a lower alkyl group, etc., $Ar^1$ and the ring B each represent an optionally substituted aromatic group, the ring A represents an optionally substituted benzene ring, the ring C represents an optionally substituted 4- to 8-membered ring which may further be condensed with an optionally substituted ring, X represents CH or N, and Y represents CH or N].

20 Claims, 2 Drawing Sheets

HETEROCYCLIC DERIVATIVES

This application is the National Phase filing of International Patent Application No. PCT/JP02/04148, filed 25 Apr. 2002.

TECHNICAL FIELD

The present invention relates to medicaments, more particularly soluble β-amyloid precursor protein secretory stimulators and apoptosis inhibitors, which are effective in treating neurodegenerative diseases such as Alzeheimer's disease, Parkinson's disease, Down's syndrome, amyotrophic lateral sclerosis, prion disease (Creutzfeldt-Jakob disease), Huntington's chorea and neuropathy (preferably, e.g., diabetic neuropathy), as well as effective in treating cerebrovascular disorder-induced neuronopathy.

BACKGROUND ART

No agent has been developed to inhibit nerve cell death in neurodegenerative diseases such as Alzeheimer's disease and Parkinson's disease and prevent these diseases from progressing.

Alzeheimer's disease is characterized by senile plaque formation and neurofibrillary degeneration along with neuronal degeneration and dropout. Senile plaques, the most characteristic pathological feature in the Alzeheimer's diseased brain, are produced by extracellular deposition of β-amyloid protein (hereinafter also abbreviated as Aβ), which is a metabolite of β-amyloid precursor protein (hereinafter also abbreviated as βAPP) (Biochem. Biophys. Res. Commun. 122, 1131 (1984); Proc. Natl. Acad. Sci. USA. 82, 4245 (1985); J. Neurochem. 46, 1820 (1986); Neuron 6, 487 (1991)). Aβ comprising 40 or 42 amino acids is known to be toxic to nerve cells (Science 250, 279 (1990); Brain Res. 563, 311 (1991); J. Neurosci. 12, 376 (1992)) and also known to induce neurofibrillary degeneration (Proc. Natl. Acad. Sci. USA. 90, 7789–7793 (1993)).

βAPP is not only metabolized to Aβ, but also metabolized in such a way as not to produce Aβ; the resulting-metabolite, soluble β-amyloid precursor protein (soluble APP, also abbreviated as sAPP), is secreted into the extracellular environment (Science 248, 492 (1990); Science 248, 1122 (1990)). There are many reports that this sAPP operate as a neurotrophic factor, i.e. stimulating the elongation of the nerve cells and inhibiting the nerve cell death by using primary cultured nerve cells or neuroblastoma PC12 cells and so on (Neuron 9, 129 (1992); Neuron 10, 243 (1993); Physiol. Rev. 77, 1081 (1997)). It is also reported that the sAPP level is reduced in the cerebral fluid of patients with Alzeheimer's disease (Lancet 340, 453 (1992); Ann. Neurol. 32, 215 (1992); Proc. Natl. Acad. Sci. USA 89, 2551 (1992); Alzheimer Disease and Associated Disorders 11, 201 (1997)). This suggests that in Alzeheimer's disease, βAPP metabolism is more likely to shift to the production of Aβ rather than sAPP, i.e., an increase and extracellular accumulation of cytotoxic Aβ, or a decrease of neurotrophic factor sAPP may play a very critical role in the onset of the disease. Thus, compounds capable of stimulating sAPP production and secretion in nerve system tissues are expected as prophylactic and/or therapeutic agents for various neurodegenerative diseases because of their ability to reduce nerve cell damage caused by various factors and/or prevent nerve cell death, with the aid of the neurotrophic action of sAPP. At the same time, such compounds also have the ability to inhibit the production of cytotoxic Aβ and are particularly expected as prophylactic and/or therapeutic agents for Alzeheimer's disease (J. Biol. Chem. 268, 22959 (1993); Ann. New York Acad. Sci. 777, 175 (1997)).

In fact, phorbol ester, which is an activator of protein kinase C (hereinafter also abbreviated as PKC), is known not only to strongly stimulate sAPP secretion, but also to inhibit the production and secretion of Aβ (Proc. Natl. Acad. Sci. USA. 87, 6003 (1990); Proc. Natl. Acad. Sci. USA. 90, 9195 (1993); J. Neurochem. 61, 2326 (1993); J. Biol. Chem. 269, 8376 (1994)).

Therefore, it has been made attempts to increase the level of sAPP by using various types of cells and brain tissue sections. For example, in addition to phorbol ester mentioned above, other compounds are also reported to stimulate sAPP secretion, including M1 muscarinic receptor agonists (Science 258, 304 (1992); Proc. Natl. Acad. Sci. USA. 89, 10075 (1992); J. Neurosci. 15, 7442 (1995)), glutamate agonists (Proc. Natl. Acad. Sci. USA. 92, 8083 (1995)) and serotonin agonists (J. Biol. Chem. 23, 4188 (1996)), it is believed since these agonists activate PKC, tyrosine kinase or phospholipase A2 through their respective receptors.

DISCLOSURE OF THE INVENTION

In view of the foregoing, it has been expected to develop sAPP secretory stimulators alternative to the above compounds.

As a result of extensive and intensive efforts, the inventors of the present invention found that novel compounds of the following Formula (I) or salts or prodrugs thereof were unexpectedly advantageous in stimulating soluble β-amyloid precursor protein secretion:

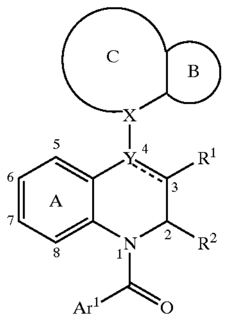

[wherein $R^1$ and $R^2$, which may be the same or different, each represent a hydrogen atom, an optionally substituted lower alkyl group or an optionally substituted hydroxy group, or $R^1$ and $R^2$ may together form a 4- to 7-membered ring together with their adjacent carbon atoms, $Ar^1$ represents an optionally substituted aromatic group, the ring A represents an optionally substituted benzene ring, the ring B represents an optionally substituted aromatic ring, the ring C represents an optionally substituted 4- to 8-membered ring which may further be condensed with an optionally substituted ring, X represents CH or N, and ═══ represents a single bond or a double bond, provided that Y represents CH or N when said bond is a single bond, and Y represents C when said bond is a double bond]. The inventors of the present invention also found that such compounds or salts or prodrugs thereof were advantageous in inhibiting apoptosis and in ameliorating nerve dysfunction. The inventors of the present invention further found that because of these advantages, such compounds or salts or prodrugs thereof were useful as prophylactic and/or therapeutic agents for neurodegenerative diseases such as Alzeheimer's disease, Parkinson's disease, prion disease or neuropathy (preferably, e.g., diabetic neuropathy), as well as for senile dementia, cerebrovascular dementia and cerebrovascular disorder-induced neuronopathy. These findings led to the completion of the present invention.

Namely, the present invention is directed to the following embodiments:

(1) a compound of the following Formula (I) or a salt or prodrug thereof:

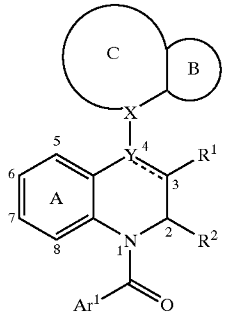

[wherein $R^1$ and $R^2$, which may be the same or different, each represent a hydrogen atom, an optionally substituted lower alkyl group or an optionally substituted hydroxy group, or $R^1$ and $R^2$ may together form a 4- to 7-membered ring together with their adjacent carbon atoms, $Ar^1$ represents an optionally substituted aromatic group, the ring A represents an optionally substituted benzene ring, the ring B represents an optionally substituted aromatic ring, the ring C represents an optionally substituted 4- to 8-membered ring which may further be condensed with an optionally substituted ring, X represents CH or N, and 

represents a single bond or a double bond, provided that Y represents CH or N when said bond is a single bond, and Y represents C when said bond is a double bond]; The inventors

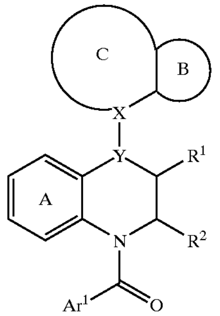

[wherein $R^1$ and $R^2$, which may be the same or different, each represent a hydrogen atom or an optionally substituted lower alkyl group, or $R^1$ and $R^2$ may together form a 4- to 7-membered ring together with their adjacent carbon atoms, $Ar^1$ represents an optionally substituted aromatic group, the ring A represents an optionally substituted benzene ring, the ring B represents an optionally substituted aromatic ring, the ring C represents an optionally substituted 4- to 8-membered ring, X represents CH or N, and Y represents CH or N];

(3) the compound of (1) above or a salt or prodrug thereof, wherein the partial structure:

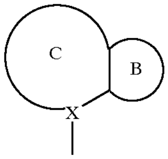

[wherein the ring B, the ring C and X are as defined in (1) above] has the following formula:

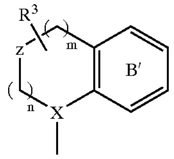

[wherein $R^3$ represents a hydrogen atom, a halogen atom, an optionally substituted lower alkyl group or an optionally substituted lower alkoxy group, the ring B' represents an optionally substituted benzene ring, X represents CH or N, Z represents an oxygen atom, a sulfur atom, $CR^4R^5$, $NR^6$ or

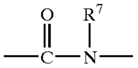 or 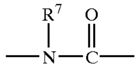

(wherein $R^4$, $R^5$, $R^6$ and $R^7$, which may be the same or different, each represent a hydrogen atom or an optionally substituted lower alkyl group), m represents 0 or 1, and n represents an integer of 1 to 4];

(4) the compound of (1) above or a salt or prodrug thereof, wherein the ring C is further condensed with a monocyclic ring in addition to the ring B;

(5) the compound of (1) above or a salt or prodrug thereof, wherein $R^1$ is a hydrogen atom;

(6) the compound of (1) above or a salt or prodrug thereof, wherein $R^1$ is a hydroxy group, an optionally substituted alkoxy group or an optionally substituted acyloxy group;

(7) the compound of (1) above or a salt or prodrug thereof, wherein $R^2$ is a hydrogen atom or an optionally substituted lower alkyl group;

(8) the compound of (1) above or a salt or prodrug thereof, wherein $Ar^1$ is an optionally substituted monocyclic aromatic group;

(9) the compound of (1) above or a salt or prodrug thereof, wherein $Ar^1$ is an optionally substituted phenyl, furyl, thienyl or pyridyl group;

(10) the compound of (1) above or a salt or prodrug thereof, wherein the ring A is an unsubstituted benzene ring;

(11) the compound of (1) above or a salt or prodrug thereof, wherein at least one of X and Y is N;

(12) the compound of (1) above or a salt or prodrug thereof, wherein X is N and Y is C;

(13) the compound of (1) above or a salt or prodrug thereof, wherein $R^1$ is a hydrogen atom, an alkyloxy group or an acyloxy group, $R^2$ is a hydrogen atom or an optionally substituted lower alkyl group, $Ar^1$ is an optionally substituted phenyl group, an optionally substituted furyl group, an optionally substituted thieny group or an optionally substituted pyridyl group, the ring A is an unsubstituted benzene ring, the ring B is an optionally substituted benzene ring, the ring C is an optionally substituted nitrogen-containing 5- to 7-membered heterocyclic ring which may be condensed with an unsubstituted benzene ring, X is N, and Y is CH;

(14) the compound of (1) above or a salt or prodrug thereof, wherein $R^1$ is a hydrogen atom or an acyloxy group, R is an unsubstituted $C_{1-6}$ alkyl group, $Ar^1$ is a phenyl group which may be substituted with an optionally halogenated $C_{1-6}$ alkoxy group, the ring A is an unsubstituted benzene ring, the ring B is an unsubstituted benzene ring, the ring C is tetrahydropyrrole, hexahydropyridine, hexahydropyrazine, tetrahydro-1,4-oxazine, tetrahydro-1,4-thiazine, perhydroazepine or pyrrole, X is N, and Y is CH;

(15) the compound of (1) above, which is any one of the following compounds or salts or prodrugs thereof:

(−)-2,4-cis-1-(3,4-dimethoxybenzoyl)-2-methyl-4-(1,2,3,4-tetrahydroquinolin-1-yl)-1,2,3,4-tetrahydroquinoline;

(−)-2,4-cis-4-(3,4-dihydro-2H-1,4-benzoxazin-4-yl)-1-(3,4-dimethoxybenzoyl)-2-methyl-1,2,3,4-tetrahydroquinoline;

2,4-cis-1-(3,4-dimethoxybenzoyl)-2-methyl-4-(1,2,3,4-tetrahydroquinolin-1-yl)-1,2,3,4-tetrahydroquinoline;

2,3-trans-2,4-cis-3-acetoxy-1-(3,4-dimethoxybenzoyl)-2-methyl-4-(1,2,3,4-tetrahydroquinolin-1-yl)-1,2,3,4-tetrahydroquinoline;

2,4-cis-4-(3,4-dihydro-2H-1,4-benzothiazin-4-yl)-1-(3,4-dimetboxybenzoyl)-2-methyl-1,2,3,4-tetrahydroquinoline;

2,4-cis-4-(1-benzyl-1,2,3,4-tetrahydroquinoxalin-4-yl)-1-(3,4-dimethoxybenzoyl)-2-methyl-1,2,3,4-tetrahydroquinoline;

2,4-cis-1-(3,4-dimethoxybenzoyl)-2-methyl-4-(2,3,4,5-tetrahydro-1H-1-benzazepinyl)-1,2,3,4-tetrahydroquinoline;

2,3-trans-2,4-cis-3-{[(benzylamino)carbonyl]oxy}-1-(3,4-dimethoxybenzoyl)-2-methyl-4-(2,3,4,5-tetrahydro-1H-1-benzazepinyl)-1,2,3,4-tetrahydroquinoline;

2,4-cis-4-(9H-9-carbazolyl)-1-(3,4-dimethoxybenzoyl)-2-methyl-1,2,3,4-tetrahydroquinoline;

(−)-2,4-cis-4-(9H-9-carbazolyl)-1-(3,4-dimethoxybenzoyl)-2-methyl-1,2,3,4-tetrahydroquinoline; and 2-butyl-4-(9H-9-carbazolyl)-1-(3,4-dimethoxybenzoyl)-1,2-dihydroquinoline;

(16) the compound of (1) above or a salt or prodrug thereof, wherein the 2- and 4-positions of Formula (I) is formed the cis(−)-configuration;

(17) a method for preparing a compound of the following formula or a salt or prodrug thereof:

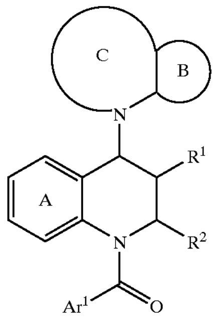

[wherein $R^1$, $R^2$, $Ar^1$ and the rings A, B and C are as defined below], which comprises reacting a compound of the following formula or a salt thereof:

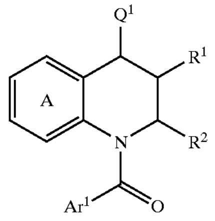

[wherein $R^1$ and $R^2$, which may be the same or different, each represent a hydrogen atom, an optionally substituted lower alkyl group or an optionally substituted hydroxy group, or $R^1$ and $R^2$ may together form a 4- to 7-membered ring together with their adjacent carbon atoms, $Ar^1$ represents an optionally substituted aromatic group, the ring A represents an optionally substituted benzene ring, and $Q^1$ represents a reactive substituent] with a compound of the following formula or a salt thereof:

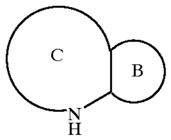

[wherein the ring B represents an optionally substituted aromatic ring, and the ring C represents an optionally substituted 4- to 8-membered ring which may further be condensed with an optionally substituted ring];

(18) a method for preparing a compound of the following formula or a salt or prodrug thereof:

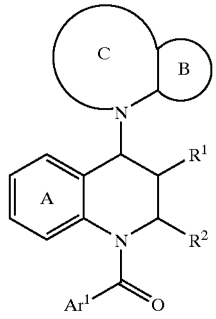

[wherein $R^1$, $R^2$, $Ar^1$ and the rings A, B and C are as defined below], which comprises reacting a compound of the following formula or a salt thereof:

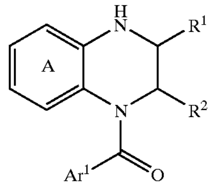

[wherein $R^1$ and $R^2$, which may be the same or different, each represent a hydrogen atom, an optionally substituted lower alkyl group or an optionally substituted hydroxy group, or $R^1$ and $R^2$ may together form a 4- to 7-membered ring together with their adjacent carbon atoms, $Ar^1$ represents an optionally substituted aromatic group, and the ring A represents an optionally substituted benzene ring] with a compound of the following formula or a salt thereof:

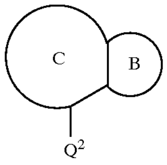

[wherein $Q^2$ represents a reactive substituent, the ring B represents an optionally substituted aromatic ring, and the ring C represents an optionally substituted 4- to 8-membered ring which may further be condensed with an optionally substituted ring];

(19) a method for preparing a compound of the following formula or a salt or prodrug thereof:

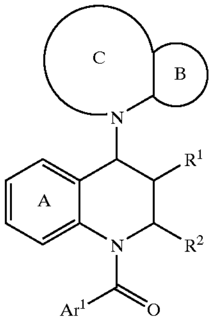

[wherein $R^1$, $R^2$, $Ar^1$ and the rings A, B and C are as defined below], which comprises reacting a compound of the following formula or a salt thereof:

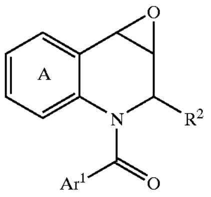

[wherein $R^2$ represents a hydrogen atom, an optionally substituted lower alkyl group or an optionally substituted hydroxy group, $Ar^1$ represents an optionally substituted aromatic group, and the ring A represents an optionally substituted benzene ring] with a compound of the following formula or a salt thereof:

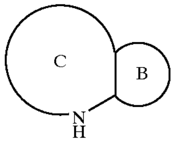

[wherein the ring B represents an optionally substituted aromatic ring, and the ring C represents an optionally substituted 4- to 8-membered ring which may further be condensed with an optionally substituted ring] to give a compound of the following formula or a salt thereof:

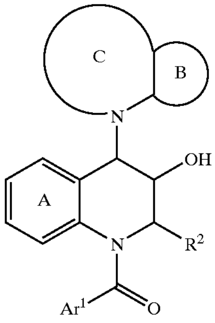

[wherein $R^2$, $Ar^1$ and the rings A, B and C are as defined above], and if necessary, replacing the hydroxy group in the above formula with $R^1$ [wherein $R^1$ represents a hydrogen atom, an optionally substituted lower alkyl group or an optionally substituted hydroxy group];

(20) a method for preparing a compound of the following formula or a salt or prodrug thereof:

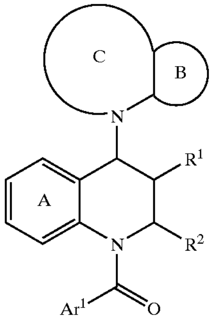

[wherein $R^1$, $R^2$, $Ar^1$ and the rings A, B and C are as defined below], which comprises reacting a compound of the following formula or a salt thereof:

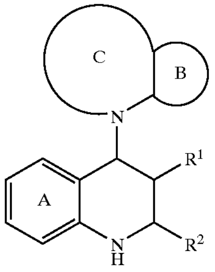

[wherein $R^1$ and $R^2$, which may be the same or different, each represent a hydrogen atom, an optionally substituted lower alkyl group or an optionally substituted hydroxy group, or $R^1$ and $R^2$ may together form a 4- to 7-membered ring together with their adjacent carbon atoms, the ring A represents an optionally substituted benzene ring, the ring B represents an optionally substituted aromatic ring, and the ring C represents an optionally substituted 4- to 8-membered ring which may further be condensed with an optionally substituted ring] with a compound of the formula: $Ar^1COOH$ [wherein $Ar^1$ represents an optionally substituted aromatic group] or a salt thereof;

(21) a method for preparing a compound of the following formula or a salt or prodrug thereof:

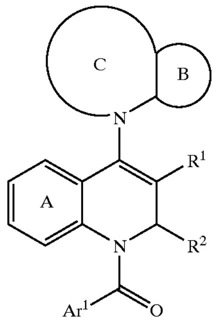

[wherein $R^2$, $Ar^1$ and the rings A, B and C are as defined below, and $R^1$ represents a hydrogen atom], which comprises reacting a compound of the following formula or a salt thereof:

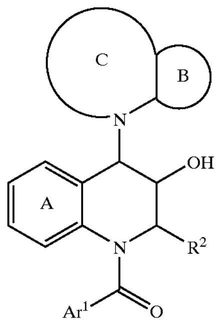

[wherein $R^2$ represents a hydrogen atom, an optionally substituted lower alkyl group or an optionally substituted hydroxy group, $Ar^1$ represents an optionally substituted aromatic group, the ring A represents an optionally substituted benzene ring, the ring B represents an optionally substituted aromatic ring, and the ring C represents an optionally substituted 4- to 8-membered ring which may further be condensed with an optionally substituted ring] with a base;

(22) a pharmaceutical composition comprising the compound of (1) above or a salt or prodrug thereof;

(23) the pharmaceutical composition of (22) above, which is a soluble β-amyloid precursor protein secretion stimulator and/or an apoptosis inhibitor;

(24) the pharmaceutical composition of (22) above, which is a prophylactic and/or therapeutic agent for Alzeheimer's disease, Parkinson's disease, neuropathy, senile dementia, cerebrovascular disorder-induced neuronopathy or cerebrovascular dementia;

(25) a therapeutic method, which comprises administering to a human or other mammalian subject an effective amount of a pharmaceutical composition comprising the compound of (1) above or a salt or prodrug thereof, wherein said pharmaceutical composition is a soluble β-amyloid precursor protein secretion stimulator and/or an apoptosis inhibitor;

(26) a prophylactic and/or therapeutic method for neurodegenerative diseases or neuronopathy, which comprises administering to a human or other mammalian subject an effective amount of a pharmaceutical composition comprising the compound of (1) above or a salt or prodrug thereof;

(27) a therapeutic method, which comprises administering to a human or other mammalian subject an effective amount of a pharmaceutical composition comprising the compound of (1) above or a salt or prodrug thereof, wherein said pharmaceutical composition is a prophylactic and/or therapeutic agent for Alzeheimer's disease, Parkinson's disease, neuropathy, senile dementia, cerebrovascular disorder-induced neuronopathy or cerebrovascular dementia;

(28) use of the compound defined in (1) above or a salt or prodrug thereof for the preparation of a pharmaceutical composition which is a soluble β-amyloid precursor protein secretion stimulator and/or an apoptosis inhibitor;

(29) use of the compound defined in (1) above or a salt or prodrug thereof for the preparation of a pharmaceutical composition which is a prophylactic and/or therapeutic agent for neurodegenerative diseases or neuronopathy; and

(30) use of the compound defined in (1) above or a salt or prodrug thereof for the preparation of a pharmaceutical composition which is a prophylactic and/or therapeutic agent for Alzeheimer's disease, Parkinson's disease, neuropathy, senile dementia, cerebrovascular disorder-induced neuronopathy or cerebrovascular dementia.

BRIEF DESCRIPTION OF THE DRAWINGS

FIG. 1(*b*) is a graph showing the stimulatory effect of Example No. 32 on sAPP secretion, as measure by Western blotting (averaged from triplicate wells).

BEST MODE FOR CARRYING OUT THE INVENTION

Figure 1:
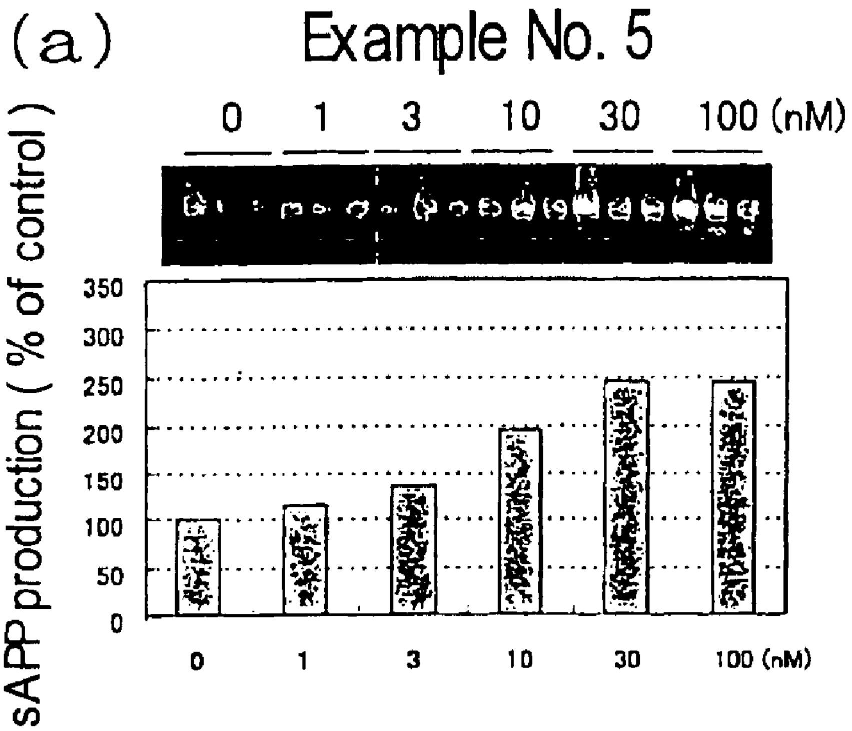
FIG. 1(*a*) is a graph showing the stimulatory effect of Example No. 5 on sAPP secretion, as measure by Western blotting (averaged from triplicate wells).
Figure 1:
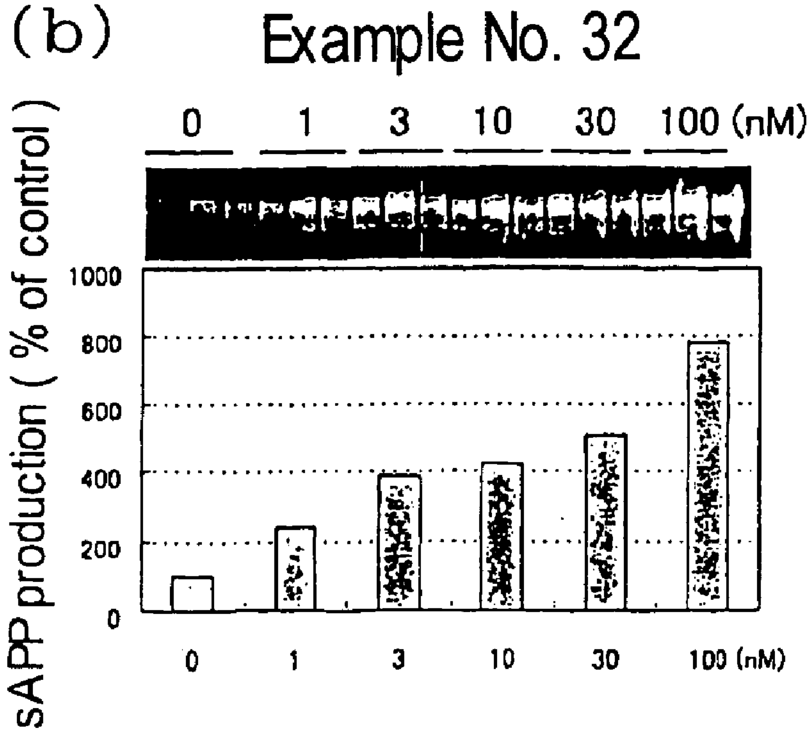

Examples of a "lower alkyl group" in the "optionally substituted lower alkyl group" represented by $R^1$ and $R^2$ include $C_{1-6}$ alkyls (e.g., methyl, ethyl, propyl, isopropyl, butyl, isobutyl, sec-butyl, tert-butyl, pentyl, hexyl), with methyl, ethyl and propyl being preferred.

In the above formulae, examples of a "substituent" on the "optionally substituted lower alkyl group" represented by $R^1$ and $R^2$ include a halogen atom (e.g., fluorine, chlorine, bromine, iodine), nitro, cyano, a $C_{1-6}$ alkyl-$C_{6-10}$ aryl-$C_{2-6}$ alkenyl (e.g., methylphenylethenyl), a $C_{1-6}$ alkyl-carbamoyl-$C_{2-6}$ alkenyl (e.g., propylcarbamoylpentenyl), an optionally halogenated $C_{3-6}$ cycloalkyl, an optionally halogenated $C_{1-6}$ alkoxy, an optionally halogenated $C_{1-6}$ alkylthio, hydroxy, an optionally substituted $C_{6-10}$ aryloxy, a $C_{6-10}$ aryl-$C_{7-16}$ aralkyloxy (e.g., phenylbenzyloxy), amino, a mono-$C_{1-6}$ alkylamino (e.g., methylamino, ethylamino, propylamino, isopropylamino, butylamino), a di-$C_{1-6}$ alkylamino (e.g., dimethylamino, diethylamino, dipropylamino, dibutylamino, ethylmethylamino), an optionally substituted 5- to 7-membered saturated cyclic amino, an acyl, an acylamino, an acyloxy, an optionally substituted $C_{6-10}$ aryl, a $C_{6-10}$ aryl-$C_{1-6}$ alkyloxy (e.g., phenylmethyloxy) and an optionally substituted silyloxy. Above all, preferred are a halogen atom, an optionally halogenated $C_{1-6}$ alkoxy, an optionally halogenated $C_{1-6}$ alkylthio, hydroxy, an optionally substituted $C_{6-10}$ aryloxy, an acyl, an acyloxy, a mono-$C_{1-6}$ alkylamino, a di-$C_{1-6}$ alkylamino, amino, an acylamino, a $C_{6-10}$ aryl, a $C_{6-10}$ aryl-$C_{1-6}$ alkyloxy and the like.

The "lower alkyl group" in the "optionally substituted lower alkyl group" represented by $R^1$ and $R^2$ may have, for example, 1 to 13 (preferably 1 to 5) of these substituents at any substitutable position(s) on the lower alkyl group. In a case where the number of substituents is at least 2, each substituent may be the same or different.

As used herein, examples of an "optionally halogenated $C_{3-6}$ cycloalkyl" include $C_{3-6}$ cycloalkyls (e.g., cyclopropyl, cyclobutyl, cyclopentyl, cyclohexyl) which may have 1 to 5, preferably 1 to 3, halogen atoms (e.g., fluorine, chlorine, bromine, iodine). Specific examples include cyclopropyl, cyclobutyl, cyclopentyl, cyclohexyl, 4,4-dichlorocyclohexyl, 2,2,3,3-tetrafluorocyclopentyl and 4-chlorocyclohexyl.

As used herein, examples of an "optionally halogenated $C_{1-6}$ alkoxy" include $C_{1-6}$ alkoxys (e.g., methoxy, ethoxy, propoxy, butoxy, pentyloxy) which may have 1 to 5, preferably 1 to 3, halogen atoms (e.g., fluorine, chlorine, bromine, iodine). Specific examples include methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, pentyloxy and hexyloxy.

As used herein, examples of an "optionally halogenated $C_{1-6}$ alkylthio" include $C_{1-6}$ alkylthios (e.g., methylthio, ethylthio, propylthio, isopropylthio, butylthio, sec-butylthio, tert-butylthio) which may have 1 to 5, preferably 1 to 3, halogen atoms (e.g., fluorine, chlorine, bromine, iodine). Specific examples include methylthio, difluoromethylthio, trifluoromethylthio, ethylthio, propylthio, isopropylthio, butylthio, 4,4,4-trifluorobutylthio, pentylthio and hexylthio.

Examples of a "$C_{6-10}$ aryloxy" in the above "optionally substituted $C_{6-10}$ aryloxy" include phenyloxy and naphthyloxy.

Examples of a "substituent" on the "optionally substituted $C_{6-10}$ aryloxy" include a halogen atom (e.g., fluorine, chlorine, bromine, iodine), a $C_{1-3}$ alkylenedioxy (e.g., methylenedioxy, ethylenedioxy), nitro, cyano, an optionally halogenated $C_{1-6}$ alkyl, an optionally halogenated $C_{3-6}$ cycloalkyl, an optionally halogenated $C_{1-6}$ alkoxy, an optionally halogenated $C_{1-6}$ alkylthio, hydroxy, amino, a mono-$C_{1-6}$ alkylamino (e.g., methylamino, ethylamino, propylamino, isopropylamino, butylamino), a di-$C_{1-6}$ alkylamino (e.g., dimethylamino, dietthylamino, dipropylamino, dibutylamino, ethylmethylamino), formyl, carboxy, carbamoyl, an optionally halogenated $C_{1-6}$ alkyl-carbonyl, a $C_{1-6}$ alkoxy-carbonyl (e.g., methoxycarbonyl, ethoxycarbonyl, propoxycarbonyl, tert-butoxycarbonyl), a mono-$C_{1-6}$ alkyl-carbamoyl (e.g., methylcarbamoyl, ethylcarbamoyl), a di-$C_{1-6}$ alkyl-carbamoyl (e.g., dimethylcarbamoyl, diethylcarbamoyl, ethylmethylcarbamoyl), an optionally halogenated $C_{1-6}$ alkylsulfonyl, formylamino, an optionally halogenated $C_{1-6}$ alkyl-carboxamide, a $C_{1-6}$ alkoxy-carboxamide (e.g., methoxycarboxamide, ethoxycarboxamide, propoxycarboxamide, butoxycarboxamide), a $C_{1-6}$ alkylsulfonylamino (e.g., methylsulfonylamino, ethylsulfonylamino), a $C_{1-6}$ alkyl-carbonyloxy (e.g., acetoxy, propanoyloxy), a $C_{1-6}$ alkoxy-carbonyloxy (e.g., methoxycarbonyloxy, ethoxycarbonyloxy, propoxycarbonyloxy, butoxycarbonyloxy), a mono-$C_{1-6}$ alkyl-carbamoyloxy (e.g., methylcarbamoyloxy, ethylcarbamoyloxy) and a di-$C_{1-6}$ alkyl-carbamoyloxy (e.g., dimethylcarbamoyloxy, diethylcarbamoyloxy), 1 to 5 of which may be used for substitution.

As used herein, examples of an "optionally halogenated $C_{1-6}$ alkyl" include $C_{1-6}$ alkyls (e.g., methyl, ethyl, propyl, isopropyl, butyl, isobutyl, sec-butyl, tert-butyl, pentyl, hexyl) which may have 1 to 5, preferably 1 to 3, halogen atoms (e.g., fluorine, chlorine, bromine, iodine). Specific examples include methyl, chloromethyl, difluoromethyl, trichloromethyl, trifluoromethyl, ethyl, 2-bromoethyl, 2,2,2-trifluoroethyl, pentafluoroethyl, propyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl and 6,6,6-trifluorohexyl.

As used herein, examples of an "optionally halogenated $C_{1-6}$ alkyl-carbonyl" include $C_{1-6}$ alkyl-carbonyls (e.g., acetyl, propanoyl, butanoyl, pentanoyl, hexanoyl) which may have 1 to 5, preferably 1 to 3, halogen atoms (e.g., fluorine, chlorine, bromine, iodine). Specific examples include acetyl, monochloroacetyl, trifluoroacetyl, trichloroacetyl, propanoyl, butanoyl, pentanoyl and hexanoyl.

As used herein, examples of an "optionally halogenated $C_{1-6}$ alkylsulfonyl" include $C_{1-6}$ alkylsulfonyls (e.g., methylsulfonyl, ethylsulfonyl, propylsulfonyl, isopropylsulfonyl, butylsulfonyl, sec-butylsulfonyl, tert-butylsulfonyl) which may have 1 to 5, preferably 1 to 3, halogen atoms (e.g., fluorine, chlorine, bromine, iodine). Specific examples include methylsulfonyl, difluoromethylsulfonyl, trifluoromethylsulfonyl, ethylsulfonyl, propylsulfonyl, isopropylsulfonyl, butylsulfonyl, 4,4,4-trifluorobutylsulfonyl, pentylsulfonyl and hexylsulfonyl.

As used herein, examples of an "optionally halogenated $C_{1-6}$ alkyl-carboxamide" include $C_{1-6}$ alkyl-carboxamides (e.g., acetamide) which may have 1 to 5, preferably 1 to 3, halogen atoms (e.g., fluorine, chlorine, bromine, iodine). Specific examples include acetamide, trifluoroacetamide, propanamide and butanamide.

Examples of a "5- to 7-membered saturated cyclic amino" in the above "optionally substituted 5- to 7-membered saturated cyclic amino" include morpholino, thiomoipholino, piperazin-1-yl, piperidino, pyrrolidin-1-yl and hexamethyleneimin-1-yl.

Examples of a "substituent" on the "optionally substituted 5- to 7-membered saturated cyclic amino" include a $C_{1-6}$ alkyl, an optionally substituted $C_{6-14}$ aryl, an optionally substituted $C_{7-19}$ aralkyl, an optionally substituted 5- to 10-membered aromatic heterocyclic group, an optionally substituted $C_{6-10}$ aryl-carbonyl, an optionally halogenated $C_{1-6}$ alkyl-carbonyl and an optionally halogenated $C_{1-6}$ alkylsulfonyl, 1 to 3 of which may be used for substitution.

Examples of a "$C_{6-14}$ aryl" in the "optionally substituted $C_{6-14}$ aryl" include phenyl, naphthyl (e.g., 1-naphthyl or 2-naphthyl), indenyl (e.g., 2-indenyl) and anthryl (e.g., 2-anthryl).

Examples of a "$C_{7-19}$ aralkyl" in the "optionally substituted $C_{7-19}$ aralkyl" include benzyl, phenethyl, diphenylmethyl, triphenylmethyl, 1-naphthylmethyl, 2-naphthylmethyl, 2,2-diphenylethyl, 3-phenylpropyl, 4-phenylbutyl and 5-phenylpentyl.

Examples of a "5- to 10-membered aromatic heterocyclic group" in the "optionally substituted 5- to 10-membered aromatic heterocyclic group" include pyridyl (e.g., 2-, 3- or 4-pyridyl), indolyl (e.g., 1-, 2- or 3-indolyl) and thienyl (e.g., 2- or 3-thienyl). Examples of a "$C_{6-10}$ aryl-carbonyl" in the "optionally substituted $C_{6-10}$ aryl-carbonyl" include benzoyl, 1-naphthoyl and 2-naphthoyl.

These "optionally substituted $C_{6-14}$ aryl", "optionally substituted $C_{7-19}$ aralkyl", "optionally substituted 5- to 10-membered aromatic heterocyclic group" and "optionally substituted $C_{6-10}$ aryl-carbonyl" may each have 1 to 5 substituents selected from a halogen atom (e.g., fluorine, chlorine, bromine, iodine), a $C_{1-3}$ alkylenedioxy (e.g., methylenedioxy, ethylenedioxy), nitro, cyano, an optionally halogenated $C_{1-6}$ alkyl, an optionally halogenated $C_{3-6}$ cycloalkyl, an optionally halogenated $C_{1-6}$ alkoxy, an optionally halogenated $C_{1-6}$ alkylthio, hydroxy, amino, a mono-$C_{1-6}$ alkylamino (e.g., methylamino, ethylamino, propylamino, isopropylamino, butylamino), a di-$C_{1-6}$ alkylamino (e.g., dimethylamino, diethylamino, dipropylamino, dibutylamino, ethylmethylamino), formyl, carboxy, carbamoyl, an optionally halogenated $C_{1-6}$ alkyl-carbonyl, a $C_{1-6}$ alkoxy-carbonyl (e.g., methoxycarbonyl, ethoxycarbonyl, propoxycarbonyl, tert-butoxycarbonyl), a mono-$C_{1-6}$ alkyl-carbamoyl (e.g., methylcarbamoyl, ethylcarbamoyl), a di-$C_{1-6}$ alkyl-carbamoyl (e.g., dimethylcarbamoyl, diethylcarbamoyl, ethylmethylcarbamoyl), an optionally halogenated $C_{1-6}$ alkylsulfonyl, formylamino, an optionally halogenated $C_{1-6}$ alkyl-carboxamide, a $C_{1-6}$ alkoxy-carboxamide (e.g., methoxycarboxamide, ethoxycarboxamide, propoxycarboxamide, butoxycarboxaamide), a $C_{1-6}$ alkylsulfonylamino (e.g., methylsulfonylamino, ethylsulfonylamino), a $C_{1-6}$ alkyl-carbonyloxy (e.g., acetoxy, propanoyloxy), a $C_{1-6}$ alkoxy-carbonyloxy (e.g., methoxycarbonyloxy, ethoxycarbonyloxy, propoxycarbonyloxy, butoxycarbonyloxy), a mono-$C_{1-6}$ alkyl-carbamoyloxy (e.g., methylcarbamoyloxy, ethylcarbamoyloxy), a di-$C_{1-6}$ alkyl-carbamoyloxy (e.g., dimethylcarbamoyloxy, diethylcarbamoyloxy) and the like.

Examples of an "acyl" in the "acyl", "acylamino" or "acyloxy" listed as a "substituent" on the above "optionally substituted lower alkyl group" represented by $R^1$ and $R^2$ include formyl, carboxy, carbamoyl, an optionally halogenated $C_{1-6}$ alkyl-carbonyl, a $C_{1-6}$ alkoxy-carbonyl (e.g., methoxycarbonyl, ethoxycarbonyl, propoxycarbonyl, tert-butoxycarbonyl), an optionally substituted $C_{6-10}$ aryl-carbonyl, an optionally substituted $C_{6-10}$ aryloxy-carbonyl, an optionally substituted $C_{7-16}$ aralkyloxy-carbonyl, an optionally substituted 5- or 6-membered heterocyclic carbonyl, an optionally substituted 5- or 6-membered heterocyclic thiocarbonyl, an optionally substituted mono-$C_{1-6}$ alkyl-carbamoyl, a di-$C_{1-6}$ alkyl-carbamoyl (e.g., dimethylcarbamoyl, diethylcarbamoyl, ethylmethylcarbamoyl), an optionally substituted $C_{6-10}$ aryl-carbamoyl, a $C_{6-10}$ aryl-$C_{1-6}$ alkyl-carbamoyl (e.g., phenylmethylcarbamoyl, phenylethylcarbamoyl), an optionally substituted 5- or 6-membered heterocyclic carbamoyl, an optionally halogenated $C_{1-6}$ alkylsulfonyl and an optionally substituted $C_{6-10}$ arylsulfonyl. Above all, preferred are an optionally halogenated $C_{1-6}$ alkyl-carbonyl, a $C_{1-6}$ alkoxy-carbonyl (e.g., ethoxycarbonyl), an optionally substituted $C_{6-10}$ aryl-carbonyl, an optionally substituted $C_{6-10}$ arylsulfonyl and the like.

Examples of a "$C_{6-10}$ aryl-carbonyl" in the above "optionally substituted $C_{6-10}$ aryl-carbonyl" include benzoyl, 1-naphthoyl and 2-naphthoyl.

Examples of a "$C_{6-10}$ aryloxy-carbonyl" in the above "optionally substituted $C_{6-10}$ aryloxy-carbonyl" include phenoxycarbonyl.

Examples of a "$C_{7-16}$ aralkyloxy-carbonyl" in the above "optionally substituted $C_{7-16}$ aralkyloxy-carbonyl" include benzyloxycarbonyl and phenethyloxycarbonyl.

Examples of a "5- or 6-membered heterocyclic carbonyl" in the above "optionally substituted 5- or 6-membered heterocyclic carbonyl" include nicotinoyl, isonicotinoyl, thenoyl (e.g., 2-thenoyl or 3-thenoyl), furoyl (e.g., 2-furoyl or 3-furoyl), morpholinocarbonyl, piperidinocarbonyl and pyrrolidin-1-ylcarbonyl.

Examples of a "mono-$C_{1-6}$ alkyl-carbamoyl" in the above "optionally substituted mono-$C_{1-6}$ alkyl-carbamoyl" include methylcarbamoyl and ethylcarbamoyl.

Examples of a "5- or 6-membered heterocyclic thiocarbonyl" in the above "optionally substituted 5- or 6-membered heterocyclic thiocarbonyl" include morpholinothiocarbonyl, piperidinothiocarbonyl, pyrrolidin-1-ylthiocarbonyl and imidazol-1-ylthiocarbonyl.

Examples of a "$C_{6-10}$ aryl-carbamoyl" in the above "optionally substituted $C_{6-10}$ aryl-carbamoyl" include phenylcarbamoyl, 1-naphthylcarbamoyl and 2-naphthylcarbamoyl.

Examples of a "5- or 6-membered heterocyclic carbamoyl" in the above "optionally substituted 5- or 6-membered heterocyclic carbamoyl" include pyridylcarbamoyl (e.g., 2-pyridylcarbamoyl, 3-pyridylcarbamoyl or 4-pyridylcarbamoyl) and thienylcarbamoyl (e.g., 2-thienylcarbamoyl or 3-thienylcarbamoyl).

Examples of a "$C_{6-10}$ arylsulfonyl" in the above "optionally substituted $C_{6-10}$ arylsulfonyl" include benzenesulfonyl, 1-naphthalenesulfonyl and 2-naphthalenesulfonyl.

These "optionally substituted $C_{6-10}$ aryl-carbonyl", "optionally substituted $C_{6-10}$ aryloxy-carbonyl", "optionally substituted $C_{7-16}$ aralkyloxy-carbonyl", "optionally substituted 5- or 6-membered heterocyclic carbonyl", "optionally substituted mono-$C_{1-6}$ alkyl-carbamoyl", "optionally substituted 5- or 6-membered heterocyclic thiocarbonyl", "optionally substituted $C_{6-10}$ aryl-carbamoyl", "optionally substituted 5- or 6-membered heterocyclic carbamoyl" and "optionally substituted $C_{6-10}$ arylsulfonyl" may each have 1 to 5 substituents, preferably 1 to 3 substituents, selected from a halogen atom, a $C_{1-3}$ alkylenedioxy, nitro, cyano, an optionally halogenated $C_{1-6}$ alkyl, an optionally halogenated $C_{1-6}$ alkoxy, an optionally halogenated $C_{1-6}$ alkylthio, hydroxy, amino, a mono-$C_{1-6}$ alkylamino, a di-$C_{1-6}$ alkylamino, formyl, carboxy, carbamoyl, an optionally halogenated $C_{1-6}$ alkyl-carbonyl, a $C_{1-6}$ alkoxy-carbonyl, a mono-$C_{1-6}$ alkyl-carbamoyl, a di-$C_{1-6}$ alkyl-carbamoyl, an optionally halogenated $C_{1-6}$ alkylsulfonyl, formylamino, an optionally halogenated $C_{1-6}$ alkyl-carboxamide, a $C_{1-6}$ alkoxy-carboxamide, a $C_{1-6}$ alkylsulfonylamino, a $C_{1-6}$ alkyl-carbonyloxy, a $C_{1-6}$ alkoxy-carbonyloxy, a mono-$C_{1-6}$ alkyl-carbamoyloxy and a di-$C_{1-6}$ alkyl-carbamoyloxy. Above all, preferred substituents are a halogen atom, an optionally halogenated $C_{1-6}$ alkyl, an optionally halogenated $C_{1-6}$ alkoxy and the like.

An "acylamino" as a "substituent" on the above "optionally substituted lower alkyl group" represented by $R^1$ and $R^2$ may be, for example, an amino group substituted with one or two of the acyl substituents specifically listed above for the "optionally substituted aromatic group." Preferred examples include formylamino, an optionally halogenated $C_{1-6}$ alkyl-carboxamide, an optionally substituted $C_{6-10}$ aryl-carboxamide (e.g., phenylcarboxamide, naphthylcarboxamide), a $C_{1-6}$ alkoxy-carboxamide (e.g., methoxycarboxamide, ethoxycarboxamide, propoxycarboxamide, butoxycarboxamide) and a $C_{1-6}$ alkylsulfonylamino (e.g., methylsulfonylamino, ethylsulfonylamino).

An "acyloxy" as a "substituent" on the above "optionally substituted lower alkyl group" represented by $R^1$ and $R^2$ may be, for example, an oxy group substituted with one of the acyl substituents specifically listed above for the "optionally substituted aromatic group." Preferred examples include a $C_{1-6}$ alkyl-carbonyloxy (e.g., acetoxy, propanoyloxy), an optionally substituted $C_{6-10}$ aryl-carbonyloxy (e.g., benzoyloxy, 1-naphthoyloxy, 2-naphthoyloxy), a $C_{1-6}$ alkoxy-carbonyloxy (e.g., methoxycarbonyloxy, ethoxycarbonyloxy, propoxycarbonyloxy, butoxycarbonyloxy), a mono-$C_{1-6}$ alkyl-carbamoyloxy (e.g., methylcarbamoyloxy, ethylcarbamoyloxy), a di-$C_{1-6}$ alkyl-carbamoyloxy (e.g., dimethylcarbamoyloxy, diethylcarbamoyloxy), an optionally substituted $C_{6-10}$ aryl-carbamoyloxy (e.g., phenylcarbamoyloxy, naphthylcarbamoyloxy) and nicotinoyloxy.

Examples of a "$C_{6-10}$ aryl" in the "optionally substituted $C_{6-10}$ aryl" as a "substituent" on the above "optionally substituted lower alkyl group" represented by $R^1$ and $R^2$ include phenyl and naphthyl.

Examples of a "substituent" on the "optionally substituted $C_{6-10}$ aryl" include a halogen atom (e.g., fluorine, chlorine, bromine, iodine), a $C_{1-3}$ alkylenedioxy (e.g., methylenedioxy, ethylenedioxy), nitro, cyano, an optionally halogenated $C_{1-6}$ alkyl, an optionally halogenated $C_{3-6}$ cycloalkyl, an optionally halogenated $C_{1-6}$ alkoxy, an optionally halogenated $C_{1-6}$ alkylthio, hydroxy, amino, a mono-$C_{1-6}$ alkylamino (e.g., methylamino, ethylamino, propylamino, isopropylamino, butylamino), a di-$C_{1-6}$ alkylamino (e.g., dimethylamino, diethylamino, dipropylamino, dibutylamino, ethylmethylamino), formyl, carboxy, carbamoyl, an optionally halogenated $C_{1-6}$ alkyl-carbonyl, a $C_{1-6}$ alkoxy-carbonyl (e.g., methoxycarbonyl, ethoxycarbonyl, propoxycarbonyl, tert-butoxycarbonyl), a mono-$C_{1-6}$ alkyl-carbamoyl (e.g., methylcarbamoyl, ethylcarbamoyl), a di-$C_{1-6}$ alkyl-carbamoyl (e.g., dimethylcarbamoyl, diethylcarbamoyl, ethylmethylcarbamoyl), an optionally halogenated $C_{1-6}$ alkylsulfonyl, formylamino, an optionally halogenated $C_{1-6}$ alkyl-carboxamide, a $C_{1-6}$ alkoxy-carboxamide (e.g., methoxycarboxamide, ethoxycarboxamide, propoxycarboxamide, butoxycarboxamide), a $C_{1-6}$ alkylsulfonylamino (e.g., methylsulfonylamino, ethylsulfonylamino), a $C_{1-6}$ alkyl-carbonyloxy (e.g., acetoxy, propanoyloxy), a $C_{1-6}$ alkoxy-carbonyloxy (e.g., methoxycarbonyloxy, ethoxycarbonyloxy, propoxycarbonyloxy, butoxycarbonyloxy), a mono-$C_{1-6}$ alkyl-carbamoyloxy (e.g., methylcarbamoyloxy, ethylcarbamoyloxy) and a di-$C_{1-6}$ alkyl-carbamoyloxy (e.g., dimethylcarbamoyloxy, diethylcarbamoyloxy), 1 to 5 of which may be used for substitution.

The "optionally substituted silyloxy" as a "substituent" on the above "optionally substituted lower alkyl group" represented by $R^1$ and $R^2$ may have 1 to 3 substituents selected from $C_{1-6}$ alkyls, $C_{6-10}$ aryls and the like.

Examples of a "substituent" on the "optionally substituted hydroxy group" represented by $R^1$ and $R^2$ include an optionally substituted lower alkyl group, an optionally substituted $C_{6-14}$ aryl group, and an acyl group.

Examples of a "lower alkyl group" in the "optionally substituted lower alkyl group" include $C_{1-6}$ alkyls (e.g., methyl, ethyl, propyl, isopropyl, butyl, isobutyl, sec-butyl, tert-butyl, pentyl, hexyl), with methyl, ethyl and propyl being preferred.

Examples of a "$C_{6-14}$ aryl group" in the "optionally substituted $C_{6-14}$ aryl group" include phenyl, naphthyl (e.g., 1-naphthyl or 2-naphthyl), indenyl (e.g., 2-indenyl) and anthryl (e.g., 2-anthryl).

An "acyl" as a "substituent" on the above "optionally substituted hydroxy group" represented by $R^1$ and $R^2$ has the same meaning as defined for the "acyl" as a "substituent" on the above "optionally substituted lower alkyl group" represented by $R^1$ and $R^2$. Above all, preferred are an optionally halogenated $C_{1-6}$ alkyl-carbonyl group, an optionally substituted carbamoyl group, an optionally substituted thiocarbamoyl group and the like.

Examples of a compound of Formula (I) wherein $R^1$ and $R^2$ may together form a 4- to 7-membered ring together with their adjacent carbon atoms include compounds having the following formula:

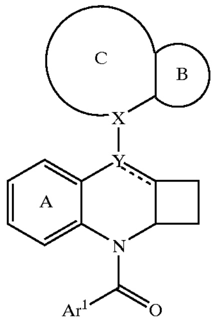
,
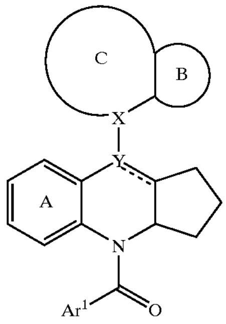
,
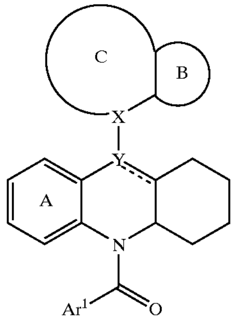
or
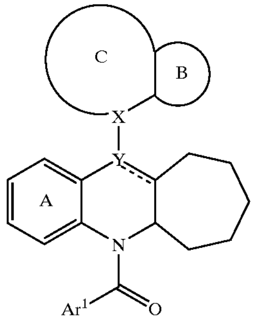

[wherein each symbol is as defined above].

$R^1$ is preferably a hydrogen atom or an optionally substituted hydroxy group. Such an optionally substituted hydroxy group is preferably an alkyloxy group or an acyloxy group. $R^2$ is preferably a hydrogen atom or an optionally substituted lower alkyl group, more preferably a hydrogen atom or a $C_{1-6}$ alkyl, and even more preferably a hydrogen atom or methyl.

Examples of an "aromatic group" in the "optionally substituted aromatic group" represented by $Ar^1$ include a monocyclic aromatic group, a ring-assembled aromatic group, and a condensed aromatic group.

Examples of the above "monocyclic aromatic group" include a monovalent group formed by removing any one hydrogen atom from a benzene ring or a 5- or 6-membered aromatic heterocyclic ring.

Examples of such a "5- or 6-membered aromatic heterocyclic ring" include those containing, in addition to carbon atoms, one or more (e.g., 1 to 3) heteroatoms selected from a nitrogen atom, a sulfur atom and an oxygen atom. Specific examples include thiophene, furan, pyrrole, imidazole, pyrazole, thiazole, oxazole, pyridine, pyrazine, pyrimidine and pyridazine.

Specific examples of the "monocyclic aromatic group" include phenyl, thienyl (e.g., 2- or 3-thienyl), furyl (e.g., 2- or 3-furyl), pyrrolyl (e.g., 1-, 2- or 3-pyrrolyl), imidazolyl (e.g., 2- or 4-imidazolyl), pyrazolyl (e.g., 3- or 4-pyrazolyl), thiazolyl (e.g., 2-, 4- or 5-thiazolyl), oxazolyl (e.g., 2-, 4- or 5-oxazolyl), pyridyl (e.g., 2-, 3- or 4-pyridyl), pyrazinyl (e.g., 2-pyrazinyl), pyrimidinyl (e.g., 2-, 4- or 5-pyrimidinyl) and pyridazinyl (e.g., 3- or 4-pyridazinyl).

Examples of the above "ring-assembled aromatic group" include a group formed by removing any one hydrogen atom from an aromatic ring assembly comprising 2 or more (preferably 2 or 3) aromatic rings directly linked via a single bond(s), in which the number of bonds linking these aromatic rings is smaller than that of the aromatic rings by one.

Examples of such an "aromatic ring" include an aromatic hydrocarbon and an aromatic heterocyclic ring.

Examples of the "aromatic hydrocarbon" include $C_{6-14}$ monocyclic or condensed polycyclic (bi- or tricyclic) aromatic hydrocarbons (e.g., benzene, naphthalene, indene, and anthracene).

Examples of the "aromatic heterocyclic ring" include 5- to 14-membered (preferably 5- to 10-membered) aromatic heterocyclic rings containing, in addition to carbon atoms, one or more (e.g., 1 to 4) heteroatoms selected from a nitrogen atom, a sulfur atom and an oxygen atom. Specific examples include aromatic heterocyclic rings such as thiophene, benzothiophene, benzofuran, benzimidazole, benzoxazole, benzothiazole, benzisothiazole, naphto[2,3-b]thiophene, furan, phenoxathiine, pyrrole, imidazole, pyrazole, oxazole, isoxazole, oxadiazole (e.g., 1,2,4-oxadiazole or 1,3,4-oxadiazole), thiadiazole (e.g., 1,2,4-thiadiazole or 1,3,4-thiadiazole), pyridine, pyrazine, pyrimidine, pyridazine, indole, isoindole, 1H-indazole, purine, 4H-quinolizine, isoquinoline, quinoline, phthalazine, naphthylizine, quinoxaline, quinazoline, cinnoline, carbazole, β-carboline, phenanthridine, acridine, phenazine, thiazole, isothiazole, phenothiazine, furazane, phenoxazine and phthalimide, or rings formed by condensation between these rings (preferably monocyclic rings) and 1 to several (preferably 1 or 2) aromatic rings (e.g., a benzene ring).

The aromatic ring assembly comprising such aromatic rings directly linked via a single bond(s) may be, for example, an aromatic ring assembly composed of 2 or 3 rings (preferably 2 rings) selected from a benzene ring, a naphthalene ring and a 5- to 10-membered (preferably 5- or 6-membered) aromatic heterocyclic ring. Preferred examples of such an aromatic ring assembly include those composed of 2 or 3 aromatic rings selected from benzene, naphthalene, pyridine, pyrimidine, thiophene, furan, thiazole, isothiazole, oxazole, oxadiazole (e.g., 1,2,4-oxadiazole or 1,3,4-oxadiazole), thiadiazole (1,2,4-thiadiazole or 1,3,4-thiadiazole), quinoline, isoquinoline, indole, benzothiophene, benzoxazole, benzothiazole and benzofuran.

Specific examples include biphenylyl (e.g., 2-, 3- or 4-biphenylyl), naphthyl-substituted oxadiazolyl (e.g., 3-(1-naphthyl)-1,2,4-oxadiazol-5-yl or 3-(2-naphthyl)-1,2,4-oxadiazol-5-yl), benzofuranyl-substituted oxadiazolyl (e.g., 3-(2-benzofuranyl)-1,2,4-oxadiazol-5-yl), phenyl-substituted oxadiazolyl (e.g., 3-phenyl-1,2,4-oxadiazol-5-yl or 5-phenyl-1,3,4-oxadiazol-2-yl), benzoxazolyl-substituted oxadiazolyl (e.g., 3-(2-benzoxazolyl)-1,2,4-oxadiazol-2-yl), indolyl-substituted oxadiazolyl (e.g., 3-(3-indolyl)-1,2,4-oxadiazol-2-yl or 3-(2-indolyl)-1,2,4-oxadiazol-2-yl), phenyl-substituted thiazolyl (e.g., 4-phenylthiazol-2-yl), benzofuranyl-substituted thiazolyl (e.g., 4-(2-benzofuranyl)thiazol-2-yl), phenyl-substituted oxazolyl (e.g., 4-phenyl-1,3-oxazol-5-yl or 5-phenyloxazol-2-yl), phenyl-substituted isothiazolyl (e.g., 5-phenyl-isothiazol-4-yl), thienyl-substituted phenyl (e.g., 4-(2-thienyl)phenyl or 4-(3-thienyl)phenyl), pyridyl-substituted phenyl (e.g., 3-(3-pyridyl)phenyl or 4-(3-pyridyl)phenyl), phenyl-substituted pyridyl (e.g., 6-phenyl-3-pyridyl), naphthyl-substituted phenyl (e.g., 4-(2-naphthyl)phenyl), benzofuranyl-substituted phenyl (e.g., 4-(2-benzofuranyl)phenyl) and terphenylyl (e.g., 4,4'-terphenylyl).

Examples of the above "condensed aromatic group" include a monovalent group formed by removing any one hydrogen atom from a condensed polycyclic (preferably bi- to tetracyclic, more preferably bi- or tricyclic) aromatic ring. Examples of such a "condensed polycyclic aromatic ring" include a condensed polycyclic aromatic hydrocarbon and a condensed polycyclic aromatic heterocyclic ring.

Examples of the "condensed polycyclic aromatic hydrocarbon" include $C_{9-14}$ condensed polycyclic (bi- or tricyclic) aromatic hydrocarbons (e.g., naphthalene, indene, and anthracene).

Examples of the "condensed polycyclic aromatic heterocyclic ring" include 9- to 14-membered (preferably 9- or 10-membered) condensed polycyclic aromatic heterocyclic rings containing, in addition to carbon atoms, one or more (e.g., 1 to 4) heteroatoms selected from a nitrogen atom, a sulfur atom and an oxygen atom. Specific examples include aromatic heterocyclic rings such as benzofuran, benzimidazole, benzoxazole, benzothiazole, benzisothiazole, naphto[2,3-b]thiophene, isoquinoline, quinoline, indole, quinoxaline, phenanthridine, phenothiazine, phenoxazine and phthalimide.

Specific examples of the above "condensed aromatic group" include naphthyl (e.g., 1-naphthyl or 2-naphthyl), quinolyl (e.g., 2-quinolyl, 3-quinolyl or 4-quinolyl), benzofuranyl (e.g., 2-benzofuranyl), benzothiazolyl (e.g., 2-benzothiazolyl), benzimidazolyl (e.g., 2-benzimidazolyl) and indolyl (e.g., 1-indolyl, 2-indolyl or 3-indolyl).

Among those listed above, preferred examples of the aromatic group represented by $Ar^1$ include:

(1) monocyclic aromatic groups such as phenyl, thienyl (e.g., 2- or 3-thienyl), furyl (e.g., 2- or 3-furyl) and pyridyl (e.g., 2-, 3- or 4-pyridyl);

(2) ring-assembled aromatic groups such as biphenylyl (e.g., 2-, 3- or 4-biphenylyl), naphthyl-substituted oxadiazolyl (e.g., 3-(1-naphthyl)-1,2,4-oxadiazol-5-yl or 3-(2-naphthyl)-1,2,4-oxadiazol-5-yl), benzofuranyl-substituted oxadiazolyl (e.g., 3-(2-benzofuranyl)-1,2,4-oxadiazol-5-yl), phenyl-substituted oxadiazolyl (e.g., 3-phenyl-1,2,4-oxadiazol-5-yl), benzoxazolyl-substituted oxadiazolyl (e.g., 3-(2-benzoxazolyl)-1,2,4-oxadiazol-2-yl), indolyl-substituted oxadiazolyl (e.g., 3-(3-indolyl)-1,2,4-oxadiazol-2-yl or 3-(2-indolyl)-1,2,4-oxadiazol-2-yl), phenyl-substituted thiazolyl (e.g., 4-phenylthiazol-2-yl), benzofuranyl-substituted thiazolyl (e.g., 4-(2-benzofuranyl)thiazol-2-yl), phenyl-substituted oxazolyl (e.g., 4-phenyl-1,3-oxazol-5-yl), thienyl-substituted phenyl (e.g., 4-(2-thienyl)phenyl), pyridyl-substituted phenyl (e.g., 4-(3-pyridyl)phenyl), naphthyl-substituted phenyl (e.g., 4-(2-naphthyl)phenyl) and terphenylyl (e.g., 4,4'-terphenylyl); and (3) condensed aromatic groups such as quinolyl (e.g., 2-, 3- or 4-quinolyl) and indolyl (e.g., 1-, 2- or 3-indolyl).

More preferred examples of the aromatic group represented by $Ar^1$ include monocyclic aromatic groups such as phenyl, thienyl (e.g., 2- or 3-thienyl), furyl (e.g., 2- or 3-furyl) and pyridyl (e.g., 2-, 3- or 4-pyridyl).

Examples of an "aromatic ring" in the "optionally substituted aromatic ring" represented by the ring B include a monocyclic aromatic ring, a ring-assembled aromatic ring, and a condensed aromatic ring.

Examples of the above "monocyclic aromatic ring" include a benzene ring and a 5- or 6-membered aromatic heterocyclic ring.

Examples of such a "5- or 6-membered aromatic heterocyclic ring" include those containing, in addition to carbon atoms, one or more (e.g., 1 to 3) heteroatoms selected from a nitrogen atom, a sulfur atom and an oxygen atom. Specific examples include thiophene, furan, pyrrole, imidazole, pyrazole, thiazole, oxazole, pyridine, pyrazine, pyrimidine and pyridazine.

Examples of the above "ring-assembled aromatic ring" include an aromatic ring assembly comprising 2 or more (preferably 2 or 3) aromatic rings directly linked via a single bond(s), in which the number of bonds linking these aromatic rings is smaller than that of the aromatic rings by one.

Examples of such an "aromatic ring" include an aromatic hydrocarbon and an aromatic heterocyclic ring.

Examples of the "aromatic hydrocarbon" include $C_{6-14}$ monocyclic or condensed polycyclic (bi- or tricyclic) aromatic hydrocarbons (e.g., benzene, naphthalene, indene, anthracene).

Examples of the "aromatic heterocyclic ring" include 5- to 14-membered (preferably 5- to 10-membered) aromatic heterocyclic rings containing, in addition to carbon atoms, one or more (e.g., 1 to 4) heteroatoms selected from a nitrogen atom, a sulfur atom and an oxygen atom. Specific examples include aromatic heterocyclic rings such as thiophene, benzothiophene, benzofuran, benzimidazole, benzoxazole, benzothiazole, benzisothiazole, naphto[2,3-b] thiophene, furan, phenoxathiine, pyrrole, imidazole, pyrazole, oxazole, isoxazole, oxadiazole (e.g., 1,2,4-oxadiazole or 1,3,4-oxadiazole), thiadiazole (e.g., 1,2,4-thiadiazole or 1,3,4-thiadiazole), pyridine, pyrazine, pyrimidine, pyridazine, indole, isoindole, 1H-indazole, purine, 4H-quinolizine, isoquinoline, quinoline, phthalazine, naphthylizine, quinoxaline, quinazoline, cinnoline, carbazole, β-carboline, phenanthridine, acridine, phenazine, thiazole, isothiazole, phenothiazine, furazane, phenoxazine and phthalimide, or rings formed by condensation between these rings (preferably monocyclic rings) and 1 to several (preferably 1 or 2) aromatic rings (e.g., a benzene ring).

The aromatic ring assembly comprising such aromatic rings directly linked via a single bond(s) may be, for example, an aromatic ring assembly composed of 2 or 3 rings (preferably 2 rings) selected from a benzene ring, a naphthalene ring and a 5- to 10-membered (preferably 5- or 6-membered) aromatic heterocyclic ring. Preferred examples of such an aromatic ring assembly include those composed of 2 or 3 aromatic rings selected from benzene, naphthalene, pyridine, pyrimidine, thiophene, furan, thiazole, isothiazole, oxazole, oxadiazole (e.g., 1,2,4-oxadiazole or 1,3,4-oxadiazole), thiadiazole (e.g., 1,2,4-thiadiazole or 1,3,4-thiadiazole), quinoline, isoquinoline, indole, benzothiophene, benzoxazole, benzothiazole and benzofuran.

Specific examples include biphenyl, naphthyl-substituted oxadiazole (e.g., 3-(1-naphthyl)-1,2,4-oxadiazole or 3-(2-naphthyl)-1,2,4-oxadiazole), benzofuranyl-substituted oxadiazole (e.g., 3-(2-benzofuranyl)-1,2,4-oxadiazole), phenyl-substituted oxadiazole (e.g., 3-phenyl-1,2,4-oxadiazole or 5-phenyl-1,3,4-oxadiazole), benzoxazolyl-substituted oxadiazole (e.g., 3-(2-benzoxazolyl)-,1,2,4-oxadiazole), indolyl-substituted oxadiazole (e.g., 3-(3-indolyl)-1,2,4-oxadiazole or 3-(2-indolyl)-1,2,4-oxadiazole), phenyl-substituted thiazole (e.g., 4-phenylthiazole), benzofuranyl-substituted thiazole (e.g., 4-(2-benzofuranyl)thiazole), phenyl-substituted oxazole (e.g., 4-phenyl-1,3-oxazole or 5-phenyloxazole), phenyl-substituted isothiazole (e.g., 5-phenyl-isothiazole), thienyl-substituted benzene (e.g., (2-thienyl)benzene or (3-thienyl)benzene), pyridyl-substituted benzene (e.g., (3-pyridyl)benzene or (3-pyridyl) benzene), phenyl-substituted pyridine (e.g., 6-phenylpyridine), naphthyl-substituted benzene (e.g., (2-naphthyl)benzene), benzofuranyl-substituted benzene (e.g., (2-benzofuranyl)benzene) and terphenyl (e.g., p-terphenyl).

Examples of the above "condensed aromatic ring" include a condensed polycyclic (preferably bi- to tetracyclic, more preferably bi- or tricyclic) aromatic ring. Examples of such a "condensed polycyclic aromatic ring" include a condensed polycyclic aromatic hydrocarbon and a condensed polycyclic aromatic heterocyclic ring.

Examples of the "condensed polycyclic aromatic hydrocarbon" include $C_{9-14}$ condensed polycyclic (bi- or tricyclic) aromatic hydrocarbons (e.g., naphthalene, indene, and anthracene).

Examples of the "condensed polycyclic aromatic heterocyclic ring" include 9- to 14-membered (preferably 9- or 10-membered) condensed polycyclic aromatic heterocyclic rings containing, in addition to carbon atoms, one or more (e.g., 1 to 4) heteroatoms selected from a nitrogen atom, a sulfur atom and an oxygen atom. Specific examples include aromatic heterocyclic rings such as benzofuran, benzimidazole, benzoxazole, benzothiazole, benzisothiazole, naphto[2,3-b]thiophene, isoquinoline, quinoline, indole, quinoxaline, phenanthridine, phenothiazine, phenoxazine and phthalimide.

Among those listed above, preferred examples of the aromatic ring represented by the ring B include:

(1) monocyclic aromatic rings such as benzene, thiophene, furan and pyridine;

(2) ring-assembled aromatic rings such as biphenyl, naphthyl-substituted oxadiazole (e.g., 3-(1-naphthyl)-1,2,4-oxadiazole or 3-(2-naphthyl)-1,2,4-oxadiazole), benzofuranyl-substituted oxadiazole (e.g., 3-(2-benzofuranyl)-1,2,4-oxadiazole), phenyl-substituted oxadiazole (e.g., 3-phenyl-1,2,4-oxadiazole), benzoxazolyl-substituted oxadiazole (e.g., 3-(2-benzoxazolyl)-1,2,4-oxadiazole), indolyl-substituted oxadiazole (e.g., 3-(3-indolyl)-1,2,4-oxadiazole or 3-(2-indolyl)-1,2,4-oxadiazole), phenyl-substituted thiazole (e.g., 4-phenylthiazole), benzofuranyl-substituted thiazole (e.g., 4-(2-benzofuranyl)thiazole), phenyl-substituted oxazole (e.g., 4-phenyl-1,3-oxazole), thienyl-substituted benzene (e.g., (2-thienyl)benzene), pyridyl-substituted benzene (e.g., (3-pyridyl)benzene), naphthyl-substituted benzene (e.g., (2-naphthyl)benzene) and terphenyl (e.g., p-terphenyl); and (3) condensed aromatic rings such as quinoline and indole.

More preferred examples of the aromatic ring represented by the ring B include monocyclic aromatic rings such as benzene.

Examples of a "4- to 8-membered ring" in the "optionally substituted 4- to 8-membered ring which may further be condensed with an optionally substituted ring" represented by the ring C include a 4- to 8-membered saturated ring and a 4- to 8-membered unsaturated ring.

Examples of such a "4- to 8-membered saturated ring" include a 4- to 8-membered saturated cyclic hydrocarbon and a 4- to 8-membered saturated heterocyclic ring.

Examples of the "4- to 8-membered saturated cyclic hydrocarbon" include cyclobutane, cyclopentane, cyclohexane, cycloheptane and cyclooctane.

Examples of the "4- to 8-membered saturated heterocyclic ring" include those containing, in addition to carbon atoms, one or more (e.g., 1 to 3) heteroatoms selected from a nitrogen atom, a sulfur atom and an oxygen atom. Specific examples include tetrahydrothiophene, tetrahydrofuran, tetrahydropyrrole, tetrahydroimidazole, tetrahydropyrazole, tetrahydrothiazole, tetrahydrooxazole, hexahydropyridine, hexahydropyrazine, hexahydropyrimidine, hexahydropyridazine, tetrahydro-1,4-oxazine, tetrahydro-1,4-thiazine, perhydroazepine, perhydro-1,4-diazepine, perhydro-1,4-oxazepine, perhydro-1,4-thiazepine and perhydroazocine.

Among those listed above, preferred is a ring of the following formula:

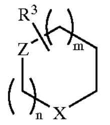

[wherein $R^3$ represents a hydrogen atom, a halogen atom, an optionally substituted lower alkyl group or an optionally substituted lower alkoxy group, X represents CH or N, Z represents an oxygen atom, a sulfur atom, $CR^4R^5$, $NR^6$ or

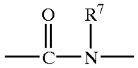

or

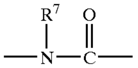

(wherein $R^4$, $R^5$, $R^6$ and $R^7$, which may be the same or different, each represent a hydrogen atom or an optionally substituted lower alkyl group), m represents 0 or 1, and n represents an integer of 1 to 4].

Examples of a "lower alkyl group" in the optionally substituted lower alkyl group represented by $R^3$, $R^4$, $R^5$, $R^6$ and $R^7$ include $C_{1-6}$ alkyls (e.g., methyl, ethyl, propyl, isopropyl, butyl, isobutyl, sec-butyl, tert-butyl, pentyl, hexyl), with methyl, ethyl and propyl being preferred.

Examples of the halogen atom as $R^3$ include fluorine, chlorine, bromine and iodine, with chlorine being preferred.

Examples of a "lower alkoxy group" in the optionally substituted lower alkoxy group represented by $R^3$ include $C_{1-6}$ alkoxys (e.g., methoxy, ethoxy, propoxy, butoxy, pentyloxy), with methoxy, ethoxy, propoxy and isopropoxy being preferred.

In the above formulae, a "substituent" on the "optionally substituted lower alkyl group" represented by $R^3$, $R^4$, $R^5$, $R^6$ and $R^7$ has the same meaning as defined for the "substituent" on the "optionally substituted lower alkyl group" represented by $R^1$ and $R^2$.

In the above formulae, examples of a "substituent" on the "optionally substituted lower alkoxy group" represented by $R^3$ include a halogen atom (e.g., fluorine, chlorine, bromine, iodine), a $C_{1-3}$ alkylenedioxy (e.g., methylenedioxy, ethylenedioxy), nitro, cyano, an optionally halogenated $C_{1-6}$ alkyl, a $C_{6-10}$ aryloxy-$C_{1-6}$ alkyl (e.g., phenoxymethyl), a $C_{1-6}$ alkyl-$C_{6-10}$ aryl-$C_{2-6}$ alkenyl (e.g., methylphenylethenyl), an optionally halogenated $C_{3-6}$ cycloalkyl, an optionally substituted $C_{7-16}$ aralkyl, an optionally halogenated $C_{1-6}$ alkoxy, an optionally halogenated $C_{1-6}$ alkylthio, hydroxy, an optionally substituted $C_{6-10}$ aryloxy, a $C_{6-10}$ aryl-$C_{7-16}$ aralkyloxy (e.g., phenylbenzyloxy), amino, a mono-$C_{1-6}$ alkylamino (e.g., methylamino, ethylamino, propylamino, isopropylamino, butylamino), a di-$C_{1-6}$ alkylamino (e.g., dimethylamino, diethylamino, dipropylamino, dibutylamino, ethylmethylamino), an optionally substituted 5- to 7-membered saturated cyclic amino, an acyl, an acylamino, and an acyloxy. Above all, preferred are a halogen atom, a $C_{1-3}$ alkylenedioxy, an optionally halogenated $C_{1-6}$ alkyl, a $C_{6-10}$ aryloxy-$C_{1-6}$ alkyl, a $C_{1-6}$ alkyl-$C_{6-10}$ aryl-$C_{2-6}$ alkenyl, an optionally substituted $C_{7-16}$ aralkyl, an optionally halogenated $C_{1-6}$ alkoxy, hydroxy, an optionally substituted $C_{6-10}$ aryloxy, an acyl, an acyloxy and the like.

The "lower alkoxy group" in the "optionally substituted lower alkoxy group" represented by $R^3$ may have, for example, 1 to 13 (preferably 1 to 5) of these substituents at any substitutable position(s) on the lower alkoxy group. In a case where the number of substituents is at least 2, each substituent may be the same or different.

Examples of a "$C_{7-16}$ aralkyl" in the above "optionally substituted $C_{7-16}$ aralkyl" include benzyl, phenethyl and naphthylmethyl.

Examples of a "$C_{6-10}$ aryloxy" in the above "optionally substituted $C_{6-10}$ aryloxy" include phenyloxy and naphthyloxy.

These "optionally substituted $C_{7-16}$ aralkyl" and "optionally substituted $C_{6-10}$ aryloxy" may each have 1 to 5 substituents selected from a halogen atom (e.g., fluorine, chlorine, bromine, iodine), a $C_{1-3}$ alkylenedioxy (e.g., methylenedioxy, ethylenedioxy), nitro, cyano, an optionally halogenated $C_{1-6}$ alkyl, an optionally halogenated $C_{3-6}$ cycloalkyl, an optionally halogenated $C_{1-6}$ alkoxy, an optionally halogenated $C_{1-6}$ alkylthio, hydroxy, amino, a mono-$C_{1-6}$ alkylamino (e.g., methylamino, ethylamino, propylamino, isopropylamino, butylamino), a di-$C_{1-6}$ alkylamino (e.g., dimethylamino, diethylamino, dipropylamino, dibutylamino, ethylmethylamino), formyl, carboxy, carbamoyl, an optionally halogenated $C_{1-6}$ alkyl-carbonyl, a $C_{1-6}$ alkoxy-carbonyl (e.g., methoxycarbonyl, ethoxycarbonyl, propoxycarbonyl, tert-butoxycarbonyl), a mono-$C_{1-6}$ alkyl-carbamoyl (e.g., methylcarbamoyl, ethylcarbamoyl), a di-$C_{1-6}$ alkyl-carbamoyl (e.g., dimethylcarbamoyl, diethylcarbamoyl, ethylmethylcarbamoyl), an optionally halogenated $C_{1-6}$ alkylsulfonyl, formylamino, an optionally halogenated $C_{1-6}$ alkyl-carboxamide, a $C_{1-6}$ alkoxy-carboxamide (e.g., methoxycarboxamide, ethoxycarboxamide, propoxycarboxamide, butoxycarboxamide), a $C_{1-6}$ alkylsulfonylamino (e.g., methylsulfonylamino, ethylsulfonylamino), a $C_{1-6}$ alkyl-carbonyloxy (e.g., acetoxy, propanoyloxy), a $C_{1-6}$ alkoxy-carbonyloxy (e.g., methoxycarbonyloxy, ethoxycarbonyloxy, propoxycarbonyloxy, butoxycarbonyloxy), a mono-$C_{1-6}$ alkyl-carbamoyloxy (e.g., methylcarbamoyloxy, ethylcarbamoyloxy), a di-$C_{1-6}$ alkyl-carbamoyloxy (e.g., dimethylcarbamoyloxy, diethylcarbamoyloxy) and the like.

Examples of a "5- to 7-membered saturated cyclic amino" in the above "optionally substituted 5- to 7-membered saturated cyclic amino" include morpholino, thiomorpholino, piperazin-1-yl, piperidino, pyrrolidin-1-yl and hexamethyleneimin-1-yl.

Examples of a "substituent" on the "optionally substituted 5- to 7-membered saturated cyclic amino" include a $C_{1-6}$ alkyl, an optionally substituted $C_{6-14}$ aryl, an optionally substituted $C_{7-19}$ aralkyl, an optionally substituted 5- to 10-membered aromatic heterocyclic group, an optionally substituted $C_{6-10}$ aryl-carbonyl, an optionally halogenated $C_{1-6}$ alkyl-carbonyl and an optionally halogenated $C_{1-6}$ alkylsulfonyl, 1 to 3 of which may be used for substitution.

Examples of a "$C_{6-14}$ aryl" in the "optionally substituted $C_{6-14}$ aryl" include phenyl, naphthyl (e.g., 1-naphthyl or 2-naphthyl), indenyl (e.g., 2-indenyl) and anthryl (e.g., 2-anthryl), with phenyl and the like being preferred.

Examples of a "$C_{7-19}$ aralkyl" in the "optionally substituted $C_{7-19}$ aralkyl" include benzyl, phenethyl, diphenylmethyl, triphenylmethyl, 1-naphthylmethyl, 2-naphthylmethyl, 2,2-diphenylethyl, 3-phenylpropyl, 4-phenylbutyl and 5-phenylpentyl, with benzyl and the like being preferred.

Examples of a "5- to 10-membered aromatic heterocyclic group" in the "optionally substituted 5- to 10-membered aromatic heterocyclic group" include pyridyl (e.g., 2-, 3- or 4-pyridyl), indolyl (e.g., 1-, 2- or 3-indolyl) and thienyl (e.g., 2- or 3-thienyl), with pyridyl (e.g., 2-, 3- or 4-pyridyl) and the like being preferred.

Examples of a "$C_{6-10}$ aryl-carbonyl" in the "optionally substituted $C_{6-10}$ aryl-carbonyl" include benzoyl, 1-naphthoyl and 2-naphthoyl.

These "optionally substituted $C_{6-14}$ aryl", "optionally substituted $C_{7-19}$ aralkyl", "optionally substituted 5- to 10-membered aromatic heterocyclic group" and "optionally substituted $C_{6-10}$ aryl-carbonyl" may each have 1 to 5 substituents selected from a halogen atom (e.g., fluorine, chlorine, bromine, iodine), a $C_{1-3}$ alkylenedioxy (e.g., methylenedioxy, ethylenedioxy), nitro, cyano, an optionally halogenated $C_{1-6}$ alkyl, an optionally halogenated $C_{3-6}$ cycloalkyl, an optionally halogenated $C_{1-6}$ alkoxy, an optionally halogenated $C_{1-6}$ alkylthio, hydroxy, amino, a mono-$C_{1-6}$ alkylamino (e.g., methylamino, ethylamino, propylamino, isopropylamino, butylamino), a di-$C_{1-6}$ alkylamino (e.g., dimethylamino, diethylamino, dipropylamino, dibutylamino, ethylmethylamino), formyl, carboxy, carbamoyl, an optionally halogenated $C_{1-6}$ alkyl-carbonyl, a $C_{1-6}$ alkoxy-carbonyl (e.g., methoxycarbonyl, ethoxycarbonyl, propoxycarbonyl, tert-butoxycarbonyl), a mono-$C_{1-6}$ alkyl-carbamoyl (e.g., methylcarbamoyl, ethylcarbamoyl), a di-$C_{1-6}$ alkyl-carbamoyl (e.g., dimethylcarbamoyl, diethylcarbamoyl, ethylmethylcarbamoyl), an optionally halogenated $C_{1-6}$ alkylsulfonyl, formylamino, an optionally halogenated $C_{1-6}$ alkyl-carboxamide, a $C_{1-6}$ alkoxy-carboxamide (e.g., methoxycarboxamide, ethoxycarboxamide, propoxycarboxamide, butoxycarboxamide), a $C_{1-6}$ alkylsulfonylamino (e.g., methylsulfonylamino, ethylsulfonylamino), a $C_{1-6}$ alkyl-carbonyloxy (e.g., acetoxy, propanoyloxy), a $C_{1-6}$ alkoxy-carbonyloxy (e.g., methoxycarbonyloxy, ethoxycarbonyloxy, propoxycarbonyloxy, butoxycarbonyloxy), a mono-$C_{1-6}$ alkyl-carbamoyloxy (e.g., methylcarbamoyloxy, ethylcarbamoyloxy), a di-$C_{1-6}$ alkyl-carbamoyloxy (e.g., dimethylcarbamoyloxy, diethylcarbamoyloxy) and the like.

Examples of an "acyl" in the "acyl", "acylamino" or "acyloxy" listed as a "substituent" on the above "optionally substituted lower alkoxy group" represented by $R^3$ include formyl, carboxy, carbamoyl, an optionally halogenated $C_{1-6}$ alkyl-carbonyl, a $C_{1-6}$ alkoxy-carbonyl (e.g., methoxycarbonyl, ethoxycarbonyl, propoxycarbonyl, tert-butoxycarbonyl), an optionally substituted $C_{6-10}$ aryl-carbonyl, an optionally substituted $C_{6-10}$ aryloxy-carbonyl, an optionally substituted $C_{7-16}$ aralkyloxy-carbonyl, an optionally substituted 5- or 6-membered heterocyclic carbonyl, a mono-$C_{1-6}$ alkyl-carbamoyl, a di-$C_{1-6}$ alkyl-carbamoyl (e.g., dimethylcarbamoyl, diethylcarbamoyl, ethylmethylcarbamoyl), an optionally substituted $C_{6-10}$ aryl-carbamoyl, an optionally substituted 5- or 6-membered heterocyclic carbamoyl, an optionally halogenated $C_{1-6}$ alkylsulfonyl, and an optionally substituted $C_{6-10}$ arylsulfonyl. Above all, preferred are an optionally halogenated $C_{1-6}$ alkyl-carbonyl, a $C_{1-6}$ alkoxy-carbonyl (e.g., ethoxycarbonyl), an optionally substituted $C_{6-10}$ aryl-carbonyl, an optionally substituted $C_{6-10}$ arylsulfonyl and the like.

Examples of a "$C_{6-10}$ aryl-carbonyl" in the above "optionally substituted $C_{6-10}$ aryl-carbonyl" include benzoyl, 1-naphthoyl and 2-naphthoyl.

Examples of a "$C_{6-10}$ aryloxy-carbonyl" in the above "optionally substituted $C_{6-10}$ aryloxy-carbonyl" include phenoxycarbonyl.

Examples of a "$C_{7-16}$ aralkyloxy-carbonyl" in the above "optionally substituted $C_{7-16}$ aralkyloxy-carbonyl" include benzyloxycarbonyl and phenethyloxycarbonyl.

Examples of a "5- or 6-membered heterocyclic carbonyl" in the above "optionally substituted 5- or 6-membered heterocyclic carbonyl" include nicotinoyl, isonicotinoyl, thenoyl (e.g., 2-thenoyl or 3-thenoyl), furoyl (e.g., 2-furoyl or 3-furoyl), morpholinocarbonyl, piperidinocarbonyl and pyrrolidin-1-ylcarbonyl.

Examples of a "$C_{6-10}$ aryl-carbamoyl" in the above "optionally substituted $C_{6-10}$ aryl-carbamoyl" include phenylcarbamoyl, 1-naphthylcarbamoyl and 2-naphthylcarbamoyl.

Examples of a "5- or 6-membered heterocyclic carbamoyl" in the above "optionally substituted 5- or 6-membered heterocyclic carbamoyl" include pyridylcarbamoyl (e.g., 2-pyridylcarbamoyl, 3-pyridylcarbamoyl or 4-pyridylcarbamoyl) and thienylcarbamoyl (e.g., 2-thienylcarbamoyl or 3-thienylcarbamoyl).

Examples of a "$C_{6-10}$ arylsulfonyl" in the above "optionally substituted $C_{6-10}$ arylsulfonyl" include benzenesulfonyl, 1-naphthalenesulfonyl and 2-naphthalenesulfonyl.

These "optionally substituted $C_{6-10}$ aryl-carbonyl", "optionally substituted $C_{6-10}$ aryloxy-carbonyl", "optionally substituted $C_{7-16}$ aralkyloxy-carbonyl", "optionally substituted 5- or 6-membered heterocyclic carbonyl", "optionally substituted $C_{6-10}$ aryl-carbamoyl", "optionally substituted 5- or 6-membered heterocyclic carbamoyl" and "optionally substituted $C_{6-10}$ arylsulfonyl" may each have 1 to 5 substituents, preferably 1 to 3 substituents, selected from a halogen atom, a $C_{1-3}$ alkylenedioxy, nitro, cyano, an optionally halogenated $C_{1-6}$ alkyl, an optionally halogenated $C_{1-6}$ alkoxy, an optionally halogenated $C_{1-6}$ alkylthio, hydroxy, amino, a mono-$C_{1-6}$ alkylamino, a di-$C_{1-6}$ alkylamino, formyl, carboxy, carbamoyl, an optionally halogenated $C_{1-6}$ alkyl-carbonyl, a $C_{1-6}$ alkoxy-carbonyl, a mono-$C_{1-6}$ alkyl-carbamoyl, a di-$C_{1-6}$ alkyl-carbamoyl, an optionally halogenated $C_{1-6}$ alkylsulfonyl, formylamino, an optionally halogenated $C_{1-6}$ alkyl-carboxamide, a $C_{1-6}$ alkoxy-carboxamide, a $C_{1-6}$ alkylsulfonylamino, a $C_{1-6}$ alkyl-carbonyloxy, a $C_{1-6}$ alkoxy-carbonyloxy, a mono-$C_{1-6}$ alkyl-carbamoyloxy and a di-$C_{1-6}$ alkyl-carbamoyloxy. Above all, preferred substituents are a halogen atom, an optionally halogenated $C_{1-6}$ alkyl, an optionally halogenated $C_{1-6}$ alkoxy and the like.

An "acylamino" as a "substituent" on the above "optionally substituted lower alkoxy group" represented by $R^3$ may be, for example, an amino group substituted with one or two of the acyl substituents specifically listed above for the "optionally substituted aromatic group." Preferred examples include formylamino, an optionally halogenated $C_{1-6}$ alkyl-carboxamide, an optionally substituted $C_{6-10}$ aryl-carboxamide (e.g., phenylcarboxamide, naphthylcarboxamide), a $C_{1-6}$ alkoxy-carboxamide (e.g., methoxycarboxamide, ethoxycarboxamide, propoxycarboxamide, butoxycarboxamide) and a $C_{1-6}$ alkylsulfonylamino (e.g., methylsulfonylamino, ethylsulfonylamino).

An "acyloxy" as a "substituent" on the above "optionally substituted lower alkoxy group" represented by $R^3$ may be, for example, an oxy group substituted with one of the acyl substituents specifically listed above for the "optionally substituted aromatic group." Preferred examples include a $C_{1-6}$ alkyl-carbonyloxy (e.g., acetoxy, propanoyloxy), an optionally substituted $C_{6-10}$ aryl-carbonyloxy (e.g., benzoyloxy, 1-naphthoyloxy, 2-naphthoyloxy), a $C_{1-6}$ alkoxy-carbonyloxy (e.g., methoxycarbonyloxy, ethoxycarbonyloxy, propoxycarbonyloxy, butoxycarbonyloxy), a mono-$C_{1-6}$ alkyl-carbamoyloxy (e.g., methylcarbamoyloxy, ethylcarbamoyloxy), a di-$C_{1-6}$ alkyl-carbamoyloxy (e.g., dimethylcarbamoyloxy, diethylcarbamoyloxy), an optionally substituted $C_{6-10}$ aryl-carbamoyloxy (e.g., phenylcarbamoyloxy, naphthylcarbamoyloxy) and nicotinoyloxy.

$R^3$, $R^4$, $R^5$, $R^6$ and $R^7$ are each preferably a hydrogen atom or a $C_{1-6}$ alkyl, and more preferably a hydrogen atom or methyl.

Examples of the "4- to 8-membered unsaturated ring" as a "4- to 8-membered ring" in the above "optionally substituted 4- to 8-membered ring which may further be condensed with an optionally substituted ring" represented by the ring C include a non-aromatic unsaturated ring and a 4- to 8-membered aromatic ring.

Examples of the "non-aromatic unsaturated ring" include hydrocarbon rings such as cyclopentene, cyclohexene, cyclohexadiene, cycloheptene and cycloheptadiene, as well as non-aromatic heterocyclic rings such as thiazine, oxazine, oxathiine, diazepine, oxazepine and thiazepine.

Examples of the "4- to 8-membered aromatic ring" include a benzene ring and a 5- or 6-membered aromatic heterocyclic ring.

Examples of such a "5- or 6-membered aromatic heterocyclic ring" include those containing, in addition to carbon atoms, one or more (e.g., 1 to 3) heteroatoms selected from a nitrogen atom, a sulfur atom and an oxygen atom. Specific examples include thiophene, furan, pyrrole, imidazole, pyrazole, thiazole, oxazole, pyridine, pyrazine, pyrimidine, pyridazine and thiazole.

Examples of an "optionally substituted ring" which may be used for condensation in the above "optionally substituted 4- to 8-membered ring which may further be condensed with an optionally substituted ring" represented by the ring C include a saturated ring and an aromatic ring.

Examples of such a "saturated ring" include a 4- to 8-membered monocyclic saturated ring, a 4- to 8-membered ring-assembled saturated ring, and a 7- to 12-membered condensed saturated ring.

Examples of the above "4- to 8-membered monocyclic saturated ring" include a 4- to 8-membered saturated cyclic hydrocarbon and a 4- to 8-membered saturated heterocyclic ring.

Examples of such a "4- to 8-membered saturated cyclic hydrocarbon" include cyclobutane, cyclopentane, cyclohexane, cycloheptane and cyclooctane.

Examples of such a "4- to 8-membered saturated heterocyclic ring" include those containing, in addition to carbon atoms, one or more (e.g., 1 to 3) heteroatoms selected from a nitrogen atom, a sulfur atom and an oxygen atom. Specific examples include tetrahydrothiophene, tetrahydrofuran, tetrahydropyrrole, tetrahydroimidazole, tetrahydropyrazole, tetrahydrothiazole, tetrahydrooxazole, hexahydropyridine, hexahydropyrazine, hexahydropyrimidine, hexahydropyridazine, tetrahydro-1,4-oxazine, tetrahydro-1,4-thiazine, perhydroazepine, perhydro-1,4-diazepine, perhydro-1,4-oxazepine, perhydro-1,4-thiazepine and perhydroazocine.

Examples of the above "4- to 8-membered ring-assembled saturated ring" include a saturated ring assembly comprising 2 or more (preferably 2) saturated rings directly linked via a single bond(s), in which the number of bonds linking these saturated rings is smaller than that of the saturated rings by one.

Examples of such a "saturated ring" include a saturated cyclic hydrocarbon and a saturated heterocyclic ring.

Examples of the "saturated cyclic hydrocarbon" include $C_{4-8}$ monocyclic or condensed polycyclic (bicyclic) saturated cyclic hydrocarbons (e.g., cyclobutane, cyclopentane).

Examples of the "saturated heterocyclic ring" include 4- to 8-membered saturated heterocyclic rings containing, in addition to carbon atoms, one or more (e.g., 1 to 4) heteroatoms selected from a nitrogen atom, a sulfur atom and an oxygen atom. Specific examples include saturated heterocyclic rings such as tetrahydrothiophene, tetrahydrofuran, tetrahydropyrrole, tetrahydroimidazole, tetrahydropyrazole, tetrahydrothiazole, tetrahydrooxazole, hexahydropyridine, hexahydropyrazine, hexahydropyrimidine, hexahydropyridazine, tetrahydro-1,4-oxazine, tetrahydro-1,4-thiazine, perhydroazepine, perhydro-1,4-diazepine, perhydro-1,4-oxazepine, perhydro-1,4-thiazepine and perhydroazocine.

The 4- to 8-membered saturated ring assembly comprising such saturated rings directly linked via a single bond(s) may be, for example, a saturated ring assembly composed of two rings selected from 4- to 8-membered saturated heterocyclic rings. Preferred examples of such a saturated ring assembly include those composed of two saturated rings selected from cyclobutane, cyclopentane, tetrahydrothiophene, tetrahydrofuran, tetrahydropyrrole, tetrahydroimidazole, tetrahydropyrazole, tetrahydrothiazole, tetrahydrooxazole, hexahydropyridine, hexahydropyrazine, hexahydropyrimidine, hexahydropyridazine, tetrahydro-1,4-oxazine, tetrahydro-1,4-thiazine, perhydroazepine, perhydro-1,4-diazepine, perhydro-1,4-oxazepine, perhydro-1,4-thiazepine and perhydroazocine.

Examples of the above "7- to 12-membered condensed saturated ring" include a condensed polycyclic (preferably bicyclic) saturated ring. Examples of such a "condensed polycyclic saturated ring" include a condensed polycyclic saturated cyclic hydrocarbon and a condensed polycyclic saturated heterocyclic ring.

Examples of the "condensed polycyclic saturated hydrocarbon" include $C_{7-12}$ condensed polycyclic (bicyclic) saturated cyclic hydrocarbons (e.g., bicyclo[4.3.0]nonane, bicyclo[4.4.0]decane).

Examples of the "condensed polycyclic saturated heterocyclic ring" include 4- to 8-membered condensed polycyclic saturated heterocyclic rings containing, in addition to carbon atoms, one or more (e.g., 1 to 4) heteroatoms selected from a nitrogen atom, a sulfur atom and an oxygen atom.

Examples of the "aromatic ring" as an "optionally substituted ring" which may be used for condensation in the above "optionally substituted 4- to 8-membered ring which may further be condensed with an optionally substituted ring" represented by the ring C include a 4- to 8-membered monocyclic aromatic ring, a 4- to 8-membered ring-assembled aromatic ring, and a 7- to 12-membered condensed aromatic ring.

Examples of the above "4- to 8-membered monocyclic aromatic ring" include a benzene ring and a 5- or 6-membered aromatic heterocyclic ring.

Examples of such a "5- or 6-membered aromatic heterocyclic ring" include those containing, in addition to carbon atoms, one or more (e.g., 1 to 3) heteroatoms selected from a nitrogen atom, a sulfur atom and an oxygen atom. Specific examples include thiophene, furan, pyrrole, imidazole, pyrazole, thiazole, oxazole, pyridine, pyrazine, pyrimidine and pyridazine.

Examples of the above "4- to 8-membered ring-assembled aromatic ring" include an aromatic ring assembly comprising 2 or more (preferably 2) aromatic rings directly linked via a single bond(s), in which the number of bonds linking these aromatic rings is smaller than that of the aromatic rings by one.

Examples of such an "aromatic ring" include an aromatic hydrocarbon and an aromatic heterocyclic ring.

Examples of the "aromatic hydrocarbon" include benzene.

Examples of the "aromatic heterocyclic ring" include 4- to 8-membered (preferably 5-membered) aromatic heterocyclic rings containing, in addition to carbon atoms, one or more (e.g., 1 to 4) heteroatoms selected from a nitrogen atom, a sulfur atom and an oxygen atom. Specific examples include aromatic heterocyclic rings such as thiophene, furan, pyrrole, imidazole, pyrazole, oxazole, isoxazole, oxadiazole (e.g., 1,2,4-oxadiazole or 1,3,4-oxadiazole), thiadiazole (e.g., 1,2,4-thiadiazole or 1,3,4-thiadiazole), thiazole, isothiazole, pyridine, pyrimidine and pyridazine.

Examples of the above "7- to 12-membered condensed aromatic ring" include a condensed polycyclic (preferably bicyclic) aromatic ring. Examples of such a "condensed polycyclic aromatic ring" include a condensed polycyclic aromatic hydrocarbon and a condensed polycyclic aromatic heterocyclic ring.

Examples of the "condensed polycyclic aromatic hydrocarbon" include $C_{7-12}$ condensed polycyclic (bicyclic) aromatic hydrocarbons.

Examples of the "condensed polycyclic aromatic heterocyclic ring" include 7- to 12-membered condensed polycyclic aromatic heterocyclic rings containing, in addition to carbon atoms, one or more (e.g., 1 to 4) heteroatoms selected from a nitrogen atom, a sulfur atom and an oxygen atom.

The "optionally substituted ring" which may be used for condensation in the above "optionally substituted 4- to 8-membered ring which may further be condensed with an optionally substituted ring" represented by the ring C is preferably a monocyclic saturated ring or a monocyclic aromatic ring.

The 4- to 8-membered ring represented by the ring C is preferably a nitrogen-containing heterocyclic ring. Above all, tetrahydropyrrole, hexahydropyridine, hexahydropyrazine, tetrahydro-1,4-oxazine, tetrahydro-1,4-thiazine, perhydroazepine and pyrrole are preferred for use.

In the above formulae, the "optionally substituted aromatic group", "optionally substituted monocyclic aromatic group" and "optionally substituted phenyl, furyl, thienyl or pyridyl group" represented by $Ar^1$, the "optionally substituted benzene ring" represented by the rings A and B', the "optionally substituted aromatic ring" represented by the ring B, and the "optionally substituted 4- to 8-membered ring" and "optionally substituted ring" in the "optionally substituted 4- to 8-membered ring which may further be condensed with an optionally substituted ring" represented by the ring C may each have a substituent(s), including a halogen atom (e.g., fluorine, chlorine, bromine, iodine), nitro, cyano, an optionally halogenated $C_{1-6}$ alkyl, a $C_{6-10}$ aryloxy-$C_{1-6}$ alkyl (e.g., phenoxymethyl), a $C_{1-6}$ alkyl-$C_{6-10}$ aryl-$C_{2-6}$ alkenyl (e.g., methylphenylethenyl), an optionally halogenated $C_{3-6}$ cycloalkyl, an optionally substituted $C_{7-16}$ aralkyl, an optionally substituted $C_{1-6}$ alkoxy, an optionally halogenated $C_{1-6}$ alkylthio, hydroxy, an optionally substituted $C_{6-10}$ aryloxy, a $C_{6-10}$ aryl-$C_{1-6}$ alkyloxy (e.g., phenylmethyloxy), a $C_{6-10}$ aryl-$C_{7-16}$ aralkyloxy (e.g., phenylbenzyloxy), amino, a mono-$C_{1-6}$ alkylamino (e.g., methylamino, ethylamino, propylamino, isopropylamino, butylamino), a di-$C_{1-6}$ alkylamino (e.g., dimethylamino, diethylamino, dipropylamino, dibutylamino, ethylmethylamino), an optionally substituted 5- to 7-membered saturated cyclic amino, an acyl, an acylamino, an acyloxy, an optionally substituted $C_{6-14}$ aryl, an optionally substituted 5- to 10-membered aromatic heterocyclic group, and a saturated heterocyclic group other than a 5- to 7-membered saturated cyclic amino (e.g., tetrahydropyran, tetrahydrofuran, 1,4-dioxane). Above all, preferred substituents are a halogen atom, an optionally halogenated $C_{1-6}$ alkyl, an optionally substituted $C_{7-16}$ aralkyl, an optionally halogenated $C_{1-6}$ alkoxy, an optionally substituted $C_{6-10}$ aryloxy, an acyl, an acylamino, phenyl, naphthyl, pyridyl, furyl, thienyl, tetrahydropyran, tetrahydrofuran and the like.

The "aromatic group" in the "optionally substituted aromatic group" represented by $Ar^1$ may have, for example, 1 to 5 (preferably 1 to 3) of these substituents at any substitutable position(s) on the aromatic group. In a case where the number of substituents is at least 2, each substituent may be the same or different. In a case where the aromatic group has a cyclic substituent, the substituent may be attached via a spiro linkage.

Likewise, the "benzene ring" in the "optionally substituted benzene ring" represented by the rings A and B' may have, for example, 1 to 4 (preferably 1 or 2) of these substituents at any substitutable position(s) on the benzene ring. In a case where the number of substituents is at least 2, each substituent may be the same or different. In a case where the benzene ring has a cyclic substituent, the substituent may be attached via a spiro linkage.

Likewise, the "aromatic ring" in the "optionally substituted aromatic ring" represented by the ring B may have, for example, 1 to 4 (preferably 1 or 2) of these substituents at any substitutable position(s) on the aromatic ring. In a case where the number of substituents is at least 2, each substituent may be the same or different. In a case where the aromatic ring has a cyclic substituent, the substituent may be attached via a spiro linkage.

Likewise, the "4- to 8-membered ring" in the "optionally substituted 4- to 8-membered ring which may further be condensed with an optionally substituted ring" represented by the ring C may have, for example, 1 to 4 (preferably 1 or 2) of these substituents at any substitutable position(s) on the ring. In a case where the number of substituents is at least 2, each substituent may be the same or different. In a case where the ring has a cyclic substituent, the substituent may be attached via a spiro linkage.

Likewise, the "optionally substituted ring" in the "optionally substituted 4- to 8-membered ring which may further be condensed with an optionally substituted ring" represented by the ring C may have, for example, 1 to 4 (preferably 1 or 2) of these substituents at any substitutable position(s) on the ring. In a case where the number of substituents is at least 2, each substituent may be the same or different. In a case where the ring has a cyclic substituent, the substituent may be attached via a spiro linkage.

Examples of a "$C_{7-16}$ aralkyl" in the above "optionally substituted $C_{7-16}$ aralkyl" include benzyl, phenethyl and naphthylmethyl.

Examples of a "$C_{1-6}$ alkoxy" in the above "optionally substituted $C_{1-6}$ alkoxy" include methoxy, ethoxy, propoxy and butoxy.

Examples of a "$C_{6-10}$ aryloxy" in the above "optionally substituted $C_{6-10}$ aryloxy" include phenyloxy and naphthyloxy.

Examples of a "$C_{6-14}$ aryl" in the above "optionally substituted $C_{6-14}$ aryl" include phenyl, naphthyl (e.g., 1-naphthyl or 2-naphthyl), indenyl (e.g., 2-indenyl) and anthryl (e.g., 2-anthryl), with phenyl and the like being preferred.

Examples of a "5- to 10-membered aromatic heterocyclic group" in the above "optionally substituted 5- to 10-membered aromatic heterocyclic group" include pyridyl (e.g., 2-, 3- or 4-pyridyl), indolyl (e.g., 1-, 2- or 3-indolyl) and thienyl (e.g., 2- or 3-thienyl), with pyridyl (e.g., 2-, 3- or 4-pyridyl) and the like being preferred.

These "optionally substituted $C_{7-16}$ aralkyl", "optionally substituted $C_{1-6}$ alkoxy", "optionally substituted $C_{6-10}$ aryloxy", "optionally substituted $C_{6-14}$ aryl" and "optionally substituted 5- to 10-membered aromatic heterocyclic group" may each have 1 to 5 substituents selected from a halogen atom (e.g., fluorine, chlorine, bromine, iodine), a $C_{1-3}$ alkylenedioxy (e.g., methylenedioxy, ethylenedioxy), nitro, cyano, an optionally halogenated $C_{1-6}$ alkyl, an optionally halogenated $C_{3-6}$ cycloalkyl, an optionally halogenated $C_{1-6}$ alkoxy, an optionally halogenated $C_{1-6}$ alkylthio, hydroxy, amino, a mono-$C_{1-6}$ alkylamino (e.g., methylamino, ethylamino, propylamino, isopropylamino, butylamino), a di-$C_{1-6}$ alkylamino (e.g., dimethylamino, diethylamino, dipropylamino, dibutylamino, ethylmethylamino), formyl, carboxy, carbamoyl, an optionally halogenated $C_{1-6}$ alkyl-carbonyl, a $C_{1-6}$ alkoxy-carbonyl (e.g., methoxycarbonyl, ethoxycarbonyl, propoxycarbonyl, tert-butoxycarbonyl), a mono-$C_{1-6}$ alkyl-carbamoyl (e.g., methylcarbamoyl, ethylcarbamoyl), a di-$C_{1-6}$ alkyl-carbamoyl (e.g., dimethylcarbamoyl, diethylcarbamoyl, ethylmethylcarbamoyl), an optionally halogenated $C_{1-6}$ alkylsulfonyl, formylamino, an optionally halogenated $C_{1-6}$ alkyl-carboxamide, a $C_{1-6}$ alkoxy-carboxamide (e.g., methoxycarboxamide, ethoxycarboxamide, propoxycarboxamide, butoxycarboxamide), a $C_{1-6}$ alkylsulfonylamino (e.g., methylsulfonylamino, ethylsulfonylamino), a $C_{1-6}$ alkyl-carbonyloxy (e.g., acetoxy, propanoyloxy), a $C_{1-6}$ alkoxy-carbonyloxy (e.g., methoxycarbonyloxy, ethoxycarbonyloxy, propoxycarbonyloxy, butoxycarbonyloxy), a mono-$C_{1-6}$ alkyl-carbamoyloxy (e.g., methylcarbamoyloxy, ethylcarbamoyloxy), a di-$C_{1-6}$ alkyl-carbamoyloxy (e.g., dimethylcarbamoyloxy, diethylcarbamoyloxy) and the like.

Examples of a "5- to 7-membered saturated cyclic amino" in the above "optionally substituted 5- to 7-membered saturated cyclic amino" include morpholino, thiomorpholino, piperazin-1-yl, piperidino, pyrrolidin-1-yl and hexamethyleneimin-1-yl.

Examples of a "substituent" on the "optionally substituted 5- to 7-membered saturated cyclic amino" include a $C_{1-6}$ alkyl, an optionally substituted $C_{6-14}$ aryl, an optionally substituted $C_{7-19}$ aralkyl, an optionally substituted 5- to 10-membered aromatic heterocyclic group, an optionally substituted $C_{6-10}$ aryl-carbonyl, an optionally halogenated $C_{1-6}$ alkyl-carbonyl and an optionally halogenated $C_{1-6}$ alkylsulfonyl, 1 to 3 of which may be used for substitution.

Examples of a "$C_{6-14}$ aryl" in the "optionally substituted $C_{6-14}$ aryl" include phenyl, naphthyl (e.g., 1-naphthyl or 2-naphthyl), indenyl (e.g., 2-indenyl) and anthryl (e.g., 2-anthryl), with phenyl and the like being preferred.

Examples of a "$C_{7-19}$ aralkyl" in the "optionally substituted $C_{7-19}$ aralkyl" include benzyl, phenethyl, diphenylmethyl, triphenylmethyl, 1-naphthylmethyl, 2-naphthylmethyl, 2,2-diphenylethyl, 3-phenylpropyl, 4-phenylbutyl and 5-phenylpentyl, with benzyl and the like being preferred.

Examples of a "5- to 10-membered aromatic heterocyclic group" in the "optionally substituted 5- to 10-membered aromatic heterocyclic group" include pyridyl (e.g., 2-, 3- or 4-pyridyl), indolyl (e.g., 1-, 2- or 3-indolyl) and thienyl (e.g., 2- or 3-thienyl), with pyridyl (e.g., 2-, 3- or 4-pyridyl) and the like being preferred.

Examples of a "$C_{6-10}$ aryl-carbonyl" in the "optionally substituted $C_{6-10}$ aryl-carbonyl" include benzoyl, 1-naphthoyl and 2-naphthoyl.

These "optionally substituted $C_{6-14}$ aryl", "optionally substituted $C_{7-19}$ aralkyl", "optionally substituted 5- to 10-membered aromatic heterocyclic group" and "optionally substituted $C_{6-10}$ aryl-carbonyl" may each have 1 to 5 substituents selected from a halogen atom (e.g., fluorine, chlorine, bromine, iodine), a $C_{1-3}$ alkylenedioxy (e.g., methylenedioxy, ethylenedioxy), nitro, cyano, an optionally halogenated $C_{1-6}$ alkyl, an optionally halogenated $C_{3-6}$ cycloalkyl, an optionally halogenated $C_{1-6}$ alkoxy, an optionally halogenated $C_{1-6}$ alkylthio, hydroxy, amino, a mono-$C_{1-6}$ alkylamino (e.g., methylamino, ethylamino, propylamino, isopropylamino, butylamino), a di-$C_{1-6}$ alkylamino (e.g., dimethylamino, diethylamino, dipropylamino, dibutylamino, ethylmethylamino), formyl, carboxy, carbamoyl, an optionally halogenated $C_{1-6}$ alkyl-carbonyl, a $C_{1-6}$ alkoxy-carbonyl (e.g., methoxycarbonyl, ethoxycarbonyl, propoxycarbonyl, tert-butoxycarbonyl), a mono-$C_{1-6}$ alkyl-carbamoyl (e.g., methylcarbamoyl, ethylcarbamoyl), a di-$C_{1-6}$ alkyl-carbamoyl (e.g., dimethylcarbamoyl, diethylcarbamoyl, ethylmethylcarbamoyl), an optionally halogenated $C_{1-6}$ alkylsulfonyl, formylamino, an optionally halogenated $C_{1-6}$ alkyl-carboxamide, a $C_{1-6}$ alkoxy-carboxamide (e.g., methoxycarboxamide, ethoxycarboxamide, propoxycarboxamide, butoxycarboxamide), a $C_{1-6}$ alkylsulfonylamino (e.g., methylsulfonylamino, ethylsulfonylamino), a $C_{1-6}$ alkyl-carbonyloxy (e.g., acetoxy, propanoyloxy), a $C_{1-6}$ alkoxy-carbonyloxy (e.g., methoxycarbonyloxy, ethoxycarbonyloxy, propoxycarbonyloxy, butoxycarbonyloxy), a mono-$C_{1-6}$ alkyl-carbamoyloxy (e.g., methylcarbamoyloxy, ethylcarbamoyloxy), a di-$C_{1-6}$ alkyl-carbamoyloxy (e.g., dimethylcarbamoyloxy, diethylcarbamoyloxy) and the like.

Examples of an "acyl" in the "acyl", "acylamino" or "acyloxy" listed as a "substituent" on the above "optionally substituted aromatic group", "optionally substituted monocyclic aromatic group" and "optionally substituted phenyl, furyl, thienyl or pyridyl group" represented by $Ar^1$, on the above "optionally substituted benzene ring" represented by the rings A and B', on the above "optionally substituted aromatic ring" represented by the ring B, and on the above "optionally substituted 4- to 8-membered ring" represented by the ring C include formyl, carboxy, carbamoyl, an optionally halogenated $C_{1-6}$ alkyl-carbonyl, a $C_{1-6}$ alkoxy-carbonyl (e.g., methoxycarbonyl, ethoxycarbonyl, propoxycarbonyl, tert-butoxycarbonyl), an optionally substituted $C_{6-10}$ aryl-carbonyl, an optionally substituted $C_{6-10}$ aryloxy-carbonyl, an optionally substituted $C_{7-16}$ aralkyloxy-carbonyl, an optionally substituted 5- or 6-membered heterocyclic carbonyl, a mono-$C_{1-6}$ alkyl-carbamoyl, a di-$C_{1-6}$ alkyl-carbamoyl (e.g., dimethylcarbamoyl, diethylcarbamoyl, ethylmethylcarbamoyl), an optionally substituted $C_{6-10}$ aryl-carbamoyl, an optionally substituted 5- or 6-membered heterocyclic carbamoyl, an optionally halogenated $C_{1-6}$ alkylsulfonyl and an optionally substituted $C_{6-10}$ arylsulfonyl. Above all, preferred are an optionally halogenated $C_{1-6}$ alkyl-carbonyl, a $C_{1-6}$ alkoxy-carbonyl (e.g., ethoxycarbonyl), an optionally substituted $C_{6-10}$ aryl-carbonyl, an optionally substituted $C_{6-10}$ arylsulfonyl and the like.

Examples of a "$C_{6-10}$ aryl-carbonyl" in the above "optionally substituted $C_{6-10}$ aryl-carbonyl" include benzoyl, 1-naphthoyl and 2-naphthoyl.

Examples of a "$C_{6-10}$ aryloxy-carbonyl" in the above "optionally substituted $C_{6-10}$ aryloxy-carbonyl" include phenoxycarbonyl.

Examples of a "$C_{7-16}$ aralkyloxy-carbonyl" in the above "optionally substituted $C_{7-16}$ aralkyloxy-carbonyl" include benzyloxycarbonyl and phenethyloxycarbonyl.

Examples of a "5- or 6-membered heterocyclic carbonyl" in the above "optionally substituted 5- or 6-membered heterocyclic carbonyl" include nicotinoyl, isonicotinoyl, thenoyl (e.g., 2-thenoyl or 3-thenoyl), furoyl (e.g., 2-furoyl or 3-furoyl), morpholinocarbonyl, piperidinocarbonyl and pyrrolidin-1-ylcarbonyl.

Examples of a "$C_{6-10}$ aryl-carbamoyl" in the above "optionally substituted $C_{6-10}$ aryl-carbamoyl" include phenylcarbamoyl, 1-naphthylcarbamoyl and 2-naphthylcarbamoyl.

Examples of a "5- or 6-membered heterocyclic carbamoyl" in the above "optionally substituted 5- or 6-membered heterocyclic carbamoyl" include pyridylcarbamoyl (e.g., 2-pyridylcarbamoyl, 3-pyridylcarbamoyl or 4-pyridylcarbamoyl) and thienylcarbamoyl (e.g., 2-thienylcarbamoyl or 3-thienylcarbamoyl).

Examples of a "$C_{6-10}$ arylsulfonyl" in the above "optionally substituted $C_{6-10}$ arylsulfonyl" include benzenesulfonyl, 1-naphthalenesulfonyl and 2-naphthalenesulfonyl.

These "optionally substituted $C_{6-10}$ aryl-carbonyl", "optionally substituted $C_{6-10}$ aryloxy-carbonyl", "optionally substituted $C_{7-16}$ aralkyloxy-carbonyl", "optionally substituted 5- or 6-membered heterocyclic carbonyl", "optionally substituted $C_{6-10}$ aryl-carbamoyl", "optionally substituted 5- or 6-membered heterocyclic carbamoyl" and "optionally substituted $C_{6-10}$ arylsulfonyl" may each have 1 to 5 substituents, preferably 1 to 3 substituents, selected from a halogen atom, a $C_{1-3}$ alkylenedioxy, nitro, cyano, an optionally halogenated $C_{1-6}$ alkyl, an optionally halogenated $C_{1-6}$ alkoxy, an optionally halogenated $C_{1-6}$ alkylthio, hydroxy, amino, a mono-$C_{1-6}$ alkylamino, a di-$C_{1-6}$ alkylamino, formyl, carboxy, carbamoyl, an optionally halogenated $C_{1-6}$ alkyl-carbonyl, a $C_{1-6}$ alkoxy-carbonyl, a mono-$C_{1-6}$ alkyl-carbamoyl, a di-$C_{1-6}$ alkyl-carbamoyl, an optionally halogenated $C_{1-6}$ alkylsulfonyl, formylamino, an optionally halogenated $C_{1-6}$ alkyl-carboxamide, a $C_{1-6}$ alkoxy-carboxamide, a $C_{1-6}$ alkylsulfonylamino, a $C_{1-6}$ alkyl-carbonyloxy, a $C_{1-6}$ alkoxy-carbonyloxy, a mono-$C_{1-6}$ alkyl-carbamoyloxy and a di-$C_{1-6}$ alkyl-carbamoyloxy. Above all, preferred substituents are a halogen atom, an optionally halogenated $C_{1-6}$ alkyl, an optionally halogenated $C_{1-6}$ alkoxy and the like.

An "acylamino" as a "substituent" on the above "optionally substituted aromatic group", "optionally substituted monocyclic aromatic group" and "optionally substituted phenyl, furyl, thienyl or pyridyl group" represented by $Ar^1$, on the above "optionally substituted benzene ring" represented by the rings A and B', on the above "optionally substituted aromatic ring" represented by the ring B, and on the above "optionally substituted 4- to 8-membered ring" represented by the ring C may be, for example, an amino group substituted with one or two of the acyl substituents specifically listed above for the "optionally substituted aromatic group." Preferred examples include formylamino, an optionally halogenated $C_{1-6}$ alkyl-carboxamide, an optionally substituted $C_{6-10}$ aryl-carboxamide (e.g., phenylcarboxamide, naphthylcarboxamide), a $C_{1-6}$ alkoxy-carboxamide (e.g., methoxycarboxamide, ethoxycarboxamide, propoxycarboxamide, butoxycarboxamide) and a $C_{1-6}$ alkylsulfonylamino (e.g., methylsulfonylamino, ethylsulfonylamino).

An "acyloxy" as a "substituent" on the above "optionally substituted aromatic group", "optionally substituted monocyclic aromatic group" and "optionally substituted phenyl, furyl, thienyl or pyridyl group" represented by $Ar^1$, on the above "optionally substituted benzene ring" represented by the rings A and B', on the above "optionally substituted aromatic ring" represented by the ring B, and on the above "optionally substituted 4- to 8-membered ring" represented by the ring C may be, for example, an oxy group substituted with one of the acyl substituents specifically listed above for the "optionally substituted aromatic group." Preferred examples include a $C_{1-6}$ alkyl-carbonyloxy (e.g., acetoxy, propanoyloxy), an optionally substituted $C_{6-10}$ aryl-carbonyloxy (e.g., benzoyloxy, 1-naphthoyloxy, 2-naphthoyloxy), a $C_{1-6}$ alkoxy-carbonyloxy (e.g., methoxycarbonyloxy, ethoxycarbonyloxy, propoxycarbonyloxy, butoxycarbonyloxy), a mono-$C_{1-6}$ alkyl-carbamoyloxy (e.g., methylcarbamoyloxy, ethylcarbamoyloxy), a di-$C_{1-6}$ alkyl-carbamoyloxy (e.g., dimethylcarbamoyloxy, diethylcarbamoyloxy), an optionally substituted $C_{6-10}$ aryl-carbamoyloxy (e.g., phenylcarbamoyloxy, naphthylcarbamoyloxy) and nicotinoyloxy.

In compounds of Formula (I), $R^1$ is preferably a hydrogen atom or an optionally substituted hydroxy group. Such an optionally substituted hydroxy group is more preferably an alkyloxy group or an acyloxy group.

$R^2$ is preferably a hydrogen atom or an optionally substituted lower alkyl group, more preferably a hydrogen atom or a $C_{1-6}$ alkyl group, and particularly preferably a methyl group.

$Ar^1$ is preferably an optionally substituted monocyclic aromatic group, more preferably an optionally substituted phenyl, furyl, thienyl or pyridyl group, and particularly preferably a phenyl group which may be substituted with a halogen atom, a $C_{1-3}$ alkylenedioxy group, an optionally halogenated $C_{1-6}$ alkyl group or an optionally halogenated $C_{1-6}$ alkoxy group.

The ring A is preferably an unsubstituted benzene ring.

The ring B is preferably an optionally substituted benzene ring, and more preferably an unsubstituted benzene ring.

The ring C is preferably an optionally substituted 5- to 7-membered saturated ring, more preferably an optionally substituted 5- to 7-membered saturated heterocyclic ring, even more preferably an optionally substituted nitrogen-containing 5- to 7-membered saturated heterocyclic ring, and particularly preferably an optionally substituted tetrahydropyrrole, hexahydropyridine, hexahydropyrazine, tetrahydro-1,4-oxazine, tetrahydro-1,4-thiazine or perhydroazepine ring. Alternatively, the ring C is preferably further condensed with an optionally substituted monocyclic ring in addition to the ring B (hereinafter, such a moiety except for the ring B, where a monocyclic ring is condensed to form a bicyclic ring, will be also simply referred to as a bicyclic condensed ring). Above all, the ring C is preferably an optionally substituted bicyclic condensed heterocyclic ring, more preferably an optionally substituted nitrogen-containing bicyclic condensed heterocyclic ring, and particularly preferably an optionally substituted indole or isoquinoline ring. In this case, the rings B and C preferably together form carbazole or 5,6-dihydrophenanthridine.

X is preferably N.

Y is preferably CH.

At least one of X and Y is preferably N.

In addition, the 2- and 4-positions of the above Formula (I) is formed the cis(−)-configuration.

A particularly preferred compound of the above Formula (I) is:

(−)-2,4-cis-1-(3,4-dimethoxybenzoyl)-2-methyl-4-(1,2,3,4-tetrahydroquinolin-1-yl)-1,2,3,4-tetrahydroquinoline;

(−)-2,4-cis-4-(3,4-dihydro-2H-1,4-benzoxazin-4-yl)-1-(3,4-dimethoxybenzoyl)-2-methyl-1,2,3,4-tetrahydroquinoline;

2,4-cis-1-(3,4-dimethoxybenzoyl)-2-methyl-4-(1,2,3,4-tetrahydroquinolin-1-yl)-1,2,3,4-tetrahydroquinoline;

2,3-trans-2,4-cis-3-acetoxy-1-(3,4-dimethoxybenzoyl)-2-methyl-4-(1,2,3,4-tetrahydroquinolin-1-yl)-1,2,3,4-tetrahydroquinoline;

2,4-cis-4-(3,4-dihydro-2H-1,4-benzothiazin-4-yl)-1-(3,4-dimethoxybenzoyl)-2-methyl-1,2,3,4-tetrahydroquinoline;

2,4-cis-4-(1-benzyl-1,2,3,4-tetrahydroquinoxalin-4-yl)-1-(3,4-dimethoxybenzoyl)-2-methyl-1,2,3,4-tetrahydroquinoline;

2,4-cis-1-(3,4-dimethoxybenzoyl)-2-methyl-4-(2,3,4,5-tetrahydro-1H-1-benzazepinyl)-1,2,3,4-tetrahydroquinoline;

2,3-trans-2,4-cis-3-{[(benzylamino)carbonyl]oxy}-1-(3,4-dimethoxybenzoyl)-2-methyl-4-(2,3,4,5-tetrahydro-1H-1-benzazepinyl)-1,2,3,4-tetrahydroquinoline;

2,4-cis-4-(9H-9-carbazolyl)-1-(3,4-dimethoxybenzoyl)-2-methyl-1,2,3,4-tetrahydroquinoline;

(−)-2,4-cis-4-(9H-9-carbazolyl)-1-(3,4-dimethoxybenzoyl)-2-methyl-1,2,3,4-tetrahydroquinoline; or 2-butyl-4-(9H-9-carbazolyl)-1-(3,4-dimethoxybenzoyl)-1,2-dihydroquinoline.

A salt of a compound of Formula (I) (hereinafter also abbreviated as Compound (I)) is preferably a pharmaceutically acceptable salt, including salts with inorganic bases, salts with organic bases, salts with inorganic acids, salts with organic acids, and salts with basic or acidic amino acids.

Preferred examples of salts with inorganic bases include alkali metal salts such as sodium salt and potassium salt, alkaline earth metal salts such as calcium salt and magnesium salt, as well as aluminum salt and ammonium salt.

Preferred examples of salts with organic bases include those which are formed with trimethylamine, triethylamine, pyridine, picoline, ethanolamine, diethanolamine, triethanolamine, dicyclohexylamine and N,N'-dibenzylethylenediamine.

Preferred examples of salts with inorganic acids include those which are formed with hydrochloric acid, hydrobromic acid, nitric acid, sulfuric acid and phosphoric acid.

Preferred examples of salts with organic acids include those which are formed with formic acid, acetic acid, trifluoroacetic acid, fumaric acid, oxalic acid, tartaric acid, maleic acid, citric acid, succinic acid, malic acid, methanesulfonic acid, benzenesulfonic acid and p-toluenesulfonic acid.

Preferred examples of salts with basic amino acids include those which are formed with arginine, lysine and ornithine. Preferred examples of salts with acidic amino acids include those which are formed with aspartic acid and glutamic acid.

A prodrug of Compound (I) refers to a compound capable of converting into Compound (I) by the action of enzymes, gastric acid and the like under in vivo physiological conditions, that is, a compound capable of converting into Compound (I) through, e.g., enzymatic oxidation, reduction and/or hydrolysis or a compound capable of converting into Compound (I) through, e.g., hydrolysis by gastric acid. Examples of a prodrug of Compound (I) include compounds obtained when an amino group of Compound (I) is acylated, alkylated or phosphorylated, such as those obtained when an amino group of Compound (I) is eicosanoylated, alanylated, pentylaminocarbonylated, (5-methyl-2-oxo-1,3-dioxolen-4-yl)methoxycarbonylated, tetrahydrofuranylated, tetrahydropyranylated, pyrrolidylmethylated, pivaloyloxymethylated or tert-butylated; compounds obtained when a hydroxy group of Compound (I) is acylated, alkylated, phosphorylated or borated, such as those obtained when a hydroxy group of Compound (I) is acetylated, palmitoylated, propanoylated, pivaloylated, succinylated, fumalylated, alanylated, dimethylaminomethylcarbonylated or tetrahydropyranylated; and compounds obtained when a carboxyl group of Compound (I) is esterified or amidated, such as those obtained when a carboxyl group of Compound (I) is ethyl esterified, phenyl esterified, carboxymethyl esterified, dimethylaminomethyl esterified, pivaloyloxymethyl esterified, ethoxycarbonyloxyethyl esterified, phthalidyl esterified, (5-methyl-2-oxo-1,3-dioxolen-4-yl)methyl esterified, cyclohexyloxycarbonylethyl esterified or methylamidated. These compounds may be prepared from Compound (I) in a known manner.

In addition, Compound (I) may be labeled with isotopes (e.g., $^{3}H$, $^{14}C$, $^{35}S$, $^{125}I$) or other labels.

Further, Compound (I) may be either in anhydride form or in hydrate form.

The preparation of Compound (I) will be illustrated below.

Although the following explanation can also be applied to the preparation of a salt or prodrug of Compound (I), such a salt and prodrug are also collectively abbreviated as Compound (I). Likewise, the same can be said for individual compounds used in the preparation of Compound (I). For example, even when expressed as Compound (II), it is also intended to include a salt and prodrug of Compound (II).

Compound (I) can be prepared using known means, for example, in the manner shown in the following preparation schemes.

The Compound (I) thus prepared may be isolated and purified from the reaction mixture by known means, including solvent extraction, concentration, neutralization, filtration, crystallization, recrystallization, column chromatography, high performance liquid chromatography and recrystallization, to give a highly purified product of interest.

Compound (I) may be either in hydrate form or in anhydride form. Examples of such a hydrate include monohydrate, 0.5-hydrate and dihydrate.

In addition, Compound (I) may be labeled with isotopes (e.g., $^{3}H$, $^{14}C$, $^{35}S$, $^{125}I$) or other labels.

In a case where Compound (I) of the present invention or a salt thereof has an asymmetric carbon atom, the resulting optically active mixture (racemate) may be resolved into individual optical isomers using conventional optical resolution means, for example, by salt formation with an optically active acid (e.g., camphorsulfonic acid) or an optically active base (e.g., 1-methylbenzylamine) or by separation means such as various chromatography techniques (e.g., liquid chromatography on an optically active column) and fractional recrystallization.

The term "room temperature" usually refers to 0° C. to 30° C.

Individual symbols in chemical structures found in the following preparation schemes have the same meanings as defined above, unless otherwise specified.

As used herein, the term "leaving group" refers to a halogen atom (e.g., chloro, bromo, iodo), an optionally halogenated $C_{1-6}$ alkylsulfonyloxy (e.g., methanesulfonyloxy, ethanesulfonyloxy, trifluoromethanesulfonyloxy), an optionally substituted $C_{6-10}$ arylsulfonyloxy, hydroxy or the like.

The "optionally substituted $C_{6-10}$ arylsulfonyloxy" may have 1 to 3 substituents selected from a halogen atom, an optionally halogenated $C_{1-6}$ alkyl or $C_{1-6}$ alkoxy and the like. Specific examples of the "optionally substituted $C_{6-10}$ arylsulfonyloxy" include benzenesulfonyloxy, p-toluenesulfonyloxy, 1-naphthalenesulfonyloxy and 2-naphthalenesulfonyloxy.

As used herein, the term "base" refers to, for example:

1) a strong base including alkali metal or alkaline earth metal hydrides (e.g., lithium hydride, sodium hydride, potassium hydride, calcium hydride), alkali metal or alkaline earth metal amides (e.g., lithium amide, sodium amide, lithium diisopropylamide, lithium dicyclohexylamide, lithium hexamethyldisilazide, sodium hexamethyldisilazide, potassium hexamethyldisilazide) and alkali metal or alkaline earth metal lower alkoxides (e.g., sodium methoxide, sodium ethoxide, potassium tert-butoxide);
2) an inorganic base including alkali metal or alkaline earth metal hydroxides (e.g., sodium hydroxide, potassium hydroxide, lithium hydroxide, barium hydroxide), alkali metal or alkaline earth metal carbonates (e.g., sodium carbonate, potassium carbonate, cesium carbonate) and alkali metal or alkaline earth metal bicarbonates (e.g., sodium bicarbonate, potassium bicarbonate); or
3) an organic base including amines such as triethylamine, diisopropylethylamine, N-methylmorpholine, dimethylaminopyridine, DBU (1,8-diazabicyclo[5.4.0]undec-7-ene) and DBN (1,5-diazabicyclo[4.3.0]non-5-ene) and basic heterocyclic compounds such as pyridine, imidazole and 2,6-lutidine.

The reactions described herein, including alkylation, hydrolysis, amination, esterification, amidation, esterification, etherification, oxidation and reduction, may be carried out in a known manner, for example, as described in ORGANIC FUNCTIONAL GROUP PREPARATIONS, 2nd ed., ACADEMIC PRESS, INC. (1989).

The preparation of Compound (I) will be shown in more detail below.

Preparation Scheme 1

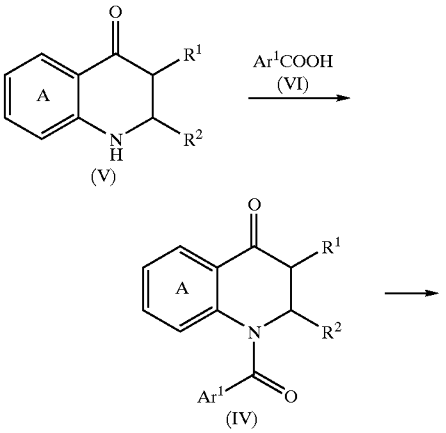

-continued

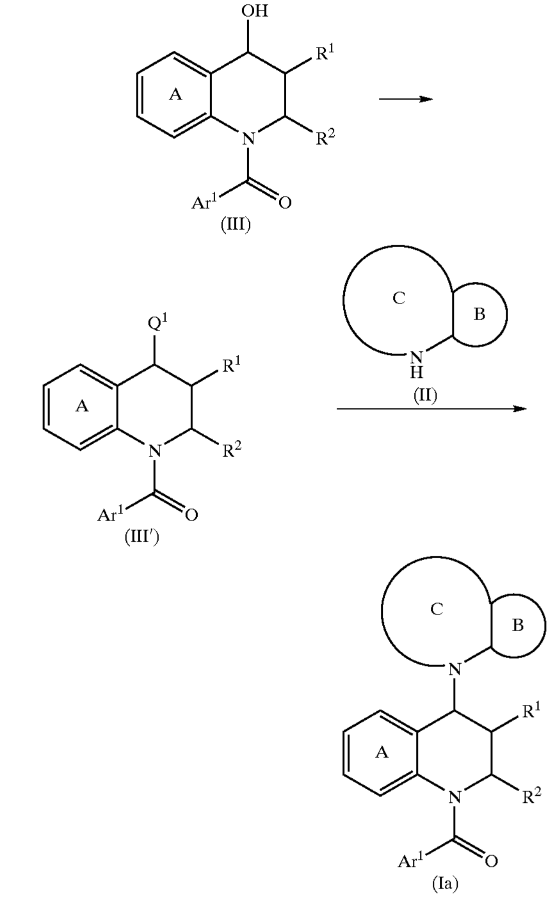

[wherein each symbol is as defined above].

Among compounds of the above Formula (I), Compound (1a) wherein X is N and Y is CH can be prepared by substituting Compound (III') with Compound (II) in the presence of a base according to the procedures as described in, e.g., Tetrahedron Lett., 38(15) 2673 (1997).

As a base, any one of those listed above may be used, but preferred are potassium carbonate, sodium carbonate, barium carbonate, sodium bicarbonate, triethylamine, N-methylmorpholine, pyridine and the like. Such a base is preferably used in an amount of 1 to 10 equivalents.

This reaction is carried out in an inert solvent. Examples of an "inert solvent" include ether solvents, halogenated hydrocarbon solvents, aromatic solvents, nitrile solvents, amide solvents, ketone solvents and sulfoxide solvents.

The reaction temperature ranges from −20° C. to 200° C., preferably from 0° C. to 50° C. The reaction time ranges from 0.1 hours to 48 hours, preferably from 1 hour to 24 hours.

Examples of Compound (II) available for use include anilines which are commercially available or synthesized as described in, e.g., New Experimental Chemistry Course, Vol. 14(III). Compound (II) is preferably used in an amount of 1 to 10 equivalents.

In the case of using Intermediate Compound (III') wherein the reactive substituent $Q^1$ is a reactive substituent other than a hydroxy group, such Compound (III') may be prepared by converting the hydroxy group of Compound (III) into the reactive substituent $Q^1$.

Examples of such a reactive substituent include a halogen atom (e.g., chlorine, bromine, iodine), an optionally halogenated $C_{1-6}$ alkylsulfonyloxy (e.g., methanesulfonyloxy, ethanesulfonyloxy, trifluoromethanesulfonyloxy) and an optionally substituted $C_{6-10}$ arylsulfonyloxy.

Examples of a "substituent" on the "optionally substituted $C_{6-10}$ arylsulfonyloxy" include a halogen atom (e.g., chlorine, bromine, iodine) and an optionally halogenated $C_{1-6}$ alkyl or $C_{1-6}$ alkoxy. The number of substituents is, for example, 1 to 3. Specific examples of the "optionally substituted $C_{6-10}$ arylsulfonyloxy" include benzenesulfonyloxy, p-toluenesulfonyloxy, 1-naphthalenesulfonyloxy and 2-naphthalenesulfonyloxy.

The "reactive substituent" is preferably a halogen atom (e.g., chlorine, bromine, and iodine), methanesulfonyloxy, trifluoromethanesulfonyloxy, p-toluenesulfonyloxy or the like.

Halogenation may be accomplished, for example, by reacting Compound (III) with 1 to 10 equivalents of a halogenating agent in an inert solvent.

Examples of such a halogenating agent include inorganic acid halides such as thionyl chloride, thionyl bromide, phosphorous trichloride, phosphorus pentachloride and phosphorus oxychloride; halogenated hydroacids such as hydrochloric acid and hydrobromic acid; or silyl halides such as iodotrimethylsilane, with iodotrimethylsilane being preferred for use.

Examples of an "inert solvent" include ether solvents, halogenated hydrocarbon solvents, aromatic solvents, nitrile solvents, amide solvents and sulfoxide solvents.

The reaction temperature ranges from −20° C. to 200° C., preferably from 0° C. to 100° C. The reaction time ranges from 0.1 hours to 48 hours, preferably from 1 hour to 24 hours.

Sulfonylation may be accomplished, for example, by reacting Compound (III) with 1 to 5 equivalents of a corresponding sulfonyl halide in an inert solvent and in the presence of a base.

Such a base is preferably potassium carbonate, sodium bicarbonate, triethylamine, N-methylmorpholine, pyridine or the like. It is preferably used in an amount of 1 to 10 equivalents.

Examples of an "inert solvent" include ether solvents, halogenated hydrocarbon solvents, aromatic solvents, nitrile solvents, amide solvents, ketone solvents and sulfoxide solvents.

The reaction temperature ranges from −20° C. to 200° C., preferably from 0° C. to 100° C. The reaction time ranges from 0.1 hours to 48 hours, preferably from 1 hour to 24 hours.

Examples of Compound (II) available for use include anilines which are commercially available or synthesized as described in, e.g., New Experimental Chemistry Course, Vol. 14 (III). Compound (II) is preferably used in an amount of 1 to 10 equivalents.

As a base, any one of those listed above may be used, but preferred are potassium carbonate, barium carbonate, sodium bicarbonate, triethylamine, N-methylmorpholine, pyridine and the like. Such a base is preferably used in an amount of 1 to 10 equivalents.

This reaction is carried out in an inert solvent. Examples of an "inert solvent" include ether solvents, halogenated hydrocarbon solvents, aromatic solvents, nitrile solvents, amide solvents, ketone solvents and sulfoxide solvents.

The reaction temperature ranges from −20° C. to 200° C., preferably from 0° C. to 50° C. The reaction time ranges from 0.1 hours to 48 hours, preferably from 1 hour to 24 hours.

Compound (III) may be prepared by reducing Compound (IV) with a suitable reducing agent in an inert solvent.

Examples of an "inert solvent" include alcohol solvents, ether solvents, halogenated hydrocarbon solvents, aromatic solvents, nitrile solvents, amide solvents and organic acid solvents. These solvents may be used in combination at an appropriate mixing ratio. Above all, methanol, ethanol and the like are preferred.

Examples of a reducing agent available for use include sodium borohydride, sodium triacetoxyborohydride, sodium cyanoborohydride and lithium aluminium hydride. Such a reducing agent is usually used in an amount of 1 to 20 equivalents, preferably 1 to 5 equivalents.

The reaction temperature ranges usually from −20° C. to 150° C., preferably from 0° C. to 50° C. The reaction time ranges usually from 5 minutes to 24 hours, preferably from 1 hour to 12 hours.

Compound (IV) may be prepared by amidation between Compound (V) and Compound (VI).

This step may be accomplished using a dehydrocondensing agent or may be mediated by conversion of Compound (VI) into a reactive derivative form before condensation.

i) In the Case of Using a Dehydrocondensing Agent:

Compound (V) or a salt thereof (1 equivalent), Compound (VI) (1 to 5 equivalents) and a dehydrocondensing agent (1 to 2 equivalents) are reacted in an inert solvent at room temperature for 10 to 24 hours. If necessary, the reaction may be carried out in the presence of 1-hydroxybenzotriazole (HOBT) in an amount of 1 to 1.5 equivalents and/or a base (e.g., triethylamine, 4-dimethylaminopyridine) in a catalytic amount up to 5 equivalents.

Examples of such a "dehydrocondensing agent" include dicyclohexylcarbodiimide (DCC) and 1-ethyl-3-(3-dimethylaminopropyl)carbodiimide hydrochloride (WSC), with WSC being particularly preferred.

Examples of an inert solvent available for use include nitrile solvents (preferably acetonitrile), amide solvents (preferably dimethylformamide (DMF)), halogenated hydrocarbon solvents (preferably dichloromethane) and ether solvents (preferably tetrahydrofuran (THF)). These solvents may be used alone or in combination.

ii) In the Case of Using a Reactive Derivative of Compound (VI):

A reactive derivative of Compound (VI) is reacted with Compound (V) (1 to 5 equivalents, preferably 1 to 3 equivalents) in an inert solvent at −20° C. to 50° C. (preferably at room temperature) for 5 minutes to 40 hours (preferably 1 to 18 hours). If necessary, the reaction may be carried out in the presence of a base in an amount of 1 to 10 equivalents, preferably 1 to 3 equivalents.

Examples of a "reactive derivative" of Compound (VI) include acid halides (e.g., acid chloride, acid bromide), mixed acid anhydrides (e.g., acid anhydrides with a $C_{1-6}$ alkyl-carboxylic acid, a $C_{6-10}$ aryl-carboxylic acid or a $C_{1-6}$ alkyl carbonic acid) and active esters (e.g., esters with an optionally substituted phenol, 1-hydroxybenzotriazole or N-hydroxysuccinimide). The "optionally substituted phenol" may have 1 to 5 substituents selected from a halogen atom, nitro, an optionally halogenated $C_{1-6}$ alkyl or an optionally halogenated $C_{1-6}$ alkoxy. Specific examples of the "optionally substituted phenol" include phenol, pentachlorophenol, pentafluorophenol and p-nitrophenol. Such a reactive derivative is preferably an acid halide.

Examples of a "base" preferred for that purpose include sodium hydride, potassium carbonate, sodium carbonate, sodium hydroxide, potassium hydroxide, sodium bicarbonate, potassium bicarbonate, triethylamine and pyridine.

Examples of an inert solvent available for use include ether solvents, halogenated hydrocarbon solvents, aromatic solvents, nitrile solvents, amide solvents, ketone solvents, sulfoxide solvents and water. These solvents may be used alone or in combination. Above all, preferred are pyridine, acetonitrile, THF, dichloromethane, chloroform and the like, and more preferred are pyridine, THF, acetonitrile and the like.

Compound (V) may be prepared in a known manner, for example, as described in Bioorganic and Medicinal Chemistry Letters, 9 1009 (1999).

Preparation Scheme 2

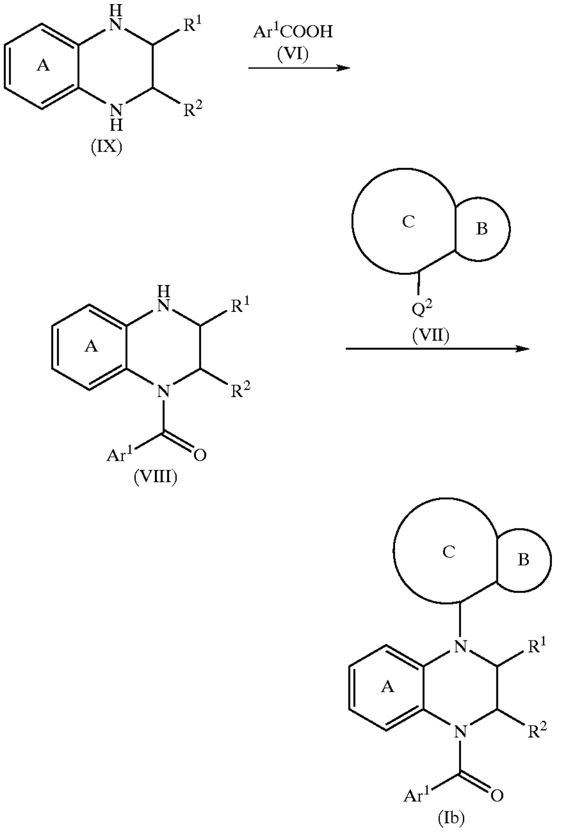

(IX) (VIII) (Ib)

[wherein each symbol is as defined above].

Among compounds of the above Formula (I), Compound (1b) wherein X is CH and Y is N can be prepared by reacting Compound (VIII) with Compound (VII) [wherein $Q^2$ has the same meaning as defined for the reactive substituent $Q^1$ in Preparation Scheme 1] in an inert solvent and in the presence of a base.

The same bases as listed above may be used for this purpose, but preferred are potassium carbonate, sodium carbonate, sodium hydroxide, potassium hydroxide, sodium hydride, potassium hydride and the like.

Such a base is preferably used in an amount of 1 to 10 equivalents.

Examples of Compound (VII) available for use include alkyl chlorides, alkyl bromides and alkyl iodides, which are commercially available or synthesized as described in, e.g., New Experimental Chemistry Course, Vol. 14(I).

Compound (VII) is preferably used in an amount of 1 to 20 equivalents.

Examples of an "inert solvent" include alcohol solvents, ether solvents, halogenated hydrocarbon solvents, aromatic solvents, nitrile solvents, amide solvents, ketone solvents and sulfoxide solvents. These solvents may be used in combination at an appropriate mixing ratio. Above all, acetonitrile, DMF, DMSO, acetone and the like are preferred.

The reaction temperature ranges usually from about −20° C. to about 100° C., preferably from room temperature to 80° C. The reaction time ranges, for example, from about 0.5 hours to about 48 hours.

Compound (VIII) may be prepared by amidation between Compound (IX) and Compound (VI) in the same manner as described in Preparation Scheme 1. Compound (IX) may be prepared in a known manner, for example, as described in Journal of Pharmaceutical Bulletin 32(6) 2421 (1984).

Preparation Scheme 3

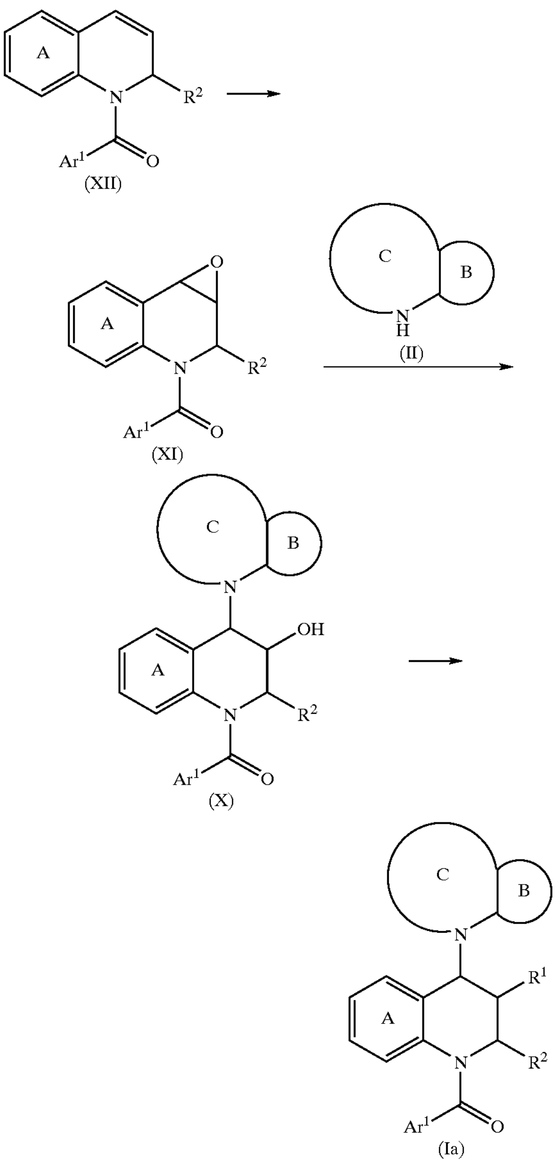

(XII) (XI) (X) (Ia)

[wherein each symbol is as defined above].

Among compounds of the above Formula (I), Compound (1a) wherein X is N and Y is CH can also be prepared by opening the oxirane ring of Compound (XI) in a manner as described in, e.g., Tetrahedron Lett. 39(21) 3459 (1998) and then converting the hydroxy group of the resulting Compound (X) into $R^1$.

The oxirane ring of Compound (XI) may be opened by treatment with Compound (II) in an inert solvent and, if necessary, in the presence of a catalyst. Examples of a catalyst include Lewis acids such as aluminum chloride, zinc bromide, zinc chloride, titanium tetrachloride, titanium tetraisopropoxide and boron trifluoride diethyl ether complex; inorganic acids such as hydrochloric acid and sulfuric acid; organic acids such as acetic acid and methanesulfonic acid; alkylaluminum reagents such as trimethylaluminum and triethylaluminum; alkali metal or alkaline earth metal hydroxides such as sodium hydroxide, potassium hydroxide and lithium hydroxide; alkali metal or alkaline earth metal carbonates such as sodium carbonate, potassium carbonate and cesium carbonate; alkali metal or alkaline earth metal bicarbonates such as sodium bicarbonate and potassium bicarbonate; perchlorates such as lithium perchlorate and sodium perchlorate; alkaline earth metal hydrides such as sodium hydride and potassium hydride; alkali metal or alkaline earth metal amides such as sodium amide, lithium diisopropylamide and lithium hexamethyldisilazide; alkali metal or alkaline earth metal lower alkoxides such as sodium methoxide, sodium ethoxide and potassium tert-butoxide; organic bases such as triethylamine and DBU; and metal complexes such as tristriphenylphosphine palladium complex and cerium(IV) diammonium nitrate. Preferred for use are trimethylaluminum, triethylaluminum, zinc bromide, lithium perchlorate, cerium(IV) diammonium nitrate, potassium hydroxide and the like.

Examples of an inert solvent include ether solvents, halogenated hydrocarbon solvents, aromatic solvents, nitrile solvents, amide solvents, ketone solvents, sulfoxide solvents and alcohol solvents. These solvents may be used in combination at an appropriate mixing ratio. Above all, acetonitrile, THF, dichloromethane, chloroform and the like are preferred.

This reaction may be carried out using Compound (II) in an amount of 1 to 20 equivalents, preferably 1.5 to 5 equivalents, and if necessary, a catalyst in an amount of 0.01 to 10 equivalents, preferably 0.1 to 2 equivalents, relative to Compound (XI).

The reaction temperature ranges usually from −50° C. to 100° C., preferably from 0° C. to 50° C. The reaction time ranges usually from 5 minutes to 48 hours, preferably from 0.5 hours to 18 hours.

Compound (1a) wherein $R^1$ is hydrogen can be prepared by converting the hydroxy group of Compound (X) into a reactive substituent and then reducing the reactive substituent in a manner as described in, e.g., Journal of Organic Chemistry 65(15) 4565 (2000) or Account of Chemical Research 25(4) 188 (1992).

Examples of such a reactive substituent include a halogen atom (e.g., chlorine, bromine, iodine), an alkylsulfonyloxy (e.g., methanesulfonyloxy, ethanesulfonyloxy, trifluoromethanesulfonyloxy), an arylsulfonyloxy (e.g., benzenesulfonyloxy, p-toluenesulfonyloxy), an alkyldithiocarbonyloxy (e.g., methyldithiocarbonyloxy), an arylthiocarbonyloxy (e.g., imidazolylthiocarbonyloxy), an aryloxythiocarbonyloxy (e.g., phenoxythiocarbonyloxy) and an arylselenoxycarbonyloxy (e.g., phenylselenoxycarbonyloxy), with methyldithiocarbonyloxy, imidazolylthiocarbonyloxy and the like being preferred.

Conversion into such a reactive substituent may be accomplished, for example, by reacting Compound (X) with 1 to 10 equivalents of an activating agent in an inert solvent and, if necessary, in the presence of a base.

Examples of an activating agent available for use include inorganic acid halides such as thionyl chloride, thionyl bromide, phosphorous trichloride, phosphorus pentachloride and phosphorus oxychloride; halogenated hydroacids such as hydrochloric acid and hydrobromic acid; silyl halides such as iodotrimethylsilane; sulfonyl chlorides such as methanesulfonyl chloride and p-toluenesulfonyl chloride; thiocarbonyldiimidazole; and a carbon disulfide/iodomethane system.

Examples of an "inert solvent" include ether solvents, halogenated hydrocarbon solvents, aromatic solvents, nitrile solvents, amide solvents and sulfoxide solvents.

The reaction temperature ranges from −50° C. to 200° C., preferably from 0° C. to 150° C. The reaction time ranges from 0.1 hours to 48 hours, preferably from 1 hour to 24 hours.

Examples of a base preferred for use include potassium carbonate, sodium bicarbonate, triethylamine, N-methylmorpholine and pyridine.

Reduction of the reactive substituent may be accomplished, for example, by reacting the reactive substituent compound with 1 to 10 equivalents or a large excess amount of a reducing agent in an inert solvent.

Examples of a reducing agent available for use include borohydride reagents such as diborane, sodium borohydride and lithium triethylborohydride; aluminium hydride reagents such as lithium aluminium hydride; tin reagents such as tributyltin hydride/AIBN; silane reagents such as tristrimethylsilylsilane and triethylsilane; and metals such as zinc and chromium acetate. Alternatively, catalytic hydrogenation may be used.

Examples an "inert solvent" include ether solvents, halogenated hydrocarbon solvents, aromatic solvents, nitrile solvents, amide solvents, sulfoxide solvents and alcohol solvents.

The reaction temperature ranges from −50° C. to 200° C., preferably from 0° C. to 150° C. The reaction time ranges from 0.1 hours to 48 hours, preferably from 1 hour to 24 hours.

Compound (1a) wherein $R^1$ is an alkoxy group or an acyloxy group can be prepared by alkylating or acylating the hydroxy group of Compound (X) in a known manner, for example, as described in ORGANIC FUNCTIONAL GROUP PREPARATIONS, 2nd ed., ACADEMIC PRESS, INC. (1989) or Comprehensive Organic Transformations, VCH Publishers Inc. (1989).

Compound (XI) may be prepared from Compound (XII) in a manner known from, e.g., Heterocycle 41(5) 897 (1995). Compound (XII) may be prepared as described in the same journal or by performing conventional dehydrogenation on Compound (III) obtained in Preparation Scheme 1.

Preparation Scheme 4

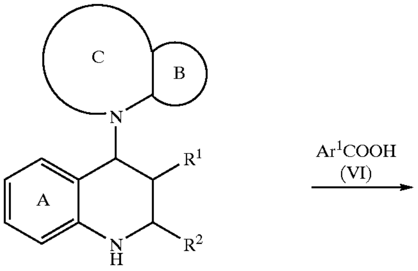

(XIII)

-continued

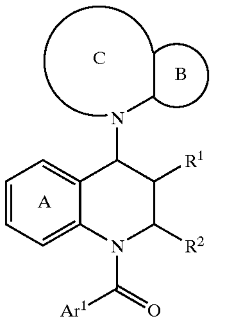

(Ia)

[wherein each symbol is as defined above].

Compound (Ia) can be prepared by amidation with Compound (VI) in the same manner as described for the preparation of Compound (IV) in Preparation Scheme 1. Compound (XIII) may be prepared in a manner known from, e.g., Journal of Organic Chemistry 60(13) 3993 (1995).

Preparation Scheme 5

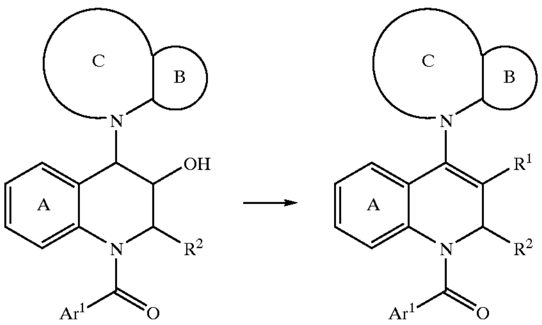

(X) (Ic)

[wherein each symbol is as defined above].

Compound (Ic) can be prepared by reacting Compound (X) with a base in an inert solvent and, if necessary, in the presence of an activating agent.

Examples of a "base" include alkali metal or alkaline earth metal hydrides (e.g., lithium hydride, sodium hydride, potassium hydride, calcium hydride), alkali metal or alkaline earth metal amides (e.g., lithium amide, sodium amide, lithium diisopropylamide, lithium dicyclohexylamide, lithium hexamethyldisilazide, sodium hexamethyldisilazide, potassium hexamethyldisilazide), alkali metal or alkaline earth metal lower alkoxides (e.g., sodium methoxide, sodium ethoxide, potassium tert-butoxide), alkali metal or alkaline earth metal hydroxides (e.g., sodium hydroxide, potassium hydroxide, lithium hydroxide, barium hydroxide), alkali metal or alkaline earth metal carbonates (e.g., sodium carbonate, potassium carbonate, cesium carbonate), alkali metal or alkaline earth metal bicarbonates (e.g., sodium bicarbonate, potassium bicarbonate), amines (e.g., triethylamine, diisopropylethylamine, N-methylmorpholine, dimethylaminopyridine, DBU (1,8-diazabicyclo[5.4.0]undec-7-ene), DBN (1,5-diazabicyclo [4.3.0]non-5-ene)) and basic heterocyclic compounds (e.g., pyridine, imidazole, 2,6-lutidine).

Among those listed above, preferred are strong bases such as sodium hydride, sodium amide and potassium hydroxide. If the reaction is carried out in the presence of an activating agent, organic bases such as triethylamine and pyridine are preferred for use.

Examples of an "inert solvent" include ether solvents, halogenated hydrocarbon solvents, aromatic solvents, nitrile solvents, amide solvents, sulfoxide solvents, alcohol solvents and water.

Examples of an activating agent available for use include inorganic acid halides such as thionyl chloride, thionyl bromide, phosphorous trichloride, phosphorus pentachloride and phosphorus oxychloride; halogenated hydroacids such as hydrochloric acid and hydrobromic acid; silyl halides such as iodotrimethylsilane; acid chlorides such as acetyl chloride and benzoyl chloride; sulfonyl chlorides such as methanesulfonyl chloride and p-toluenesulfonyl chloride; chlorocarbonates such as ethyl chlorocarbonate; acid anhydrides such as acetic anhydride and trifluoromethanesulfonic anhydride; isocyanates and thioisocyanates such as methyl isocyanate; carbonyldiimidazole; and thiocarbonyldiimidazole.

This reaction may be carried out using a base in an amount of 1 to 20 equivalents, preferably 1.5 to 5 equivalents, and an activating agent in an amount of 0.01 to 10 equivalents, preferably 1 to 2 equivalents, relative to Compound (X). The reaction temperature ranges usually from −50° C. to 200° C., preferably from 0° C. to 150° C. The reaction time ranges usually from 5 minutes to 48 hours, preferably from 0.5 hours to 18 hours.

Compound (I) or a salt or prodrug thereof is excellent in stimulating soluble β-amyloid precursor protein secretion and is less toxic; it can therefore be used as a soluble β-amyloid precursor protein secretion stimulator that is safe for humans and mammals (e.g., mouse, rat, guinea pig, rabbit, dog, cat, cattle, pig, sheep, monkey, chimpanzee). It can also be used as an apoptosis inhibitor or a nerve dysfunction ameliorator.

Thus, Compound (I) or a salt or prodrug thereof can be safely used in humans and mammals as a prophylactic and/or therapeutic agent for neurodegenerative diseases such as Alzeheimer's disease, Parkinson's disease, prion disease or neuropathy (preferably, e.g., diabetic neuropathy), as well as for senile dementia, cerebrovascular dementia and cerebrovascular disorder-induced neuronopathy.

In a case where Compound (I) or a salt or prodrug thereof is used as a medicament, it can be safely administered by oral or parenteral route, either alone or as a pharmaceutical composition in an oral dosage form [e.g., powders, granules, tablets, capsules (including soft capsules and microcapsules), syrups] or in a parenteral dosage form [e.g., injections, external preparations (e.g., transnasal or percutaneous formulations), suppositories (e.g., rectal or vaginal suppositories), pellets], in combination with appropriate pharmaceutically acceptable carriers, excipients, diluents, etc.

These dosage forms may be prepared, for example, by applying known procedures commonly used for formulation. The percentage of Compound (I) formulated will vary depending on the intended dosage form, but it is preferably about 10% to 95% by weight in the above oral dosage forms and about 0.001% to 95% by weight in the above parenteral dosage forms, by way of example.

To prepare injections, for example, Compound (I) may be formulated in a routine manner into aqueous injections in combination with solubilizers (e.g., β-cyclodextrins), dispersants (e.g., Tween 80 (Atlas Powder, USA), HCO60 (Nikko Chemicals Co., Ltd., Japan), carboxyinethylcellulose, sodium alginate), preservatives (e.g., methylparaben, propylparaben, benzyl alcohol, chlorobutanol), isotonizing agents (e.g., sodium chloride, glycerine, sorbitol, glucose) and the like or may be formulated into oil injections by appropriately dissolving, suspending or emulsifying it in vegetable oils (e.g., olive oil, sesame oil, peanut oil, cottonseed oil, corn oil), propylene glycol or the like.

To prepare oral dosage forms, for example, Compound (I) may be compressed and molded as appropriate together with excipients (e.g., lactose, sucrose, starch), disintegrating agents (e.g., starch, calcium carbonate), binders (e.g., starch, gum arabic, carboxymethylcellulose, polyvinylpyrrolidone, hydroxypropylcellulose) or lubricants (e.g., talc, magnesium stearate, polyethylene glycol 6000) and then, if necessary, coated in a known manner for the purpose of taste masking, enteric coating or sustained release. Examples of a coating agent appropriate for use include hydroxypropylmethylcellulose, ethylcellulose, hydroxymethylcellulose, hydroxypropylcellulose, polyoxyethylene glycol, Tween 80, Pluronic F68, cellulose acetate phthalate, hydroxypropylmethylcellulose phthalate, hydroxymethylcellulose acetate succinate, Eudragit (Rohm, West Germany, a copolymer of methacrylate and acrylate) and dyes (e.g., titanium oxide, iron oxide red).

Compound (I) of the present invention may also be used as a solid, semisolid or liquid preparation for external application.

To prepare solid preparations for external application, for example, Compound (I) may be formulated alone or in combination with excipients (e.g., glycol, mannitol, starch, microcrystalline cellulose), thickeners (e.g., natural gums, cellulose derivatives, acrylate polymers) to give powdered compositions. Semisolid preparations for external application may be prepared in a routine manner and preferably used as aqueous or oil gels or ointments. Liquid preparations for external application may be prepared in the same or equivalent manner as used for the preparation of injections to give oil or aqueous suspensions.

Such solid, semisolid or liquid preparations for external application may also be supplemented as appropriate with pH adjusters (e.g., carbonic acid, phosphoric acid, citric acid, hydrochloric acid, sodium hydroxide), antiseptics (e.g., p-hydroxybenzoic esters, chlorobutanol, benzalkonium chloride) and the like. More specifically, Compound (I) of the present invention may be used as an ointment usually containing Compound (I) in an amount of about 0.1 mg to about 100 mg per gram of matrix such as vaseline or lanolin.

Compound (I) may also be formulated into oil or aqueous solid, semisolid or liquid suppositories. Examples of an oleaginous base appropriate for use in suppository preparation include glycerides of higher fatty acids (e.g., cacao butter, Witepsols (Dynamite Noble)), medium fatty acids (e.g., miglyols (Dynamite Noble)) and vegetable oils (e.g., sesame oil, soybean oil, cottonseed oil). Examples of an aqueous base appropriate for this purpose include polyethylene glycols and propylene glycol. Examples of an aqueous gel base appropriate for this purpose include natural gums, cellulose derivatives, vinyl polymers and acrylate polymers.

The dose of Compound (I) or a salt or prodrug thereof will vary depending on target diseases, subjects (human or mammal) to be administered, symptoms, age, body weight, symptoms, the intended dosage form, the intended route of administration, the period of administration, etc. For oral administration in the treatment of Alzeheimer's disease, Compound (I) or a salt or prodrug thereof is usually administered, per 60 kg of body weight of human or mammalian subjects, in an amount of about 0.1 to 100 mg, preferably about 0.1 to 50 mg, more preferably about 1 to 50 mg, and particularly preferably about 2.5 to 50 mg, in one to three divided doses per day. Of course, it may be administered in a smaller amount than that mentioned above to achieve successful results or may be administered in an amount beyond the range because the dose will vary depending on various conditions, as stated above.

EXAMPLES

The present invention will be further described in more detail in the following Examples and Experimental Example, which are not intended to limit the scope of the invention.

Reference Example 1 cis-1-(3,4-Dimethoxybenzoyl)-2-methyl-1,2,3,4-tetrahydro-4-quinolinol

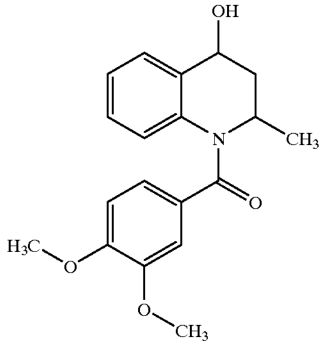

1) 1-(3,4-Dimethoxybenzoyl)-2-methyl-2,3-dihydro-4(1H)-quinolinone

2-Methyl 2,3-dihydro-4(1H)-quinolone (1.19 g, 7.38 mmol) was synthesized in the published manner (Bioorganic and Medicinal Chemistry Letters 9 1009 (1999)) and dissolved in pyridine (15 ml). To this solution, 3,4-dimethoxybenzoyl chloride (1.63 g, 8.12 mmol) was added and stirred at room temperature for 16 hours. The reaction mixture was concentrated and extracted by addition of ethyl acetate and water. After the organic layer was dried and concentrated, the residue was applied to silica gel column chromatography (developing solvent: ethyl acetate/hexane=1/2) and the resulting eluate was recrystallized from ethyl acetate-hexane to give the product of interest, i.e., cis-1-(3,4-dimethoxybenzoyl)-2-methyl-2,3-dihydro-4(1H)-quinolinone (1.57 g, yield: 65%) as a white crystal.

Elementary Analysis for $C_{19}H_{19}NO_4$: Calculated: C, 70.14; H, 5.89; N, 4.31. Found: C, 70.18; H, 5.86; N, 4.46.

2) cis-1-(3,4-Dimethoxybenzoyl)-2-methyl-1,2,3,4-tetrahydro-4-quinolinol cis-1-(3,4-Dimethoxybenzoyl)-2-methyl-2,3-dihydro-4(1H)-quinolinone (4.65 g, 14.3 mmol) prepared in 1) above was dissolved in a solvent mixture of methanol (40 ml) and THF (80 ml), to which sodium borohydride (540 mg, 14.3 mmol) was then added and stirred at room temperature for 2 hours. The reaction mixture was poured into water and extracted with ethyl acetate. After the organic layer was dried and concentrated, the residue was recrystallized from THF-hexane to give the product of interest, i.e., cis-1-(3,4-dimethoxy-benzoyl)-2-methyl-1,2,3,4-tetrahydro-4-quinolinol (3.84 g, yield: 82%) as a white crystal.

Elementary Analysis for $C_{19}H_{21}NO_4$: Calculated: C, 69.71; H, 6.47; N, 4.28. Found: C, 69.88; H, 6.51; N, 4.18.

Reference Example 2

1-(3,4-Dimethoxybenzoyl)-1,2,3,4-tetrahydro-4-quinolinol

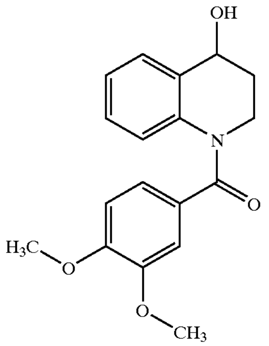

1) 1-(3,4-Dimethoxybenzoyl)-2,3-dihydro-4(1H)-quinolinone

Starting with 2,3-dihydro-4(1H)-quinolone (2.60 g, 16.54 mmol), the same procedure as shown in Reference Example 1-1) was repeated to give 1-(3,4-dimethoxybenzoyl)-2,3-dihydro-4(1H)-quinolinone (4.42 g, yield: 86%) as a white crystal.

$^1$H-NMR ($CDCl_3$) δ: 2.90 (2H, t, J=6.3 Hz), 3.80 (3H, s), 3.90 (3H, s), 4.35 (2H, t, J=6.3 Hz), 6.76 (1H, d, J=8.4 Hz), 6.95 (1H, d, J=7.5 Hz), 7.03–7.29 (4H, m), 8.01 (1H, dd, J=1.2 Hz, 7.8 Hz).

2) 1-(3,4-Dimethoxybenzoyl)-1,2,3,4-tetrahydro-4-quinolinol

Starting with 1-(3,4-dimethoxybenzoyl)-2,3-dihydro-4 (1H)-quinolinone (2.00 g, 14.3 mmol) prepared in 1) above, the same procedure as shown in Reference Example 1-2) was repeated to give 1-(3,4-dimethoxybenzoyl)-1,2,3,4-tetrahydro-4-quinolinol (1.54 g, yield: 77%) as a white crystal.

$^1$H-NMR ($CDCl_3$) δ: 2.05–2.13 (1H, m), 2.21–2.27 (1H, m), 3.76 (3H, s), 3.76–3.84 (1H, m), 3.88 (3H, s), 4.09–4.20 (1H, m), 4.89–4.90 (1H, m), 6.74 (1H, d, J=7.8 Hz), 6.88 (1H, d, J=7.8 Hz), 6.96–7.12 (4H, m), 7.45 (1H, d, J=6.0 Hz).

Example 1

4-(Tetrahydroquinolin-1-yl)-1-(3,4-dimethoxybenzoyl)-1,2,3,4-tetrahydroquinoline

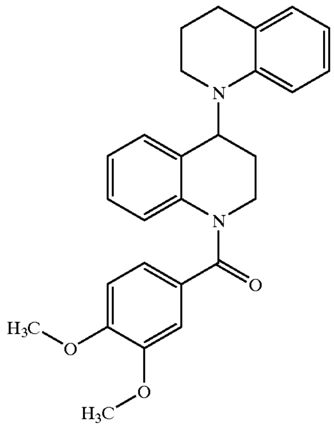

1-(3,4-Dimethoxybenzoyl)-1,2,3,4-tetrahydro-4-quinolinol (400 mg, 1.28 mmol) prepared in Reference Example 2 was dissolved in chloroform (10 ml), to which iodotrimethylsilane (638 mg, 3.19 mmol) was then added on ice and stirred for 2 hours. After the reaction mixture was concentrated, the residue was dissolved in THF (10 ml) and mixed with 1,2,3,4-tetrahydroquinoline (511 mg, 3.84 mmol) and barium carbonate (505 mg, 2.56 mmol), followed by stirring at room temperature for 48 hours. After the reaction mixture was filtered to remove insoluble products and concentrated, the residue was applied to silica gel column chromatography (developing solvent: ethyl acetate/hexane=1/3) and the resulting eluate was recrystallized from diethyl ether-hexane to give the product of interest, i.e., 4-(tetrahydroquinolin-1-yl)-1-(3,4-dimethoxybenzoyl)-1,2,3,4-tetrahydro-quinoline (202 mg, yield: 37%) as a white crystal.

Elementary Analysis for $C_{22}H_{21}N_3O$ 0.20$H_2O$: Calculated: C, 75.05; H, 6.62; N, 6.48. Found: C, 74.88; H, 6.65; N, 6.31.

Melting point: 88° C.–90° C. (crystallization solvent: diethyl ether-hexane)

Example 2

4-(2,3-Dihydro-1H-indol-1-yl)-1-(3,4-dimethoxybenzoyl)-1,2,3,4-tetrahydroquinoline

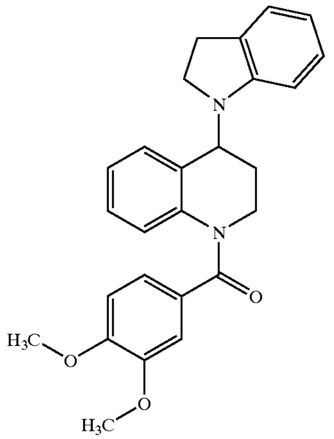

Starting with 1-(3,4-dimethoxybenzoyl)-1,2,3,4-tetrahydro-4-quinolinol (390 mg, 1.19 mmol) prepared in Reference Example 2 and indoline (425 mg, 3.57 mmol), the same procedure as shown in Example 1 was repeated to give the product of interest, i.e., 4-(2,3-dihydro-1H-indol-1-yl)-1-(3,4-dimethoxybenzoyl)-1,2,3,4-tetrahydroquinoline (268 mg, yield: 54%) as a white crystal.

Melting point: 121° C.–123° C. (crystallization solvent: ethyl acetate-hexane)

FABMS(pos) 415.1 [M+H$^+$]

Example 3

4-(1'-Benzylspiro[indoline-3,4'-piperidin]-1-yl)-1-(3,4-dimethoxybenzoyl)-1,2,3,4-tetrahydroquinoline

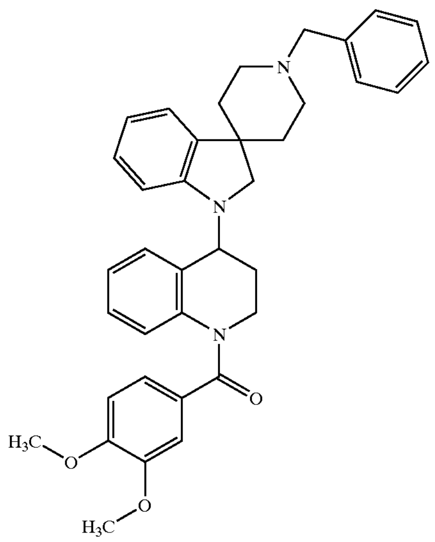

Starting with 1-(3,4-dimethoxybenzoyl)-1,2,3,4-tetrahydro-4-quinolinol (250 mg, 0.76 mmol) prepared in Reference Example 2 and 1'-benzylspiro[indoline-3,4'-piperidine] (532 mg, 1.91 mmol), the same procedure as shown in Example 1 was repeated to give the product of interest, i.e., 4-(1'-benzylspiro[indoline-3,4'-piperidin]-1-yl)-1-(3,4-dimethoxybenzoyl)-1,2,3,4-tetrahydroquinoline (211 mg, yield: 48%) as a white crystal.

Melting point: 155° C.–157° C. (crystallization solvent: diisopropyl ether-hexane)

FABMS(pos) 574.2 [M+H$^+$]

Example 4

1-(3,4-Dimethoxybenzoyl)-2-methyl-4-(tetrahydroquinolin-1-yl)-1,2,3,4-tetrahydroquinoline

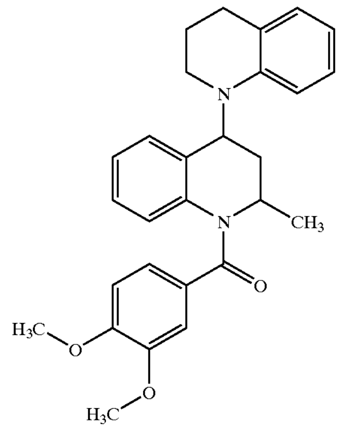

Starting with cis-1-(3,4-dimethoxybenzoyl)-2-methyl-1,2,3,4-tetrahydro-4-quinolinol (400 mg, 1.22 mmol) prepared in Reference Example 1 and 1,2,3,4-tetrahydroquinoline (487 mg, 3.66 mmol), the same procedure as shown in Example 1 was repeated to give the product of interest, i.e., 1-(3,4-dimethoxybenzoyl)-2-methyl-4-(tetrahydroquinolin-1-yl)-1,2,3,4-tetrahydroquinoline (216 mg, yield: 40%) as a colorless oil. (cis:trans=1.6:1)

FABMS(pos) 465.2 [M+Na$^+$]

Reference Example 3

3-(3,4-Dimethoxybenzoyl)-2-methyl-1a,2,3,7b-tetrahydrooxyleno[2,3-c]quinoline

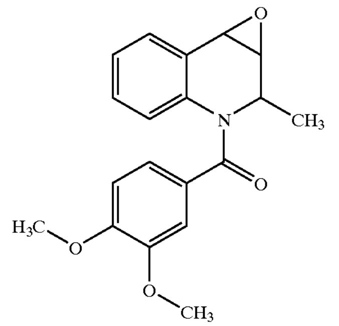

1-(3,4-Dimethoxybenzoyl)-2-methyl-1,2-dihydroquinoline (10.2 g, 0.033 mol) was synthesized in the published manner and dissolved in chloroform (50 ml). To this solution, m-perbenzoic acid (17.08 g, 0.099 mol) was added on ice over 1 hour. After stirring for 6 hours, the reaction mixture was partitioned between ethyl acetate and aqueous sodium thiosulfate. The organic layer was washed with aqueous sodium bicarbonate and water, and then concentrated. The residue was applied to silica gel column chromatography (developing solvent: chloroform) and the resulting eluate was recrystallized from diisopropyl ether-hexane to give the titled compound (7.3 g, yield: 68%) as a white crystal.

Melting point: 123° C.–124° C.

Reference Example 4

2,4-cis-4-(9H-9-Carbazolyl)-2-methyl-1,2,3,4-tetrahydroquinoline

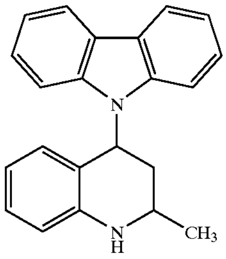

In the published manner (*J. Org Chem.* 1995, 60, 3993), benzotriazole (11.9 g, 100 mmol) and aniline (9.1 ml, 100 mmol) were dissolved in diethyl ether (200 ml), and acetaldehyde (6.1 ml, 110 mmol) was added dropwise thereto on ice. The reaction mixture was stirred at room temperature for 15 minutes and then allowed to stand overnight at −20° C. The crystallized product was collected by filtration, washed with diethyl ether and then dried to give α-methyl-N-phenyl-1H-benzotriazole-1-methanamine (22.3 g) as a white crystal. The resulting α-methyl-N-phenyl-1H-benzotriazole-1-methanamine (2.31 g, 10 mmol) and 9-vinylcarbazole (1.93 g, 10 mmol) were suspended in chloroform (10 ml), to which p-toluenesulfonic acid monohydrate (20 mg, 0.105 mmol) was then added and stirred at room temperature for 2 hours. After addition of water, the reaction mixture was extracted with chloroform. The organic layer was washed with 10% aqueous sodium carbonate and water, and then concentrated. The residue was applied to silica gel column chromatography (developing solvent: ethyl acetate/hexane=1/10) to give the titled compound (644 mg, yield over 2 steps: 20%) as a white crystal.

$^1$H NMR ($CDCl_3$) δ 1.27 (d, J=6.3 Hz, 3H), 2.04–2.16 (m, 1H), 2.45 (q, J=11.8 Hz, 1H), 3.74–3.85 (m, 1H), 3.90 (br s, 1H), 6.13 (dd, J=11.9, 6.4 Hz, 1H), 6.47 (t, J=8.2 Hz, 1H), 6.63 (d, J=8.3 Hz, 2H), 6.86–6.88 (m, 1H), 7.04 (t, J=7.7 Hz, 1H), 7.15 (dt, J=7.3, 1.4 Hz, 2H), 7.22–7.30 (m, 1H), 7.40–7.60 (m, 2H), 8.08–8.15 (m, 2H)

Reference Example 5

2,4-cis-4-(9H-9-Carbazolyl)-2-ethyl-1,2,3,4-tetrahydroquinoline

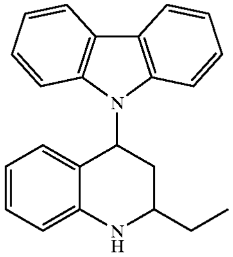

Starting with propylaldehyde (0.91 g, 15 mmol), the same procedure as shown in Reference Example 4 was repeated to give the titled compound (1.79 g, yield over 2 steps: 39%) as a white crystal.

$^1$H NMR ($CDCl_3$) δ 0.98 (t, J=7.4 Hz, 3H), 1.56–1.66 (m, 2H), 2.15–2.22 (m, 2H), 2.41 (q, J=12.0 Hz, 1H), 3.54–3.62 (m, 1H), 3.95 (br s, 1H), 6.13 (dd, J=11.8, 6.3 Hz, 1H), 6.47 (t, J=7.4 Hz, 1H), 6.64 (t, J=7.0 Hz, 2H), 6.80–7.51 (m, 7H), 8.08–8.15 (m, 2H).

Reference Example 6

2,4-cis-4-(9H-9-Carbazolyl)-2-propyl-1,2,3,4-tetrahydroquinoline

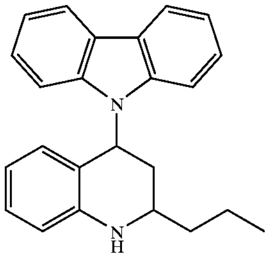

Starting with butylaldehyde (3.54 g, 40 mmol), the same procedure as shown in Reference Example 4 was repeated to give the titled compound (1.67 g, yield over 2 steps: 27%) as a white crystal.

$^1$H NMR ($CDCl_3$) δ 0.97 (t, J=7.2 Hz, 3H), 1.30–1.60 (m, 4H), 2.10–2.25 (m, 1H), 2.45 (q, J=12.0 Hz, 1H), 3.60–3.75 (m, 1H), 3.95 (br s, 1H), 6.13 (dd, J=11.8, 6.3 Hz, 1H), 6.47 (t, J=7.4 Hz, 1H), 6.64 (t, J=7.0 Hz, 2H), 6.80–7.60 (m, 7H), 8.08–8.15 (m, 2H).

FABMS(pos) 340.2 [$M^+$]

Reference Example 7

2,4-cis-2-Butyl-4-(9H-9-carbazolyl)-1,2,3,4-tetrahydroquinoline

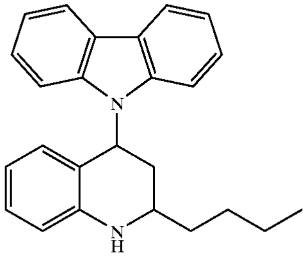

Starting with valeric aldehyde (3.45 g, 40 mmol), the same procedure as shown in Reference Example 4 was repeated to give the titled compound (2.12 g, yield over 2 steps: 23%) as a white crystal.

$^1$H NMR ($CDCl_3$) δ 0.91 (t, J=6.8 Hz, 3H), 1.20–1.80 (m, 6H), 2.10–2.25 (m, 1H), 2.44 (q, J=11.7 Hz, 1H), 3.70–3.85 (m, 1H), 3.95 (br s, 1H), 6.12 (dd, J=11.8, 6.2 Hz, 1H), 6.40–6.70 (m, 3H), 6.80–6.90 (m, 1H), 7.00–7.50 (m, 6H), 8.00–8.15 (m, 2H).

FABMS(pos) 354.1 [$M^+$]

Reference Example 8

2,4-cis-4-(9H-9-Carbazolyl)-2-isobutyl-1,2,3,4-tetrahydroquinoline

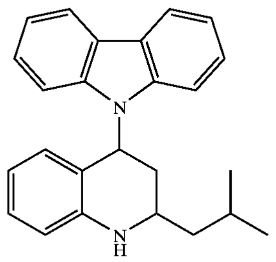

Starting with isovaleric aldehyde (3.54 g, 40 mmol), the same procedure as shown in Reference Example 4 was repeated to give the titled compound (2.52 g, yield over 2 steps: 54%) as a white crystal.

$^1$H NMR ($CDCl_3$) δ 0.95–0.98 (m, 6H), 1.35–1.60 (m, 2H), 1.70–1.85 (m, 1H), 2.10–2.20 (m, 1H), 2.38–2.50 (m, 1H), 3.70–3.80 (m, 1H), 3.95 (br s, 1H), 6.13 (dd, J=11.8, 6.3 Hz, 1H), 6.40–6.90 (m, 4H), 7.00–7.40 (m, 6H), 7.40–7.60 (m, 2H), 8.00–8.20 (m, 2H).

Reference Example 9

2,4-cis-4-(9H-9-Carbazolyl)-2-(2-phenylethyl)-1,2,3,4-tetrahydroquinoline

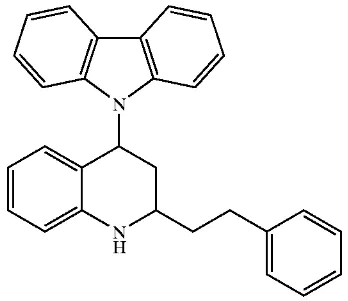

Starting with 3-phenylpropionaldehyde (5.37 g, 40 mmol), the same procedure as shown in Reference Example 4 was repeated to give the titled compound (2.98 g, yield over 2 steps: 60%) as a colorless oil.

$^1$H NMR ($CDCl_3$) δ 1.80–2.00 (m, 2H), 2.15–2.30 (m, 1H), 2.50–2.80 (m, 2H), 3.55–3.75 (m, 1H), 4.16(br s, 1H), 6.11 (dd, J=11.9, 6.3 Hz, 1H), 6.45–6.70 (m, 4H), 6.80–6.90 (m, 1H), 7.00–7.50 (m, 7H), 7.80–7.90 (m, 1H), 8.00–8.15 (m, 3H).

Reference Example 10

2,4-cis-2-[(Benzyloxy)methyl]-4-(9H-9-carbazolyl)-1,2,3,4-tetrahydroquinoline

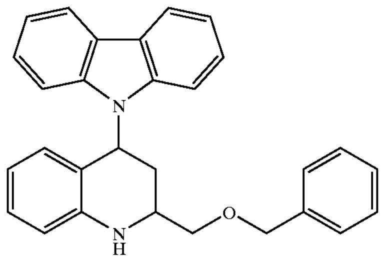

Starting with benzyloxyacetaldehyde (10 g, 66.6 mmol), the same procedure as shown in Reference Example 4 was repeated to give the titled compound (10.9 g, yield over 2 steps: 60%) as a colorless oil.

$^1$H NMR ($CDCl_3$) δ 2.00–2.12 (m, 1H), 2.44 (q, J=11.9 Hz, 1H), 3.47 (t, J=9.0 Hz, 1H), 3.59 (dd, J=9.0, 3.6 Hz, 1H), 3.9–4.15 (m, 1H), 4.58 (s, 2H), 6.17 (dd, J=13.9, 6.5 Hz, 1H), 6.40–6.90 (m, 4H), 7.00–7.50 (m, 11H), 8.07–8.14 (m, 2H).

Reference Example 11

2,4-cis-4-(9H-9-Carbazolyl)-2-(2-cyanoethyl)-1,2,3,4-tetrahydroquinoline

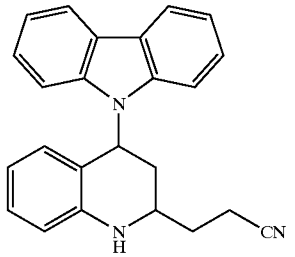

Starting with β-cyanopropionaldehyde (7.73 g, 93.0 mmol), the same procedure as shown in Reference Example 4 was repeated to give the titled compound (2.95 g, yield over 2 steps: 25%) as a white crystal.

Melting point: 178° C.–179° C. (crystallization solvent: diethyl ether-hexane)

$^1$H NMR ($CDCl_3$) δ 1.93–2.10 (m, 2H), 2.10–2.18 (m, 1H), 2.35–3.65 (m, 3H), 3.80–4.00 (m, 2H), 6.15 (dd, J=11.6, 6.2 Hz, 1H), 6.53 (t, J=7.5 Hz, 1H), 6.68 (t, J=7.6 Hz, 2H), 6.79–6.86 (m, 1H), 7.08 (t, J=7.5 Hz, 2H), 7.13–7.39 (m, 3H), 7.52 (d, J=Hz, 2H), 8.08–8.15 (m, 2H).

Reference Example 12

2,4-cis-4-(9H-9-Carbazolyl)-5,7-dimethoxy-2-methyl-1,2,3,4-tetrahydroquinoline

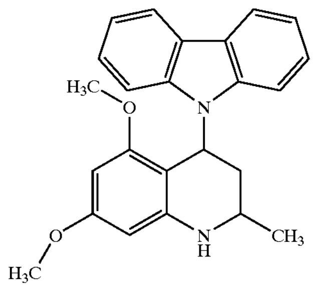

Starting with 3,5-dimethoxyaniline (5.50 g, 35.9 mmol), the same procedure as shown in Reference Example 4 was repeated to give the titled compound (1.18 g, yield over 2 steps: 9%) as a white crystal.

$^1$H NMR ($CDCl_3$) δ 1.24 (d, J=6.2, 3H), 2.31–2.37 (m, 2H), 2.95 (s, 3H), 2.56 (m, 1H), 3.73 (s, 3H), 3.88 (s, 1H), 5.66 (s, 1H), 5.87 (s, 1H), 6.09 (t, J=9.7 Hz, 1H), 6.79–6.86 (m, 1H), 7.10–7.22 (m, 4H), 7.46–7.57 (m, 2H), 8.03–8.09 (m, 2H).

Reference Example 13

2,4-cis-4-(9H-9-Carbazolyl)-5,8-dimethoxy-2-methyl-1,2,3,4-tetrahydroquinoline

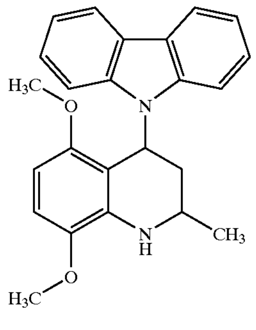

Starting with 2,5-dimethoxyaniline (1.70 g, 11.1 mmol), the same procedure as shown in Reference Example 4 was repeated to give the titled compound (1.60 g, yield over 2 steps: 38%) as a white crystal.

$^1$H NMR ($CDCl_3$) δ 1.30 (d, J=6.2, 3H), 2.36–2.44 (m, 2H), 2.86 (s, 3H), 3.55 (m, 1H), 3.87 (s, 3H), 4.51 (s, 1H), 5.95 (d, J=8.7 Hz, 1H), 6.17 (t, J=9.4 Hz, 1H), 6.61 (d, J=8.7 Hz, 1H), 7.06–7.23 (m, 4H), 7.47–7.58 (m, 2H), 8.02–8.09 (m, 2H).

Reference Example 14

2,4-cis-4-(9H-9-Carbazolyl)-8-methoxy-2-methyl-1,2,3,4-tetrahydroquinoline

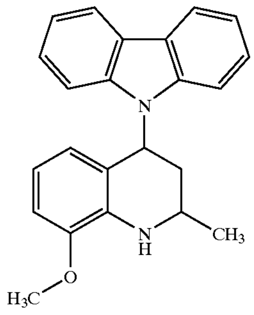

Starting with 2-methoxyaniline (2.11 g, 13.8 mmol), the same procedure as shown in Reference Example 4 was repeated to give the titled compound (1.74 g, yield over 2 steps: 44%) as a white crystal.

$^1$H NMR ($CDCl_3$) δ 1.32 (d, J=6.3, 3H), 2.14 (dd, J=12.7, 6.4 Hz, 1H), 2.48 (m, 1H), 3.77 (m, 1H), 3.90 (s, 3H), 4.41 (s, 1H), 6.18 (m, 1H), 6.29 (t, J=7.8 Hz, 1H), 6.44 (t, J=7.9 Hz, 1H), 6.68 (d, J=7.8 Hz, 1H), 6.88 (d, J=7.8 Hz, 1H), 7.13–7.25 (m, 2H), 7.48–7.50 (m, 2H), 8.09–8.14 (m, 2H).

Reference Example 15

2,4-cis-4-(9H-9-Carbazolyl)-6-methoxy-2-methyl-1,2,3,4-tetrahydroquinoline

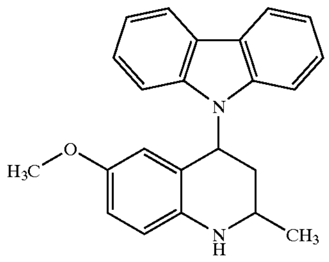

Starting with 4-methoxyaniline (2.94 g, 23.9 mmol), the same procedure as shown in Reference Example 4 was repeated to give the titled compound (2.3 g, yield over 2 steps: 35%) as a white crystal (cis/trans mixture).

2,4-cis:

$^1$H NMR ($CDCl_3$) δ 1.19 (d, J=6.3 Hz, 3H), 2.01–2.12 (m, 1H), 2.35 (q, J=12.0 Hz, 1H), 3.35 (s, 3H), 3.59 (br s, 1H), 3.65–3.72 (m, 1H), 6.07 (m, 1H), 6.24 (m, 1H), 6.60–7.00 (m, 3H), 7.10–7.47 (m, 5H), 8.00–8.12 (m, 2H).

2,4-trans:

$^1$H NMR ($CDCl_3$) δ 1.14 (d, J=6.3 Hz, 3H), 1.80–2.10 (m, 1H), 2.34–2.37 (m, 1H), 3.46 (s, 3H), 3.43–3.52 (m, 1H), 3.85 (br s, 1H), 5.87–5.90 (m, 1H), 6.50 (m, 1H), 6.60–7.00 (m, 3H), 7.10–7.47 (m, 5H), 8.00–8.12 (m, 2H).

Example 5

(−)-2,4-cis-1-(3,4-Dimethoxybenzoyl)-2-methyl-4-(1,2,3,4-tetrahydroquinolin-1-yl)-1,2,3,4-tetrahydroquinoline

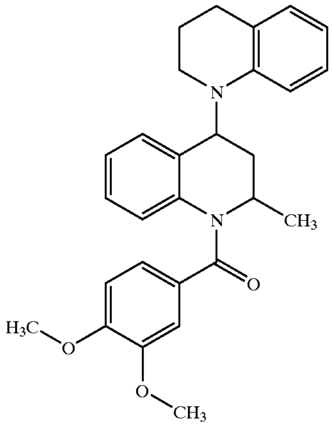

2,4-cis-1-(3,4-Dimethoxybenzoyl)-2-methyl-4-(1,2,3,4-tetrahydroquinolin-1-yl)-1,2,3,4-tetrahydroquinoline (145 mg) prepared in Example 4 was separated by chiral HPLC (column: CHIRALPAK AD; developing solvent: ethanol/hexane=1/1) and then concentrated to dryness to give the titled compound (23 mg) as a white powder. When analyzed for optical rotation with a Shodex OR-2 (wavelength: 470 nm), this compound was shown to be (−)-form.

$^1$H-NMR ($CDCl_3$) δ: 1.38 (d, J=6.2 Hz, 3H), 1.69–1.80 (m, 1H), 1.97–2.16 (m, 2H), 2.69–2.77 (m, 1H), 2.84–2.92 (m, 2H), 3.34–3.38 (m, 2H), 3.61 (s, 3H), 3.86 (s, 3H), 4.77–4.89 (m, 2H), 6.49 (d, J=8.2 Hz, 1H), 6.60–6.66 (m, 3H), 6.73 (d, J=8.4 Hz, 1H), 6.94–7.10 (m, 6H).

[α]D=−449.2° (C=1.01, EtOH)

Example 6

(+)-2,4-cis-1-(3,4-Dimethoxybenzoyl)-2-methyl-4-(1,2,3,4-tetrahydroquinolin-1-yl)-1,2,3,4-tetrahydroquinoline

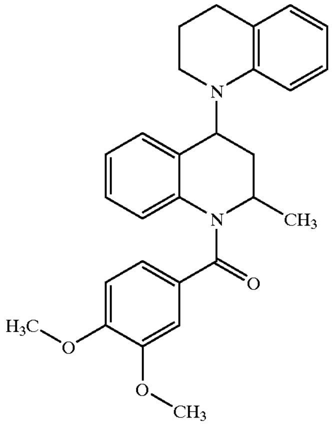

2,4-cis-1-(3,4-Dimethoxybenzoyl)-2-methyl-4-(1,2,3,4-tetrahydroquinolin-1-yl)-1,2,3,4-tetrahydroquinoline (145 mg) prepared in Example 4 was separated by chiral HPLC (column: CHIRALPAK AD; developing solvent: ethanol/hexane=1/1) and then concentrated to dryness to give the titled compound (24 mg) as a white powder. When analyzed for optical rotation with a Shodex OR-2 (wavelength: 470 nm), this compound was shown to be (+)-form.

$^1$H-NMR ($CDCl_3$) δ: 1.38 (d, J=6.2 Hz, 3H), 1.69–1.80 (m, 1H), 1.97–2.16 (m, 2H), 2.69–2.77 (m, 1H), 2.84–2.92 (m, 2H), 3.34–3.38 (m, 2H), 3.61 (s, 3H), 3.86 (s, 3H), 4.77–4.89 (m, 2H), 6.49 (d, J=8.2 Hz, 1H), 6.60–6.66 (m, 3H), 6.73 (d, J=8.4 Hz, 1H), 6.94–7.10 (m, 6H).

[α]D=+408.2° (C=1.00, EtOH)

Example 7

(−)-2,4-trans-1-(3,4-dimethoxybenzoyl)-2-methyl-4-(1,2,3,4-tetrahydroquinolin-1-yl)-1,2,3,4-tetrahydroquinoline

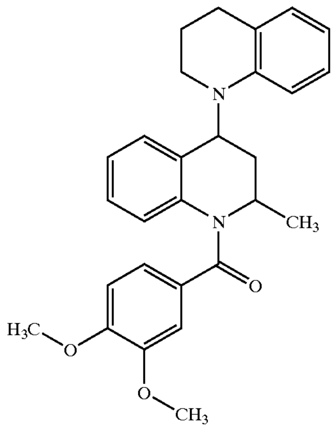

2,4-cis-1-(3,4-dimethoxybenzoyl)-2-methyl-4-(1,2,3,4-tetrahydroquinolin-1-yl)-1,2,3,4-tetrahydroquinoline (145 mg) prepared in Example 4 was separated by chiral HPLC (column: CHIRALPAK AD; developing solvent: ethanol/hexane=1/1) and then concentrated to dryness to give the titled compound (36 mg) as a white powder. When analyzed for optical rotation with a Shodex OR-2 (wavelength: 470 nm), this compound was shown to be (−)-form.

$^1$H-NMR ($CDCl_3$) δ: 1.37 (d, J=6.9 Hz, 3H), 1.80–2.00 (m, 2H), 2.09–2.17 (m, 1H), 2.25–2.40 (m, 1H), 2.80–2.84 (m, 2H), 3.14 (t, J=5.2 Hz, 2H), 3.76 (s, 3H), 3.89 (s, 3H), 5.00–5.20 (m, 1H), 5.34 (dd, J=11.2, 7.4 Hz, 1H), 6.63 (t, J=7.3 Hz, 1H), 6.71–6.80 (m, 3H), 6.85–7.10 (m, 6H), 7.34 (d, J=7.4 Hz, 1H).

Example 8

(+)-2,4-trans-1-(3,4-Dimethoxybenzoyl)-2-methyl-4-(1,2,3,4-tetrahydroquinolin-1-yl)-1,2,3,4-tetrahydroquinoline

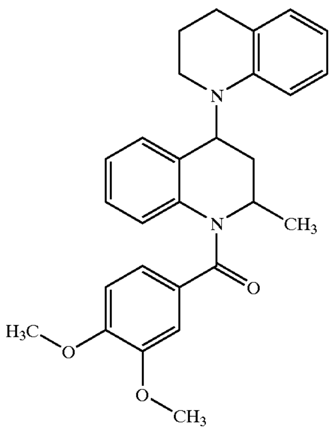

2,4-cis-1-(3,4-Dimethoxybenzoyl)-2-methyl-4-(1,2,3,4-tetrahydroquinolin-1-yl)-1,2,3,4-tetrahydroquinoline (145 mg) prepared in Example 4 was separated by chiral HPLC (column: CHIRALPAK AD; developing solvent: ethanol/hexane=1/1) and then concentrated to dryness to give the titled compound (36 mg) as a white powder. When analyzed for optical rotation with a Shodex OR-2 (wavelength: 470 nm), this compound was shown to be (+)form.

$^1$H-NMR ($CDCl_3$) δ: 1.37 (d, J=6.9 Hz, 3H), 1.80–2.00 (m, 2H), 2.09–2.17 (m, 1H), 2.25–2.40 (m, 1H), 2.80–2.84 (m, 2H), 3.14 (t, J=5.2 Hz, 2H), 3.76 (s, 3H), 3.89 (s, 3H), 5.00–5.20 (m, 1H), 5.34 (dd, J=11.2, 7.4 Hz, 1H), 6.63 (t, J=7.3 Hz, 1H), 6.71–6.80 (m, 3H), 6.85–7.10 (m, 6H), 7.34 (d, J=7.4 Hz, 1H).

Example 9

4-(3,4-Dihydro-2H-1,4-benzoxazin-4-yl)-1-(3,4-dimethoxybenzoyl)-2-methyl-1,2,3,4-tetrahydroquinoline

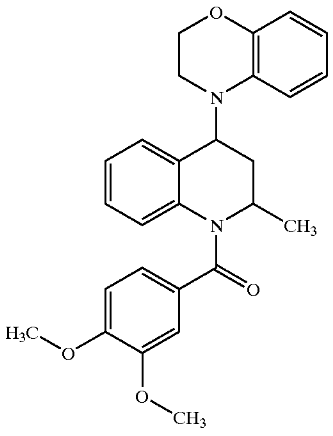

Starting with cis-1-(3,4-dimethoxybenzoyl)-2-methyl-1,2,3,4-tetrahydro-4-quinolinol (400 mg, 1.22 mmol) prepared in Reference Example 1 and 3,4-dihydro-2H-1,4-benzoxazine (495 mg, 3.66 mmol), the same procedure as shown in Example 1 was repeated to give the titled compound (320 mg, yield: 59%) as a colorless oil. (cis:trans=1:2.3)

Elementary Analysis for $C_{27}H_{28}N_2O_4$: Calculated: C, 72.95; H, 6.35; N, 6.30. Found: C, 72.76; H, 6.37; N, 6.24.

Example 10

(−)-2,4-cis-4-(3,4-Dihydro-2H-1,4-benzoxazin-4-yl)-1-(3,4-dimethoxybenzoyl)-2-methyl-1,2,3,4-tetrahydroquinoline

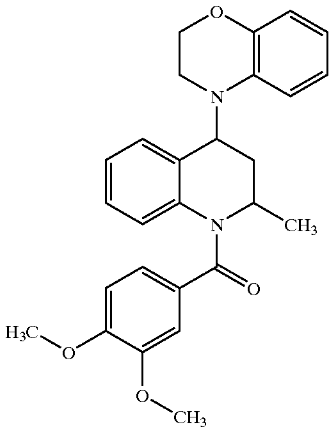

4-(3,4-Dihydro-2H-1,4-benzoxazin-4-yl)-1-(3,4-dimethoxybenzoyl)-2-methyl-1,2,3,4-tetrahydroquinoline (320 mg) prepared in Example 9 was separated by chiral HPLC (column: CHIRALPAK AD; developing solvent: ethanol/hexane=1/1) and then concentrated to dryness to give the titled compound (21 mg) as a white powder. When analyzed for optical rotation with a Shodex OR-2 (wavelength: 470 nm), this compound was shown to be (−)-form.

$^1$H-NMR ($CDCl_3$) δ: 1.38 (d, J=6.2 Hz, 3H), 1.50–1.80 (m, 1H), 2.67–2.75 (m, 1H), 3.49 (brs, 2H), 3.62 (s, 3H), 3.86 (s, 3H), 4.36 (brs, 2H), 4.75–4.95 (m, 2H), 6.60–6.80 (m, 6H), 6.89–6.97 (m, 3H), 7.02–7.10 (m, 2H).

Example 11

(+)-2,4-cis-4-(3,4-Dihydro-2H-1,4-benzoxazin-4-yl)-1-(3,4-dimethoxybenzoyl)-2-methyl-1,2,3,4-tetrahydroquinoline

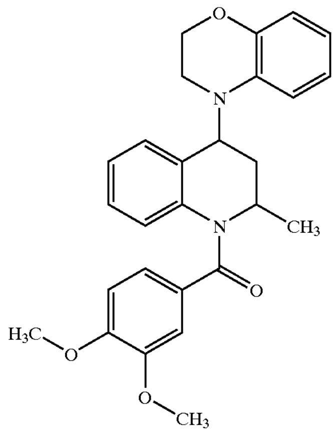

4-(3,4-Dihydro-2H-1,4-benzoxazin-4-yl)-1-(3,4-dimethoxybenzoyl)-2-methyl-1,2,3,4-tetrahydroquinoline (320 mg) prepared in Example 9 was separated by chiral HPLC (column: CHIRALPAK AD; developing solvent: ethanol/hexane=1/1) and then concentrated to dryness to give the titled compound (26 mg) as a white powder. When analyzed for optical rotation with a Shodex OR-2 (wavelength: 470 nm), this compound was shown to be (+)-form.

$^1$H-NMR ($CDCl_3$) δ: 1.38 (d, J=6.2 Hz, 3H), 1.50–1.80 (m, 1H), 2.67–2.75 (m, 1H), 3.49 (brs, 2H), 3.62 (s, 3H), 3.86 (s, 3H), 4.36 (brs, 2H), 4.75–4.95 (m, 2H), 6.60–6.80 (m, 6H), 6.89–6.97 (m, 3H), 7.02–7.10 (m, 2H).

Example 12

(−)-2,4-trans-4-(3,4-dihydro-2H-1,4-benzoxazin-4-yl)-1-(3,4-dimethoxybenzoyl)-2-methyl-1,2,3,4-tetrahydroquinoline

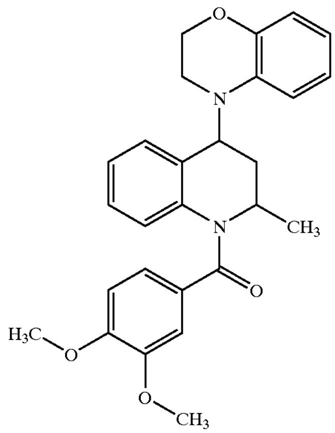

4-(3,4-Dihydro-2H-1,4-benzoxazin-4-yl)-1-(3,4-dimethoxybenzoyl)-2-methyl-1,2,3,4-tetrahydroquinoline (320 mg) prepared in Example 9 was separated by chiral HPLC (column: CHIRALPAK AD; developing solvent: ethanol/hexane=1/1) and then concentrated to dryness to give the titled compound (50 mg) as a white powder. When analyzed for optical rotation with a Shodex OR-2 (wavelength: 470 nm), this compound was shown to be (−)-form.

$^1$H-NMR ($CDCl_3$) δ: 1.31 (d, J=6.9 Hz, 3H), 2.10–2.28 (m, 2H), 3.13–3.29 (m, 2H), 3.20–3.35 (m, 1H), 3.80 (s, 3H), 3.89 (s, 3H), 4.24 (t, J=4.8 Hz, 2H), 5.30 (dd, J=11.0, 7.6 Hz, 1H), 6.60–6.70 (m, 1H), 6.76–6.87 (m, 5H), 6.90–7.03 (m, 3H), 7.09 (d, J=1.8 Hz, 1H), 7.36 (d, J=7.2 Hz, 1H).

Example 13

(+)-2,4-trans-4-(3,4-Dihydro-2H-1,4-benzoxazin-4-yl)-1-(3,4-dimethoxybenzoyl)-2-methyl-1,2,3,4-tetrahydroquinoline

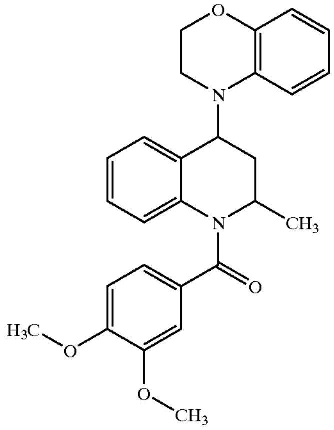

4-(3,4-Dihydro-2H-1,4-benzoxazin-4-yl)-1-(3,4-dimethoxybenzoyl)-2-methyl-1,2,3,4-tetrahydroquinoline (320 mg) prepared in Example 9 was separated by chiral HPLC (column: CHIRALPAK AD; developing solvent: ethanol/hexane=1/1) and then concentrated to dryness to give the titled compound (56 mg) as a white powder. When analyzed for optical rotation with a Shodex OR-2 (wavelength: 470 nm), this compound was shown to be (+)-form.

$^1$H-NMR ($CDCl_3$) δ: 1.31 (d, J=6.9 Hz, 3H), 2.10–2.28 (m, 2H), 3.13–3.29 (m, 2H), 3.20–3.35 (m, 1H), 3.80 (s, 3H), 3.89 (s, 3H), 4.24 (t, J=4.8 Hz, 2H), 5.30 (dd, J=11.0, 7.6 Hz, 1H), 6.60–6.70 (m, 1H), 6.76–6.87 (m, 5H), 6.90–7.03 (m, 3H), 7.09 (d, J=1.8 Hz, 1H), 7.36 (d, J=7.2 Hz, 1H).

Example 14

2,3-trans-2,4-cis-1-(3,4-Dimethoxybenzoyl)-3-hydroxy-2-methyl-4-(1,2,3,4-tetrahydroquinolin-1-yl)-1,2,3,4-tetrahydroquinoline

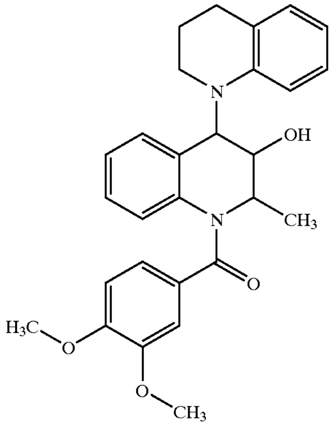

3-(3,4-Dimethoxybenzoyl)-2-methyl-1a,2,3,7b-tetrahydrooxyleno[2,3-c]quinoline (500 mg, 1.54 mmol) prepared in Reference Example 3 and 1,2,3,4-tetrahydroquinoline (409 mg, 3.07 mmol) were dissolved in THF (20 ml), to which trimethylaluminum (0.98 M in hexane, 0.79 ml, 0.77 mmol) was then added dropwise on ice under nitrogen atmosphere, and stirring was continued at room temperature for 3 hours. Water (1.5 ml) was added to the reaction mixture and stirred for 30 minutes, followed by addition of anhydrous magnesium sulfate, and stirring was continued for an additional 20 minutes. After insoluble products were removed by filtration, the filtrate was concentrated. The residue was applied to silica gel column chromatography (developing solvent: ethyl acetate/hexane=1/2) and the resulting eluate was recrystallized from diethyl ether-hexane to give the titled compound (229 mg, 33%) (yield: 37%) as a white crystal.

FABMS(pos) 458.2 [$M^+$]

Example 15

2,3-trans-2,4-cis-1-(3,4-Dimethoxybenzoyl)-3-[(1H-imidazol-1-ylcarbothioyl)oxy]-2-methyl-4-(1,2,3,4-tetrahydroquinolin-1-yl)-1,2,3,4-tetrahydroquinoline

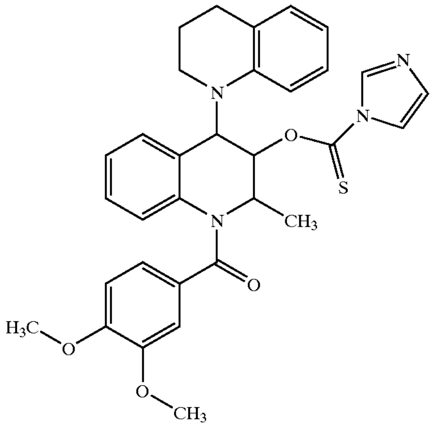

2,3-trans-2,4-cis-1-(3,4-Dimethoxybenzoyl)-3-hydroxy-2-methyl-4-(1,2,3,4-tetrahydroquinolin-1-yl)-1,2,3,4-tetrahydroquinoline (560 mg, 1.22 mmol) prepared in Example 14 and 1,1'-thiocarbonyldiimidazole (617 mg, 0.872 mmol) were dissolved in 1,2-dichloroethane (25 ml) and heated at reflux for 18 hours. The reaction mixture was concentrated and the residue was applied to silica gel column chromatography (developing solvent: ethyl acetate/hexane=1/1) to give the titled compound (370 mg, yield: 53%) as a yellow oil.

FABMS(pos) 568.1 [$M^+$]

Example 16

2,4-cis-1-(3,4-Dimethoxybenzoyl)-2-methyl-4-(1,2,3,4-tetrahydroquinolin-1-yl)-1,2,3,4-tetrahydroquinoline

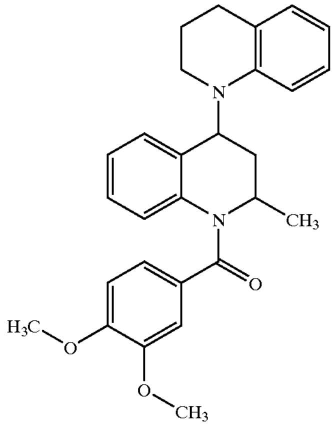

A toluene (10 ml) solution of tributyltin hydride (0.095 ml, 0.352 mmol) and 2,2'-azobisisobutyronitrile (2 mg, 0.012 mmol) was heated at reflux for 30 minutes under nitrogen atmosphere, followed by dropwise addition over 30 minutes of a toluene (10 ml) solution of 2,3-trans-2,4-cis-1-(3,4-dimethoxybenzoyl)-3-[(1H-imidazol-1-ylcarbothioyl)-oxy]-2-methyl-4-(1,2,3,4-tetrahydroquinolin-1-yl)-1,2,3,4-tetrahydroquinoline (100 mg, 0.176 mg) prepared in Example 15. After the reaction mixture was heated at reflux for 4 hours and concentrated, the residue was applied to silica gel column chromatography (developing solvent: ethyl acetate/hexane=1/3) and the resulting eluate was recrystallized from diethyl ether-hexane to give the titled compound (27.5 mg, yield: 35%) as a white crystal.

Melting point: 187° C.–189° C.

Example 17

2,3-trans-2,4-cis-3-Acetoxy-1-(3,4-dimethoxybenzoyl)-2-methyl-4-(1,2,3,4-tetrahydroquinolin-1-yl)-1,2,3,4-tetrahydroquinoline

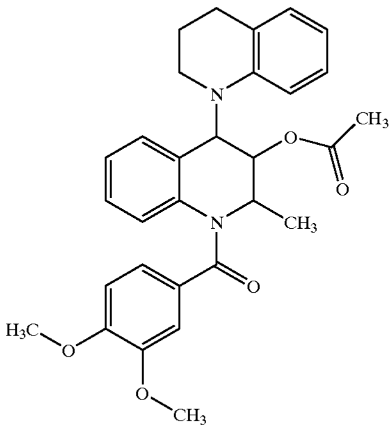

2,3-trans-2,4-cis-1-(3,4-Dimethoxybenzoyl)-3-hydroxy-2-methyl-4-(1,2,3,4-tetrahydroquinolin-1-yl)-1,2,3,4-tetrahydroquinoline (250 mg, 0.55 mmol) prepared in Example 14 was dissolved in pyridine (5 ml), to which acetic anhydride (2 ml) was then added dropwise and stirred at room temperature for 4 hours. After the reaction mixture was concentrated, the residue was dissolved in ethyl acetate, washed with saturated aqueous sodium bicarbonate and then concentrated. The residue was applied to silica gel column chromatography (developing solvent: ethyl acetate/hexane=1/2) and the resulting eluate was recrystallized from diethyl ether-hexane to give the titled compound (27.5 mg, yield: 35%) as a white crystal.

FABMS(pos) 500.1 [$M^+$]

Melting point: 130° C.–131° C. (crystallization solvent: diethyl ether-hexane)

Example 18

2,3-trans-2,4-cis-4-(3,4-Dihydro-2H-1,4-benzothiazin-4-yl)-1-(3,4-dimethoxybenzoyl)-3-hydroxy-2-methyl-1,2,3,4-tetrahydroquinoline

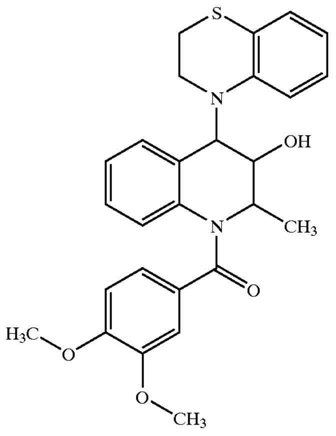

Starting with 3,4-dihydro-2H-1,4-benzothiazine (930 mg, 6.14 mmol), the same procedure as shown in Example 14 was repeated to give the titled compound (764 mg, yield: 52%) as a white crystal.

$^1$H-NMR ($CDCl_3$) δ: 1.45 (d, J=6.0 Hz, 3H), 2.50–2.65 (m, 1H), 3.00–3.15 (m, 1H), 3.20–3.35 (m, 1H), 3.55–3.86 (m, 9H), 4.55–4.65 (m, 1H), 4.75–4.90 (m, 1H), 6.50–7.40 (m, 11H).

Example 19

2,3-trans-2,4-cis-4-(3,4-Dihydro-2H-1,4-benzothiazin-4-yl)-1-(3,4-dimethoxybenzoyl)-3-[(1H-imidazol-1-ylcarbothioyl)oxy]-2-methyl-1,2,3,4-tetrahydroquinoline

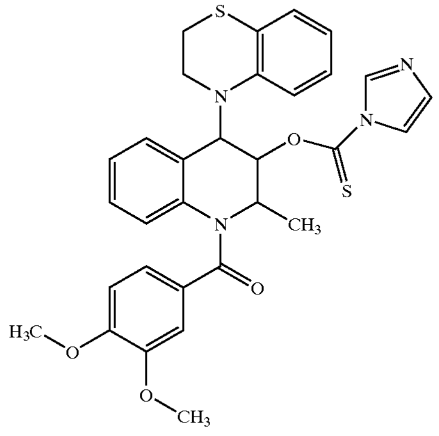

Starting with 2,3-trans-2,4-cis-4-(3,4-dihydro-2H-1,4-benzothiazin-4-yl)-1-(3,4-dimethoxybenzoyl)-3-hydroxy-2-methyl-1,2,3,4-tetrahydroquinoline (500 mg, 1.05 mmol) prepare in Example 18, the same procedure as shown in Example 15 was repeated to give the titled compound (580 mg, yield: 94%) as a yellow oil.

FABMS(pos) 587.1 [M+$H^+$]

Example 20

2,4-cis-4-(3,4-Dihydro-2H-1,4-benzothiazin-4-yl)-1-(3,4-dimethoxybenzoyl)-2-methyl-1,2,3,4-tetrahydroquinoline

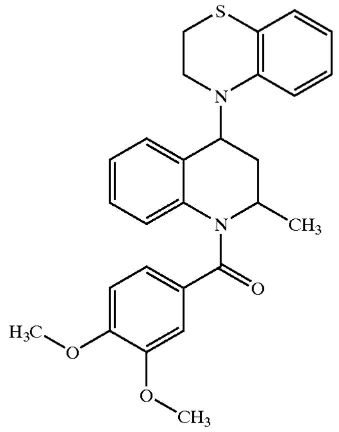

Starting with 2,3-trans-2,4-cis-4-(3,4-dihydro-2H-1,4-benzothiazin-4-yl)-1-(3,4-dimethoxybenzoyl)-3-[(1H-imidazol-1-ylcarbothioyl)oxy]-2-methyl-1,2,3,4-tetrahydroquinoline (580 mg, 0.94 mmol) prepared in Example 19, the same procedure as shown in Example 16 was repeated to give the titled compound (30 mg, yield: 7%) as a white crystal.

Elementary Analysis for $C_{27}H_{28}N_2O_3S$: Calculated: C, 70.41; H, 6.13; N, 6.08. Found: C, 69.91; H, 6.02; N, 6.97.

Melting point: 178° C.–180° C. (crystallization solvent: diethyl ether-hexane)

The titled compounds of Examples 5 to 20 are summarized in Table 1 below.

Table 1

TABLE 1

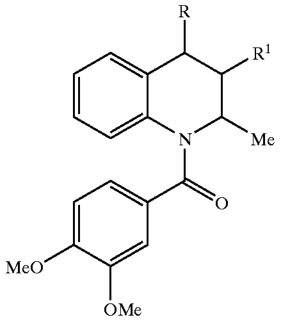

| Example | R | $R^1$ | Stereochemistry |
|---|---|---|---|
| 5 | 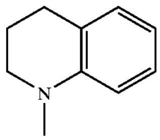 | H | 2,4-cis (−) |
| 6 | 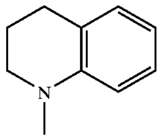 | H | 2,4-cis (+) |
| 7 | 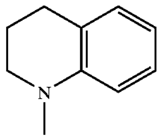 | H | 2,4-trans (−) |
| 8 | 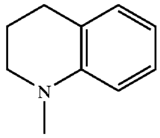 | H | 2,4-trans (+) |
| 9 | 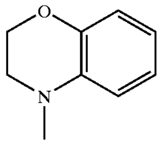 | H | 2,4-cis/trans = 2.3/1 (±) |

TABLE 1-continued

| Example | R | $R^1$ | Stereochemistry |
|---|---|---|---|
| 10 | 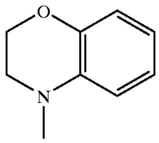 | H | 2,4-cis (−) |
| 11 | 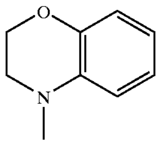 | H | 2,4-cis (+) |
| 12 | 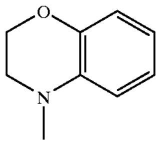 | H | 2,4-trans (−) |
| 13 | 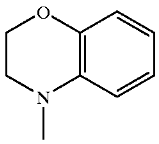 | H | 2,4-trans (+) |
| 14 | 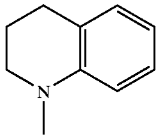 | OH | 2,3-trans 2,4-cis (±) |
| 15 | 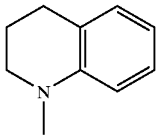 | OCSIm | 2,3-trans 2,4-cis (±) |
| 16 | 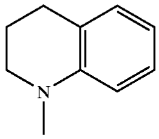 | H | 2,4-cis (±) |
| 17 | 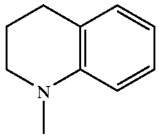 | OAc | 2,3-trans 2,4-cis (±) |
| 18 | 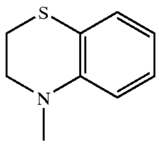 | OH | 2,3-trans 2,4-cis (±) |
| 19 | 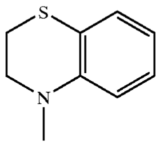 | OCSIm | 2,3-trans 2,4-cis (±) |

TABLE 1-continued

| | | | |
|---|---|---|---|
| 20 | 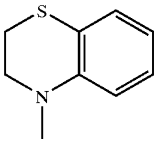 | H | 2,4-cis (±) |

OCSIm =

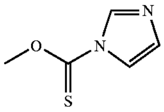

Example 21

2,3-trans-2,4-cis-4-(1-Benzyl-1,2,3,4-tetrahydroquinoxalin-4-yl)1-(3,4-dimethoxybenzoyl)-3-hydroxy-2-methyl-1,2,3,4-tetrahydroquinoline

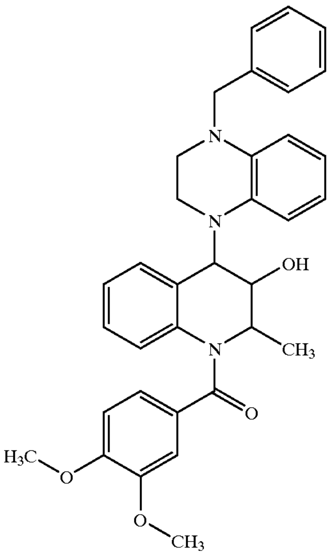

Starting with 4-benzyl-1,2,3,4-tetrahydroquinoxaline (630 mg, 2.81 mmol), the same procedure as shown in Example 14 was repeated to give the titled compound (720 mg, yield: 61%) as a white crystal.

Melting point: 99° C.–102° C.

Example 22

2,3-trans-2,4-cis-4-(1-Benzyl-1,2,3,4-tetrahydroquinoxalin-4-yl)1-(3,4-dimethoxybenzoyl)-3-[(1H-imidazol-1-ylcarbothioyl)oxy]-2-methyl-1,2,3,4-tetrahydroquinoline

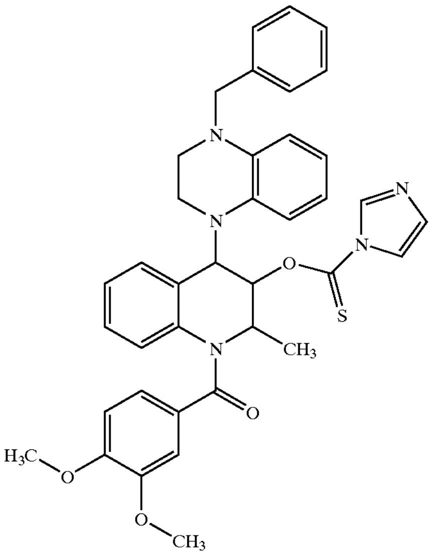

Starting with 2,3-trans-2,4-cis-4-(1-benzyl-1,2,3,4-tetrahydroquinoxalin-4-yl)1-(3,4-dimethoxybenzoyl)-3-hydroxy-2-methyl-1,2,3,4-tetrahydroquinoline (600 mg, 1.09 mmol) prepared in Example 21, the same procedure as shown in Example 15 was repeated to give the titled compound (596 mg, yield: 83%) as a yellow oil.

$^1$H-NMR ($CDCl_3$) δ: 1.42 (d, J=7.0 Hz, 3H), 3.20–3.57 (m, 4H), 3.73 (s, 3H), 3.83 (s, 3H), 4.30–4.50 (m, 2H), 5.05–5.20 (m, 1H), 5.35–5.51 (m, 1H), 5.80–5.95 (m, 1H), 6.58–6.75 (m, 6H), 6.89–7.00 (m, 3H), 7.02–7.32 (m, 7H), 7.30–7.42 (m, 2H), 8.14 (brs, 1H).

Example 23

2,4-cis-4-(1-Benzyl-1,2,3,4-tetrahydroquinoxalin-4-yl)-1-(3,4-dimethoxybenzoyl)-2-methyl-1,2,3,4-tetrahydroquinoline

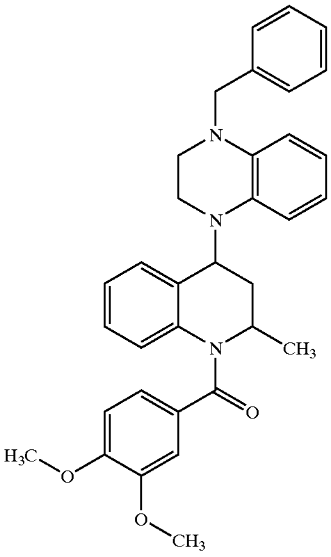

Starting with 2,3-trans-2,4-cis-4-(1-benzyl-1,2,3,4-tetrahydroquinoxalin-4-yl)-1-(3,4-dimethoxybenzoyl)-3-[(1H-imidazol-1-ylcarbothioyl)oxy]-2-methyl-1,2,3,4-tetrahydroquinoline (590 mg, 0.89 mmol) prepared in Example 22, the same procedure as shown in Example 16 was repeated to give the titled compound (340 mg, yield: 71%) as a white crystal.

Melting point: 192° C.–194° C.

Example 24

2,3-trans-2,4-cis-1-(3,4-Dimethoxybenzoyl)-3-hydroxy-2-methyl-4-(2,3,4,5-tetrahydro-1H-1-benzazepinyl)-1,2,3,4-tetrahydroquinoline

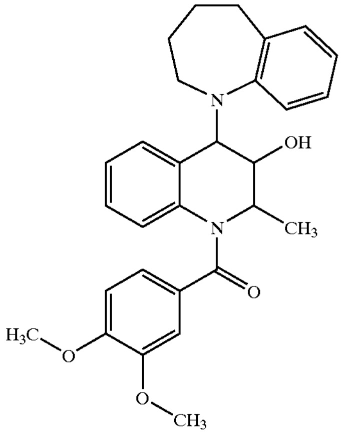

Starting with 2,3,4,5-tetrahydro-1H-1-benzazepine (520 mg, 3.53 mmol), the same procedure as shown in Example 14 was repeated to give the titled compound (300 mg, yield: 26%) as a white crystal.

Melting point: 88° C.–92° C.

Example 25

2,3-trans-2,4-cis-1-(3,4-Dimethoxybenzoyl)-3-[(1H-imidazol-1-ylcarbothioyl)oxy]-2-methyl-4-(2,3,4,5-tetrahydro-1H-1-benzazepinyl)-1,2,3,4-tetrahydroquinoline

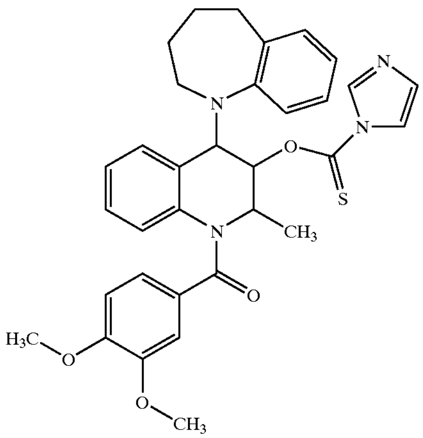

Starting with 2,3-trans-2,4-cis-1-(3,4-dimethoxybenzoyl)-3-hydroxy-2-methyl-4-(2,3,4,5-tetrahydro-1H-1-benzazepinyl)-1,2,3,4-tetrahydroquinoline (190 mg, 0.41 mmol) prepared in Example 24, the same procedure as shown in Example 15 was repeated to give the titled compound (130 mg, yield: 54%) as a yellow oil.

$^1$H-NMR ($CDCl_3$) δ: 1.40 (d, J=7.0 Hz, 3H), 1.50–1.65 (m, 2H), 1.75–1.90 (m, 2H), 2.41–2.50 (m, 1H), 2.60–2.75 (m, 1H), 3.16–3.24 (m, 1H), 3.59–3.63 (m, 1H), 3.76 (s, 3H), 3.88 (s, 3H), 4.99 (d, J=8.8 Hz, 1H), 5.10–5.16 (m, 1H), 5.73 (d, J=8.7 Hz, 1H), 6.65–7.70 (m, 1H), 6.75 (d, J=8.4 Hz, 1H), 6.85–6.95 (m, 3H), 6.95–7.08 (m, 3H), 7.10–7.15 (m, 2H), 7.15–7.21 (m, 1H), 7.42–7.46 (m, 1H), 7.50 (s, 1H), 8.24 (s, 1H).

Example 26

2,4-cis-1-(3,4-Dimethoxybenzoyl)-2-methyl-4-(2,3,4,5-tetrahydro-1H-1-benzazepinyl)-1,2,3,4-tetrahydroquinoline

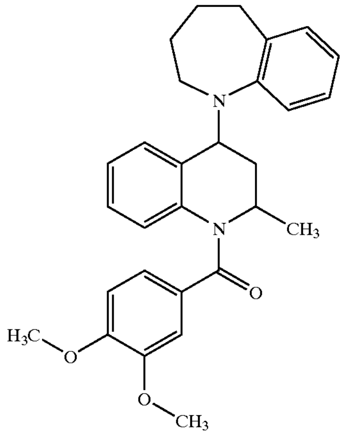

Starting with 2,3-trans-2,4-cis-1-(3,4-dimethoxybenzoyl)-3-[(1H-imidazol-1-ylcarbothioyl)oxy]-2-methyl-4-(2,3,4,5-tetrahydro-1H-1-benzazepinyl)-1,2,3,4-tetrahydro-quinoline (130 mg, 0.22 mmol) prepared in Example 25, the same procedure as shown in Example 16 was repeated to give the titled compound (61 mg, yield: 60%) as a white crystal.

Melting point: 150° C.–151° C.

Example 27

2,3-trans-2,4-cis-1-(3,4-Dimethoxybenzoyl)-3-{[(hexylamino)carbonyl]oxy}-2-methyl-4-(2,3,4,5-tetrahydro-1H-1-benzazepinyl)-1,2,3,4-tetrahydroquinoline

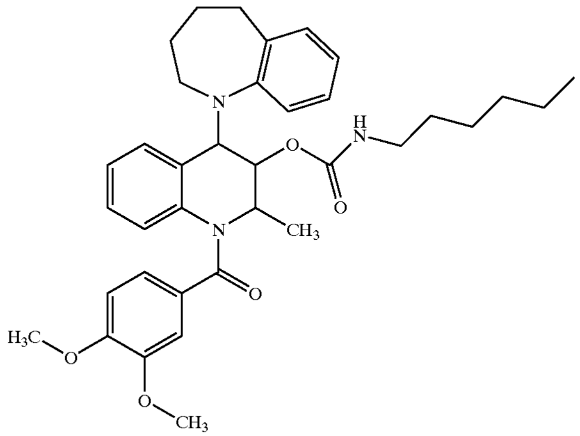

2,3-trans-2,4-cis-1-(3,4-Dimethoxybenzoyl)-3-hydroxy-2-methyl-4-(2,3,4,5-tetrahydro-1H-1-benzazepinyl)-1,2,3,4-tetrahydroquinoline (150 mg, 0.33 mmol) prepared in Example 24 and triethylamine (101 mg, 1 mmol) were dissolved in toluene (10 ml), to which hexylisocyanate (124 mg, 0.98 mmol) was then added and stirred at 80° C. for 5 hours. After the reaction mixture was concentrated under reduced pressure, the residue was applied to silica gel column chromatography (developing solvent: ethyl acetate/hexane=3/7) and the resulting eluate was recrystallized from hexane to give the titled compound (159 mg, yield: 83%) as a white crystal.

Melting point: 152° C.–154° C.

Example 28

2,3-trans-2,4-cis-3-{[(Benzylamino)carbonyl]oxy}-1-(3,4-dimethoxybenzoyl)-2-methyl-4-(2,3,4,5-tetrahydro-1H-1-benzazepinyl)-1,2,3,4-tetrahydroquinoline

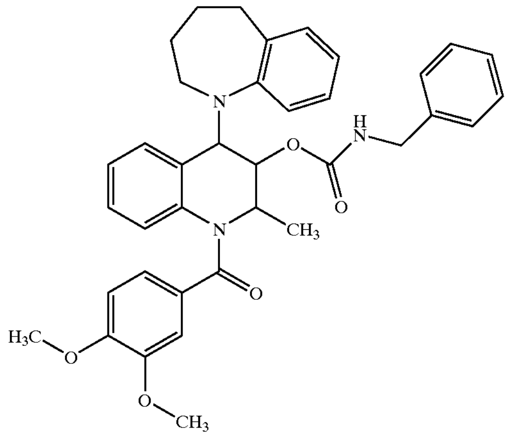

Starting with benzylisocyanate (75 mg, 0.50 mmol), the same procedure as shown in Example 27 was repeated to give the titled compound (133 mg, yield: 78%) as a white crystal.

Melting point: 173° C.–174° C.

Example 29

2,3-trans-2,4-cis-4-(2,3-Dihydro-1H-indol-1-yl)-1-(3,4-dimethoxybenzoyl)-3-hydroxy-2-methyl-1,2,3,4-tetrahydroquinoline

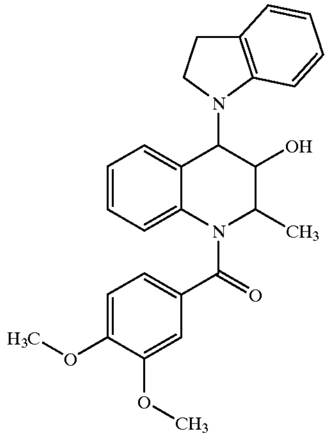

Starting with 2,3-dihydro-1H-indole (190 mg, 1.60 mmol), the same procedure as shown in Example 14 was repeated to give the titled compound (443 mg, yield: 81%) as a white crystal.

Melting point: 182° C.–183° C.

Example 30

2,4-cis-1-(3,4-Dimethoxybenzoyl)-4-(1H-indol-1-yl)-2-methyl-1,2,3,4-tetrahydroquinoline

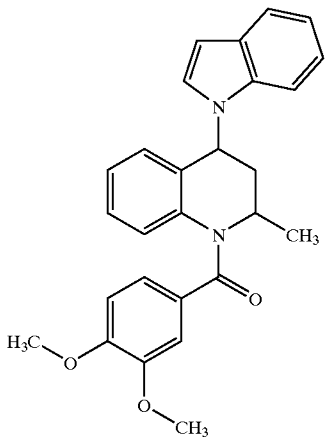

Starting with 2,3-trans-2,4-cis-4-(2,3-dihydro-1H-indol-1-yl)-1-(3,4-dimethoxy-benzoyl)-3-hydroxy-2-methyl-1,2,3,4-tetrahydroquinoline prepared in Example 29, the same procedures as shown in Examples 15 and 16 were repeatedto give a mixture of 2,4-cis-4-(2,3-dihydro-1H-indol-1-yl)-1-(3,4-dimethoxybenzoyl)-2-methyl-1,2,3,4-tetrahydroquinoline and the titled compound (mixing ratio: 2:1). This mixture (85 mg) was dissolved in toluene (5 ml), to which o-chloranil (68 mg) was then added and stirred at room temperature for 2 hours. After the reaction mixture was concentrated under reduced pressure, the residue was applied to silica gel column chromatography (developing solvent: ethyl acetate/hexane=1/3) and the resulting eluate was recrystallized from diisopropyl ether-hexane to give the titled compound (50 mg) as a white crystal.

Melting point: 226° C.–227° C.

Example 31

2,3-trans-2,4-cis-4-(2,3-Dihydro-1H-indol-1-yl)-1-(3,4-dimethoxybenzoyl)-2-methyl-3-({[(2-phenylethyl)amino]carbonyl}oxy)-1,2,3,4-tetrahydroquinoline

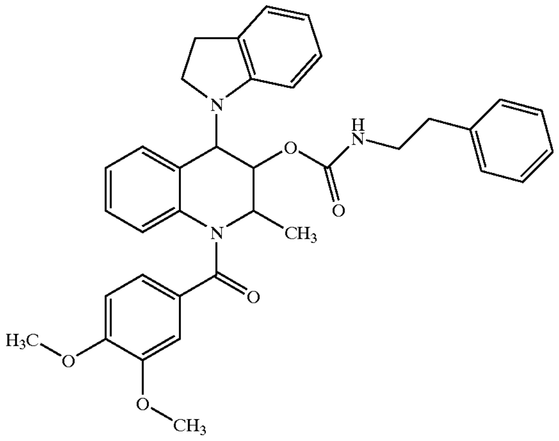

Starting with 2,3-trans-2,4-cis-4-(2,3-dihydro-1H-indol-1-yl)-1-(3,4-dimethoxy-benzoyl)-3-hydroxy-2-methyl-1,2,3,4-tetrahydroquinoline (150 mg, 0.34 mmol) prepared in Example 29 and phenethylisocyanate (149 mg, 1.01 mmol), the same procedure as shown in Example 27 was repeated to give the titled compound (190 mg, yield: 95%) as a white crystal.

Melting point: 146° C.–149° C.

The titled compounds of Examples 21 to 31 are summarized in Table 2 below.

Table 2

TABLE 2

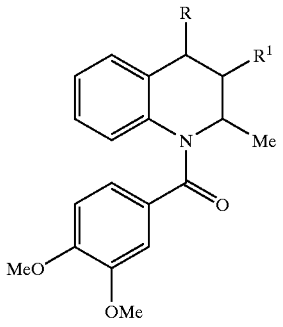

| Example | R | $R^1$ | Stereo-chemistry |
|---|---|---|---|
| 21 | 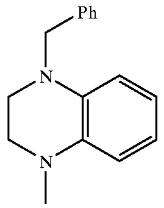 | OH | 2,3-trans 2,4-cis (±) |
| 22 | 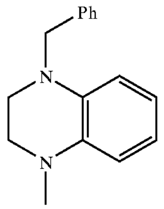 | OCSIm | 2,3-trans 2,4-cis (±) |
| 23 | 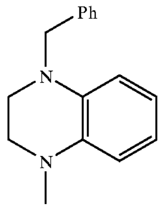 | H | 2,4-cis (±) |
| 24 | 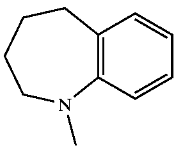 | OH | 2,3-trans 2,4-cis (±) |
| 25 | 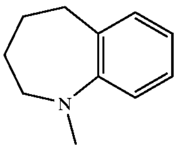 | OCSIm | 2,3-trans 2,4-cis (±) |
| 26 | 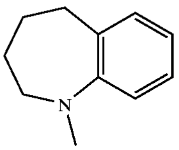 | H | 2,4-cis (±) |

TABLE 2-continued

| | | | |
|---|---|---|---|
| 27 | 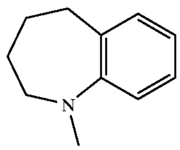 | $OCONHC_6H_{13}$ | 2,3-trans 2,4-cis (±) |
| 28 | 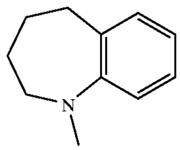 | $OCONHCH_2Ph$ | 2,3-trans 2,4-cis (±) |
| 29 | 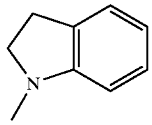 | OH | 2,3-trans 2,4-cis (±) |
| 30 | 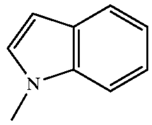 | H | 2,4-cis (±) |
| 31 | 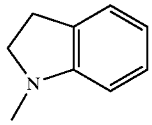 | $OCONHCH_2CH_2Ph$ | 2,3-trans 2,4-cis (±) |

Example 32

2,4-cis-4-(9H-9-Carbazolyl)-1-(3,4-dimethoxybenzoyl)-2-methyl-1,2,3,4-tetrahydroquinoline

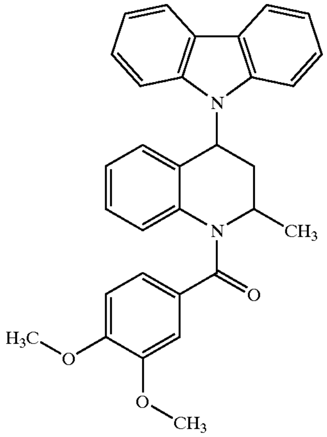

2,4-cis-4-(9H-9-Carbazolyl)-2-methyl-1,2,3,4-tetrahydroquinoline (361 mg, 1.16 mmol) prepared in Reference Example 4 was dissolved in pyridine (15 ml), to which 3,4-dimethoxybenzoyl chloride (279 mg, 1.39 mmol) was then added on ice and stirred at 60° C. for 4 hours. After the reaction mixture was concentrated, the residue was extracted by addition of ethyl acetate and water. After the organic layer was washed with water and concentrated, the residue was recrystallized from ethyl acetate-hexane to give the titled compound (155 mg, yield: 28%) as a white crystal.

Melting point: 229° C.–231° C. (crystallization solvent: ethyl acetate-hexane)

Elementary Analysis for $C_{31}H_{28}N_2O_3 0.25H_2O$: Calculated: C, 77.40; H, 5.97; N, 5.82. Found: C, 77.44; H, 5.70; N, 5.86.

Example 33

(−)-2,4-cis-4-(9H-9-Carbazolyl)-1-(3,4-dimethoxybenzoyl)-2-methyl-1,2,3,4-tetrahydroquinoline

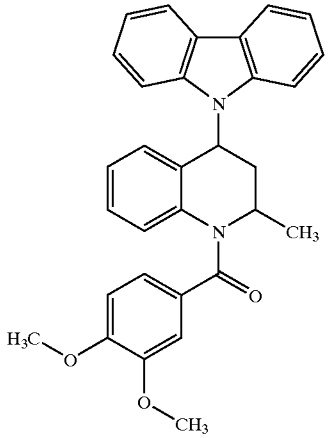

2,4-cis-4-(9H-9-Carbazolyl)-1-(3,4-dimethoxybenzoyl)-2-methyl-1,2,3,4-tetrahydro-quinoline (1.1 g) prepared in Example 32 was separated by chiral HPLC (column: CHIRALPAK AD; developing solvent: ethanol/hexane=1/1) and then concentrated to dryness to give the titled compound (430 mg) as a white crystal. When analyzed for optical rotation with a Shodex OR-2 (wavelength: 470 nm), this compound was shown to be (−)-form.

Melting point: 278° C.–280° C.

Example 34

(+)-2,4-cis-4-(9H-9-Carbazolyl)-1-(3,4-dimethoxybenzoyl)-2-methyl-1,2,3,4-tetrahydroquinoline

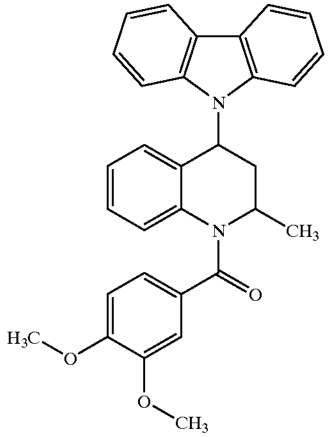

2,4-cis-4-(9H-9-Carbazolyl)-1-(3,4-dimethoxybenzoyl)-2-methyl-1,2,3,4-tetrahydro-quinoline (1.1 g) prepared in Example 32 was separated by chiral HPLC (column: CHIRALPAK AD; developing solvent: ethanol/hexane=1/1) and then concentrated to dryness to give the titled compound (470 mg) as a white crystal. When analyzed for optical rotation with a Shodex OR-2 (wavelength: 470 nm), this compound was shown to be (+)-form.

Melting point: 279° C.–280° C.

Example 35

2,4-cis-4-(9H-9-Carbazolyl)-1-(3,4-dimethoxybenzoyl)-2-ethyl-1,2,3,4-tetrahydroquinoline

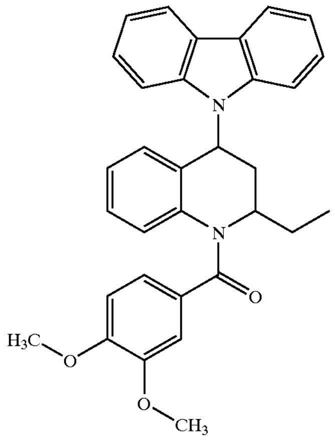

Starting with 2,4-cis-4-(9H-9-carbazolyl)-2-ethyl-1,2,3,4-tetrahydroquinoline (1.47 g, 4.50 mmol) prepared in Reference Example 5, the same procedure as shown in Example 32 was repeated to give the titled compound (0.93 g, yield: 42%) as a white crystal.

$^1$H NMR ($CDCl_3$) δ 0.99 (t, J=7.3 Hz, 3H), 1.65 (m, 1H), 1.93 (m, 1H), 2.62 (m, 1H), 2.75 (m, 1H), 3.67 (s, 3H), 3.85 (s, 3H), 4.97 (m, 1H), 5.91 (m, 1H), 6.70 (t, J=8.5 Hz, 2H), 6.80–7.35 (m, 9H), 7.50 (m, 2H), 8.19 (d, J=7.6 Hz, 2H),

FABMS(pos) 491.2 [M$^+$]

Example 36

(−)-2,4-cis-4-(9H-9-Carbazolyl)-1-(3,4-dimethoxybenzoyl)-2-ethyl-1,2,3,4-tetrahydroquinoline

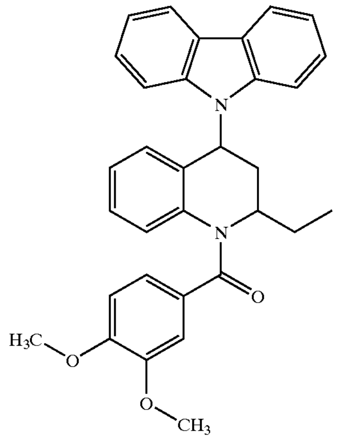

2,4-cis-4-(9H-9-Carbazolyl)-1-(3,4-dimethoxybenzoyl)-2-ethyl-1,2,3,4-tetrahydro-quinoline (1.21 g) prepared in Example 35 was separated by chiral HPLC (column: CHIRALPAK AD; developing solvent: ethanol/hexane=1/1) and then concentrated to dryness to give the titled compound (0.50 g) as a white crystal. When analyzed for optical rotation with a Shodex OR-2 (wavelength: 470 nm), this compound was shown to be (−)-form.

Elementary Analysis for $C_{32}H_{30}N_2O_3 0.25H_2O$: Calculated: C, 77.63; H, 6.21; N, 5.66. Found: C, 77.98; H, 6.08; N, 5.55.

Example 37

(+)-2,4-cis-4-(9H-9-Carbazolyl)-1-(3,4-dimethoxybenzoyl)-2-ethyl-1,2,3,4-tetrahydroquinoline

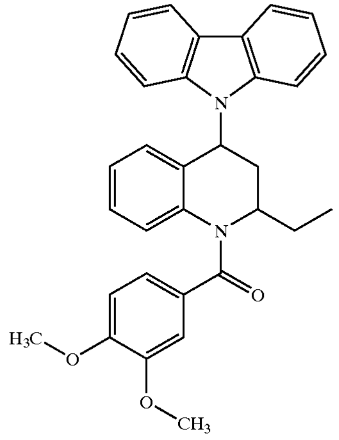

2,4-cis-4-(9H-9-Carbazolyl)-1-(3,4-dimethoxybenzoyl)-2-ethyl-1,2,3,4-tetrahydroquinoline (1.21 g) prepared in Example 35 was separated by chiral HPLC (column: CHIRALPAK AD; developing solvent: ethanol/hexane=1/1) and then concentrated to dryness to give the titled compound (0.47 g) as a white crystal. When analyzed for optical rotation with a Shodex OR-2 (wavelength: 470 nm), this compound was shown to be (+)-form.

Elementary Analysis for $C_{32}H_{30}N_2O_3 0.25H_2O$: Calculated: C, 77.63; H, 6.21; N, 5.66. Found: C, 77.83; H, 6.40; N, 5.57.

Example 38

2,4-cis-4-(9H-9-Carbazolyl)-1-(3,4-dimethoxybenzoyl)-2-propyl-1,2,3,4-tetrahydroquinoline

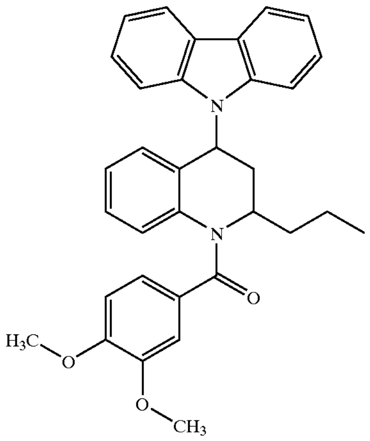

Starting with 2,4-cis-4-(9H-9-carbazolyl)-2-propyl-1,2,3,4-tetrahydroquinoline (1.63 g, 4.90 mmol) prepared in Reference Example 6, the same procedure as shown in Example 32 was repeated to give the titled compound (471 mg, yield: 20%) as a white crystal.

Melting point: 195° C.–196° C. (crystallization solvent: ethyl acetate-hexane)

Elementary Analysis for $C_{35}H_{32}N_2O_3 0.5H_2O$: Calculated: C, 77.17; H, 6.48; N, 5.45. Found: C, 77.36; H, 6.50; N, 5.16.

Example 39

(−)-2,4-cis-4-(9H-9-Carbazolyl)-1-(3,4-dimethoxybenzoyl)-2-propyl-1,2,3,4-tetrahydroquinoline

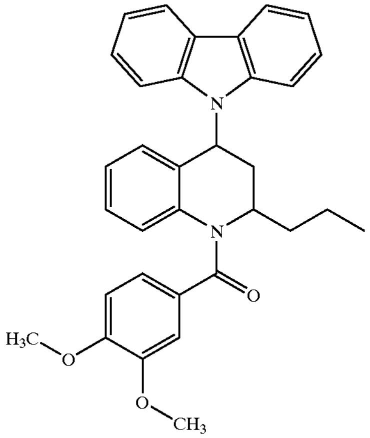

2,4-cis-4-(9H-9-Carbazolyl)-1-(3,4-dimethoxybenzoyl)-2-propyl-1,2,3,4-tetrahydroquinoline (345 mg) prepared in Example 38 was separated by chiral HPLC (column: CHIRALPAK AD; developing solvent: ethanol/hexane=1/1) and then concentrated to dryness to give the titled compound (137 mg) as a white crystal. When analyzed for optical rotation with a Shodex OR-2 (wavelength: 470 nm), this compound was shown to be (−)-form.

Melting point: 194° C.–195° C.

Example 40

2,4-cis-2-Butyl-4-(9H-9-carbazolyl)-1-(3,4-dimethoxybenzoyl)-1,2,3,4-tetrahydroquinoline

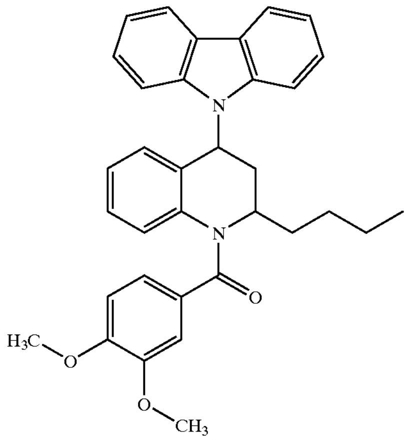

Starting with 2,4-cis-2-butyl-4-(9H-9-carbazolyl)-1,2,3,4-tetrahydroquinoline (2.12 g, 5.98 mmol) prepared in Reference Example 7, the same procedure as shown in Example 32 was repeated to give the titled compound (920 mg, yield: 30%) as a white crystal.

Melting point: 213° C. (crystallization solvent: ethyl acetate-hexane)

Elementary Analysis for $C_{34}H_{34}N_2O_3$: Calculated: C, 78.74; H, 6.61; N, 5.40. Found: C, 78.35; H, 6.53; N, 5.36.

Example 41

2,4-cis-4-(9H-9-Carbazolyl)-1-(3,4-dimethoxybenzoyl)-2-isobutyl-1,2,3,4-tetrahydroquinoline

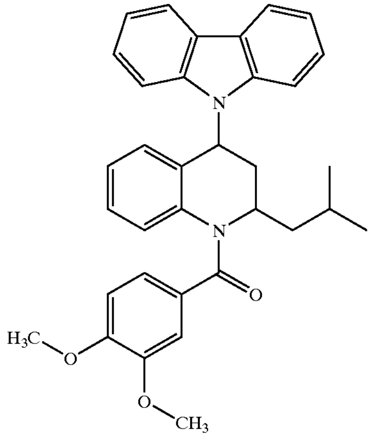

Starting with 2,4-cis-4-(9H-9-carbazolyl)-2-isobutyl-1,2,3,4-tetrahydroquinoline (1.10 g, 3.10 mmol) prepared in Reference Example 8, the same procedure as shown in Example 32 was repeated to give the titled compound (636 mg, yield: 40%) as a white crystal.

Melting point: 191° C.–193° C. (crystallization solvent: THF-hexane)

Elementary Analysis for $C_{34}H_{34}N_2O_3H_2O$: Calculated: C, 77.39; H, 6.69; N, 5.31. Found: C, 77.77; H, 7.01; N, 5.03.

Example 42

2,4-cis-4-(9H-9-Carbazolyl)-1-(3,4-dimethoxybenzoyl)-2-(2-phenylethyl)-1,2,3,4-tetrahydroquinoline

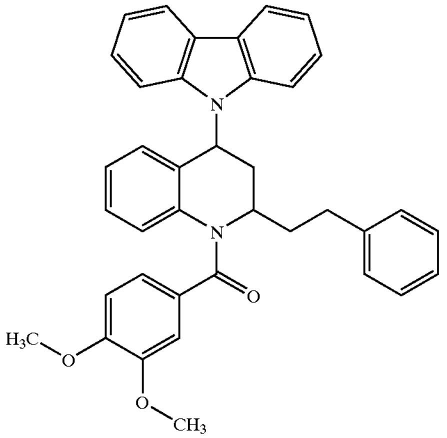

Starting with 2,4-cis-4-(9H-9-carbazolyl)-2-(2-phenylethyl)-1,2,3,4-tetrahydroquinoline (2.98 g, 7.40 mmol) prepared in Reference Example 9, the same procedure as shown in Example 32 was repeated to give the titled compound (886 mg, yield: 22%) as a white crystal.

Melting point: 223–225° C. (crystallization solvent: ethyl acetate-hexane)

Elementary Analysis for $C_{38}H_{34}N_2O_{33}$: Calculated: C, 80.54; H, 6.05; N, 4.94. Found: C, 80.29; H, 6.00; N, 5.05.

Example 43

2-[(Benzyloxy)methyl]-4-(9H-9-carbazolyl)-1-(3,4-dimethoxybenzoyl)-1,2,3,4-tetrahydroquinoline

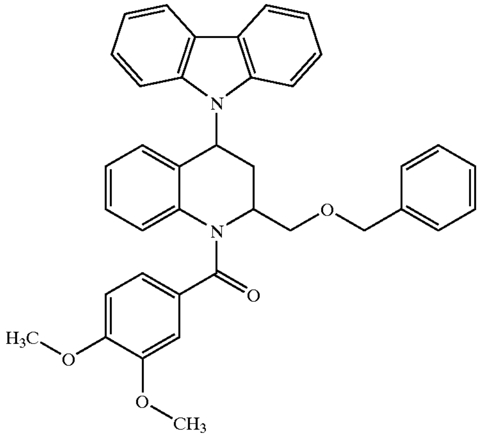

Starting with 2,4-cis-2-[(benzyloxy)methyl]-4-(9H-9-carbazolyl)-1,2,3,4-tetrahydroquinoline (3.27 g, 7.81 mmol) prepared in Reference Example 10, the same procedure as shown in Example 32 was repeated to give the titled compound (1.01 g, yield: 22%) as a white crystal. (cis:trans=1:1)

Melting point: 203° C.–204° C. (crystallization solvent: diethyl ether-ethyl acetate)

Elementary Analysis for $C_{38}H_{34}N_2O_4$: Calculated: C, 78.33; H, 5.83; N, 4.81. Found: C, 77.90; H, 5.83; N, 4.76.

Example 44

2,4-cis-4-(9H-9-Carbazolyl)-2-(2-cyanoethyl)-1-(3,4-dimethoxybenzoyl)-1,2,3,4-tetrahydroquinoline

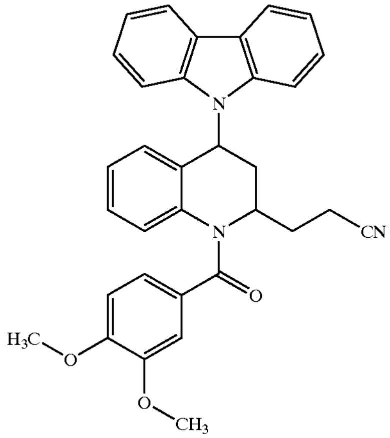

Starting with 2,4-cis-4-(9H-9-carbazolyl)-2-(2-cyanoethyl)-1,2,3,4-tetrahydroquinoline (2.00 g, 5.69 mmol) prepared in Reference Example 11, the same procedure as shown in Example 32 was repeated to give the titled compound (1.61 g, yield: 55%) as a white crystal.

Melting point: 181° C.–182° C. (crystallization solvent: ethyl acetate-hexane)

FABMS(pos) 544.2 $[M+H^+]$

Example 45

2,4-cis-2-{3-[(t-Butoxycarbonyl)amino]propyl}-4-(9H-carbazol-9-yl)-1-(3,4-dimethoxybenzoyl)-1,2,3,4-tetrahydroquinoline

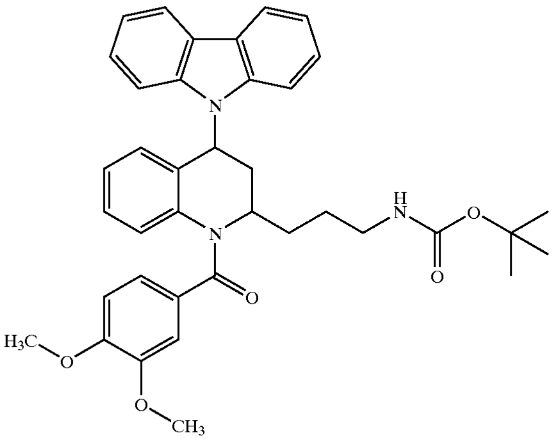

2,4-cis-4-(9H-9-Carbazolyl)-2-(2-cyanoethyl)-1-(3,4-dimethoxybenzoyl)-1,2,3,4-tetrahydroquinoline (400 mg, 0.78 mmol) prepared in Example 44, nickel(II) chloride hexahydrate (370 mg, 1.56 mmol) and di-t-butyl dicarbonate (340 mg, 1.56 mmol) were dissolved in a solvent mixture of methanol (10 ml) and THF (20 ml), to which sodium borohydride (590 mg, 15.6 mmol) was then added and stirred overnight at room temperature. The reaction mixture was poured into water and extracted with ethyl acetate. After the organic layer was dried and concentrated, the residue was recrystallized from ethyl acetate-hexane to give the titled compound (282 mg, yield: 56%) as a white crystal.

Melting point: 180° C.–181° C. (crystallization solvent: ethyl acetate-hexane)

Elementary Analysis for $C_{35}H_{35}N_3O_4 0.3H_2O$: Calculated: C, 73.01; H, 6.71; N, 6.72. Found: C, 73.19; H, 7.10; N, 6.42.

Example 46

2,4-cis-2-(3-Aminopropyl)-4-(9H-carbazol-9-yl)-1-(3,4-dimethoxybenzoyl)-1,2,3,4-tetrahydroquinoline hydrochloride

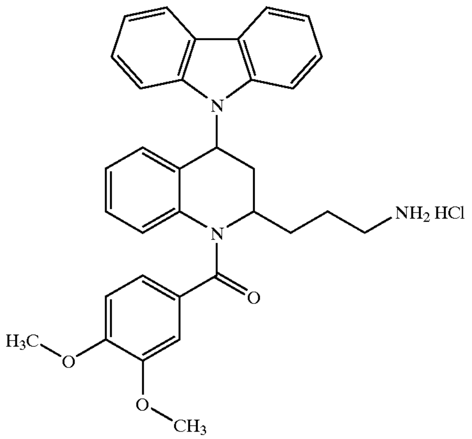

2,4-cis-2-{3-[(t-Butoxycarbonyl)amino]propyl}-4-(9H-carbazol-9-yl)-1-(3,4-dimethoxybenzoyl)-1,2,3,4-tetrahydroquinoline (250 mg, 0.403 mmol) prepared in Example 45 was dissolved in THF (5 ml), to which a 4N ethyl acetate solution of hydrogen chloride (5 ml, 20 mmol) was then added and stirred at room temperature for 5 hours. After the reaction mixture was concentrated, the residue was recrystallized from ethyl acetate-hexane to give the titled compound (141 mg, yield: 67%) as a white crystal.

Melting point: 203° C.–204° C. (crystallization solvent: ethyl acetate-hexane)

Elementary Analysis for $C_{33}H_{34}N_3O_3Cl1.0H_2O$: Calculated: C, 69.04; H, 6.32; N, 7.32; Cl, 6.18. Found: C, 69.20; H, 6.09; N, 7.31; Cl, 6.12.

The titled compounds of Examples 32 to 46 are summarized in Table 3 below.

TABLE 3

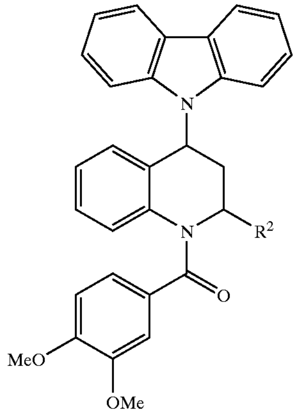

| Example | $R^2$ | Stereochemistry |
|---|---|---|
| 32 | $CH_3$ | 2,4-cis (±) |
| 33 | $CH_3$ | 2,4-cis (−) |
| 34 | $CH_3$ | 2,4-cis (+) |
| 35 | $C_2H_5$ | 2,4-cis (±) |
| 36 | $C_2H_5$ | 2,4-cis (−) |
| 37 | $C_2H_5$ | 2,4-cis (+) |
| 38 | $C_3H_7$ | 2,4-cis (±) |
| 39 | $C_3H_7$ | 2,4-cis (−) |
| 40 | $C_4H_9$ | 2,4-cis (±) |
| 41 | $CH_2CH(CH_3)_2$ | 2,4-cis (±) |
| 42 | $CH_2CH_2Ph$ | 2,4-cis (±) |
| 43 | $CH_2OCH_2Ph$ | 2,4-cis/trans = 1/1 (±) |
| 44 | $CH_2CH_2CN$ | 2,4-cis (±) |
| 45 | $CH_2CH_2CH_2NHCOOC_4H_9$ | 2,4-cis (±) |
| 46 | $CH_2CH_2CH_2NH_2$ | 2,4-cis (±) |

Example 47

2,4-cis-4-(9H-9-Carbazolyl)-5,7-dimethoxy-1-(3,4-dimethoxybenzoyl)-2-methyl-1,2,3,4-tetrahydroquinoline

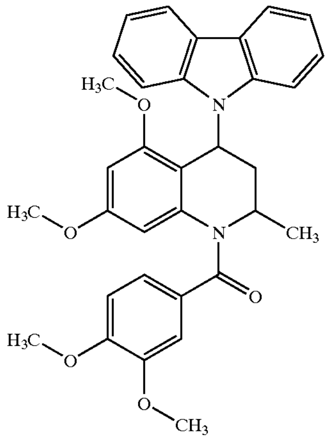

Starting with 2,4-cis-4-(9H-9-carbazolyl)-5,7-dimethoxy-2-methyl-1,2,3,4-tetrahydroquinoline (0.83 g, 2.22 mmol) prepared in Reference Example 12, the same procedure as shown in Example 32 was repeated to give the titled compound (0.26 g, yield: 22%) as a white crystal.

Elementary Analysis for $C_{33}H_{32}N_2O_5 0.5H_2O$: Calculated: C, 72.64; H, 6.10; N, 5.13. Found: C, 72.94; H, 5.86; N, 5.18.

Example 48

2,4-cis-4-(9H-9-Carbazolyl)-5,8-dimethoxy-1-(3,4-dimethoxybenzoyl)-2-methyl-1,2,3,4-tetrahydroquinoline

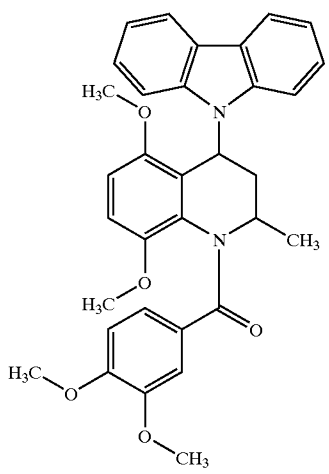

Starting with 2,4-cis-4-(9H-9-carbazolyl)-5,8-dimethoxy-2-methyl-1,2,3,4-tetrahydroquinoline (1.10 g, 2.95 mmol) prepared in Reference Example 13, the same procedure as shown in Example 32 was repeated to give the titled compound (0.19 g, yield: 12%) as a white crystal.

Elementary Analysis for $C_{33}H_{32}N_2O_5$: Calculated: C, 73.86; H, 6.01; N, 5.22. Found: C, 73.56; H, 6.06; N, 5.05.

Example 49

2,4-cis-4-(9H-9-Carbazolyl)-1-(3,4-dimethoxybenzoyl)-8-methoxy-2-methyl-1,2,3,4-tetrahydroquinoline

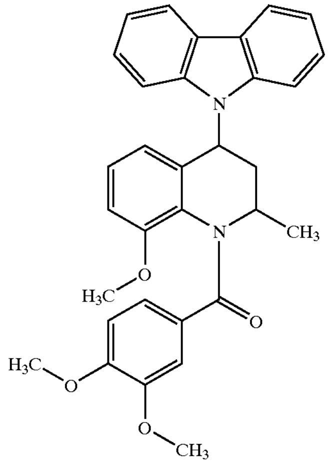

Starting with 2,4-cis-4-(9H-9-carbazolyl)-8-methoxy-2-methyl-1,2,3,4-tetrahydro-quinoline (685 mg, 2.0 mmol) prepared in Reference Example 14, the same procedure as shown in Example 32 was repeated to give the titled compound (100 mg, yield: 10%) as a white crystal.

Elementary Analysis for $C_{32}H_{30}N_2O_4 0.25H_2O$: Calculated: C, 75.20; H, 6.01; N, 5.48. Found: C, 75.36; H, 6.11; N, 5.40.

Example 50

4-(9H-9-Carbazolyl)-1-(3,4-dimethoxybenzoyl)-6-methoxy-2-methyl-1,2,3,4-tetrahydroquinoline

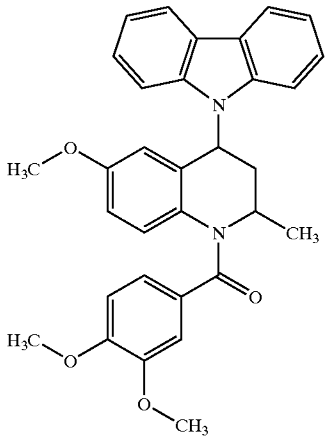

Starting with 4-(9H-9-carbazolyl)-6-methoxy-2-methyl-1,2,3,4-tetrahydroquinoline (800 mg, 2.34 mmol) prepared in Reference Example 15, the same procedure as shown in Example 32 was repeated to give the titled compound (306 mg, yield: 26%) as a white crystal (cis/trans mixture).

Elementary Analysis for $C_{32}H_{30}N_2O_4 0.6H_2O$: Calculated: C, 74.28; H, 6.08; N, 5.41. Found: C, 74.62; H, 6.17; N, 5.02.

Example 51

2,4-cis-4-(9H-9-Carbazolyl)-1-(2-furoyl)-2-methyl-1,2,3,4-tetrahydroquinoline

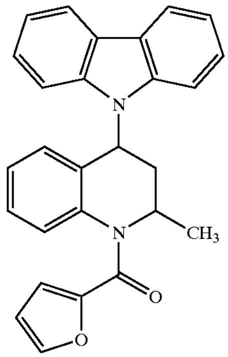

Starting with 2,4-cis-4-(9H-9-carbazolyl)-2-methyl-1,2,3,4-tetrahydroquinoline (600 mg, 1.90 mmol) prepared in Reference Example 4, the same procedure as shown in Example 32 was repeated to give the titled compound (379 mg, yield: 49%) as a white crystal.

Elementary Analysis for $C_{27}H_{22}N_2O_2 0.1\ H_2O$: Calculated: C, 79.43; H, 5.48; N, 6.86. Found: C, 79.42; H, 5.54; N, 6.76.

Melting point: 202° C.–203° C.

Example 52

2,4-cis-4-(9H-9-Carbazolyl)-2-methyl-1-(2-thienoyl)-1,2,3,4-tetrahydroquinoline

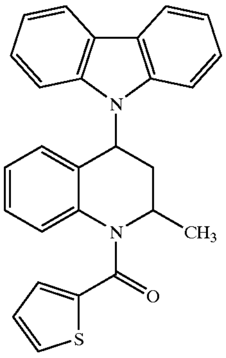

Starting with 2,4-cis-4-(9H-9-carbazolyl)-2-methyl-1,2,3,4-tetrahydroquinoline (600 mg, 1.90 mmol) prepared in Reference Example 4, the same procedure as shown in Example 32 was repeated to give the titled compound (250 mg, yield: 31%) as a white crystal.

Elementary Analysis for $C_{27}H_{22}N_2O_1S0.2H_2O$: Calculated: C, 76.10; H, 5.30; N, 6.57. Found: C, 76.40; H, 5.21; N, 6.33.

Example 53

2,4-cis-4-(9H-9-Carbazolyl)-2-ethyl-1-(3-thienoyl)-1,2,3,4-tetrahydroquinoline

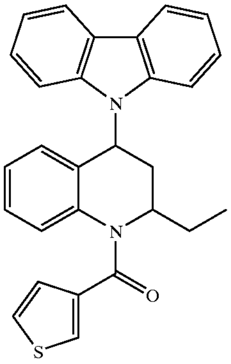

Starting with 2,4-cis-4-(9H-9-carbazolyl)-2-ethyl-1,2,3,4-tetrahydroquinoline (200 mg, 0.61 mmol) prepared in Reference Example 5, the same procedure as shown in Example 32 was repeated to give the titled compound (90 mg, yield: 33%) as a white crystal.

Mass m/z 437.2 ($MH^+$)

The titled compounds of Examples 47 to 53 are summarized in Table 4 below.

TABLE 4

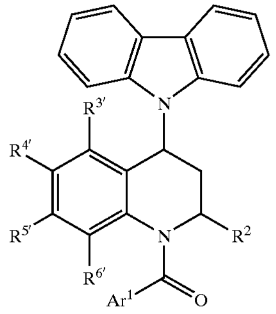

| Example | $Ar^1$ | $R^2$ | $R^{3'}$ | $R^{4'}$ | $R^{5'}$ | $R^{6'}$ | Stereochemistry |
|---|---|---|---|---|---|---|---|
| 47 | 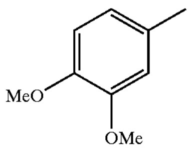 | $CH_3$ | $OCH_3$ | H | $OCH_3$ | H | 2,4-cis (±) |
| 48 | 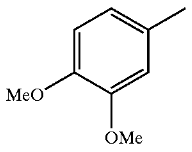 | $CH_3$ | $OCH_3$ | H | H | $OCH_3$ | 2,4-cis (±) |
| 49 | 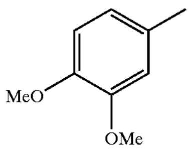 | $CH_3$ | H | H | H | $OCH_3$ | 2,4-cis (±) |

TABLE 4-continued

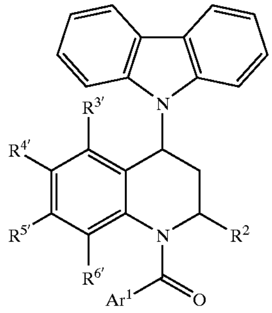

| Example | $Ar^1$ | $R^2$ | $R^{3'}$ | $R^{4'}$ | $R^{5'}$ | $R^{6'}$ | Stereochemistry |
|---|---|---|---|---|---|---|---|
| 50 | 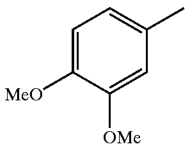 | $CH_3$ | H | $OCH_3$ | H | H | 2,4-cis/trans = 1/1 (±) |
| 51 | 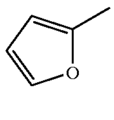 | $CH_3$ | H | H | H | H | 2,4-cis (±) |
| 52 | 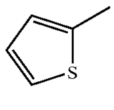 | $CH_3$ | H | H | H | H | 2,4-cis (±) |
| 53 | 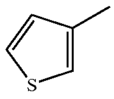 | $C_2H_5$ | H | H | H | H | 2,4-cis (±) |

Example 54

1-(3,4-Dimethoxybenzoyl)-2-methyl-4-(1,2,3,4-tetrahydroquinolin-1-yl)-1,2-dihydroquinoline

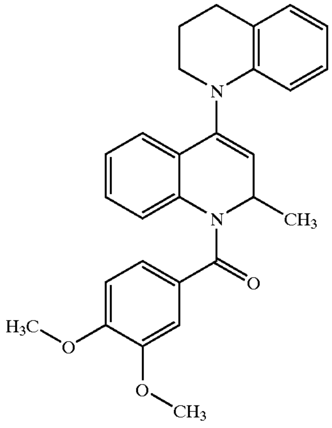

2,3-trans-2,4-cis-1-(3,4-Dimethoxybenzoyl)-3-hydroxy-2-methyl-4-(1,2,3,4-tetrahydroquinolin-1-yl)-1,2,3,4-tetrahydroquinoline (560 mg, 1.22 mmol) prepared in Example 14 and 1,1'-thiocarbonyldiimidazole (617 mg, 0.872 mmol) were dissolved in 1,2-dichloroethane (25 ml) and heated at reflux for 18 hours. After the reaction mixture was concentrated, the residue was applied to silica gel column chromatography (developing solvent: ethyl acetate/hexane=1/5) to give the titled compound (66 mg, yield: 12%) as a yellow oil.

Elementary Analysis for $C_{28}H_{28}N_2O_3 0.5H_2O$: Calculated: C, 74.81; H, 6.50; N, 6.23. Found: C, 74.53; H, 6.29; N, 6.48.

FABMS(pos) 441.2 $[M+H^+]$

Example 55

1-(3,4-Dimethoxybenzoyl)-2-methyl-4-(2,3,4,5-tetrahydro-1H-1-benzazepinyl)-1,2-dihydroquinoline

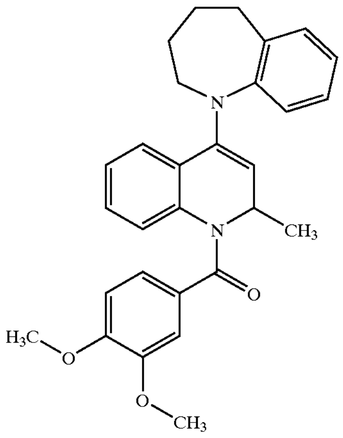

Starting with 2,3-trans-2,4-cis-1-(3,4-dimethoxybenzoyl)-3-hydroxy-2-methyl-4-(2,3,4,5-tetrahydro-1H-1-benzazepinyl)-1,2,3,4-tetrahydroquinoline (190 mg, 0.41 mmol) prepared in Example 24, the same procedure as shown in Example 54 was repeated to give the titled compound (27 mg, yield: 15%) as a white crystal.

Melting point: 151° C.–152° C.

Example 56

4-(3,4-Dihydro-2H-1,4-benzothiazin-4-yl)-1-(3,4-dimethoxybenzoyl)-2-methyl-1,2-dihydroquinoline

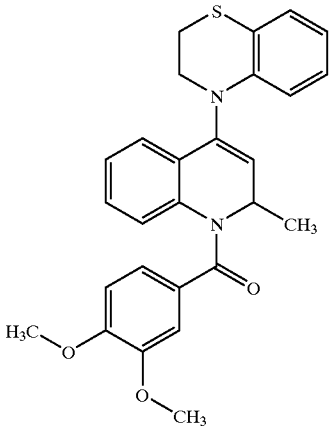

Starting with 2,3-trans-2,4-cis-4-(3,4-dihydro-2H-1,4-benzothiazin-4-yl)-1-(3,4-dimethoxybenzoyl)-3-[(1H-imidazol-1-ylcarbothioyl)oxy]-2-methyl-1,2,3,4-tetrahydroquinoline (580 mg, 0.94 mmol) prepared in Example 19, the same procedure as shown in Example 16 was repeated to give the titled compound (42 mg, yield: 10%) as a white crystal.

Melting point: 166° C.–168° C. (crystallization solvent: diethyl ether-hexane)

Example 57

2,3-trans-2,4-cis-4-(5,6-Dihydrophenanthrdin-5-yl)-1-(3,4-dimethoxybenzoyl)-3-hydroxy-2-methyl-1,2,3,4-tetrahydroquinoline

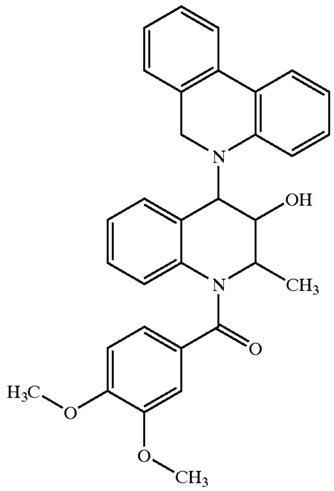

Starting with 5,6-dihydro-phenanthrdine (579 mg, 3.20 mmol), the same procedure as shown in Example 14 was repeated to give the titled compound (950 mg, yield: 76%) as a white crystal.

Melting point: 120° C.–123° C.

Example 58

4-(5,6-Dihydrophenanthrdin-5-yl)-1-(3,4-dimethoxybenzoyl)-2-methyl-1,2-dihydroquinoline

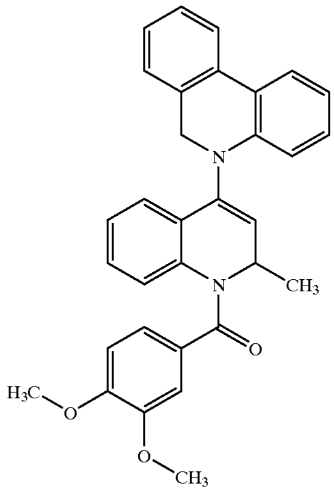

Starting with 2,3-trans-2,4-cis-4-(5,6-dihydrophenanthrdin-5-yl)-1-(3,4-dimethoxybenzoly)-3-hydroxy-2-methyl-1,2,3,4-tetrahydroquinoline (550 mg, 1.09 mmol) prepared in Example 57, the same procedure as shown in Example 54 was repeated to give the titled compound (120 mg, yield: 23%) as a white crystal.

Melting point: 196° C.–198° C.

Example 59

2-Butyl-4-(9H-9-carbazolyl)-1-(3,4-dimethoxybenzoyl)-1,2-dihydroquinoline

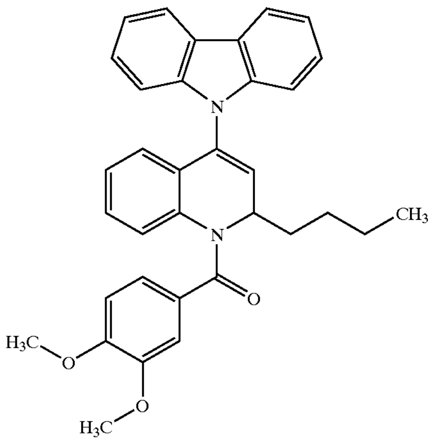

2-Butyl-3-(3,4-dimethoxybenzoyl)-1a,2,3,7b-tetrahydrooxyleno[2,3-c]quinoline (1 g, 2.7 mmol) prepared in Reference Example 18 was dissolved in THF (30 ml) and potassium carbazole (554 mg, 2.7 mmol) was added thereto, followed by heating at reflux for 24 hours. The reaction mixture was concentrated under reduced pressure, diluted with water and then extracted twice with ethyl acetate. The organic layer was washed with water and saturated brine, dried over sodium sulfate and then concentrated under reduced pressure. The resulting residue was applied to silica gel column chromatography (developing solvent: hexane/ethyl acetate=80/20) and the resulting eluate was recrystallized from hexane-ethyl acetate to give the titled compound (105 mg, yield: 8%) as a white crystal.

Elementary Analysis for $C_{34}H_{32}N_2O_3$: Calculated: C, 79.04; H, 6.24; N, 5.42. Found: C, 78.81; H, 6.26; N, 5.32.

Melting point: 174° C.–175° C.

The titled compounds of Examples 54 to 59 are summarized in Table 5 below.

TABLE 5

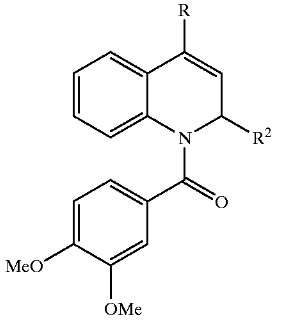

| Example | R | $R^2$ |
|---|---|---|
| 54 | 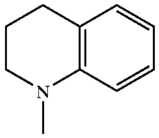 | $CH_3$ |

TABLE 5-continued

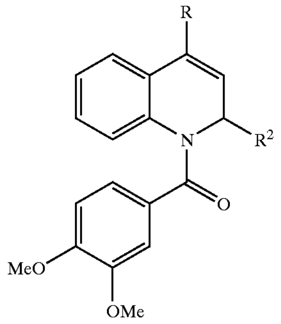

| Example | R | $R^2$ |
|---|---|---|
| 55 | 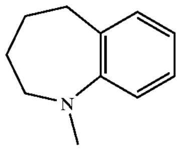 | $CH_3$ |
| 56 | 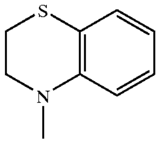 | $CH_3$ |
| 57* | 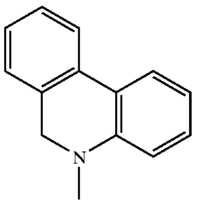 | $CH_3$ |
| 58 | 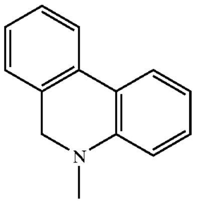 | $CH_3$ |
| 59 | 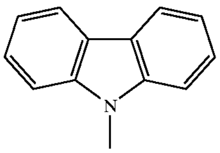 | $C_4H_9$ |

*

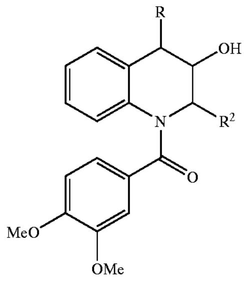

Reference Example 16

2,4-trans-4-(Benzotriazol-1-yl)-2-methyl-1,2,3,4-tetrahydroquinoline

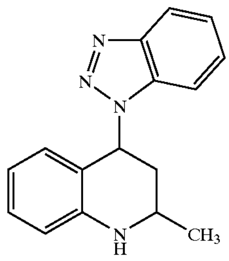

Benzotriazole (5.0 g, 4.20 mmol) and aniline (3.91 g, 4.20 mmol) were dissolved in diethyl ether (85 ml), and acetaldehyde (2.03 g, 4.62 mmol) was added dropwise thereto on ice. The reaction mixture was stirred at room temperature for 15 minutes and then allowed to stand overnight at −20° C. The crystallized product was collected by filtration, washed with diethyl ether and then dried to give α-methyl-N-phenyl-1H-benzotriazole-1-methanamine (8.7 g) as a white crystal. The resulting α-methyl-N-phenyl-1H-benzotriazole-1-methanamine (2.86 g, 12 mmol) and vinylphthalimide (2860 mg, 12.0 mmol) were suspended in chloroform (10 ml), to which p-toluenesulfonic acid monohydrate (190 mg, 1.0 mmol) was then added and stirred at room temperature for 10 hours. After addition of water, the reaction mixture was extracted with chloroform. The organic layer was washed with saturated aqueous sodium carbonate and water, and then concentrated. The residue was applied to silica gel column chromatography to give the titled compound (1.03 g, yield over 2 steps: 25%) as a white crystal.

$^1$H-NMR ($CDCl_3$) δ 1.21 (d, J=6.2 Hz, 3H), 2.14 (m, 1H), 2.41 (d, J=13.7 Hz, 1H), 3.41 (m, 1H), 4.15 (s, 1H), 6.22 (dd, J=4.4, 3.2 Hz, 1H), 6.64–6.72 (m, 2H), 6.88 (d, J=7.1 Hz, 1H), 7.00 (t, J=7.1 Hz, 1H), 7.19–7.29 (m, 3H), 8.03 (m, 1H), 8.03 (m, 1H).

FABMS(pos) 264.1 [M+]

Reference Example 17

3-(3,4-Dimethoxybenzoyl)-2-propyl-1a,2,3,7b-tetrahydrooxyleno[2,3-c]quinoline

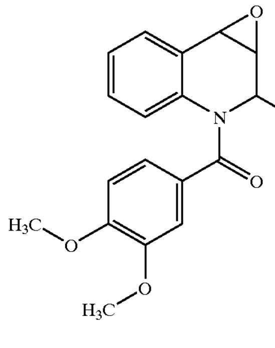

Starting with 1-(3,4-dimethoxybenzoyl)-2-propyl-1,2-dihydroquinoline (850 mg, 0.023 mol) synthesized in the published manner, the same procedure as shown in Reference Example 3 was repeated to give the titled compound (540 mg, yield: 61%) as a white crystal.

$^1$H-NMR ($CDCl_3$) δ 0.93 (t, J=7.3 Hz, 3H), 1.15–1.30 (m, 1H), 1.35–1.58 (m, 3H), 3.66)s, 3H), 3.83 (s, 3H), 3.86 (dd, J=2.3, 4.2 Hz, 1H), 3.96 (d, J=4.2 Hz, 1H), 5.22–5.28 (m, 1H), 6.47 (d, J=7.8 Hz, 1H), 6.66 (d, J=7.8 Hz, 1H), 6.89 (d, J=2.0 Hz, 1H), 6.94–7.08 (m, 3H), 7.42 (dd, J=1.6, 7.2 Hz, 1H).

Reference Example 18

2-Butyl-3-(3,4-dimethoxybenzoyl)-1a,2,3,7b-tetrahydrooxyleno[2,3-c]quinoline

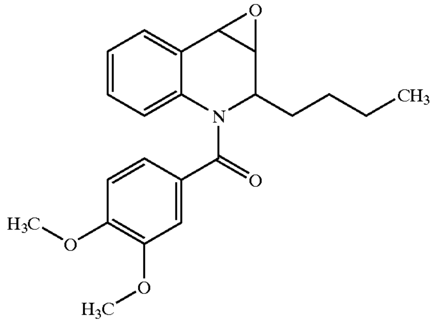

Starting with 2-butyl-1-(3,4-dimethoxybenzoyl)-1,2-dihydroquinoline (8.00 g, 0.023 mol) synthesized in the published manner, the same procedure as shown in Reference Example 3 was repeated to give the titled compound (6.12 g, yield: 73%) as a white crystal.

Melting point: 133° C.–134° C.

Reference Example 19

1-(4-Ethoxy-3-methoxybenzoyl)-2-methyl-1,2,3,4-tetrahydro-4-quinolinol

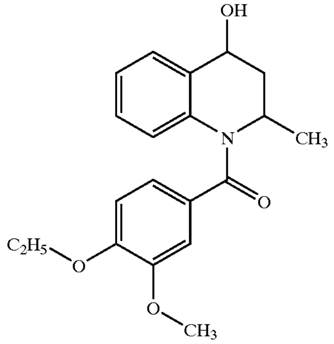

2-Methyl-1,2,3,4-tetrahydro-4-quinolinol (7.1 g, 43.5 mmol) synthesized in the published manner was dissolved in pyridine (50 ml), followed by addition of 4-ethoxy-3-methoxybenzoyl chloride prepared from 4-ethoxy-3-methoxybenzoic acid (9.2 g, 46.4 mmol). After stirring at room temperature for 16 hours, the reaction mixture was concentrated and extracted by addition of ethyl acetate and water. After the organic layer was dried and concentrated, the residue was applied to silica gel column chromatography (developing solvent: ethyl acetate/hexane=1/1) and the resulting eluate was recrystallized from ethyl acetate-hexane to give the titled compound (4.4 g, yield: 30%) as a white crystal.

$^1$H NMR ($CDCl_3$) δ 1.29 (d, J=6.4 Hz, 3H), 1.43 (t, J=6.9 Hz, 3H), 1.44–1.55 (m, 1H), 2.00 (d, J=6.2 Hz, 1H), 2.73–2.82 (m, 1H), 3.64 (s, 3H), 4.04 (q, J=6.4 Hz, 2H), 4.79–4.88 (m, 2H), 6.57 (d, J=7.9 Hz, 1H), 6.63 (d, J=8.9 Hz, 1H), 6.75–6.77 (m, 2H), 6.96 (dd, J=7.7, 7.7 Hz, 1H), 7.15 (dd, J=7.5, 7.5 Hz, 1H), 7.53 (d, J=7.5 Hz, 1H)

Reference Example 20

1-(3,4-Diethoxybenzoyl)-2-methyl-1,2,3,4-tetrahydro-4-quinolinol

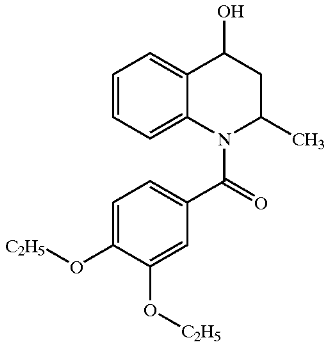

Starting with 2-methyl-1,2,3,4-tetrahydro-4-quinolinol (10.0 g, 61.3 mmol) synthesized in the published manner, the same procedure as shown in Reference Example 19 was repeated to give the titled compound (4.67 g, yield: 21%) as a white crystal.

Melting point: 164° C.–165° C.

Reference Example 21

1-(3-Methoxybenzoyl)-2-methyl-1,2,3,4-tetrahydro-4-quinolinol

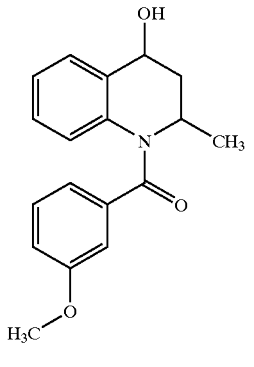

Starting with 2-methyl-1,2,3,4-tetrahydro-4-quinolinol (3.00 g, 18.3 mmol) synthesized in the published manner and 3-methoxybenzoic acid (3.34 g, 22.0 mmol), the same procedure as shown in Reference Example 19 was repeated to give the titled compound (1.45 g, yield: 27%) as a white crystal. (cis:trans=1:1)

Melting point: 148° C.–149° C.

Reference Example 22

1-(3,4,5-Trimethoxybenzoyl)-2-methyl-1,2,3,4-tetrahydro-4-quinolinol

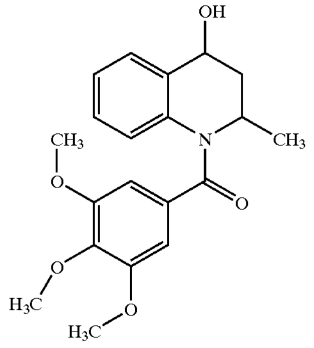

Starting with 2-methyl-1,2,3,4-tetrahydro-4-quinolinol (3.00 g, 18.3 mmol) synthesized in the published manner and 3,4,5-trimethoxybenzoic acid (2.0 g, 10.9 mmol), the same procedure as shown in Reference Example 19 was repeated to give the titled compound (1.30 g, yield: 33%) as a white crystal. (cis:trans=1:1)

Reference Example 23

1-(3,4-Dimethylbenzoyl)-2-methyl-1,2,3,4-tetrahydro-4-quinolinol

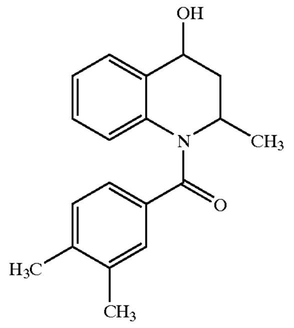

Starting with 2-methyl-1,2,3,4-tetrahydro-4-quinolinol (1.00 g, 6.12 mmol) synthesized in the published manner and 3,4-dimethylbenzoic acid (1.20 g, 7.96 mmol), the same procedure as shown in Reference Example 19 was repeated to give the titled compound (1.13 g, yield: 48%) as an oil. (cis:trans=1:1)

$^1$H NMR ($CDCl_3$) δ 1.25–1.28 (m, 3H), 1.44–2.78 (m, 9H), 4.86–4.94 (m, 2H), 6.57–7.53 (m, 7H).

Reference Example 24

9-[2,4-cis-2-(3-Phenylpropyl)-1,2,3,4-tetrahydroquinolin-4-yl]-9H-carbazole

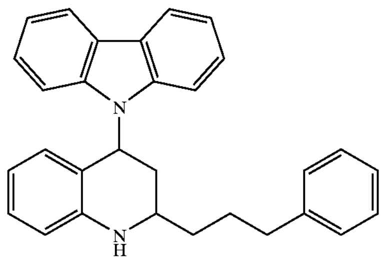

Starting with 4-phenylbutylaldehyde (6.48 g, 43.7 mmol), the same procedure as shown in Reference Example 4 was repeated to give the titled compound (4.40 g, yield over 2 steps: 24%) as a colorless oil.

$^1$H NMR ($CDCl_3$) δ 1.50–1.80 (m, 2H), 2.10–2.25 (m, 1H), 2.30–2.50 (m, 1H), 2.50–2.80 (m, 4H), 3.60–3.75 (m, 1H), 6.10 (dd, J=11.9, 6.4 Hz, 1H), 6.40–8.20 (m, 17H).

Reference Example 25

9-[2,4-cis-2-[3-[[tert-Butyl(diphenyl)silyl]oxy]propyl]-1,2,3,4-tetrahydroquinolin-4-yl]-9H-carbazole

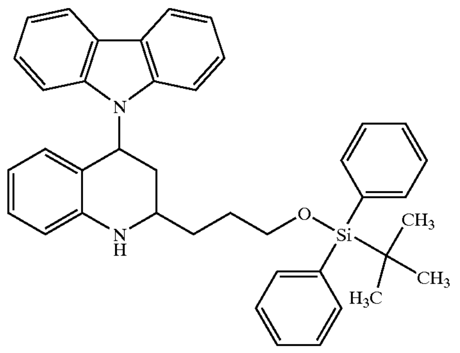

Starting with 4-[[tert-butyl(diphenyl)silyl]oxy]butanal (6.10 g, 18.7 mmol), the same procedure as shown in Reference Example 4 was repeated to give the titled compound (1.08 g, yield over 2 steps: 10%) as a colorless oil.

$^1$H NMR ($CDCl_3$) δ 1.03–1.06 (m, 9H), 1.70–1.85 (m, 2H), 2.10–2.20 (m, 1H), 2.30–2.50 (m, 1H), 3.60–3.80 (m, 3H), 3.96 (br s, 1H), 6.09 (dd, J=11.8, 6.2 Hz, 1H), 6.40–8.20 (m, 22H),

Example 60

4-(1'-Benzylspiro[indoline-3,4'-piperidin]-1-yl)-1-(3,4-dimethoxybenzoyl)-2-methyl-1,2,3,4-tetrahydroquinoline

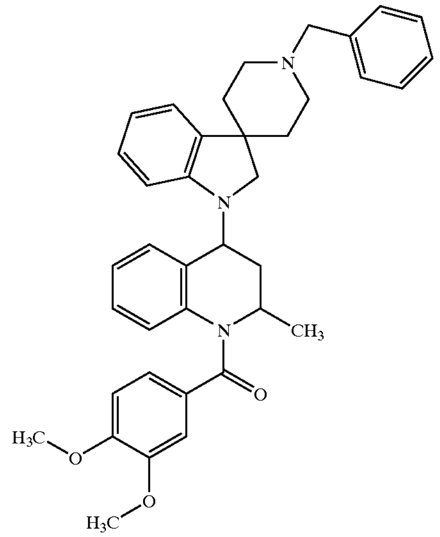

Starting with cis-1-(3,4-dimethoxybenzoyl)-2-methyl-1,2,3,4-tetrahydro-4-quinolinol (400 mg, 1.22 mmol) prepared in Reference Example 1 and 1'-benzylspiro[indoline-3,4'-piperidine] (849 mg, 3.05 mmol), the same procedure as shown in Example 1 was repeated to give the titled compound (376 mg, yield: 44%) as a colorless oil. (cis:trans=1:1.5)

FABMS(pos) 588.2 [M+H$^+$]

Example 61

4-(2,3-Dihydro-1H-indol-1-yl)-1-(3,4-dimethoxybenzoyl)-2-methyl-1,2,3,4-tetrahydroquinoline

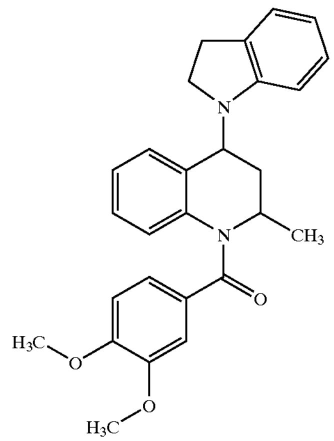

Starting with cis-1-(3,4-dimethoxybenzoyl)-2-methyl-1,2,3,4-tetrahydro-4-quinolinol (400 mg, 1.22 mmol) prepared in Reference Example 1 and indoline (436 mg, 3.66 mmol), the same procedure as shown in Example 1 was repeated to give the titled compound (267 mg, yield: 51%) as a white crystal. (cis:trans=1:1.8)

Melting point: 147° C.–148° C. (crystallization solvent: diethyl ether-hexane)

FABMS(pos) 451.2 [M+Na$^+$]

Example 62

1-(3,4-Dimethoxybenzoyl)-2-methyl-4-(2,3,4,5-tetrahydro-1H-benzazepin-1-yl)-1,2,3,4-tetrahydroquinoline

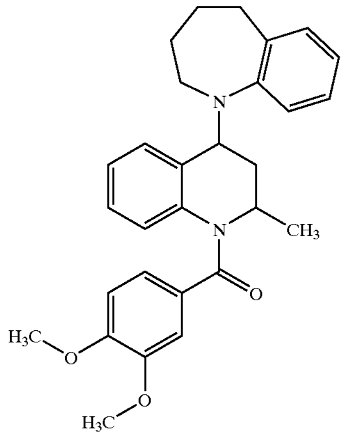

Starting with cis-1-(3,4-dimethoxybenzoyl)-2-methyl-1,2,3,4-tetrahydro-4-quinolinol (280 mg, 0.82 mmol) prepared in Reference Example 1 and 2,3,4,5-tetrahydro-1H-1-benzazepine (362 mg, 2.46 mmol), the same procedure as shown in Example 1 was repeated to give the titled compound (32 mg, yield: 9%) as a colorless oil. (cis:trans=1:1.5)

FABMS(pos) 479.2 [M+Na$^+$]

Example 63

(+)-2,4-trans-1-(3,4-Dimethoxybenzoyl)-2-methyl-4-(2,3,4,5-tetrahydro-1H-benzazepin-1-yl)-1,2,3,4-tetrahydroquinoline

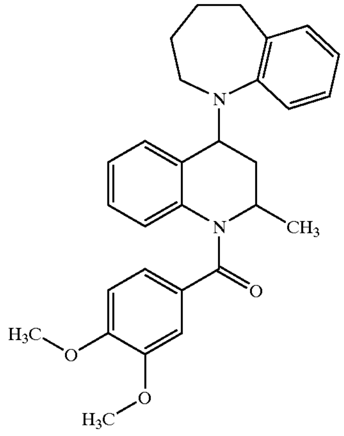

Starting with 1-(3,4-dimethoxybenzoyl)-2-methyl-4-(2,3,4,5-tetrahydro-1H-benzazepin-1-yl)-1,2,3,4- tetrahydroquinoline (431 mg) prepared in Example 62, the same procedure as shown in Example 5 was repeated to give the titled compound (198 mg). When analyzed for optical rotation with a Shodex OR-2 (wavelength: 470 nm), this compound was shown to be (+)-form.

$^1$H NMR ($CDCl_3$) δ (d, J=6.6 Hz, 3H), 1.50–1.80 (m, 4H), 1.99–2.05 (m, 1H), 2.55–2.60 (m, 1H), 2.78–2.81 (m, 2H), 2.92–2.98 (m, 1H), 3.00–3.20 (m, 1H), 3.62 (s, 3H), 3.87 (s, 3H), 4.82 (dd, J=8.1, 5.5 Hz, 1H), 4.89–4.95 (m, 1H), 6.63 (d, J=8.0 Hz, 1H), 6.72 (d, J=8.3 Hz, 1H), 6.89–7.15 (m, 8H), 7.51 (d, J=7.2 Hz, 1H).

Example 64

(−)-2,4-trans-1-(3,4-Dimethoxybenzoyl)-2-methyl-4-(2,3,4,5-tetrahydro-1H-benzazepin-1-yl)-1,2,3,4-tetrahydroquinoline

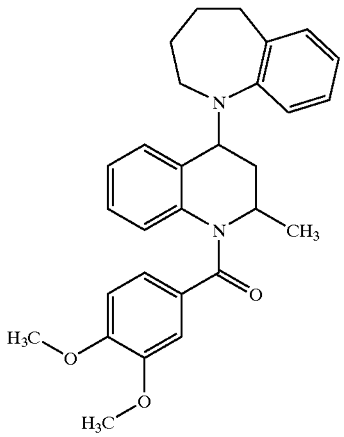

Starting with 1-(3,4-dimethoxybenzoyl)-2-methyl-4-(2,3,4,5-tetrahydro-1H-benzazepin-1-yl)-1,2,3,4-tetrahydroquinoline (431 mg) prepared in Example 62, the same procedure as shown in Example 5 was repeated to give the titled compound (199 mg). When analyzed for optical rotation with a Shodex OR-2 (wavelength: 470 nm), this compound was shown to be (−)-form.

$^1$H NMR ($CDCl_3$) δ (d, J=6.6 Hz, 3H), 1.50–1.80 (m, 4H), 1.99–2.05 (m, 1H), 2.55–2.60 (m, 1H), 2.78–2.81 (m, 2H), 2.92–2.98 (m, 1H), 3.00–3.20 (m, 1H), 3.62 (s, 3H), 3.87 (s, 3H), 4.82 (dd, J=8.1, 5.5 Hz, 1H), 4.89–4.95 (m, 1H), 6.63 (d, J=8.0 Hz, 1H), 6.72 (d, J=8.3 Hz, 1H), 6.89–7.15 (m, 8H), 7.51 (d, J=7.2 Hz, 1H).

Example 65

4-(6-Chloro-1,2,3,4-tetrahydroquinolin-1-yl)-1-(3,4-dimethoxybenzoyl)-2-methyl-1,2,3,4-tetrahydroquinoline

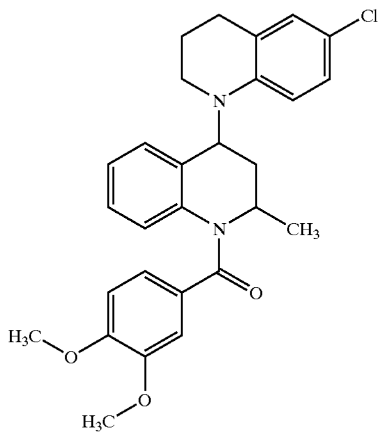

Starting with cis-1-(3,4-dimethoxybenzoyl)-2-methyl-1,2,3,4-tetrahydro-4-quinolinol (400 mg, 1.22 mmol) prepared in Reference Example 1 and 6-chloro-1,2,3,4-tetrahydroquinoline (614 mg, 3.66 mmol), the same procedure as shown in Example 1 was repeated to give the titled compound (216 mg, yield: 37%) as a colorless oil. (cis:trans=3.4:1)

Elementary Analysis for $C_{28}H_{29}N_2O_3Cl$: Calculated: C, 70.50; H, 6.13; N, 5.87. Found: C, 70.32; H, 6.17; N, 5.86.

Example 66

(+)-2,4-trans-4-(6-Chloro-1,2,3,4-tetrahydroquinolin-1-yl)-1-(3,4-dimethoxybenzoyl)-2-methyl-1,2,3,4-tetrahydroquinoline

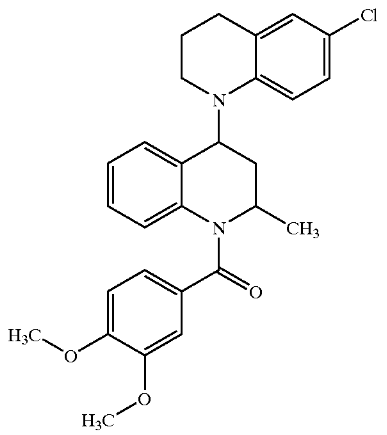

Starting with 4-(6-chloro-1,2,3,4-tetrahydroquinolin-1-yl)-1-(3,4-dimethoxybenzoyl)-2-methyl-1,2,3,4- tetrahydroquinoline (150 mg) prepared in Example 65, the same procedure as shown in Example 5 was repeated to give the titled compound (55 mg). When analyzed for optical rotation with a Shodex OR-2 (wavelength: 470 nm), this compound was shown to be (+)-form.

$^1$H NMR ($CDCl_3$) δ 1.36 (d, J=6.9 Hz, 3H), 1.80–2.00 (m, 2H), 2.06–2.14 (m, 1H), 2.22–2.31 (m, 1H), 2.76–2.80 (m, 2H), 3.13 (t, J=5.6 Hz, 2H), 3.77 (s, 3H), 3.89 (s, 3H), 5.00–5.15 (m, 1H), 5.26 (dd, J=11.2 Hz, 7.4 Hz, 1H), 6.67–6.79 (m, 3H), 6.90–7.05 (m, 6H), 7.29 (d, J=7.2 Hz, 1H).

Example 67

(−)-2,4-trans-4-(6-Chloro-1,2,3,4-tetrahydroquinolin-1-yl)-1-(3,4-dimethoxybenzoyl)-2-methyl-1,2,3,4-tetrahydroquinoline

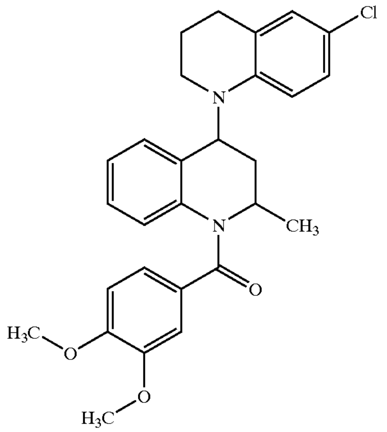

Starting with 4-(6-chloro-1,2,3,4-tetrahydroquinolin-1-yl)-1-(3,4-dimethoxybenzoyl)-2-methyl-1,2,3,4-tetrahydroquinoline (150 mg) prepared in Example 65, the same procedure as shown in Example 5 was repeated to give the titled compound (53 mg). When analyzed for optical rotation with a Shodex OR-2 (wavelength: 470 nm), this compound was shown to be (−)-form.

$^1$H NMR ($CDCl_3$) δ 1.36 (d, J=6.9 Hz, 3H), 1.80–2.00 (m, 2H), 2.06–2.14 (m, 1H), 2.22–2.31 (m, 1H), 2.76–2.80 (m, 2H), 3.13 (t, J=5.6 Hz, 2H), 3.77 (s, 3H), 3.89 (s, 3H), 5.00–5.15 (m, 1H), 5.26 (dd, J=11.2 Hz, 7.4 Hz, 1H), 6.67–6.79 (m, 3H), 6.90–7.05 (m, 6H), 7.29 (d, J=7.2 Hz, 1H).

Example 68

(+)-2,4-cis-4-(6-Chloro-1,2,3,4-tetrahydroquinolin-1-yl)-1-(3,4-dimethoxybenzoyl)-2-methyl-1,2,3,4-tetrahydroquinoline

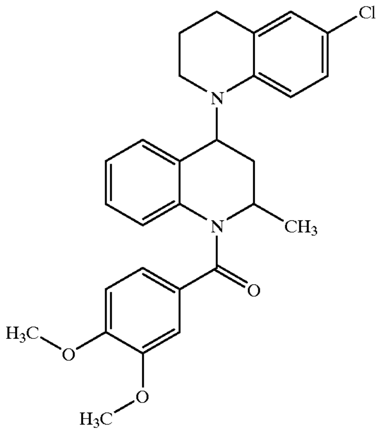

Starting with 4-(6-chloro-1,2,3,4-tetrahydroquinolin-1-yl)-1-(3,4-dimethoxybenzoyl)-2-methyl-1,2,3,4-tetrahydroquinoline (150 mg) prepared in Example 65, the same procedure as shown in Example 5 was repeated to give the titled compound (18 mg). When analyzed for optical rotation with a Shodex OR-2 (wavelength: 470 nm), this compound was shown to be (+)-form.

$^1$H NMR ($CDCl_3$) δ 1.38 (d, J=6.2 Hz, 3H), 1.60–1.80 (m, 1H), 1.90–2.20 (m, 2H), 2.68–2.76 (m, 1H), 2.80–2.90 (m, 2H), 3.33–3.37 (m, 2H), 3.62 (s, 3H), 3.86 (s, 3H), 4.73–4.90 (m, 2H), 6.38 (d, J=8.8 Hz, 1H), 6.62 (d, J=7.7 Hz, 1H), 6.60–6.73 (m, 2H), 6.85–7.10 (m, 6H).

Example 69

(−)-2,4-cis-4-(6-Chloro-1,2,3,4-tetrahydroquinolin-1-yl)-1-(3,4-dimethoxybenzoyl)-2-methyl-1,2,3,4-tetrahydroquinoline

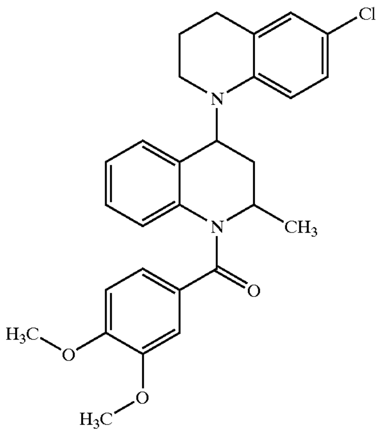

Starting with 4-(6-chloro-1,2,3,4-tetrahydroquinolin-1-yl)-1-(3,4-dimethoxybenzoyl)-2-methyl-1,2,3,4-tetrahydroquinoline (150 mg) prepared in Example 65, the same procedure as shown in Example 5 was repeated to give the titled compound (17 mg). When analyzed for optical rotation with a Shodex OR-2 (wavelength: 470 nm), this compound was shown to be (−)-form.

$^1$H NMR ($CDCl_3$) δ 1.38 (d, J=6.2 Hz, 3H), 1.60–1.80 (m, 1H), 1.90–2.20 (m, 2H), 2.68–2.76 (m, 1H), 2.80–2.90 (m, 2H), 3.33–3.37 (m, 2H), 3.62 (s, 3H), 3.86 (s, 3H), 4.73–4.90 (m. 2H), 6.38 (d, J=8.8 Hz, 1H), 6.62 (d, J=7.7 Hz, 1H), 6.60–6.73 (m, 2H), 6.85–7.10 (m, 6H).

Example 70

1-(3,4-Dimethoxybenzoyl)-2-methyl-4-(6-methyl-1,2,3,4-tetrahydroquinolin-1-yl)-1,2,3,4-tetrahydroquinoline

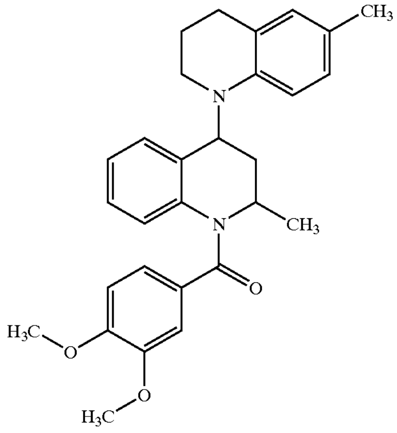

Starting with cis-1-(3,4-dimethoxybenzoyl)-2-methyl-1,2,3,4-tetrahydro-4-quinolinol (500 mg, 1.53 mmol) prepared in Reference Example 1 and 6-methyl-1,2,3,4-tetrahydroquinoline (676 mg, 4.59 mmol), the same procedure as shown in Example 1 was repeated to give the titled compound (117 mg, yield: 18%) as a white crystal. (cis:trans=1.6:1)

Elementary Analysis for $C_{29}H_{32}N_3O_3$: Calculated: C, 76.29; H, 7.06; N, 6.14. Found: C, 75.89; H, 6.94; N, 6.25.

Melting point: 139° C.–140° C. (crystallization solvent: diethyl ether-hexane)

Example 71

N-[1-[1-(3,4-Dimethoxybenzoyl)-2-methyl-1,2,3,4-tetrahydroquinolin-4-yl]-1,2,3,4-tetrahydroquinolin-6-yl]acetamide

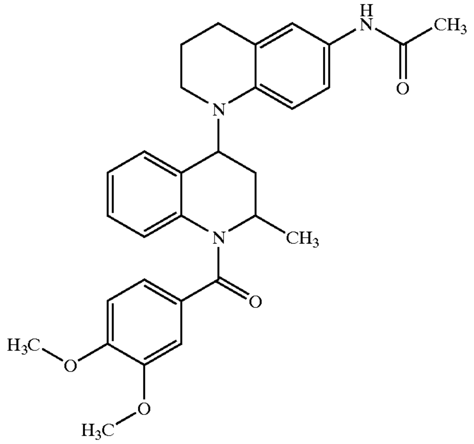

Starting with cis-1-(3,4-dimethoxybenzoyl)-2-methyl-1,2,3,4-tetrahydro-4-quinolinol (350 mg, 1.07 mmol) prepared in Reference Example 1 and N-(1,2,3,4-tetrahydro-quinolin-6-yl)acetamide (475 mg, 2.50 mmol), the same procedure as shown in Example 1 was repeated to give the titled compound (38 mg, yield: 7%) as a colorless oil. (cis:trans=1:1.7)

FABMS(pos) 522.1 [M+Na$^+$]

Example 72

4-[1-(3,4-Dimethoxybenzoyl)-2-methyl-1,2,3,4-tetrahydroquinolin-4-yl]-3,4-dihydro-2H-1,4-benzothiazine

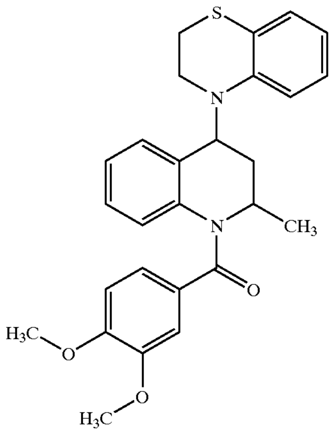

Starting with cis-1-(3,4-dimethoxybenzoyl)-2-methyl-1,2,3,4-tetrahydro-4-quinolinol (1.00 g, 2.93 mmol) prepared in Reference Example 1 and 3,4-dihydro-2H-1,4-benzothiazine (1.22 g, 8.07 mmol), the same procedure as shown in Example 1 was repeated to give the titled compound (335 mg, yield: 25%) as a white crystal. (cis:trans=1.5:1)

FABMS(pos) 483.1 [M+Na$^+$]

Melting point: 113° C.–114° C. (crystallization solvent: diisopropyl ether-hexane)

Example 73

1-(3,4-Dimethoxybenzoyl)-2-methyl-4-(1,2,3,4-tetrahydroisoquinolin-2-yl)-1,2,3,4-tetrahydroquinoline

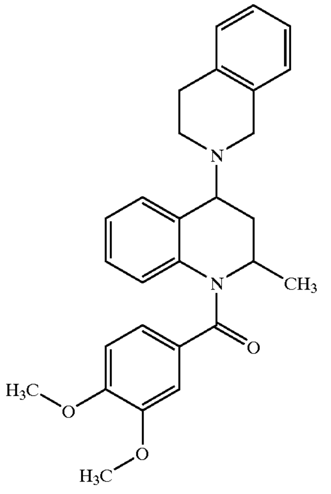

Starting with cis-1-(3,4-dimethoxybenzoyl)-2-methyl-1,2,3,4-tetrahydro-4-quinolinol (400 mg, 1.22 mmol) prepared in Reference Example 1 and 1,2,3,4-tetrahydroisoquinoline (487 mg, 3.66 mmol), the same procedure as shown in Example 1 was repeated to give the titled compound (210 mg, yield: 39%) as a white crystal. (cis:trans=1:1)

Elementary Analysis for $C_{28}H_{30}N_2O_3$: Calculated: C, 75.99; H, 6.83; N, 6.33. Found: C, 75.86; H, 7.20; N, 6.32.

Melting point: 128° C.–129° C. (crystallization solvent: diethyl ether-hexane)

The titled compounds of Examples 60 to 73 are summarized in Table 6 below.

TABLE 6

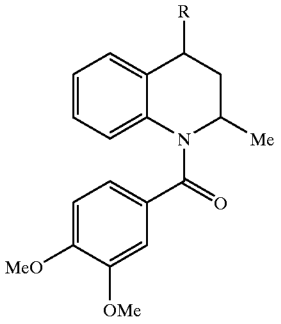

| Example No. | R | Stereochemistry |
|---|---|---|
| 60 | 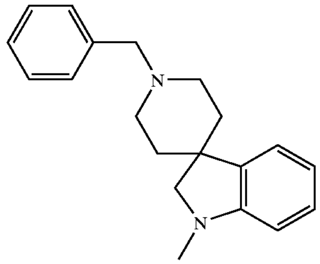 | cis/trans = 1/1.5 |
| 61 | 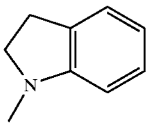 | cis/trans = 1/1.8 |
| 62 | 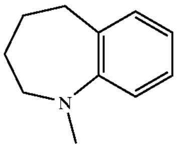 | cis/trans = 1/1.5 |
| 63 | 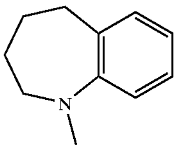 | trans (+) |
| 64 | 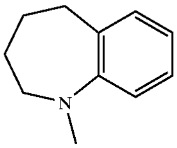 | trans (−) |
| 65 | 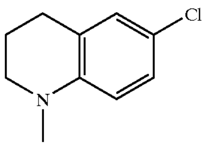 | cis/trans = 3.4/1 |
| 66 | 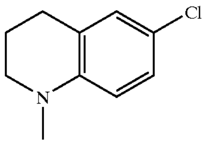 | trans (+) |

TABLE 6-continued

| | | |
|---|---|---|
| 67 | 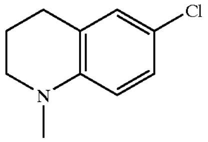 | trans (−) |
| 68 | 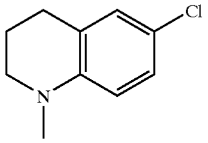 | cis (+) |
| 69 | 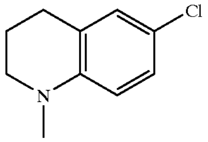 | cis (−) |
| 70 | 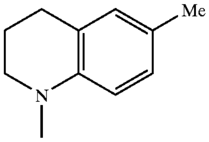 | cis/trans = 1.6/1 |
| 71 | 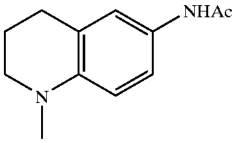 | cis/trans = 1/1.7 |
| 72 | 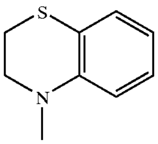 | cis/trans = 1.5/1 |
| 73 | 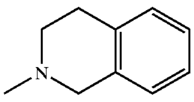 | cis/trans = 1/1 |

Example 74

2,3-trans-2,4-cis-1-(3,4-Dimethoxybenzoyl)-3-hydroxy-2-propyl-4-(1,2,3,4-tetrahydroquinolin-1-yl)-1,2,3,4-tetrahydroquinoline

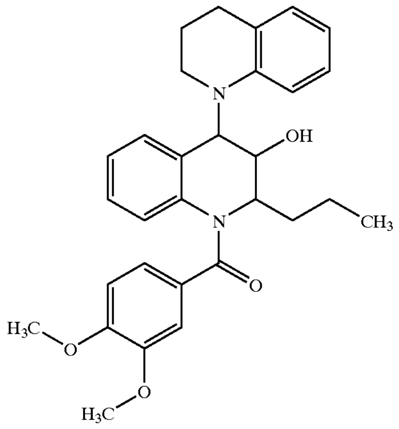

Starting with 3-(3,4-dimethoxybenzoyl)-2-propyl-1a,2,3,7b-tetrahydrooxyleno[2,3-c]quinoline (400 mg, 1.13 mmol) prepared in Reference Example 17, the same procedure as shown in Example 14 was repeated to give the titled compound (169 mg, yield: 31%) as a white crystal.

Elementary Analysis for $C_{30}H_{34}N_2O_4 0.25H_2O$: Calculated: C, 73.37; H, 7.08; N, 5.70. Found: C, 73.65; H, 7.04; N, 5.44.

Melting point: 160° C.–162° C. (crystallization solvent: diisopropyl ether-hexane)

Example 75

2,4-cis-1-(3,4-Dimethoxybenzoyl)-2-propyl-4-(1,2,3,4-tetrahydroquinolin-1-yl)-1,2,3,4-tetrahydroquinoline

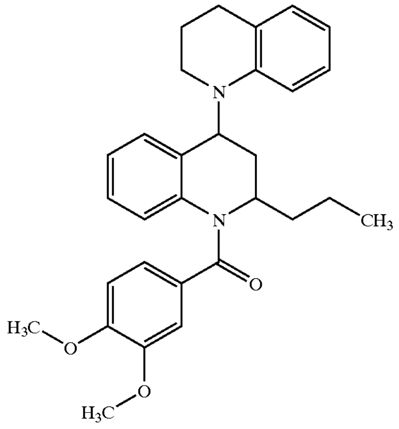

Starting with 2,3-trans-2,4-cis-1-(3,4-dimethoxybenzoyl)-3-hydroxy-2-propyl-4-(1,2,3,4-tetrahydroquinolin-1-yl)-1,2,3,4-tetrahydroquinoline (353 mg, 0.72 mmol) prepared in Example 74, the same procedures as shown in Examples 15 and 16 were repeated to give the titled compound (131 mg, yield over 2 steps: 39%) as a white crystal.

Elementary Analysis for $C_{30}H_{34}N_2O_3$: Calculated: C, 76.57; H, 7.28; N, 5.95. Found: C, 76.36; H, 7.41; N, 5.98.

Melting point: 176° C.–177° C. (crystallization solvent: ethyl acetate-hexane)

Example 76

2,3-trans-2,4-cis-2-Butyl-1-(3,4-dimethoxybenzoyl)-3-hydroxy-4-(1,2,3,4-tetrahydroquinolin-1-yl)-1,2,3,4-tetrahydroquinoline

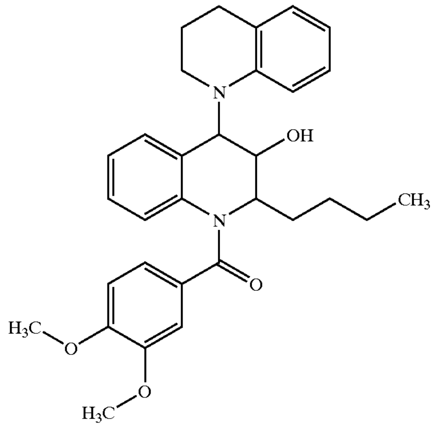

Starting with 2-butyl-3-(3,4-dimethoxybenzoyl)-1a,2,3,7b-tetrahydrooxyleno[2,3-c]quinoline (1.10 g, 3.00 mmol) prepared in Reference Example 18 and 1,2,3,4-tetrahydroquinoline, the same procedure as shown in Example 14 was repeated to give the titled compound (1.11 g, yield: 74%) as a white crystal.

Elementary Analysis for $C_{31}H_{36}N_2O_4$: Calculated: C, 74.37; H, 7.25; N, 5.60. Found: C, 74.24; H, 7.46; N, 5.43.

Melting point: 200° C.–202° C. (crystallization solvent: ethyl acetate-hexane)

Example 77

2,4-cis-2-Butyl-1-(3,4-dimethoxybenzoyl)-4-(1,2,3,4-tetrahydroquinolin-1-yl)-1,2,3,4-tetrahydroquinoline

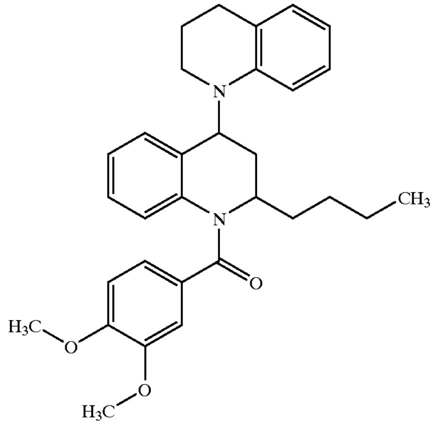

Starting with 2,3-trans-2,4-cis-2-butyl-1-(3,4-dimethoxybenzoyl)-3-hydroxy-4-(1,2,3,4-tetrahydroquinolin-1-yl)-1,2,3,4-tetrahydroquinoline (500 mg, 1.00 mmol) prepared in Example 76, the same procedures as shown in Examples 15 and 16 were repeated to give the titled compound (560 mg, yield over 2 steps: 62%) as a white crystal.

Elementary Analysis for $C_{31}H_{36}N_2O_3$: Calculated: C, 76.83; H, 7.49; N, 5.78. Found: C, 76.68; H, 7.53; N, 5.68.

Melting point: 159° C.–160° C. (crystallization solvent: ethyl acetate-hexane)

Example 78

2,3-trans-2,4-cis-1-(3,4-Dimethoxybenzoyl)-3-[[(isopropylamino)carbonyl]oxy]-2-methyl-4-(1,2,3,4-tetrahydroquinolin-1-yl)-1,2,3,4-tetrahydroquinoline

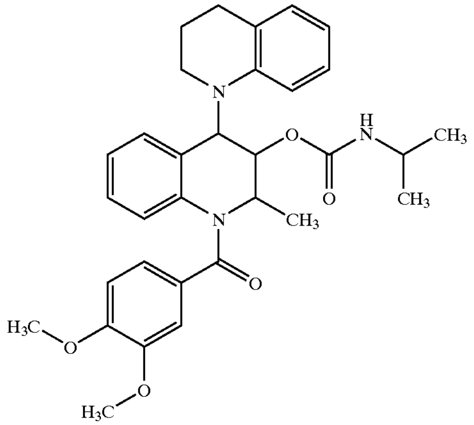

Starting with 2,3-trans-2,4-cis-1-(3,4-dimethoxybenzoyl)-3-hydroxy-2-methyl-4-(1,2,3,4-tetrahydroquinolin-1-yl)-1,2,3,4-tetrahydroquinoline (200 mg, 0.44 mmol) prepared in Example 14 and isopropylisocyanate (170 mg, 2.0 mmol), the same procedure as shown in Example 27 was repeated to give the titled compound (190 mg, yield: 80%) as a white crystal.

Melting point: 183° C.–184° C.

Example 79

2,3-trans-2,4-cis-1-(3,4-Dimethoxybenzoyl)-2-methyl-3-[[(phenylamino)carbonyl]oxy]-4-(1,2,3,4-tetrahydroquinolin-1-yl)-1,2,3,4-tetrahydroquinoline

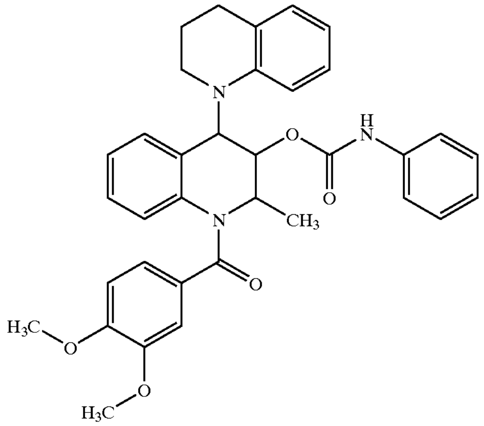

Starting with 2,3-trans-2,4-cis-1-(3,4-dimethoxybenzoyl)-3-hydroxy-2-methyl-4-(1,2,3,4-tetrahydroquinolin-1-yl)-1,2,3,4-tetrahydroquinoline (200 mg, 0.44 mmol) prepared in Example 14 and phenylisocyanate (138 mg, 2.0 mmol), the same procedure as shown in Example 27 was repeated to give the titled compound (138 mg, yield: 55%) as a white crystal.

Melting point: 233° C.–234° C.

Example 80

2,3-trans-2,4-cis-1-(3,4-Dimethoxybenzoyl)-3-hydroxy-2-methyl-4-(7-methyl-1,2,3,4-tetrahydroquinolin-1-yl)-1,2,3,4-tetrahydroquinoline

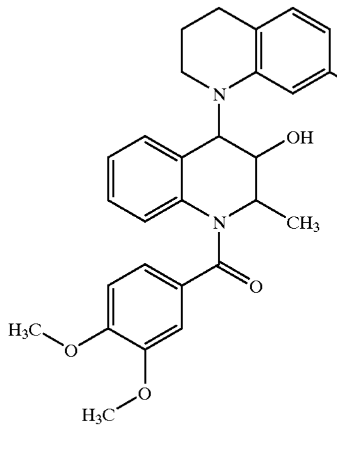

Starting with 3-(3,4-dimethoxybenzoyl)-2-methyl-1a,2,3,7b-tetrahydrooxyleno[2,3-c]quinoline (976 mg, 3.00 mmol) prepared in Reference Example 3 and 7-methyl-1,2,3,4-tetrahydroquinoline (883 mg, 6.00 mmol), the same procedure as shown in Example 14 was repeated to give the titled compound (372 mg, yield: 26%) as a white crystal.

Elementary Analysis for $C_{29}H_{32}N_2O_4 0.25H_2O$: Calculated: C, 73.01; H, 6.87; N, 5.87. Found: C, 73.15; H, 7.08; N, 5.87.

Melting point: 130° C.–131° C. (crystallization solvent: diisopropyl ether-hexane)

Example 81

2,4-cis-1-(3,4-Dimethoxybenzoyl)-2-methyl-4-(7-methyl-1,2,3,4-tetrahydroquinolin-1-yl)-1,2,3,4-tetrahydroquinoline

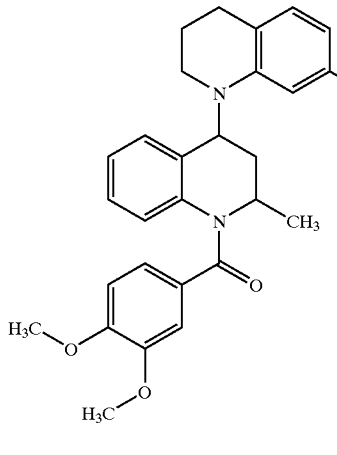

Starting with 2,3-trans-2,4-cis-1-(3,4-dimethoxybenzoyl)-3-hydroxy-2-methyl-4-(7-methyl-1,2,3,4-tetrahydroquinolin-1-yl)-1,2,3,4-tetrahydroquinoline (473 mg, 1.00 mmol) prepared in Example 80, the same procedures as shown in Examples 15 and 16 were repeated to give the titled compound (320 mg, yield over 2 steps: 70%) as a white crystal.

Elementary Analysis for $C_{29}H_{32}N_2O_3$: Calculated: C, 76.29; H, 7.06; N, 6.14. Found: C, 76.00; H, 7.27; N, 5.93.

Melting point: 197° C.–198° C. (crystallization solvent: diisopropyl ether-hexane)

Example 82

2,3-trans-2,4-cis-1-(3,4-Dimethoxybenzoyl)-3-hydroxy-2-methyl-4-(6-methyl-1,2,3,4-tetrahydroquinolin-1-yl)-1,2,3,4-tetrahydroquinoline

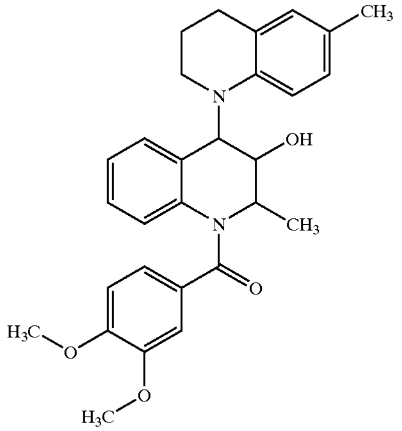

Starting with 3-(3,4-dimethoxybenzoyl)-2-methyl-1 a,2,3,7b-tetrahydrooxyleno[2,3-c]quinoline (813 mg, 2.50 mmol) prepared in Reference Example 3 and 6-methyl-1,2,3,4-tetrahydroquinoline (552 mg, 3.74 mmol), the same procedure as shown in Example 14 was repeated to give the titled compound (679 mg, yield: 57%) as a white crystal.

Elementary Analysis for $C_{29}H_{32}N_2O_4$: Calculated: C, 73.70; H, 6.83; N, 5.93. Found: C, 73.39; H, 6.98; N, 5.91.

Example 83

2,4-cis-1-(3,4-Dimethoxybenzoyl)-2-methyl-4-(6-methyl-1,2,3,4-tetrahydroquinolin-1-yl)-1,2,3,4-tetrahydroquinoline

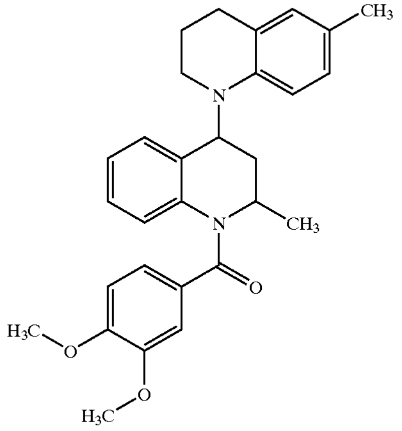

Starting with 2,3-trans-2,4-cis-1-(3,4-dimethoxybenzoyl)-3-hydroxy-2-methyl-4-(6-methyl-1,2,3,4-tetrahydroquinolin-1-yl)-1,2,3,4-tetrahydroquinoline (600 mg, 1.27 mmol) prepared in Example 82, the same procedures as shown in Examples 15 and 16 were repeated to give the titled compound (169 mg, yield: 30%) as a white crystal.

Melting point: 184° C.–185° C. (crystallization solvent: ethyl acetate-hexane) Elementary Analysis for $C_{29}H_{32}N_2O_3$: Calculated: C, 76.29; H, 7.06; N, 6.14. Found: C, 76.14; H, 6.99; N, 6.12.

Example 84

2,3-trans-2,4-cis-1-(3,4-Dimethoxybenzoyl)-3-hydroxy-4-(6-isopropyl-1,2,3,4-tetrahydroquinolin-1-yl)-2-methyl-1,2,3,4-tetrahydroquinoline

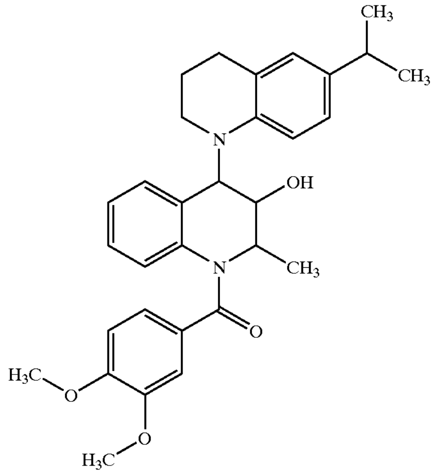

Starting with 3-(3,4-dimethoxybenzoyl)-2-methyl-1a,2,3,7b-tetrahydrooxyleno[2,3-c]quinoline (976 mg, 3.00 mmol) prepared in Reference Example 3 and 6-isopropyl-1,2,3,4-tetrahydroquinoline (789 mg, 4.50 mmol), the same procedure as shown in Example 14 was repeated to give the titled compound (1.06 g, yield: 71%) as a white crystal.

Elementary Analysis for $C_{31}H_{36}N_2O_4$: Calculated: C, 74.37; H, 7.25; N, 5.60. Found: C, 74.11; H, 7.61; N, 5.35.

Melting point: 165° C.–166° C. (crystallization solvent: ethyl acetate-hexane)

Example 85

2,4-cis-4-(6-Isopropyl-1,2,3,4-tetrahydroquinolin-1-yl)-1-(3,4-dimethoxybenzoyl)-2-methyl-1,2,3,4-tetrahydroquinoline

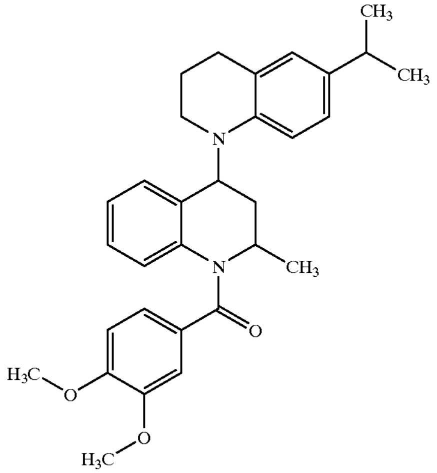

Starting with 2,3-trans-2,4-cis-1-(3,4-dimethoxybenzoyl)-3-hydroxy-4-(6-isopropyl-1,2,3,4-tetrahydroquinolin-1-yl)-2-methyl-1,2,3,4-tetrahydroquinoline (499 mg, 1.00 mmol) prepared in Example 84, the same procedures as shown in Examples 15 and 16 were repeated to give the titled compound (240 mg, yield over 2 steps: 50%) as a white crystal.

Elementary Analysis for $C_{31}H_{36}N_2O_3$: Calculated: C, 76.83; H, 7.49; N, 5.78. Found: C, 76.45; H, 7.57; N, 5.88.

Melting point: 187° C.–188° C. (crystallization solvent: ethyl acetate-hexane)

Example 86

2,3-trans-2,4-cis-4-(5-Chloro-1,2,3,4-tetrahydroquinolin-1-yl)-1-(3,4-dimethoxybenzoyl)-3-hydroxy-2-methyl-1,2,3,4-tetrahydroquinoline

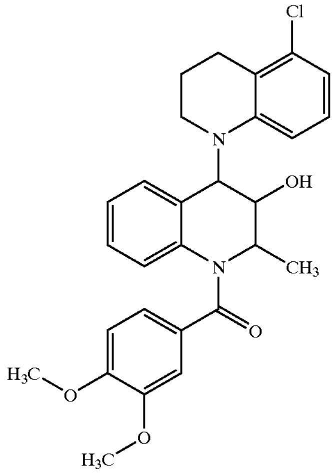

Starting with 3-(3,4-dimethoxybenzoyl)-2-methyl-1a,2,3,7b-tetrahydrooxyleno[2,3-c]quinoline (976 mg, 3.00 mmol) prepared in Reference Example 3 and 5-chloro-1,2,3,4-tetrahydroquinoline (754 mg, 4.50 mmol), the same procedure as shown in Example 14 was repeated to give the titled compound (1.01 g, yield: 69%) as a white crystal.

Elementary Analysis for $C_{28}H_{29}N_2O_4$: Calculated: C, 68.22; H, 5.93; N, 5.68. Found: C, 68.17; H, 5.94; N, 5.56.

Melting point: 205° C.–206° C. (crystallization solvent: tetrahydrofuran-hexane)

Example 87

2,4-cis-4-(5-Chloro-1,2,3,4-tetrahydroquinolin-1-yl)-1-(3,4-dimethoxybenzoyl)-2-methyl-1,2,3,4-tetrahydroquinoline

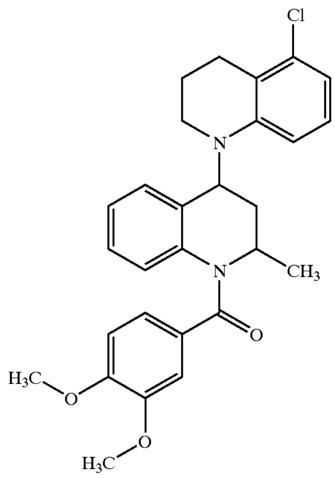

Starting with 2,3-trans-2,4-cis-4-(5-chloro-1,2,3,4-tetrahydroquinolin-1-yl)-1-(3,4-dimethoxybenzoyl)-3-hydroxy-2-methyl-1,2,3,4-tetrahydroquinoline (493 mg, 1.00 mmol) prepared in Example 86, the same procedures as shown in Examples 15 and 16 were repeated to give the titled compound (172 mg, yield over 2 steps: 36%) as a white crystal.

Elementary Analysis for $C_{28}H_{29}ClN_2O_3 0.25H_2O$: Calculated: C, 69.84; H, 6.18; N, 5.82. Found: C, 69.64; H, 5.89; N, 5.61.

Melting point: 194° C.–195° C. (crystallization solvent: diethyl ether-hexane)

Example 88

2,3-trans-2,4-cis-1-(3,4-Dimethoxybenzoyl)-3-hydroxy-2-methyl-4-(1,2,4,5-tetrahydro-3H-3-benzazepin-3-yl)-1,2,3,4-tetrahydroquinoline

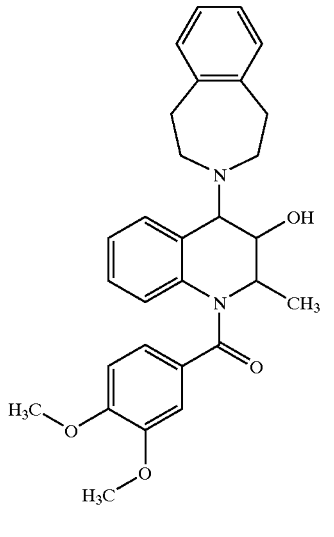

Starting with 3-(3,4-dimethoxybenzoyl)-2-methyl-1a,2,3,7b-tetrahydrooxyleno[2,3-c]quinoline (813 mg, 2.50 mmol) prepared in Reference Example 3 and 2,3,4,5-tetrahydro-1H-3-benzazepine (552 mg, 3.75 mmol), the same procedure as shown in Example 14 was repeated to give the titled compound (624 mg, yield: 53%) as a white crystal.

Melting point: 191° C.–192° C. (crystallization solvent: ethyl acetate-hexane)

$^1$H NMR ($CDCl_3$) δ 1.32 (d, J=6.6 Hz, 3H), 2.93–3.30 (m, 9H), 3.65–3.76 (m, 4H), 3.83 (s, 3H), 3.89 (d, J=8.7 Hz, 1H), 4.55–4.63 (m, 1H), 6.54–6.62 (m, 2H), 6.71 (dd, J=8.3, 1.8 Hz, 1H), 6.83 (d, J=1.7 Hz, 1H), 6.91 (t, J=7.6 Hz, 1H), 7.09 (t, J=7.4 Hz, 1H), 7.20 (br s. 4H), 7.53 (d, J=7.6 Hz, 1H).

Example 89

2,3-trans-2,4-cis-1-(3,4-Dimethoxybenzoyl)-3-hydroxy-2-methyl-4-(1,2,3,4-tetrahydroisoquinolin-2-yl)-1,2,3,4-tetrahydroquinoline

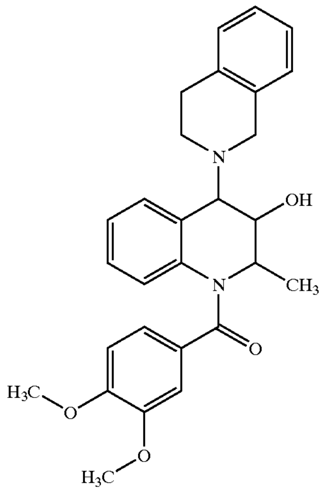

Starting with 3-(3,4-dimethoxybenzoyl)-2-methyl-1a,2,3,7b-tetrahydrooxyleno[2,3-c]quinoline (813 mg, 2.50 mmol) prepared in Reference Example 3 and 1,2,3,4-tetrahydroisoquinoline (499 mg, 3.75 mmol), the same procedure as shown in Example 14 was repeated to give the titled compound (623 mg, yield: 54%) as an amorphous powder.

$^1$H-NMR ($CDCl_3$) δ 1.32 (d, J=6.6 Hz, 3H), 2.90–3.30 (m, 5H), 3.67 (s, 3H), 3.83 (s, 3H), 3.85–3.89 (m, 1H), 4.02 (d, J=8.3 Hz, 1H), 4.19 (d, J=15.0 Hz, 1H), 4.34 (d, J=150 Hz, 1H), 4.67–4.70 (m, 1H), 6.57–6.63 (m, 2H), 6.76–6.80 (m, 1H), 6.85 (m, 1H), 6.93 (t, J=7.7 Hz, 1H), 7.06–7.11 (m, 2H), 7.15–7.19 (m, 3H), 7.57 (d, J=7.7 Hz, 1H).

FABMS(pos) 459.2 [M+H$^+$]

The titled compounds of Examples 74 to 89 are summarized in Table 7 below.

TABLE 7
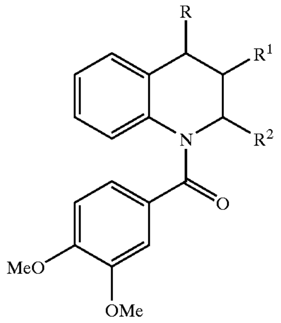
| Example No. | R | $R^1$ | $R^2$ | Stereochemistry |
| --- | --- | --- | --- | --- |
| 74 | 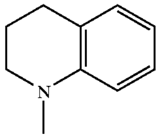 | OH | $C_3H_7$ | 2,3-trans 2,4-cis |
| 75 | 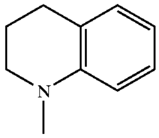 | H | $C_3H_7$ | 2,4-cis |
| 76 | 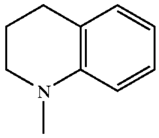 | OH | $C_4H_9$ | 2,3-trans 2,4-cis |
| 77 | 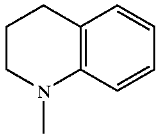 | H | $C_4H_9$ | 2,4-cis |
| 78 | 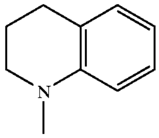 | $OCONHCH(CH_3)_2$ | $CH_3$ | 2,3-trans 2,4-cis |
| 79 | 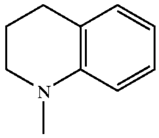 | OCONHPh | $CH_3$ | 2,3-trans 2,4-cis |
| 80 | 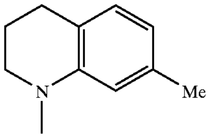 | OH | $CH_3$ | 2,3-trans 2,4-cis |

TABLE 7-continued
| | | | | |
|---|---|---|---|---|
| 81 | 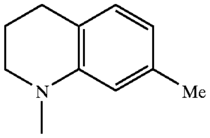 | H | $CH_3$ | 2,4-cis |
| 82 | 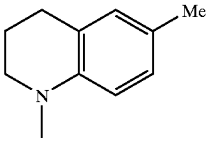 | OH | $CH_3$ | 2,3-trans<br>2,4-cis |
| 83 | 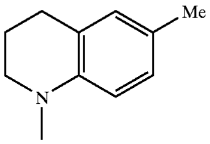 | H | $CH_3$ | 2,4-cis |
| 84 | 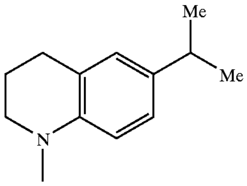 | OH | $CH_3$ | 2,3-trans<br>2,4-cis |
| 85 | 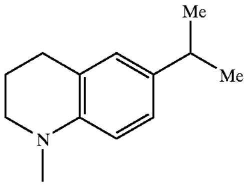 | H | $CH_3$ | 2,4-cis |
| 86 | 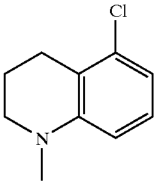 | OH | $CH_3$ | 2,3-trans<br>2,4-cis |
| 87 | 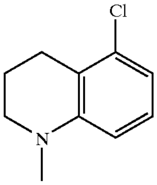 | H | $CH_3$ | 2,4-cis |
| 88 | 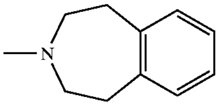 | OH | $CH_3$ | 2,3-trans<br>2,4-cis |
| 89 | 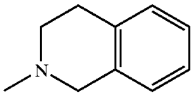 | OH | $CH_3$ | 2,3-trans<br>2,4-cis |

Example 90

(+)-2,4-cis-1-(3,4-Dimethoxybenzoyl)-2-methyl-4-(1,2,3,4-tetrahydroisoquinolin-2-yl)-1,2,3,4-tetrahydroquinoline

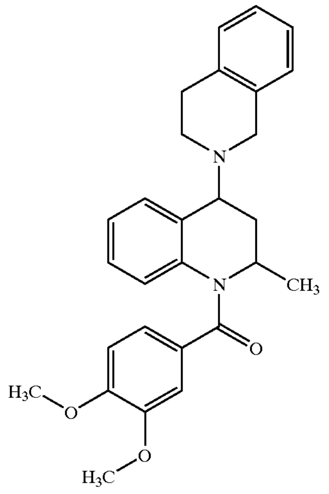

Starting with 1-(3,4-dimethoxybenzoyl)-2-methyl-4-(1,2,3,4-tetrahydroisoquinolin-2-yl)-1,2,3,4-tetrahydroquinoline (1.7 g) prepared in Example 73, the same procedure as shown in Example 5 was repeated to give the titled compound (343 mg). When analyzed for optical rotation with a Shodex OR-2 (wavelength: 470 nm), this compound was shown to be (+)-form.

$^1$H NMR ($CDCl_3$) δ 1.34 (d, J=6.4 Hz, 3H), 1.64–1.72 (m, 1H), 2.69–2.78 (m, 1H), 2.85–2.94 (m, 4H), 3.57 (s, 3H), 3.65–3.74 (m, 2H), 3.82 (s, 3H), 3.90 (d, J=14.7 Hz, 1H), 4.77–4.84 (m, 1H), 6.59–6.63 (m, 2H), 6.79 (d, J=1.7 Hz, 1H), 6.96–7.10 (m, 7H), 7.33 (dd, J=7.4, 1.2 Hz, 1H).

Example 91

(−)-2,4-cis-1-(3,4-Dimethoxybenzoyl)-2-methyl-4-(1,2,3,4-tetrahydroisoquinolin-2-yl)-1,2,3,4-tetrahydroquinoline

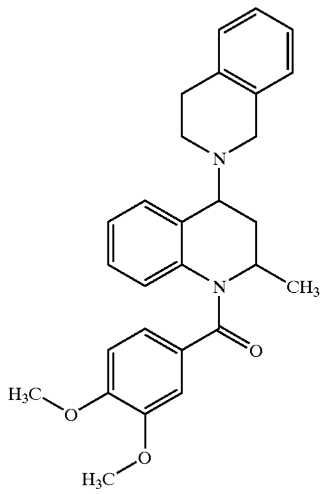

Starting with 1-(3,4-dimethoxybenzoyl)-2-methyl-4-(1,2,3,4-tetrahydroisoquinolin-2-yl)-1,2,3,4-tetrahydroquinoline (1.7 g) prepared in Example 73, the same procedure as shown in Example 5 was repeated to give the titled compound (314 mg). When analyzed for optical rotation with a Shodex OR-2 (wavelength: 470 nm), this compound was shown to be (−)-form.

$^1$H NMR ($CDCl_3$) δ 1.34 (d, J=6.4 Hz, 3H), 1.64–1.72 (m, 1H), 2.69–2.78 (m, 1H), 2.85–2.94 (m, 4H), 3.57 (s, 3H), 3.65–3.74 (m, 2H), 3.82 (s, 3H), 3.90 (d, J=14.7 Hz, 1H), 4.77–4.84 (m, 1H), 6.59–6.63 (m, 2H), 6.79 (d, J=1.7 Hz, 1H), 6.96–7.10 (m, 7H), 7.33 (dd, J=7.4, 1.2 Hz, 1H).

Example 92

(+)-2,4-trans-1-(3,4-Dimethoxybenzoyl)-2-methyl-4-(1,2,3,4-tetrahydroisoquinolin-2-yl)-1,2,3,4-tetrahydroquinoline

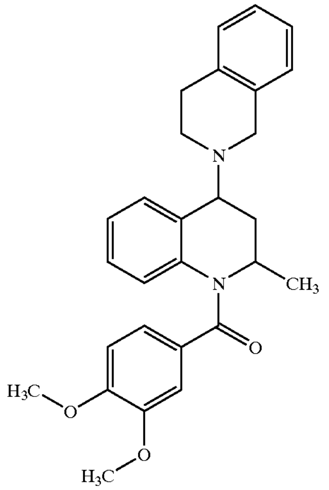

Starting with 1-(3,4-dimethoxybenzoyl)-2-methyl-4-(1,2,3,4-tetrahydroisoquinolin-2-yl)-1,2,3,4-tetrahydroquinoline (1.7 g) prepared in Example 73, the same procedure as shown in Example 5 was repeated to give the titled compound (411 mg). When analyzed for optical rotation with a Shodex OR-2 (wavelength: 470 nm), this compound was shown to be (+)-form.

$^1$H NMR ($CDCl_3$) δ 1.27–1.42 (m, 4H), 2.71–2.82 (m, 2H), 2.93–3.16 (m, 3H), 3.62 (s, 3H), 3.86 (s, 3H), 3.86–3.96 (m, 2H), 4.11 (d, J=14.7 Hz, 1H), 4.77–4.84 (m, 1H) 6.55–6.62 (m, 2H), 6.72–6.76 (m, 2H), 6.92 (t, J=7.5 Hz, 1H), 7.08–7.18 (m, 5H), 7.52 (d, J=7.5 Hz, 1H).

Example 93

(−)-2,4-trans-1-(3,4-Dimethoxybenzoyl)-2-methyl-4-(1,2,3,4-tetrahydroisoquinolin-2-yl)-1,2,3,4-tetrahydroquinoline

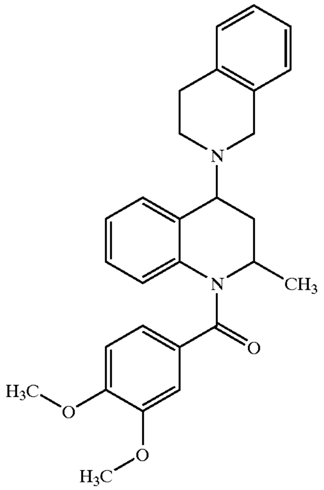

Starting with 1-(3,4-dimethoxybenzoyl)-2-methyl-4-(1,2,3,4-tetrahydroisoquinolin-2-yl)-1,2,3,4-tetrahydroquinoline (1.7 g) prepared in Example 73, the same procedure as shown in Example 5 was repeated to give the titled compound (451 mg). When analyzed for optical rotation with a Shodex OR-2 (wavelength: 470 nm), this compound was shown to be (−)-form.

$^1$H NMR ($CDCl_3$) δ 1.27–1.42 (m, 4H), 2.71–2.82 (m, 2H), 2.93–3.16 (m, 3H), 3.62 (s, 3H), 3.86 (s, 3H), 3.86–3.96 (m, 2H), 4.11 (d, J=14.7 Hz, 1H), 4.77–4.84 (m, 1H), 6.55–6.62 (m, 2H), 6.72–6.76 (m, 2H), 6.92 (t, J=7.5 Hz, 1H), 7.08–7.18 (m, 5H), 7.52 (d, J=7.5 Hz, 1H).

Example 94

Ethyl 5-[[1-[1-(3,4-dimethoxybenzoyl)-2-methyl-1,2,3,4-tetrahydro-4-quinolinyl]-1,2,3,4-tetrahydro-6-quinolinyl]oxy]pentanoate

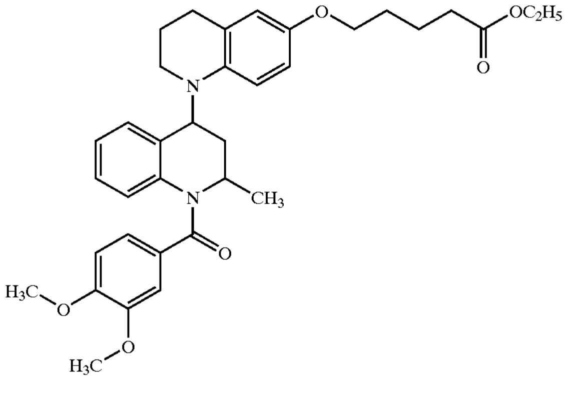

Starting with cis-1-(3,4-dimethoxybenzoyl)-2-methyl-1,2,3,4-tetrahydro-4-quinolinol (1.0 g, 3.05 mmol) prepared in Reference Example 1 and ethyl 5-[(1,2,3,4-tetrahydro-6-quinolinyl)oxy]pentanoate (487 mg, 3.66 mmol), the same procedure as shown in Example 1 was repeated to give the titled compound (760 mg, yield: 42%) as a colorless oil. (cis:trans=1:1.2)

FABMS(pos) 586.2 [$M^+$]

Example 95

5-[[1-[1-(3,4-Dimethoxybenzoyl)-2-methyl-1,2,3,4-tetrahydro-4-quinolinyl]-1,2,3,4-tetrahydro-6-quinolinyl]oxy]pentanoic aicd

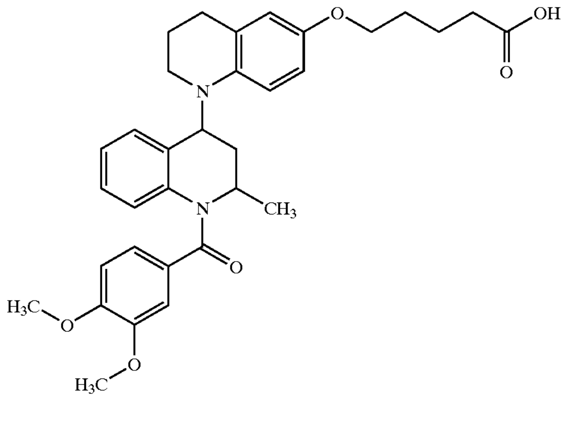

Ethyl 5-[[1-[1-(3,4-dimethoxybenzoyl)-2-methyl-1,2,3,4-tetrahydro-4-quinolinyl]-1,2,3,4-tetrahydro-6-quinolinyl]oxy]pentanoate (100 mg, 0.17 mmol) prepared in Example 94 was dissolved in THF (3 ml), ethanol (2 ml) and water (2 ml), to which lithium hydroxide monohydrate (21 mg, 0.51 mmol) was then added and stirred at room temperature for 3 hours. The reaction mixture was neutralized with 1N hydrochloric acid and then extracted with ethyl acetate. After the organic layer was dried and concentrated, the residue was applied to silica gel column chromatography (developing solvent: ethyl acetate/hexane=4/1) to give the titled compound (33 mg, yield: 35%) as a colorless oil. (cis:trans=1:1.5)

FABMS(pos) 558.2 [$M^+$]

Example 96

5-[[1-[1-(3,4-Dimethoxybenzoyl)-2-methyl-1,2,3,4-tetrahydro-4-quinolinyl]-1,2,3,4-tetrahydro-6-quinolinyl]oxy]-N-propylpentanamide

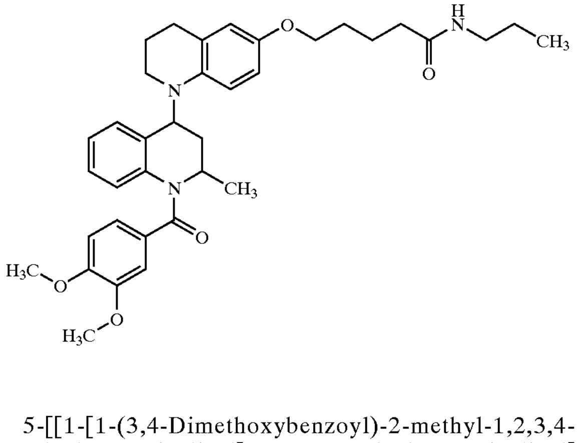

5-[[1-[1-(3,4-Dimethoxybenzoyl)-2-methyl-1,2,3,4-tetrahydro-4-quinolinyl]-1,2,3,4-tetrahydro-6-quinolinyl]oxy]pentanoic acid (197 mg, 0.35 mmol) prepared in Example 95 was dissolved in THF (10 ml), to which oxalyl chloride (0.079 ml, 1.05 mmol) and DMF (0.1 ml) were then added on ice and stirred at room temperature for 1 hour.

After the reaction mixture was concentrated, the residue was dissolved in pyridine (10 ml) on ice and propylamine (62 mg, 1.05 mmol) was added thereto, followed by stirring at room temperature for 16 hours. After the reaction mixture was diluted with ethyl acetate, washed with water, dried and concentrated, the residue was applied to silica gel column chromatography (developing solvent: ethyl acetate/hexane=4/1) to give the titled compound (51 mg, yield: 24%) as a colorless oil. (cis:trans=1:2.8)

FABMS(pos) 599.2 [$M^+$]

Example 97

N,N-Dimethylcarbamic acid [1-[1-(3,4-dimethoxybenzoyl)-2-methyl-1,2,3,4-tetrahydro-4-quinolinyl]-1,2,3,4-tetrahydro-6-quinolinyl]

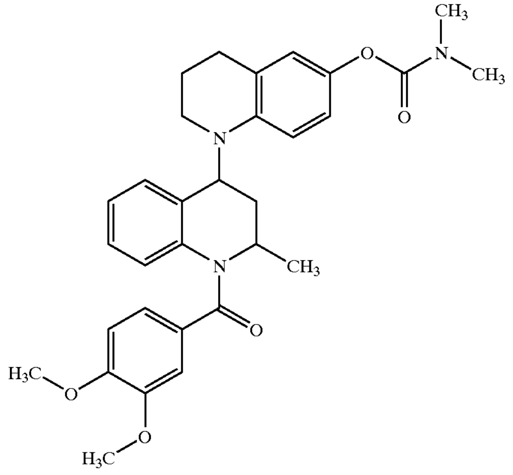

Starting with cis-1-(3,4-dimethoxybenzoyl)-2-methyl-1,2,3,4-tetrahydro-4-quinolinol (600 mg, 1.83 mmol) prepared in Reference Example 1 and N,N-dimethylcarbamic acid (1,2,3,4-tetrahydro-6-quinolinyl) (1.00 g, 4.58 mmol), the same procedure as shown in Example 1 was repeated to give the titled compound (290 mg, yield: 29%) as a white crystal. (cis:trans=3.3:1)

Elementary Analysis for $C_{31}H_{35}N_3O_5$ $0.2H_2O$: Calculated: C, 69.83; H, 6.69; N, 7.88. Found: C, 69.88; H, 6.79; N, 7.66.

Example 98 tert-Butyl N-[1-[1-(3,4-dimethoxybenzoyl)-2-methyl-1,2,3,4-tetrahydro-4-quinolinyl]-1,2,3,4-tetrahydro-6-quinolinyl]carbamate

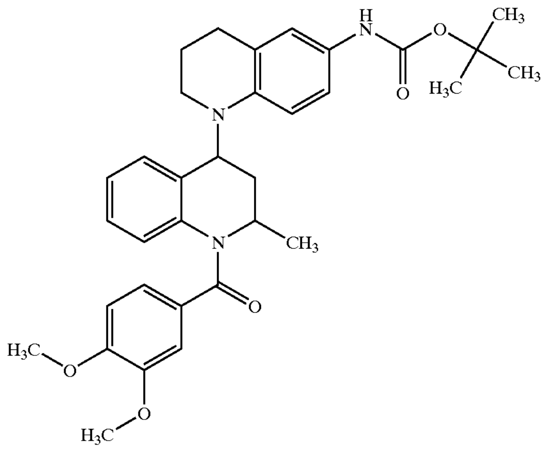

Starting with cis-1-(3,4-dimethoxybenzoyl)-2-methyl-1,2,3,4-tetrahydro-4-quinolinol (712 mg, 2.18 mmol) prepared in Reference Example 1 and tert-butyl N-(1,2,3,4-tetrahydro-6-quinolinyl)carbamate (1.35 g, 5.44 mmol), the same procedure as shown in Example 1 was repeated to give the titled compound (157 mg, yield: 13%) as a white crystal. (cis:trans=4.8:1)

Melting point: 192° C.–193° C. (crystallization solvent: diethyl ether-hexane)

Example 99

N-[1-[1-(3,4-Dimethoxybenzoyl)-2-methyl-1,2,3,4-tetrahydro-4-quinolinyl]-1,2,3,4-tetrahydro-6-quinolinyl]butanamide

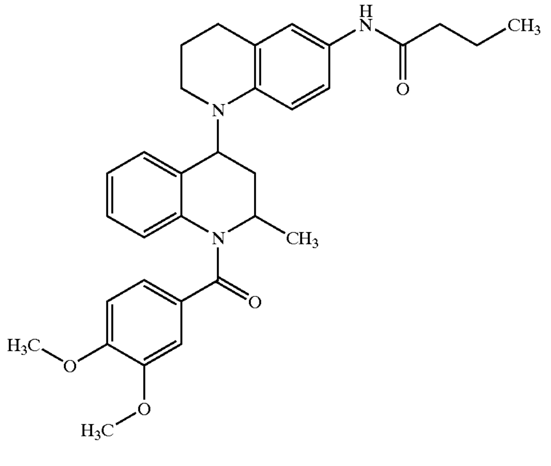

Starting with cis-1-(3,4-dimethoxybenzoyl)-2-methyl-1,2,3,4-tetrahydro-4-quinolinol (800 mg, 2.44 mmol) prepared in Reference Example 1 and N-(1,2,3,4-tetrahydro-6-quinolinyl)butanamide (1.33 g, 6.1 mmol), the same procedure as shown in Example 1 was repeated to give the titled compound (463 mg, yield: 36%) as a colorless oil. (cis:trans=1:1.3)

$^1H$ NMR ($CDCl_3$) δ 0.90–1.10 (m, 3H), 1.30–1.38 (m, 3H), 1.60–2.40 (m, 11H), 3.05–3.20 (m, 1.14H), 3.30–3.40 (m, 0.86H), 3.62 (s, 1.29H), 3.77 (s, 1.71H), 3.86 (s, 1.29H), 3.89 (s, 1.71H), 4.76–4.83 (m, 0.86H), 5.10 (br s, 0.57H), 5.25–5.31 (m, 0.57H), 6.40–7.33 (m, 10H).

Example 100

2,4-trans-4-(Benzotriazol-1-yl)-1-(3,4-dimethoxybenzoyl)-2-methyl-1,2,3,4-tetrahydroquinoline

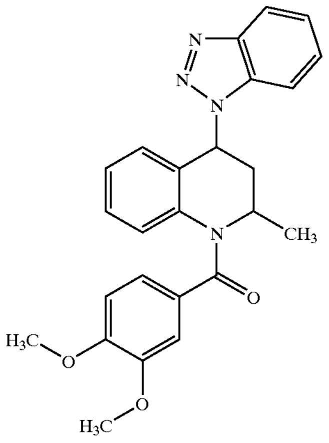

Starting with 2,4-trans-4-(benzotriazol-1-yl)-2-methyl-1,2,3,4-tetrahydroquinoline (440 mg, 1.50 mmol) prepared in Reference Example 16, the same procedure as shown in Example 32 was repeated to give the titled compound (630 mg, yield: 98%) as a white crystal.

Elementary Analysis for $C_{25}H_{24}N_4O_3$ $0.25H_2O$: Calculated: C, 69.35; H, 5.70; N, 12.94. Found: C, 69.01; H, 5.71; N, 12.69.

Example 101

2,4-cis-4-(6-Benzyloxy-1,2,3,4-tetrahydroquinolin-1-yl)-1-(3,4-dimethoxybenzoyl)-2-methyl-1,2,3,4-tetrahydroquinoline

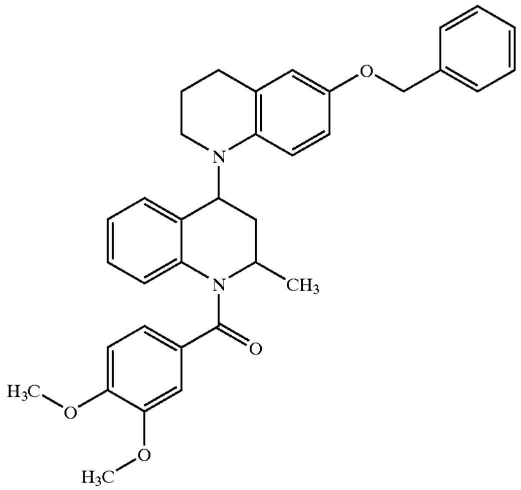

Starting with cis-1-(3,4-dimethoxybenzoyl)-2-methyl-1,2,3,4-tetrahydro-4-quinolinol (830 mg, 2.6 mmol) prepared in Reference Example 1 and 6-benzyloxy-1,2,3,4-tetrahydroquinoline (1.90 g, 8.0 mmol), the same procedure as shown in Example 1 was repeated to give the titled compound (283 mg, yield: 20%) as a white crystal.

Elementary Analysis for $C_{35}H_{36}N_2O_4$ $0.2H_2O$: Calculated: C, 76.12; H, 6.64; N, 5.07. Found: C, 76.24; H, 6.46; N, 4.88.

Melting point: 164° C.–165° C.

The titled compounds of Examples 90 to 101 are summarized in Table 8 below.

TABLE 8

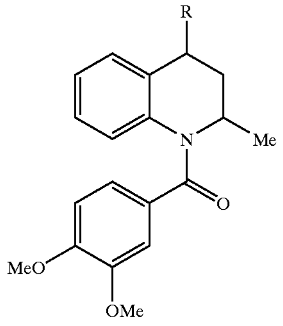

| Example No. | R | Stereochemistry |
|---|---|---|
| 90 | 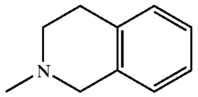 | cis (+) |
| 91 | 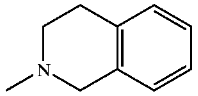 | cis (−) |
| 92 | 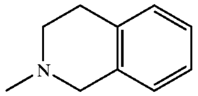 | trans (+) |

TABLE 8-continued
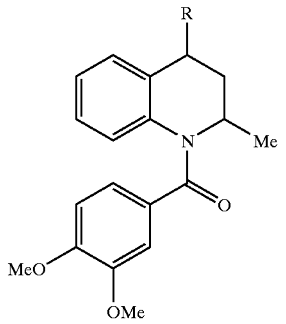
| Example No. | R | Stereochemistry |
|---|---|---|
| 93 | 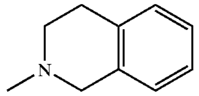 | trans (−) |
| 94 | 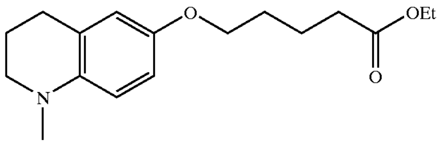 | cis/trans = 1/1.2 |
| 95 | 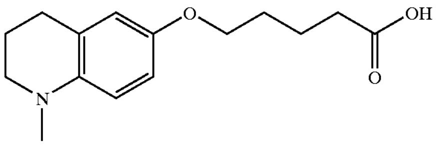 | cis/trans = 1/1.5 |
| 96 | 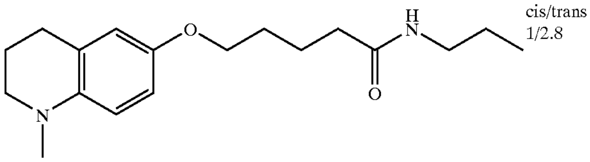 | cis/trans = 1/2.8 |
| 97 | 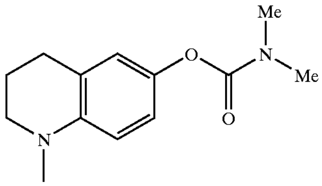 | cis/trans = 3.3/1 |
| 98 | 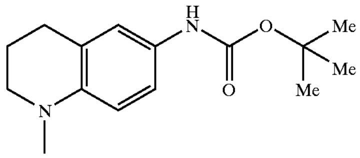 | cis/trans = 4.8/1 |
| 99 | 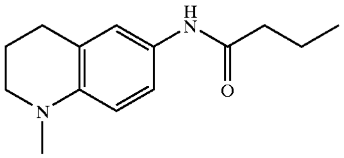 | cis/trans = 1/1.3 |

TABLE 8-continued

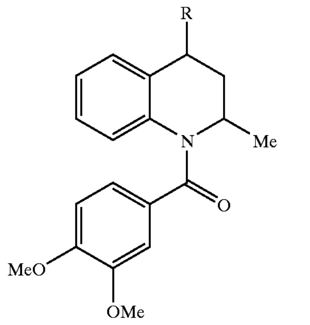

| Example No. | R | Stereochemistry |
|---|---|---|
| 100 | 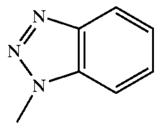 | cis |
| 101 | 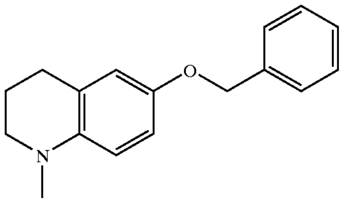 | cis |

Example 102

1-(3,4-Diethoxybenzoyl)-2-methyl-4-(1,2,3,4-tetrahydroquinolin-1-yl)-1,2,3,4-tetrahydroquinoline

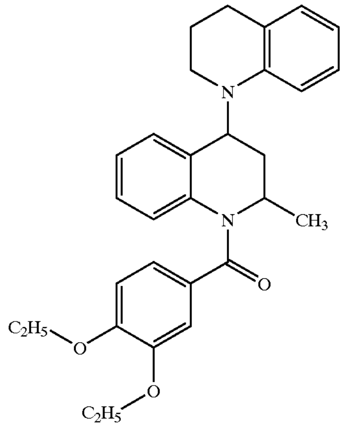

Starting with 1-(3,4-diethoxybenzoyl)-2-methyl-1,2,3,4-tetrahydro-4-quinolinol (600 mg, 1.70 mmol) prepared in Reference Example 20 and 1,2,3,4-tetrahydroquinoline (679 mg, 5.23 mmol), the same procedure as shown in Example 1 was repeated to give the titled compound (267 mg, yield: 34%) as a white crystal. (cis:trans=1:1.4)

Elementary Analysis for $C_{30}H_{34}N_2O_3$: Calculated: C, 76.57; H, 7.28; N, 5.95. Found: C, 76.49; H, 7.38; N, 5.99.

Melting point: 157° C.–158° C.

Example 103

1-(4-Ethoxy-3-methoxybenzoyl)-2-methyl-4-(1,2,3,4-tetrahydroquinolin-1-yl)-1,2,3,4-tetrahydroquinoline

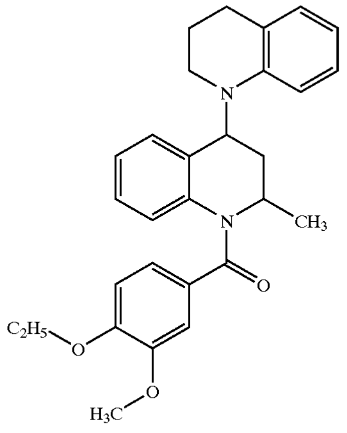

Starting with 1-(4-ethoxy-3-methoxybenzoyl)-2-methyl-1,2,3,4-tetrahydro-4-quinolinol (600 mg, 1.76 mmol) prepared in Reference Example 19 and 1,2,3,4-tetrahydroquinoline (703 mg, 5.28 mmol), the same procedure as shown in Example 1 was repeated to give the titled compound (288 mg, yield: 36%) as a white crystal. (cis:trans=2:3)

Elementary Analysis for $C_{29}H_{32}N_2O_3$ $0.25H_2O$: Calculated: C, 75.54; H, 7.10; N, 6.08. Found: C, 75.56; H, 7.05; N, 6.10.

Melting point: 140° C.–142° C.

Example 104

Ethyl 5-[[1-[1-(3-methoxybenzoyl)-2-methyl-1,2,3,4-tetrahydro-4-quinolinyl]-1,2,3,4-tetrahydro-6-quinolinyl]oxy]pentanoate

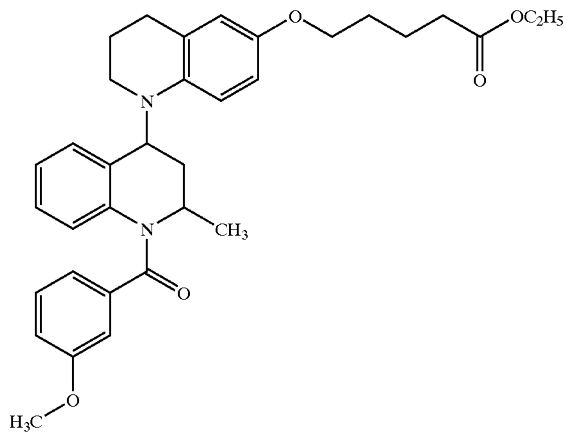

Starting with 1-(3-methoxybenzoyl)-2-methyl-1,2,3,4-tetrahydro-4-quinolinol (1.0 g, 3.36 mmol) prepared in Reference Example 21 and ethyl 5-[(1,2,3,4-tetrahydro-6-quinolinyl)oxy]pentanoate (2.14 g, 7.73 mmol), the same procedure as shown in Example 1 was repeated to give the titled compound (479 mg, yield: 26%) as a colorless oil. (cis:trans=1:3.5)

FABMS(pos) 556.2 [$M^+$]

Example 105

Ethyl 5-[[1-[2-methyl-1-(3,4,5-trimethoxybenzoyl)-1,2,3,4-tetrahydro-4-quinolinyl]-1,2,3,4-tetrahydro-6-quinolinyl]oxy]pentanoate

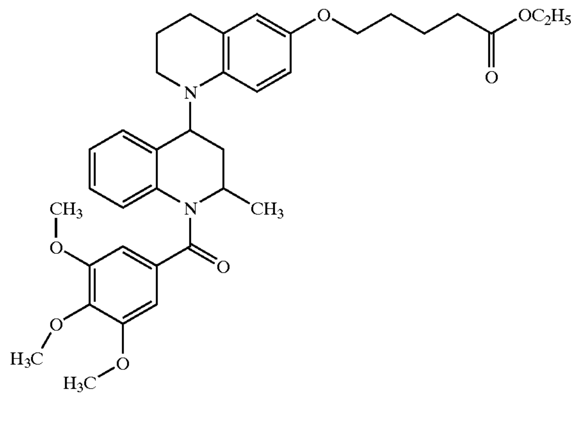

Starting with 2-methyl-1-(3,4,5-trimethoxybenzoyl)-1,2,3,4-tetrahydro-4-quinolinol (1.3 g, 3.6 mmol) prepared in Reference Example 22 and ethyl 5-[(1,2,3,4-tetrahydro-6-quinolinyl)oxy]pentanoate (2.30 g, 8.28 mmol), the same procedure as shown in Example 1 was repeated to give the titled compound (806 mg, yield: 40%) as a colorless oil. (cis:trans=1:1.3)

Example 106

5-[[1-[1-(3-Methoxybenzoyl)-2-methyl-1,2,3,4-tetrahydro-4-quinolinyl]-1,2,3,4-tetrahydro-6-quinolinyl]oxy]pentanoic acid

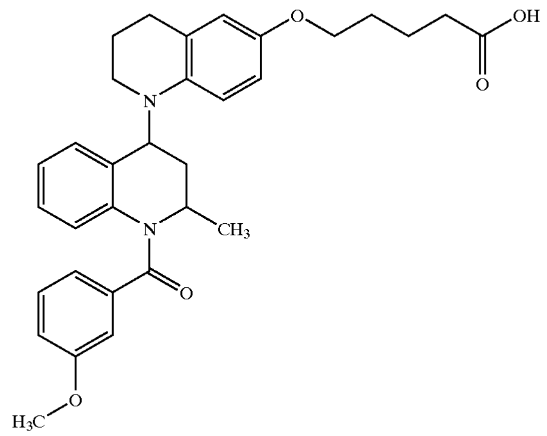

Starting with ethyl 5-[[1-[1-(3-methoxybenzoyl)-2-methyl-1,2,3,4-tetrahydro-4-quinolinyl]-1,2,3,4-tetrahydro-6-quinolinyl]oxy]pentanoate (450 mg, 0.81 mmol) prepared in Example 104, the same procedure as shown in Example 95 was repeated to give the titled compound (280 mg, yield: 65%) as a colorless oil. (cis:trans=1:3.2)

FABMS(pos) 528.1 [$M^+$]

Example 107

5-[[1-[2-Methyl-1-(3,4,5-trimethoxybenzoyl)-1,2,3,4-tetrahydro-4-quinolinyl]-1,2,3,4-tetrahydro-6-quinolinyl]oxy]pentanoic acid

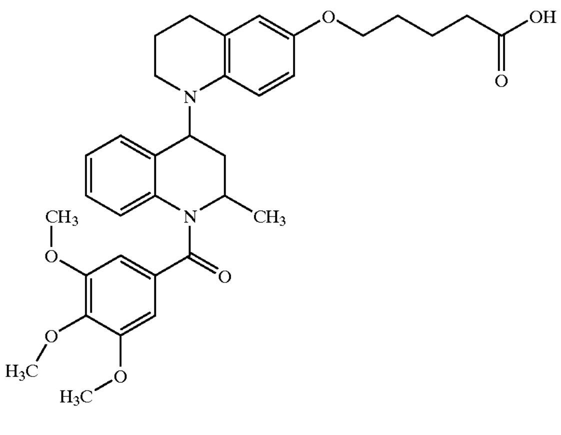

Starting with ethyl 5-[[1-[2-methyl-1-(3,4,5-trimethoxybenzoyl)-1,2,3,4-tetrahydro-4-quinolinyl]-1,2,3,4-tetrahydro-6-quinolinyl]oxy]pentanoate (780 mg, 1.26 mmol) prepared in Example 105, the same procedure as shown in Example 95 was repeated to give the titled compound (422 mg, yield: 57%) as a colorless oil. (cis:trans=1:1.3)

Example 108

5-[[1-[1-(3-Methoxybenzoyl)-2-methyl-1,2,3,4-tetrahydro-4-quinolinyl]-1,2,3,4-tetrahydro-6-quinolinyl]oxy]-N-propylpentanamide

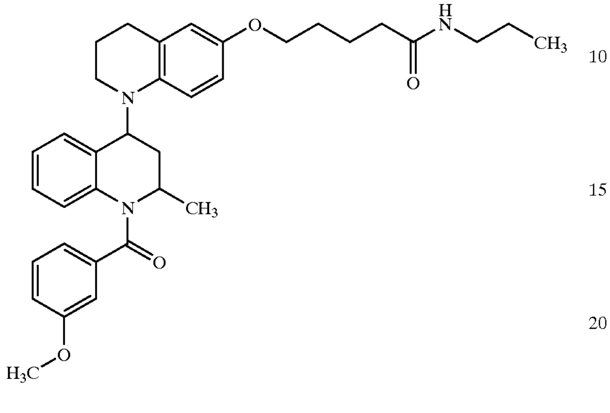

Starting with 5-[[1-[1-(3-methoxybenzoyl)-2-methyl-1,2,3,4-tetrahydro-4-quinolinyl]-1,2,3,4-tetrahydro-6-quinolinyl]oxy]pentanoic acid (260 mg, 0.49 mmol) prepared in Example 106, the same procedure as shown in Example 96 was repeated to give the titled compound (38 mg, yield: 12%) as a colorless oil. (cis:trans=1:4.5)

$^1$H NMR ($CDCl_3$) δ 0.93 (t, J=7.4, 1H), 1.35 (d, J=6.9, 1H), 1.48–3.30 (m, 18H), 3.64 (s, 0.54H), 3.76 (s, 2.46H), 3.93 (br s, 2H), 4.70–4.90 (m, 0.36H), 5.03 (br s, 0.82H), 5.22 (dd, J=11.1, 7.1, 0.82H), 5.52 (br s, 1H), 6.40–7.40 (m, 11H).

Example 109

5-[[1-[2-Methyl-1-(3,4-dimethylbenzoyl)-1,2,3,4-tetrahydro-4-quinolinyl]-1,2,3,4-tetrahydro-6-quinolinyl]oxy]-N-propylpentanamide

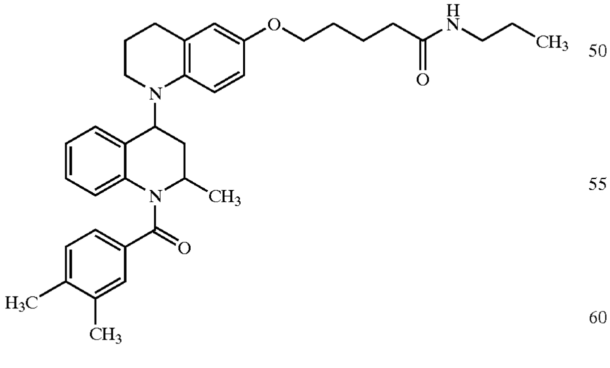

5-[[1-[1-(3,4-Dimethylbenzoyl)-2-methyl-1,2,3,4-tetrahydro-4-quinolinyl]-1,2,3,4-tetrahydro-6-quinolinyl]oxy]pentanoic acid (0.20 g, 0.37 mmol) prepared in Example 164 and 1-hydroxybenzotriazole (50 mg, 0.37 mmol) were dissolved in N,N-dimethylformamide (3 ml). To this solution, 1-ethyl-3-(3-dimethylaminopropyl) carbodiimide hydrochloride (WSC) (92 mg, 0.48 mmol) was added and the resulting mixture was stirred at room temperature for 10 minutes. After addition of propylamine (91 μl), the mixture was stirred at room temperature for an additional 15 hours. Aqueous sodium bicarbonate was added to the reaction mixture, which was then extracted with ethyl acetate. The extracted solution was washed with water and concentrated under reduced pressure. The residue was purified by silica gel column chromatography (hexane:ethyl acetate=1:1 to 4:1) to give the titled compound (0.14 g, yield: 68%) as an amorphous powder. (cis:trans=3:2)

$^1$H NMR ($CDCl_3$) δ 0.92 (t, J=7.4 Hz, 3H), 1.24–1.35 (m, 3H), 1.46–1.57 (m, 2H)m 1.74–2.27 (m, 16H), 2.62–3.34 (m, 6H), 3.88–3.94 (m, 2H), 4.71–4.89 (m, 0.8H), 5.00 (br s, 0.6H), 5.18–5.24 (m, 0.6H), 5.54 (br s, 1H), 6.44–7.38 (m, 10H).

Example 110

5-[[1-[2-Methyl-1-(3,4,5-trimethoxybenzoyl)-1,2,3,4-tetrahydro-4-quinolinyl]-1,2,3,4-tetrahydro-6-quinolinyl]oxy]-N-propylpentanamide

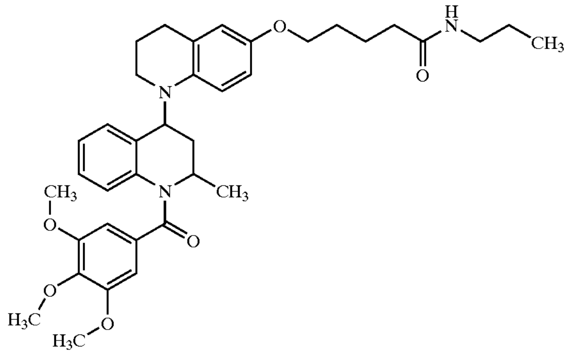

Starting with 5-[[1-[2-methyl-1-(3,4,5-trimethoxybenzoyl)-1,2,3,4-tetrahydro-4-quinolinyl]-1,2,3,4-tetrahydro-6-quinolinyl]oxy]pentanoic acid (0.37 g, 0.62 mmol) prepared in Example 107, the same procedure as shown in Example 109 was repeated to give the titled compound (0.22 g, yield: 56%). (cis:trans=1:1)

Melting point: 124° C.–133° C. (recrystallized from hexane-ethyl acetate) $^1$H NMR ($CDCl_3$) δ 0.90–0.95 (m, 3H), 1.34–1.39 (m, 3H), 1.46–1.58 (m, 2H), 1.73–2.32 (m, 10H), 2.68–3.38 (m, 6H), 3.62–3.93 (m, 11H), 4.70–4.88 (m, 1H), 5.10 (br s, 0.5H), 5.21–5.29 (m, 0.5H), 5.51 (br s, 1H), 6.37–7.39 (m, 9H).

The titled compounds of Examples 102 to 110 are summarized in Table 9 below.

TABLE 9
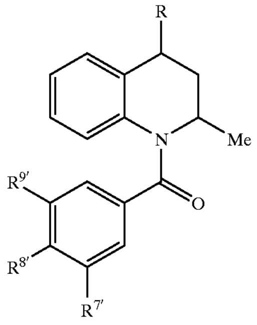
| Example No. | R | $R^{7'}$ | $R^{8'}$ | $R^{9'}$ | Stereochemistry |
|---|---|---|---|---|---|
| 102 | 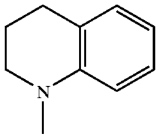 | $OC_2H_5$ | $OC_2H_5$ | H | cis/trans = 2/3 |
| 103 | 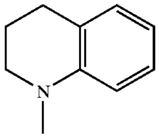 | $OCH_3$ | $OC_2H_5$ | H | cis/trans = 2/3 |
| 104 | 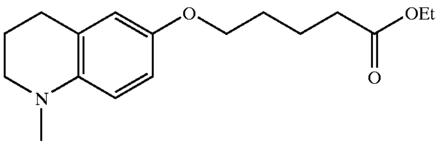 | $OCH_3$ | H | H | cis/trans = 1/3.5 |
| 105 | 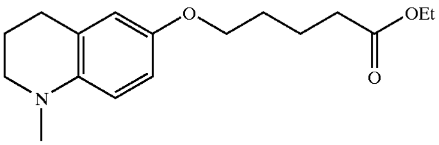 | $OCH_3$ | $OCH_3$ | $OCH_3$ | cis/trans = 1/1.1 |
| 106 | 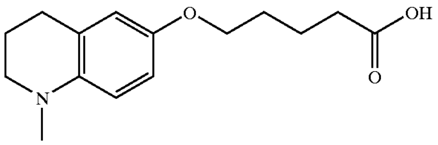 | $OCH_3$ | H | H | cis/trans = 1/3.2 |
| 107 | 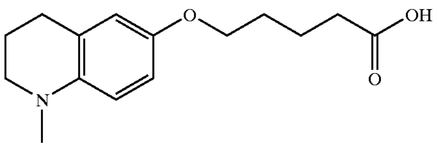 | $OCH_3$ | $OCH_3$ | $OCH_3$ | cis/trans = 1/1.3 |
| 108 | 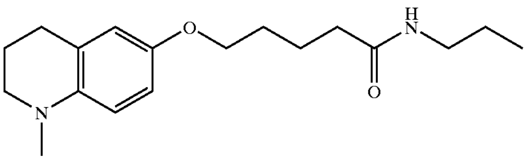 | $OCH_3$ | H | H | cis/trans = 1/4.5 |

TABLE 9-continued

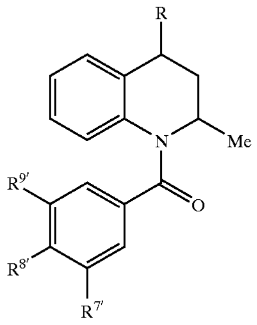

| Example No. | R | $R^{7'}$ | $R^{8'}$ | $R^{9'}$ | Stereochemistry |
|---|---|---|---|---|---|
| 109 | 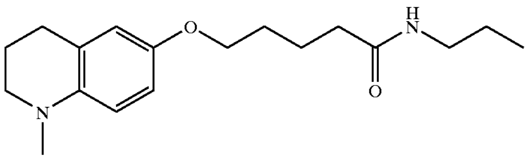 | $CH_3$ | $CH_3$ | H | cis/trans = 3/2 |
| 110 | 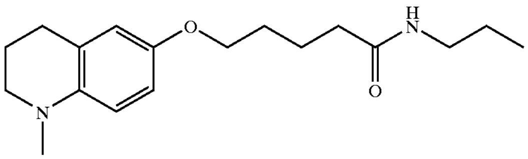 | $OCH_3$ | $OCH_3$ | $OCH_3$ | cis/trans = 1/1 |

Example 111

(+)-2,4-cis-4-(9H-9-Carbazolyl)-1-(3,4-dimethoxybenzoyl)-2-propyl-1,2,3,4-tetrahydroquinoline

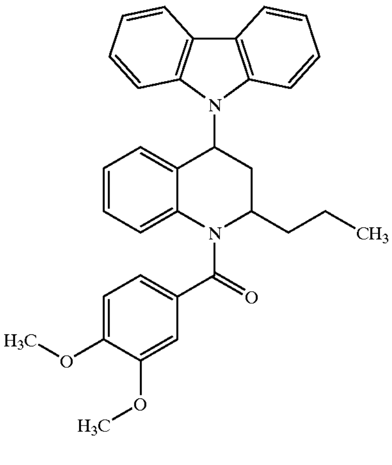

Starting with 2,4-cis-4-(9H-9-carbazolyl)-1-(3,4-dimethoxybenzoyl)-2-propyl-1,2,3,4-tetrahydroquinoline (345 mg) prepared in Example 38, the same procedure as shown in Example 5 was repeated to give the titled compound (111 mg). When analyzed for optical rotation with a Shodex OR-2 (wavelength: 470 nm), this compound was shown to be (+)-form.

Melting point: 191° C.–192° C.

Example 112

(+)-2,4-cis-2-[(Benzyloxy)methyl]-4-(9H-9-carbazolyl)-1-(3,4-dimethoxybenzoyl)-1,2,3,4-tetrahydroquinoline

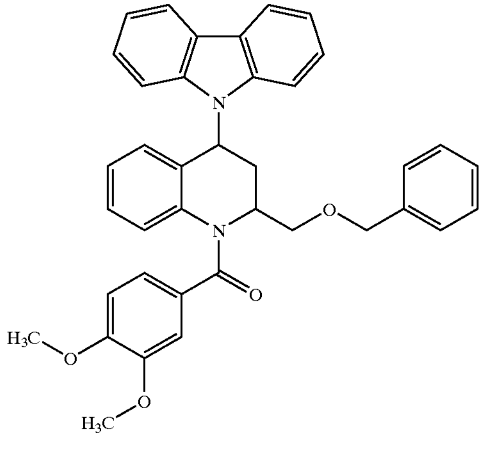

Starting with 2-[(benzyloxy)methyl]-4-(9H-9-carbazolyl)-1-(3,4-dimethoxybenzoyl)-1,2,3,4-tetrahydroquinoline (250 mg) prepared in Example 43, the same procedure as shown in Example 5 was repeated to give the titled compound (29 mg). When analyzed for optical rotation with a Shodex OR-2 (wavelength: 470 nm), this compound was shown to be (+)-form.

Example 113

(−)-2,4-cis-2-[(Benzyloxy)methyl]-4-(9H-9-carbazolyl)-1-(3,4-dimethoxybenzoyl)-1,2,3,4-tetrahydroquinoline

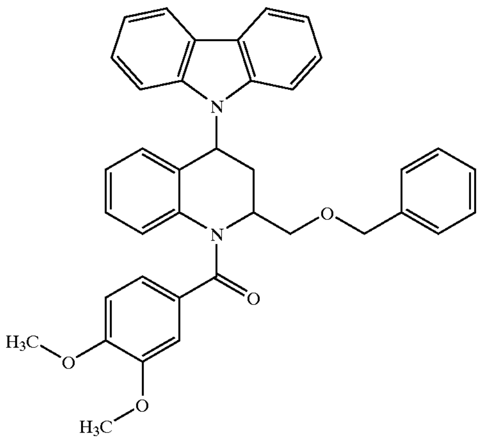

Starting with 2-[(benzyloxy)methyl]-4-(9H-9-carbazolyl)-1-(3,4-dimethoxybenzoyl)-1,2,3,4-tetrahydroquinoline (250 mg) prepared in Example 43, the same procedure as shown in Example 5 was repeated to give the titled compound (21 mg). When analyzed for optical rotation with a Shodex OR-2 (wavelength: 470 nm), this compound was shown to be (−)-form.

Example 114

(+)-2,4-trans-2-[(Benzyloxy)methyl]-4-(9H-9-carbazolyl)-1-(3,4-dimethoxybenzoyl)-1,2,3,4-tetrahydroquinoline

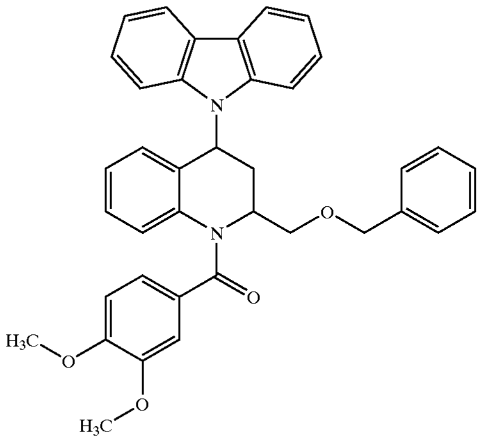

Starting with 2-[(benzyloxy)methyl]-4-(9H-9-carbazolyl)-1-(3,4-dimethoxybenzoyl)-1,2,3,4-tetrahydroquinoline (250 mg) prepared in Example 43, the same procedure as shown in Example 5 was repeated to give the titled compound (17 mg). When analyzed for optical rotation with a Shodex OR-2 (wavelength: 470 nm), this compound was shown to be (+)-form.

Example 115

(−)-2,4-trans-2-[(Benzyloxy)methyl]-4-(9H-9-carbazolyl)-1-(3,4-dimethoxybenzoyl)-1,2,3,4-tetrahydroquinoline

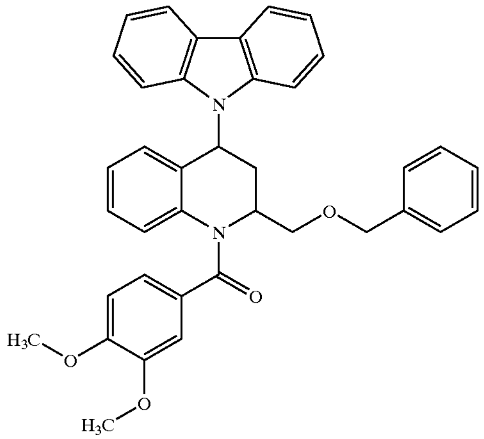

Starting with 2-[(benzyloxy)methyl]-4-(9H-9-carbazolyl)-1-(3,4-dimethoxybenzoyl)-1,2,3,4-tetrahydroquinoline (250 mg) prepared in Example 43, the same procedure as shown in Example 5 was repeated to give the titled compound (14 mg). When analyzed for optical rotation with a Shodex OR-2 (wavelength: 470 nm), this compound was shown to be (−)-form.

Example 116

9-[2,4-cis-1-(3,4-Dimethoxybenzoyl)-2-(3phenylpropyl)-1,2,3,4-tetrahydroquinolin-4-yl]-9H-carbazole

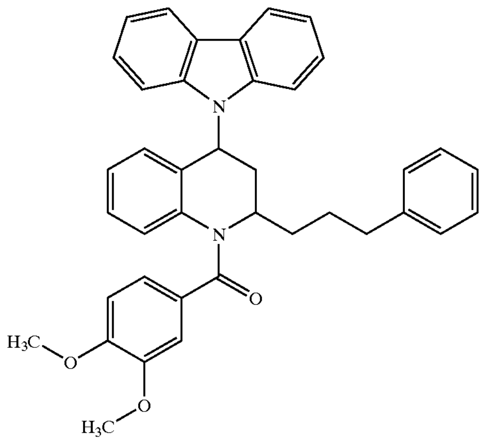

Starting with 9-[2,4-cis-2-(3-phenylpropyl)-1,2,3,4-tetrahydroquinolin-4-yl]-9H-carbazole (2.00 g, 4.80 mmol) prepared in Reference Example 24, the same procedure as shown in Example 32 was repeated to give the titled compound (527 mg, yield: 19%) as a white crystal.

Melting point: 225° C.–226° C. (crystallization solvent: ethyl acetate-hexane) Elementary Analysis for $C_{39}H_{36}N_2O_3$ $0.5H_2O$: Calculated: C, 79.34; H, 6.32; N, 4.75. Found: C, 79.38; H, 6.41; N, 4.57.

Example 117

9-[2,4-cis-2-[3-[[tert-Butyl(diphenyl)silyl]oxy]propyl]-1-(3,4-dimethoxybenzoyl)-1,2,3,4-tetrahydroquinolin-4-yl]-9H-carbazole

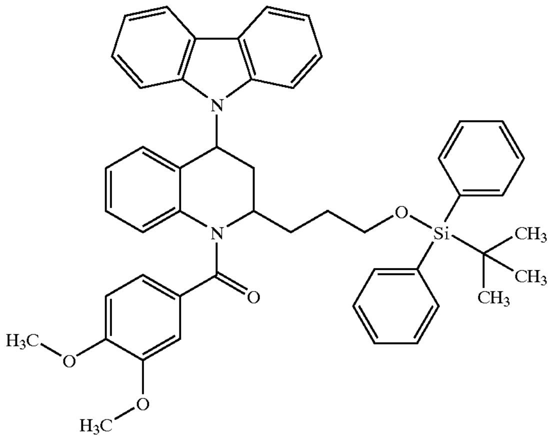

Starting with 9-[2,4-cis-2-[3-[[tert-butyl(diphenyl)silyl]oxy]propyl]-1,2,3,4-tetrahydroquinolin-4-yl]-9H-carbazole (1.08 g, 1.82 mmol) prepared in Reference Example 25, the same procedure as shown in Example 32 was repeated to give the titled compound (382 mg, yield: 27%) as a white crystal.

Melting point: 209° C.–211° C. (crystallization solvent: ethyl acetate-hexane)

$^1$H NMR ($CDCl_3$) δ 1.00 (s, 9H), 1.67 (br s, 3H), 1.85–2.00 (m, 1H), 2.51–2.61 (m, 1H), 2.68–2.78 (m, 1H), 3.44–3.71 (m, 5H), 3.85 (s, 3H), 5.01–5.06 (m, 1H), 5.90 (dd, J=12.0, 6.7 Hz, 1H), 6.68 (d, J=8.2 Hz, 2H), 6.82–6.90 (m, 3H), 6.90–7.00 (m, 2H), 7.00–7.10 (m, 1H), 7.20–7.50 (m, 9H), 7.50–7.55 (m, 2H), 7.59–7.63 (m, 4H), 8.20 (d, J=6.7 Hz, 2H).

Example 118

3-[2,4-cis-4-(9H-9-Carbazolyl)-1-(3,4-dimethoxybenzoyl)-1,2,3,4-tetrahydroquinolin-2-yl]-1-propanol

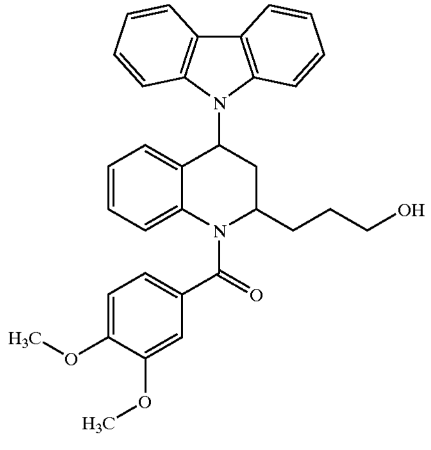

9-[2,4-cis-2-[3-[[tert-Butyl(diphenyl)silyl]oxy]propyl]-1-(3,4-dimethoxybenzoyl)-1,2,3,4-tetrahydroquinolin-4-yl]-9H-carbazole (350 mg, 0.461 mmol) prepared in Example 117 was dissolved in THF (10 ml), to which a 1N THF solution of tetrabutylammonium fluoride (0.92 ml, 0.922 mmol) was then added on ice and stirred at room temperature for 4 hours. After the reaction mixture was diluted with ethyl acetate, washed with water, dried and concentrated, the residue was applied to silica gel column chromatography (developing solvent: ethyl acetate) and the resulting eluate was recrystallized from ethyl acetate-diethyl ether to give the titled compound (156 mg, yield: 65%) as a white crystal.

Melting point: 192° C.–194° C. (crystallization solvent: ethyl acetate-diethyl ether)

FABMS(pos) 521.2 [M+H$^+$]

Example 119

3-[2,4-cis-4-(9H-9-Carbazolyl)-1-(3,4-dimethoxybenzoyl)-1,2,3,4-tetrahydroquinolin-2-yl]-propanal

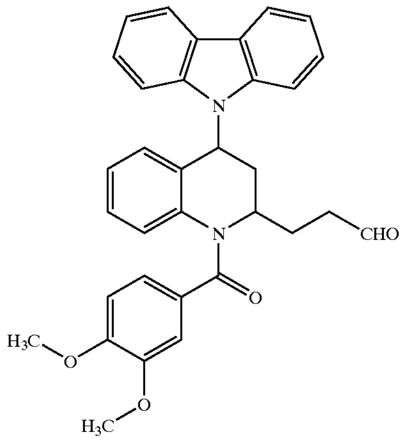

To a chloroform (10 ml) suspension of PCC (1.94 g, 9 mmol), a chloroform (10 ml) solution of 3-[2,4-cis-4-(9H-9-carbazolyl)-1-(3,4-dimethoxybenzoyl)-1,2,3,4-tetrahydroquinolin-2-yl]-1-propanol (520 mg, 1 mmol) prepared in Example 118 was added and stirred at room temperature for 6 hours. After addition of ethyl acetate and anhydrous magnesium sulfate, the reaction mixture was stirred for 10 minutes, filtered to remove insoluble products, and then concentrated. The residue was applied to silica gel column chromatography (developing solvent: ethyl acetate/hexane=1/1) and the resulting eluate was recrystallized from ethyl acetate-hexane to give the titled compound (216 mg, yield: 42%) as a white crystal.

FABMS(pos) 519.2 [M+H$^+$]

$^1H$ NMR ($CDCl_3$) δ 1.90–2.20 (m, 2H), 2.55–2.86 (m, 2H), 2.55–2.86 (m, 4H), 3.65 (s, 3H), 3.85 (s, 3H), 5.04–5.14 (m, 1H), 5.92 (dd, J=6.1, 11.9 Hz, 1H), 6.67–6.73 (m, 2H), 6.83–6.85 (m, 3H), 6.95–7.10 (m, 3H), 7.26–7.34 (m, 3H), 7.40–7.60 (m, 2H), 8.19 (d, J=7.3 Hz, 2H), 9.85 (s, 1H).

Example 120

(Z)-8-[2,4-cis-4-(9H-9-Carbazolyl)-1-(3,4-dimethoxybenzoyl)-1,2,3,4-tetrahydroquinolin-2-yl]-N-propyl-5-octenamide

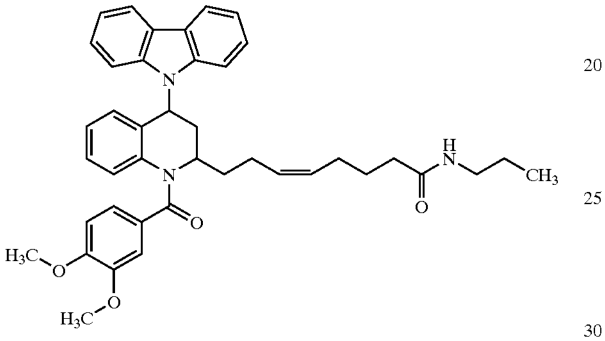

To a suspension of (4-carboxybutyl) triphenylphosphonium bromide (89 mg, 0.2 mmol) in THF (3 ml) and DMSO (1 ml), n-butyllithium (1.56 M in hexane, 0.25 ml, 0.39 mmol) was added dropwise on ice and stirred for 30 minutes. A THF (4 ml) solution of 3-[2,4-cis-4-(9H-9-carbazolyl)-1-(3,4-dimethoxybenzoyl)-1,2,3,4-tetrahydroquinolin-2-yl]-propanal (52 mg, 0.1 mmol) prepared in Example 119 was added and stirring was continued at room temperature for an additional 18 hours. After addition of 1N aqueous hydrochloric acid, the reaction mixture was extracted with ethyl acetate. After the organic layer was dried and concentrated, the residue was applied to silica gel column chromatography (developing solvent: ethyl acetate) and the resulting eluate was recrystallized from ethyl acetate-hexane to give (Z)-8-[2,4-cis-4-(9H-9-carbazolyl)-1-(3,4-dimethoxybenzoyl)-1,2,3,4-tetrahydroquinolin-2-yl]-5-octenoic acid as a colorless oil. Starting with the resulting (Z)-8-[2,4-cis-4-(9H-9-carbazolyl)-1-(3,4-dimethoxybenzoyl)-1,2,3,4-tetrahydroquinolin-2-yl]-5-octenoic acid (90 mg, 0.149 mmol) and n-propylamine (22 mg, 0.373 mmol), the same procedure as shown in Example 109 was repeated to give the titled compound (6.8 mg, yield over 2 steps: 11%) as a white crystal.

$^1H$ NMR ($CDCl_3$) δ 0.85–0.91 (m, 3H), 1.40–1.80 (m, 4H), 1.90–2.30 (m, 7H), 2.50–2.90 (m, 2H), 3.13–3.20 (m, 2H), 3.65 (s, 3H), 3.86 (s, 3H), 4.95–5.10 (m, 1H), 5.30–5.50 (m, 2H), 5.62 (br s, 1H), 5.92 (dd, J=11.7, 5.9, 1H), 6.68–7.11 (m, 9H), 7.20–7.60 (m, 4H), 8.21–8.18 (m, 2H).

Example 121

N-[3-[2,4-cis-4-(9H-9-Carbazolyl)-1-(3,4-dimethoxybenzoyl)-1,2,3,4-tetrahydroquinolin-2-yl]propyl]acetamide

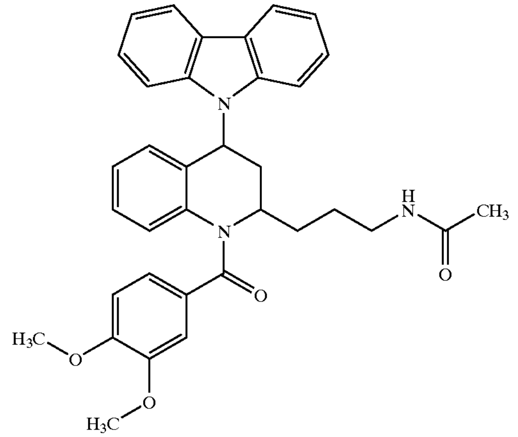

Starting with 2,4-cis-4-(9H-9-carbazolyl)-2-(2-cyanoethyl)-1-(3,4-dimethoxybenzoyl)-1,2,3,4-tetrahydroquinoline (300 mg, 0.58 mmol) prepared in Example 44 and acetic anhydride (118 mg, 1.16 mmol), the same procedure as shown in Example 45 was repeated to give the titled compound (108 mg, yield: 34%) as a white crystal.

Melting point: 203° C.–204° C. (crystallization solvent: ethyl acetate-hexane)

Elementary Analysis for $C_{37}H_{39}N_3O_4$ $0.5H_2O$: Calculated: C, 73.66; H, 6.36; N, 7.36. Found: C, 73.90; H, 6.08; N, 7.18.

Example 122

N-[3-[2,4-cis-4-(9H-9-Carbazolyl)-1-(3,4-dimethoxybenzoyl)-1,2,3,4-tetrahydroquinolin-2-yl]propyl]butanamide

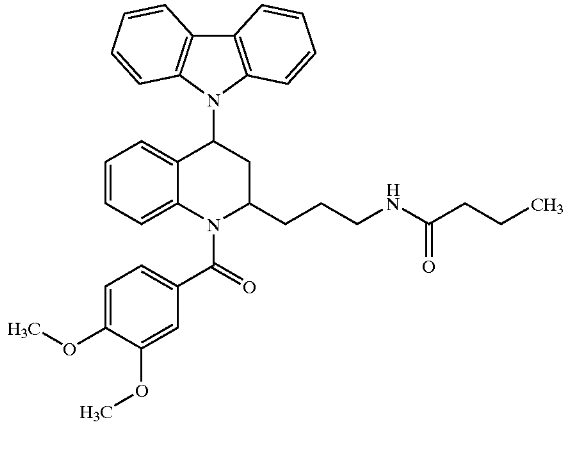

2,4-cis-2-(3-Aminopropyl)-4-(9H-carbazolyl-9-yl)-1-(3,4-dimethoxybenzoyl)-1,2,3,4-tetrahydroquinoline hydrochloride (80 mg, 0.154 mmol) prepared in Example 46 was dissolved in pyridine (4 ml), to which n-butyryl chloride was then added on ice and stirred at room temperature for 3 hours. The reaction mixture was diluted with ethyl acetate, washed with water, dried and concentrated. The residue was recrystallized from diethyl ether to give the titled compound (61 mg, yield: 67%) as a white crystal.

Melting point: 199° C.–201° C. (crystallization solvent: diethyl ether)

Elementary Analysis for $C_{37}H_{39}N_3O_4$ $0.4H_2O$: Calculated: C, 74.45; H, 6.72; N, 7.04. Found: C, 74.63; H, 6.69; N, 6.75.

Example 123

N-[3-[2,4-cis-4-(9H-9-Carbazolyl)-1-(3,4-dimethoxybenzoyl)-1,2,3,4-tetrahydroquinolin-2-yl]propyl]decanamide

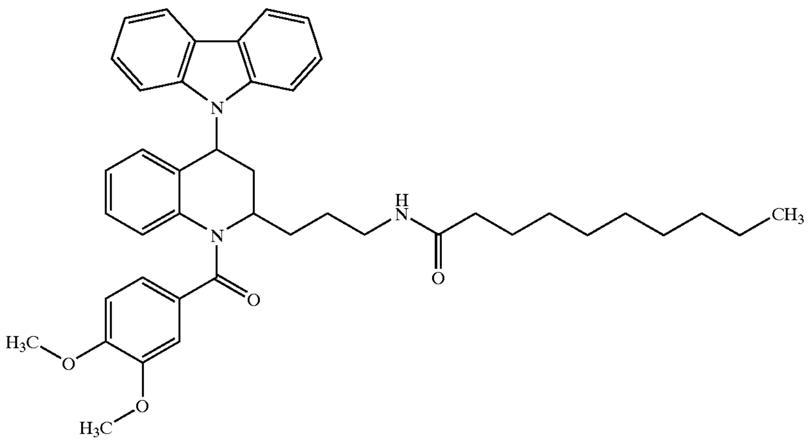

Starting with 2,4-cis-2-(3-aminopropyl)-4-(9H-carbazolyl-9-yl)-1-(3,4-dimethoxybenzoyl)-1,2,3,4-tetrahydroquinoline hydrochloride (200 mg, 0.385 mmol) prepared in Example 46 and decanoyl chloride (110 mg, 0.577 mmol), the same procedure as shown in Example 122 was repeated to give the titled compound (136 mg, yield: 53%) as a white crystal.

$^1$H NMR ($CDCl_3$) δ 0.86 (t, J=6.7 Hz, 3H), 1.20–1.40 (m, 12H), 1.50–1.80 (m, 5H), 1.90–2.10 (m, 1H), 2.20 (t, J=7.3 Hz, 2H), 2.53–2.64 (m, 1H), 2.74–2.84 (m, 1H), 3.20–3.50 (m, 2H), 3.65 (s, 3H), 3.86 (s, 3H), 4.95–5.10 (m, 1H), 5.91 (dd, J=11.9, 5.9 Hz, 1H), 6.00–6.10 (m, 1H), 6.68–6.72 (m, 2H), 6.83–6.90 (m, 3H), 6.90–7.10 (m, 3H), 7.20–7.40 (m, 3H), 7.50–7.65 (m, 2H), 8.19 (d, J=7.3 Hz, 2H).

Example 124

N-[3-[2,4-cis-4-(9H-9-Carbazolyl)-1-(3,4-dimethoxybenzoyl)-1,2,3,4-tetrahydroquinolin-2-yl]propyl]-benzamide

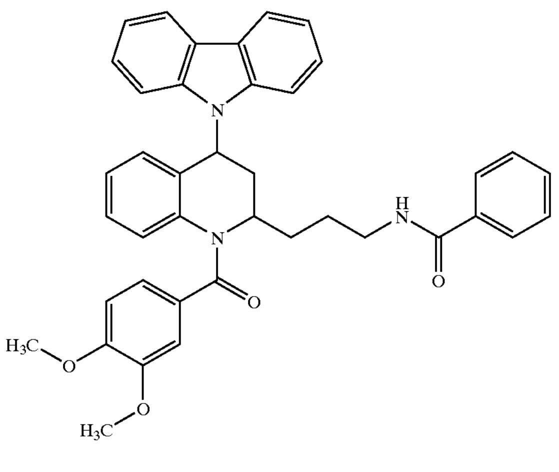

Starting with 2,4-cis-2-(3-aminopropyl)-4-(9H-carbazolyl-9-yl)-1-(3,4-dimethoxybenzoyl)-1,2,3,4-tetrahydroquinoline hydrochloride (100 mg, 0.192 mmol) prepared in Example 46 and benzoyl chloride (0.044 ml, 0.385 mmol), the same procedure as shown in Example 122 was repeated to give the titled compound (39.4 mg, yield: 33%) as a white crystal.

Melting point: 236° C.–237° C. (crystallization solvent: ethyl acetate-hexane)

Elementary Analysis for $C_{40}H_{37}N_3O_4$ $0.5H_2O$: Calculated: C, 75.93; H, 6.05; N, 6.64. Found: C, 76.26; H, 5.99; N, 6.54.

Example 125

2,4-cis-2-[(Benzyloxy)methyl]-4-(9H-9-carbazolyl)-1-(3,4-dimethoxybenzoyl)-1,2,3,4-tetrahydroquinoline

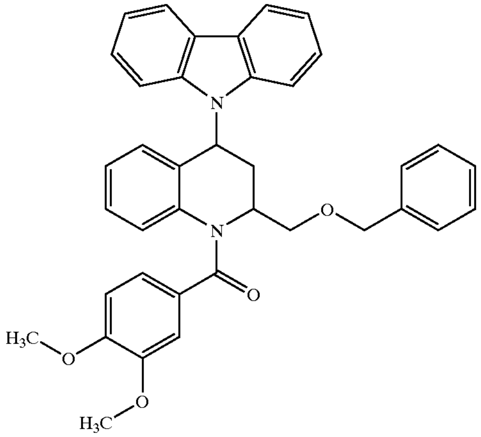

2,4-cis-2-[(Benzyloxy)methyl]-4-(9H-9-carbazolyl)-1,2,3,4-tetrahydroquinoline (5.40 g, 12.9 mmol) prepared in Reference Example 10 was dissolved in pyridine (60 ml), to which 3,4-dimethoxybenzoyl chloride (2.85 g, 14.2 mmol) was then added on ice and stirred overnight at room temperature. After methanol (1 ml) was added to stop the reaction, the reaction mixture was evaporated to remove the solvent and partitioned between ethyl acetate and aqueous sodium bicarbonate. The organic layer was washed with water, dried over anhydrous magnesium sulfate and then evaporated to remove the solvent. The residue was applied to silica gel column chromatography (developing solvent: ethyl acetate/hexane=1/10) to give the titled compound (5.39 g, yield: 72%) as a white crystal.

Melting point: 243° C.–244° C.

Example 126

Ethyl 4-[2-[4-(9H-9-Carbazolyl)-1-(3,4-dimethoxybenzoyl)-1,2,3,4-tetrahydro-2-quinolinyl]ethyl]benzoate

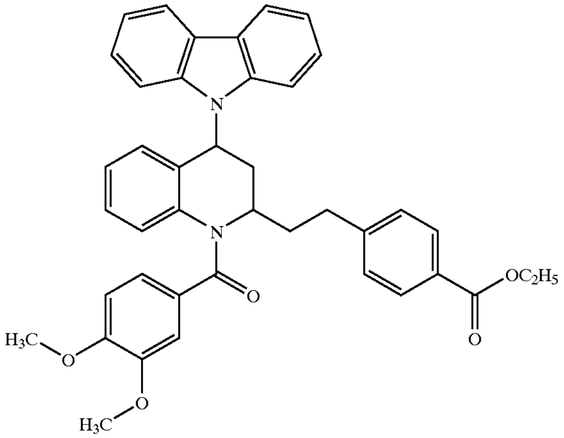

Starting with ethyl 4-(3-formylpropyl)benzoate (4.50 g, 21.8 mmol), the same procedures as shown in Reference Example 4 and Example 32 were repeated to give the titled compound (1.67 g, overall yield: 12%) as a white crystal (cis:trans=11:1).

Melting point: 247° C.–249° C.

The titled compounds of Examples 111 to 126 are summarized in Table 10 below.

TABLE 10

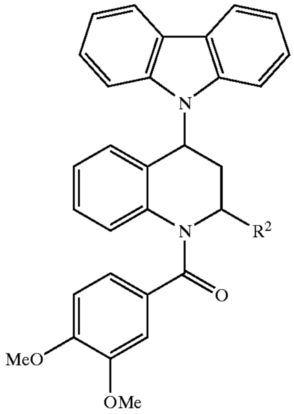

| Example No. | $R^2$ | Stereochemistry |
|---|---|---|
| 111 | $C_3H_7$ | cis (+) |
| 112 | $CH_2OCH_2Ph$ | cis (+) |
| 113 | $CH_2OCH_2Ph$ | cis (−) |

TABLE 10-continued

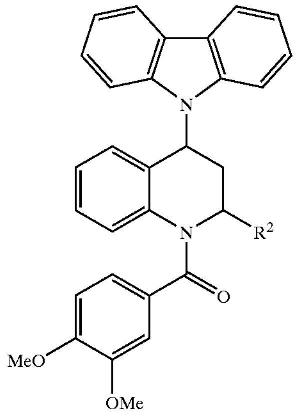

| Example No. | $R^2$ | Stereochemistry |
|---|---|---|
| 114 | $CH_2OCH_2Ph$ | trans (+) |
| 115 | $CH_2OCH_2Ph$ | trans (−) |
| 116 | $CH_2CH_2CH_2Ph$ | cis |
| 117 | $CH_2CH_2CH_2OTBDPS$ | cis |
| 118 | $CH_2CH_2CH_2OH$ | cis |
| 119 | $CH_2CH_2CHO$ | cis |
| 120 | $CH_2CH_2CH{=}CHCH_2CH_2CH_2CONHC_3H_7$ (Z) | cis |
| 121 | $CH_2CH_2CH_2NHAc$ | cis |
| 122 | $CH_2CH_2CH_2NHCOC_3H_7$ | cis |
| 123 | $CH_2CH_2CH_2NHCOC_9H_{19}$ | cis |
| 124 | $CH_2CH_2CH_2NHCOPh$ | cis |
| 125 | $CH_2OCH_2Ph$ | cis |
| 126 | 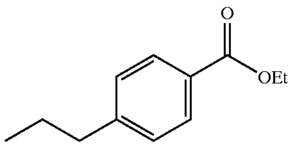 | cis/trans = 11/1 |

Example 127

Ethyl 5-[4-(9H-9-Carbazolyl)-1-(3,4-dimethoxybenzoyl)-1,2,3,4-tetrahydro-2-quinolinyl]pentanoate

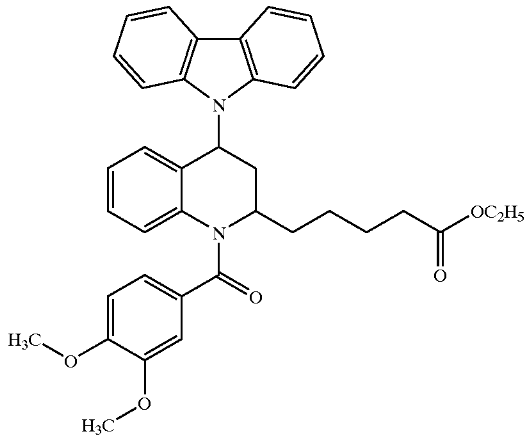

Starting with ethyl 6-formylhexanoate (7.20 g, 45.5 mmol), the same procedures as shown in Reference Example 4 and Example 32 were repeated to give the titled compound (3.50 g, overall yield: 13%) as a white crystal (cis:trans=3:2).

Melting point: 195° C.–196° C.

Example 128

5-[4-(9H-9-Carbazolyl)-1-(3,4-dimethoxybenzoyl)-1,2,3,4-tetrahydro-2-quinolinyl]pentanoic acid

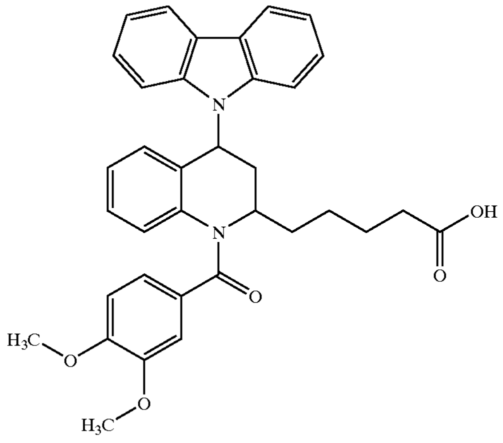

Ethyl 5-[4-(9H-9-carbazolyl)-1-(3,4-dimethoxybenzoyl)-1,2,3,4-tetrahydro-2-quinolinyl]pentanoate (0.20 g, 0.34 mmol) prepared in Example 127 was dissolved in tetrahydrofuran (10 ml), to which 1N NaOH (5 ml) and tetrabutylammonium bromide (0.11 g, 0.34 mmol) were then added and stirred at room temperature for 4 hours and then at 60° C. for 4 hours. After the reaction mixture was partitioned between ethyl acetate and 1N HCl, the organic layer was washed with saturated brine and dried over anhydrous magnesium sulfate. After distilling off the solvent, the residue was applied to silica gel column chromatography (developing solvent: ethyl acetate/hexane=1/5) to give the titled compound (0.14 g, yield: 74%) as a white crystal (cis:trans=4:1).

Melting point: 226° C.–228° C.

Example 129

5-[4-(9H-9-Carbazolyl)-1-(3,4-dimethoxybenzoyl)-1,2,3,4-tetrahydro-2-quinolinyl]-N-methylpentanamide

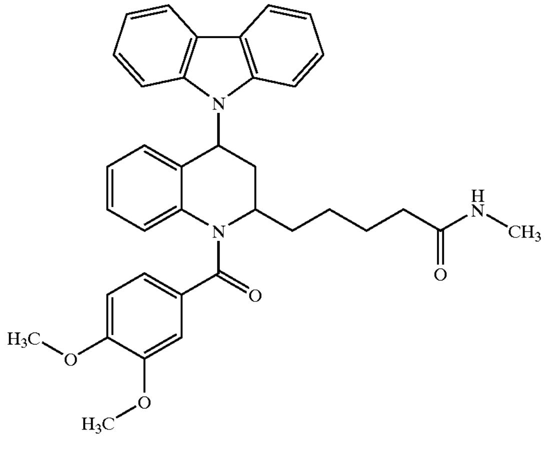

5-[4-(9H-9-Carbazolyl)-1-(3,4-dimethoxybenzoyl)-1,2,3,4-tetrahydro-2-quinolinyl]-pentanoic acid (0.12 g, 0.21 mmol) prepared in Example 128 was mixed with dichloromethane (5 ml), N,N-dimethylformamide (100 μl) and thionyl chloride (24 μl). The resulting mixture was stirred at 50° C. for 30 minutes and then cooled on ice, followed by addition of a 40% methylamine/methanol solution (1 ml), and stirring was continued at room temperature for an additional 4 hours. The reaction mixture was partitioned between ethyl acetate and saturated brine, washed and dried over anhydrous magnesium sulfate. After distilling off the solvent, the residue was applied to silica gel column chromatography (developing solvent: ethyl acetate/hexane=1/4) to give the titled compound (0.10 g, yield: 83%) as a white crystal (cis:trans=4:1).

Melting point: 224° C.–225° C.

Example 130

5-[4-(9H-9-Carbazolyl)-1-(3,4-dimethoxybenzoyl)-1,2,3,4-tetrahydro-2-quinolinyl]-N-propylpentanamide

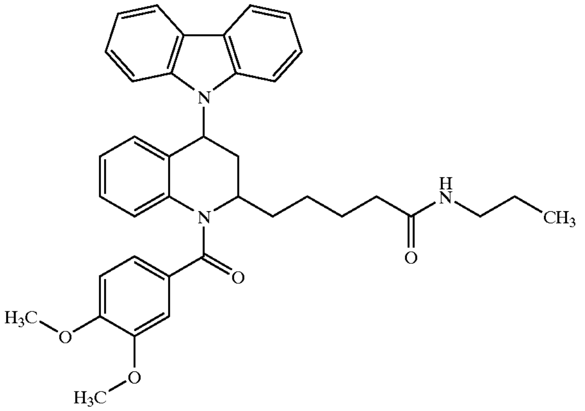

Starting with 5-[4-(9H-9-carbazolyl)-1-(3,4-dimethoxybenzoyl)-1,2,3,4-tetrahydro-2-quinolinyl]pentanoic acid (0.09 g, 0.16 mmol) prepared in Example 128 and n-propylamine (52 μl), the same procedure as shown in Example 129 was repeated to give the titled compound (0.09 g, overall yield: 93%) as a white powder (cis:trans=5:2).

FABMS 604.3 $[M+H^+]$

Example 131

Ethyl 3-[[5-[4-(9H-9-carbazolyl)-1-(3,4-dimethoxybenzoyl)-1,2,3,4-tetrahydro-2-quinolinyl]pentanoyl]amino]propionate

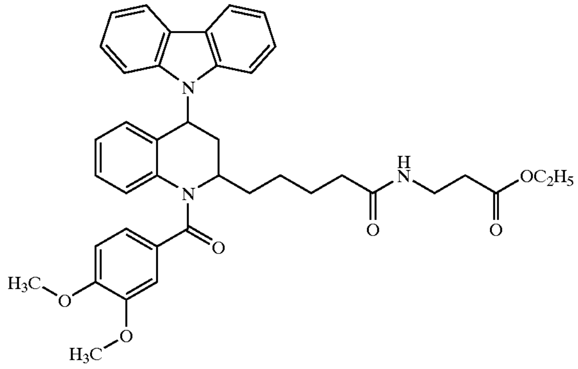

5-[4-(9H-9-Carbazolyl)-1-(3,4-dimethoxybenzoyl)-1,2,3,4-tetrahydro-2-quinolinyl]-pentanoic acid (0.50 g, 0.89 mmol) prepared in Example 128 was mixed with β-alanine ethyl ester hydrochloride (0.15 g, 1 mmol), N,N-dimethylformamide (10 ml), 1-hydroxybenzotriazole (0.14 g, 1 mmol) and 1-ethyl-3-(3-dimethylaminopropyl) carbodiimide hydrochloride (WSC) (0.19 g, 1 mmol), followed by stirring overnight at room temperature. After distilling off the solvent, the residue was partitioned between ethyl acetate and saturated brine, washed and dried over anhydrous magnesium sulfate. After distilling off the solvent, the residue was applied to silica gel column chromatography (developing solvent: ethyl acetate/hexane=1/7) to give the titled compound (0.48 g, yield: 81%) as a white powder (cis:trans=3:1).

FABMS 662.1 $[M+H^+]$

Example 132

3-[[5-[4-(9H-9-Carbazolyl)-1-(3,4-dimethoxybenzoyl)-1,2,3,4-tetrahydro-2-quinolinyl]pentanoyl]amino]propionic acid

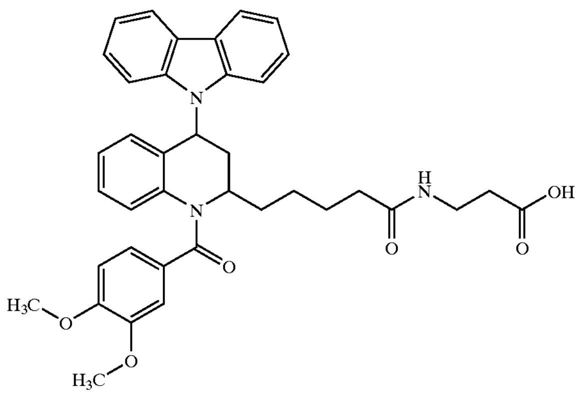

Starting with ethyl 3-[[5-[4-(9H-9-carbazolyl)-1-(3,4-dimethoxybenzoyl)-1,2,3,4-tetrahydro-2-quinolinyl]pentanoyl]amino]propionate (0.45 g, 0.68 mmol) prepared in Example 131, the same procedure as shown in Example 128 was repeated to give the titled compound (0.29 g, yield: 67%) as a white powder (cis:trans=3:1).

FABMS 634.1 [$M+H^+$]

Example 133

5-[4-(9H-9-Carbazolyl)-1-(3,4-dimethoxybenzoyl)-1,2,3,4-tetrahydro-2-quinolinyl]-N,N-dimethylpentanamide

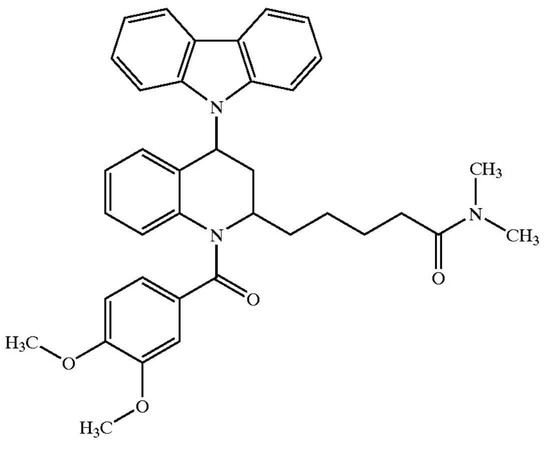

Starting with 5-[4-(9H-9-carbazolyl)-1-(3,4-dimethoxybenzoyl)-1,2,3,4-tetrahydro-2-quinolinyl]pentanoic acid (0.20 g, 0.34 mmol) prepared in Example 128 and a 2M dimethylamine/tetrahydrofuran solution (1 ml), the same procedure as shown in Example 129 was repeated to give the titled compound (0.12 g, yield: 60%) as a white powder (cis:trans=5:1).

FABMS 590.1 [$M+H^+$]

Example 134

5-[4-(9H-9-Carbazolyl)-1-(3,4-dimethoxybenzoyl)-1,2,3,4-tetrahydro-2-quinolinyl]-N-hexyl-N-methylpentanamide

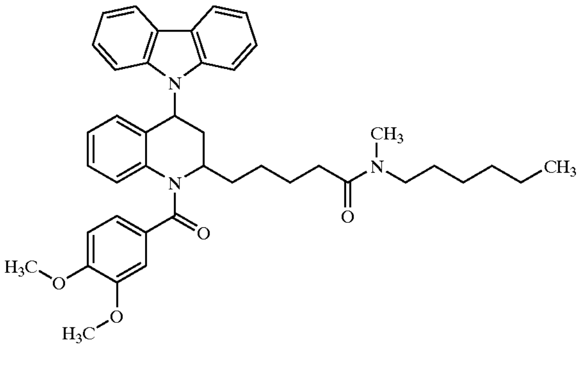

Starting with 5-[4-(9H-9-carbazolyl)-1-(3,4-dimethoxybenzoyl)-1,2,3,4-tetrahydro-2-quinolinyl]pentanoic acid (0.12 g, 0.21 mmol) prepared in Example 128 and N-hexyl-N-methylamine (0.3 ml), the same procedure as shown in Example 129 was repeated to give the titled compound (0.10 g, yield: 71%) as a white powder (cis:trans=3:1).

FABMS 660.3 [$M+H^+$]

Example 135

5-[4-(9H-9-Carbazolyl)-1-(3,4-dimethoxybenzoyl)-1,2,3,4-tetrahydro-2-quinolinyl]-1-pentanol

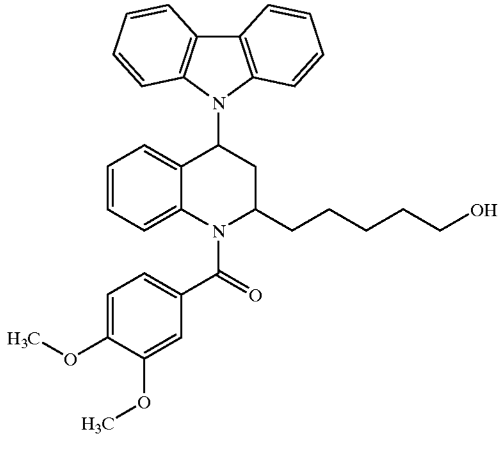

5-[4-(9H-9-Carbazolyl)-1-(3,4-dimethoxybenzoyl)-1,2,3,4-tetrahydro-2-quinolinyl]-pentanoic acid (0.30 g, 0.53 mmol) prepared in Example 128 was mixed with N-hydroxysuccinimide (64 mg, 0.56 mmol), N,N-dimethylformamide (5 ml) and WSC (113 mg, 0.59 mmol), followed by stirring overnight at room temperature. To the resulting mixture, tetrahydrofuran (5 ml) and sodium borohydride (61 mg, 1.6 mmol) were added and stirred at room temperature for 4 hours. The reaction mixture was poured into 10% citric acid, extracted with ethyl acetate, washed with saturated brine, and then dried over anhydrous magnesium sulfate. After distilling off the solvent, the residue was applied to silica gel column chromatography (developing solvent: ethyl acetate/hexane=1/10) to give the titled compound (0.17 g, yield: 59%) as a white crystal (cis:trans=4:1).

Melting point: 239° C.–240° C.

Example 136

5-[4-(9H-9-Carbazolyl)-1-(3,4-dimethoxybenzoyl)-1,2,3,4-tetrahydro-2-quinolinyl]-N,N-dimethyl-1-pentanamine

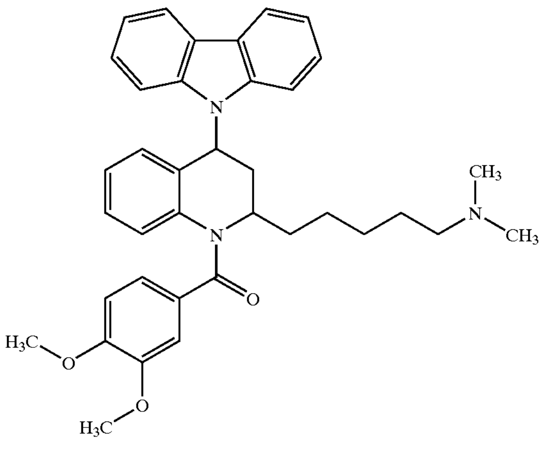

5-[4-(9H-9-Carbazolyl)-1-(3,4-dimethoxybenzoyl)-1,2,3,4-tetrahydro-2-quinolinyl]-1-pentanol (0.36 g, 0.66 mmol) prepared in Example 135 was mixed with triphenylphosphine (198 mg, 0.75 mmol), carbon tetrabromide (249 mg, 0.75 mmol) and tetrahydrofuran (10 ml), followed by stirring at room temperature for 4 hours. The resulting mixture was filtered and evaporated to remove the solvent. A 2M dimethylamine/tetrahydrofuran solution (10 ml) was added to the residue, followed by stirring overnight at room temperature. After distilling off the solvent, the residue was partitioned between chloroform and saturated brine, and the organic layer was washed with water and dried over anhydrous magnesium sulfate. After distilling off the solvent, the residue was applied to silica gel column chromatography (developing solvent: ethyl acetate/hexane=1/5) to give the titled compound (0.11 g, yield: 29%) as a white crystal (cis:trans=4:1).

Melting point: 198° C.–200° C.

Example 137

9-[1-(3,4-Dimethoxybenzoyl)-2-[5-[4-(4-fluorophenyl)-1-piperazinyl]pentyl]-1,2,3,4-tetrahydro-4-quinolinyl]-9H-carbazole

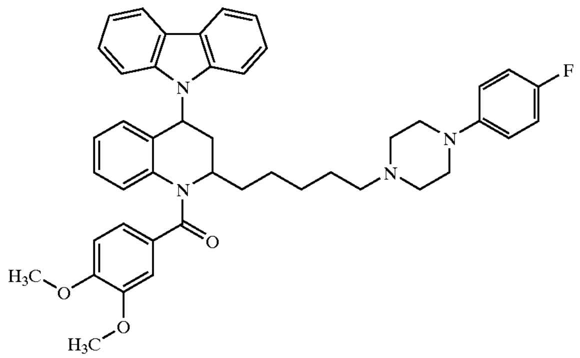

Starting with 5-[4-(9H-9-carbazolyl)-1-(3,4-dimethoxybenzoyl)-1,2,3,4-tetrahydro-2-quinolinyl]-1-pentanol (0.13 g, 0.22 mmol) prepared in Example 135 and 4-(4-fluorophenyl)piperazine (79 mg, 0.44 mmol), the same procedure as shown in Example 136 was repeated to give the titled compound (0.08 g, yield: 51%) as a white crystal (cis:trans=4:1).

Melting point: 178° C.–179° C.

Example 138

9-[1-(3,4-Dimethoxybenzoyl)-2-[5-[4-[3-(trifluoromethyl)phenyl]-1-piperidinyl]pentyl]-1,2,3,4-tetrahydro-4-quinolinyl]-9H-carbazole

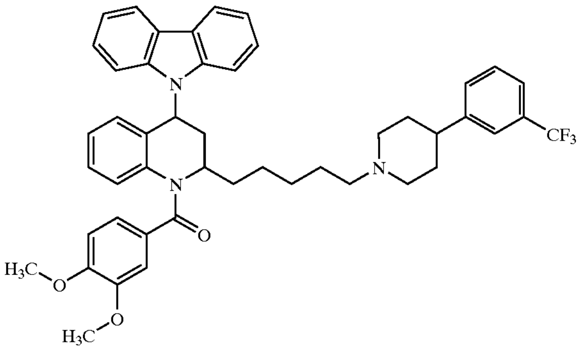

Starting with 5-[4-(9H-9-carbazolyl)-1-(3,4-dimethoxybenzoyl)-1,2,3,4-tetrahydro-2-quinolinyl]-1-pentanol (0.19 g, 0.32 mmol) prepared in Example 135 and 4-[3-(trifluoromethyl)phenyl]piperidine (0.23 g, 1 mmol), the same procedure as shown in Example 136 was repeated to give the titled compound (0.13 g, yield: 53%) as a white crystal (cis:trans=3:1).

Melting point: 149° C.–150° C.

Example 139

N-[5-[4-(9H-9-Carbazolyl)-1-(3,4-dimethoxybenzoyl)-1,2,3,4-tetrahydro-2-quinolinyl]pentyl]-N-methylacetamide

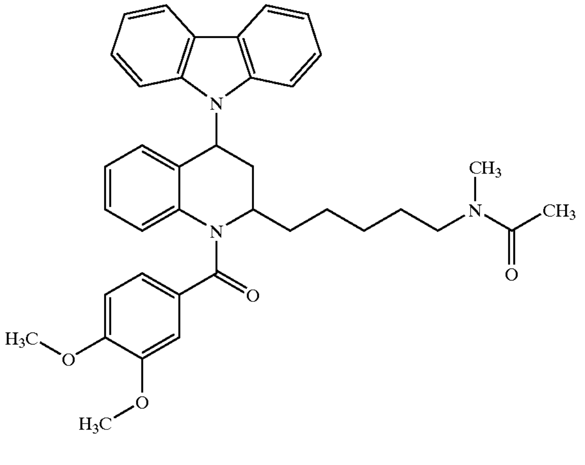

5-[4-(9H-9-Carbazolyl)-1-(3,4-dimethoxybenzoyl)-1,2,3,4-tetrahydro-2-quinolinyl]-1-pentanol (0.12 g, 0.22 mmol) prepared in Example 135 was mixed with triphenylphosphine (66 mg, 0.25 mmol), carbon tetrabromide (83 mg, 0.25 mmol) and tetrahydrofuran (3 ml), followed by stirring at room temperature for 4 hours. The resulting mixture was filtered and evaporated to remove the solvent. To the residue, a 40% methylamine/methanol solution (10 ml) was added and stirred overnight at room temperature. After distilling off the solvent, the residue was dissolved in pyridine (3 ml), mixed with acetic anhydride (1 ml) and stirred overnight at room temperature, followed by addition of methanol (1 ml) to stop the reaction. After distilling off the solvent, the residue was partitioned between ethyl acetate and saturated aqueous sodium bicarbonate, and the organic layer was washed with water and dried over anhydrous magnesium sulfate. After distilling off the solvent, the residue was applied to silica gel column chromatography (developing solvent: ethyl acetate/hexane=1/5) to give the titled compound (0.09 g, yield: 69%) as a white crystal (cis:trans=4:1).

Melting point: 173° C.–175° C.

Example 140

9-[1-(3,4-Dimethoxybenzoyl)-2-[5-(hexylthio)pentyl]-1,2,3,4-tetrahydro-4-quinolinyl]-9H-carbazole

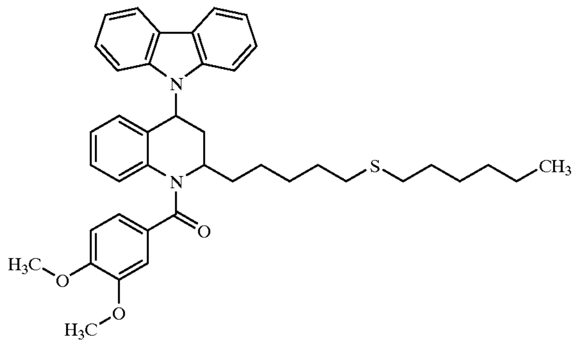

Starting with 5-[4-(9H-9-carbazolyl)-1-(3,4-dimethoxybenzoyl)-1,2,3,4-tetrahydro-2-quinolinyl]-1-pentanol (0.08 g, 0.15 mmol) prepared in Example 135 and n-hexylmercaptan (0.3 ml), the same procedure as shown in Example 136 was repeated to give the titled compound (0.01 g, yield: 7%) as a white crystal (cis:trans=6:1).

Melting point: 231° C.–232° C.

Example 141

9-[1-(3,4-Dimethoxybenzoyl)-2-[5-(4-fluorophenoxy)pentyl]-1,2,3,4-tetrahydro-4-quinolinyl]-9H-carbazole

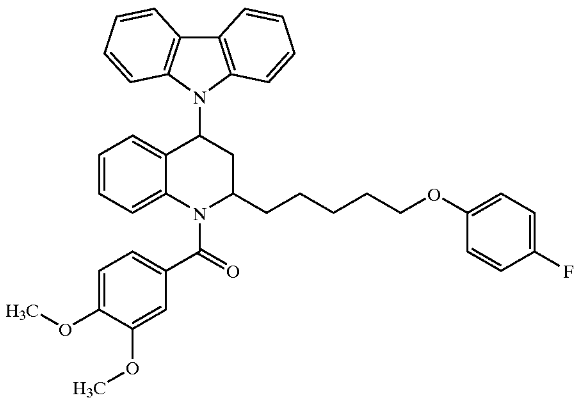

5-[4-(9H-9-Carbazolyl)-1-(3,4-dimethoxybenzoyl)-1,2,3,4-tetrahydro-2-quinolinyl]-1-pentanol (0.12 g, 0.22 mmol) prepared in Example 135 was mixed with 4-fluorophenol (50 mg, 0.44 mmol), tetrahydrofuran (4 ml), diethyl azodicarboxylate (69 μl, 0.44 mmol) and triphenylphosphine (0.11 g, 0.44 mmol), followed by stirring overnight at room temperature. After distilling off the solvent, the residue was partitioned between ethyl acetate and water, and the organic layer was washed with water, dried over anhydrous magnesium sulfate and then evaporated to remove the solvent. The residue was applied to silica gel column chromatography (developing solvent: ethyl acetate/hexane=1/10) to give the titled compound (0.13 g, yield: 93%) as a white crystal (cis:trans=4:1).

Melting point: 157° C.–159° C.

Example 142

2,4-trans-9-{1-(3,4-Dimethoxybenzoyl)-2-[5-(4-fluorophenoxy)pentyl]-1,2,3,4-tetrahydro-4-quinolinyl}-9H-carbazole

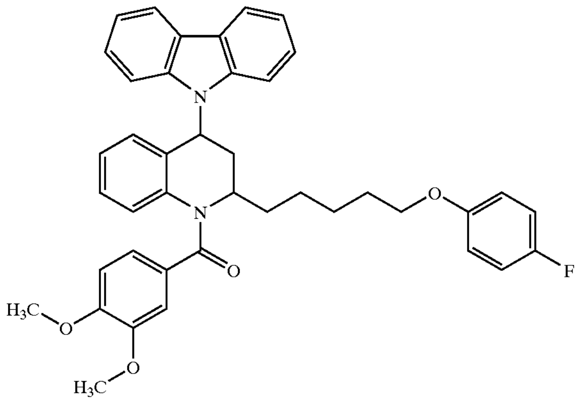

The recrystallization mother liquor of 5-[4-(9H-9-carbazolyl)-1-(3,4-dimethoxybenzoyl)-1,2,3,4-tetrahydro-2-quinolinyl]-1-pentanol prepared in Example 135 was concentrated, and the resulting residue was applied to silica gel column chromatography (developing solvent: ethyl acetate/hexane=1/10) to give the trans-form. Starting with this trans-form (0.15 g, 0.27 mmol), the same procedure as shown in Example 141 was repeated to give the titled compound (0.09 g, 56%) as a colorless oil.

Elementary Analysis for $C_{41}H_{39}N_2O_4$: Calculated: C, 76.61; H, 6.12; N, 4.36. Found: C, 76.55; H, 6.41; N, 4.28.

FABMS 643.2 $[M+H^+]$

The titled compounds of Examples 127 to 142 are summarized in Table 11 below.

TABLE 11

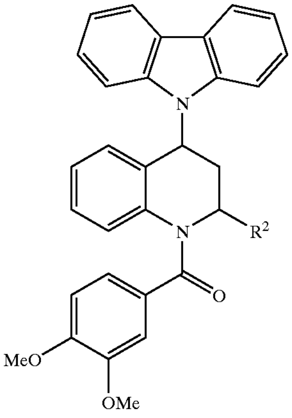

| Example No. | $R^2$ | Stereochemistry |
|---|---|---|
| 127 | $CH_2CH_2CH_2CH_2COOEt$ | cis/trans = 3/2 |
| 128 | $CH_2CH_2CH_2CH_2COOH$ | cis/trans = 4/1 |
| 129 | $CH_2CH_2CH_2CH_2CONHCH_3$ | cis/trans = 4/1 |
| 130 | $CH_2CH_2CH_2CH_2CONHC_3H_7$ | cis/trans = 5/2 |
| 131 | $CH_2CH_2CH_2CH_2CONHCH_2CH_2COOEt$ | cis/trans = 3/1 |
| 132 | $CH_2CH_2CH_2CH_2CONHCH_2CH_2COOH$ | cis/trans = 3/1 |
| 133 | $CH_2CH_2CH_2CH_2CON(CH_3)_2$ | cis/trans = 5/1 |
| 134 | $CH_2CH_2CH_2CH_2CONH(CH_3)C_6H_{13}$ | cis/trans = 3/1 |
| 135 | $CH_2CH_2CH_2CH_2CH_2OH$ | cis/trans = 4/1 |
| 136 | $CH_2CH_2CH_2CH_2CH_2N(CH_3)_2$ | cis/trans = 4/1 |
| 137 | 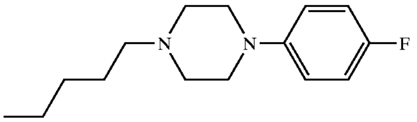 | cis/trans = 4/1 |
| 138 | 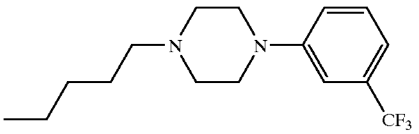 | cis/trans = 3/1 |
| 139 | $CH_2CH_2CH_2CH_2CH_2N(CH_3)Ac$ | cis/trans = 4/1 |
| 140 | $CH_2CH_2CH_2CH_2CH_2SC_6H_{13}$ | cis/trans = 6/1 |
| 141 | 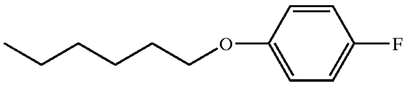 | cis/trans = 4/1 |
| 142 | 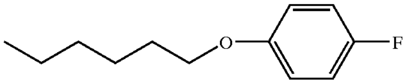 | trans |

Example 143

2,4-cis-4-(9H-9-Carbazolyl)-1-(4-ethoxy-3-methoxybenzoyl)-2-methyl-1,2,3,4-tetrahydroquinoline

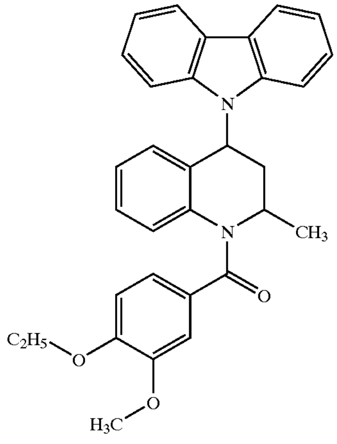

Starting with 2,4-cis-4-(9H-9-carbazolyl)-2-methyl-1,2,3,4-tetrahydroquinoline (600 mg, 1.92 mmol) prepared in Reference Example 4, the same procedure as shown in Reference Example 19 was repeated to give the titled compound (234 mg, yield: 26%) as a white crystal.

Elementary Analysis for $C_{32}H_{30}N_2O_3$ $0.45H_2O$: Calculated: C, 77.06; H, 6.25; N, 5.61. Found: C, 77.39; H, 6.58; N, 5.28.

Melting point: 214° C.–215° C.

Example 144

2,4-cis-4-(9H-9-Carbazolyl)-1-(3,4-diethoxybenzoyl)-2-methyl-1,2,3,4-tetrahydroquinoline

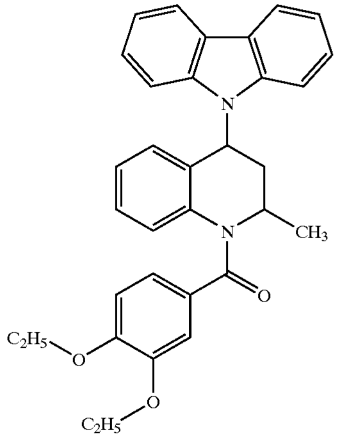

Starting with 2,4-cis-4-(9H-9-carbazolyl)-2-methyl-1,2,3,4-tetrahydroquinoline (600 mg, 1.92 mmol) prepared in Reference Example 4, the same procedure as shown in Reference Example 20 was repeated to give the titled compound (215 mg, yield: 23%) as a white crystal.

Elementary Analysis for $C_{33}H_{32}N_2O_3$ $0.3H_2O$: Calculated: C, 77.71; H, 6.44; N, 5.49. Found: C, 77.84; H, 6.72; N, 5.16.

Melting point: 240° C.–241° C.

Example 145

2,4-cis-4-(9H-9-Carbazolyl)-1-(3,4-diethoxybenzoyl)-2-ethyl-1,2,3,4-tetrahydroquinoline

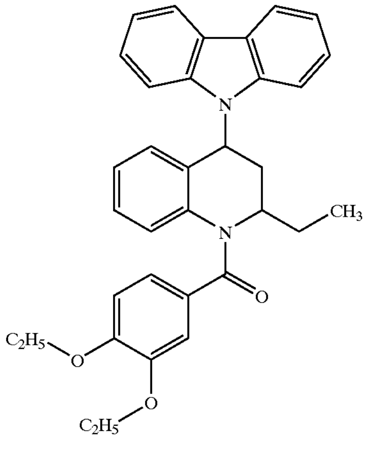

Starting with 2,4-cis-4-(9H-9-carbazolyl)-2-ethyl-1,2,3,4-tetrahydroquinoline (570 mg, 1.75 mmol) prepared in Reference Example 5, the same procedure as shown in Reference Example 19 was repeated to give the titled compound (517 mg, yield: 57%) as a white crystal.

$^1H$ NMR ($CDCl_3$) δ 0.98 (t, J=7.4 Hz, 3H), 1.30 (t, J=6.9 Hz, 3H), 1.42 (t, J=6.9 Hz, 3H), 1.63 (m, 1H), 1.93 (m, 1H), 2.63 (m, 1H), 2.77 (m, 1H), 3.77 (m, 1H), 3.90 (m, 1H), 4.02–4.13 (m, 2H), 4.95 (m, 1H), 5.90 (m, 1H), 6.68–6.72 (m, 2H), 6.82–7.00 (m, 5H), 7.10–7.13 (m, 1H), 7.93 (m, 3H), 8.35–8.45 (m, 2H), 8.84 (d, J=5.2 Hz, 2H).

Example 146

2,4-cis-4-(9H-9-Carbazolyl)-1-(4-ethoxy-3-methoxybenzoyl)-2-propyl-1,2,3,4-tetrahydroquinoline

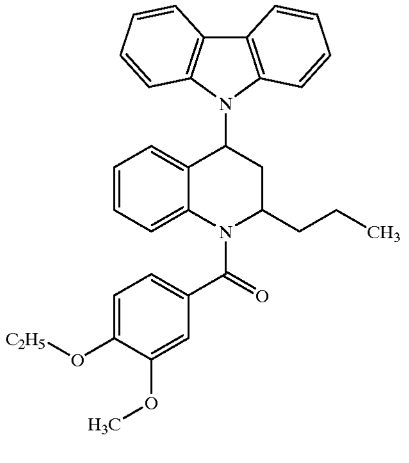

Starting with 2,4-cis-4-(9H-9-carbazolyl)-2-propyl-1,2,3,4-tetrahydroquinoline (500 mg, 1.47 mmol) prepared in Reference Example 6, the same procedure as shown in Reference Example 19 was repeated to give the titled compound (44 mg, yield: 6%) as a white crystal.

Elementary Analysis for $C_{34}H_{34}N_2O_3$: Calculated: C, 78.74; H, 6.61; N, 5.40. Found: C, 78.44; H, 6.48; N, 5.28.

Melting point: 221° C.–222° C.

Example 147

2,4-cis-4-(9H-9-Carbazolyl)-1-(3,4-diethoxybenzoyl)-2-propyl-1,2,3,4-tetrahydroquinoline

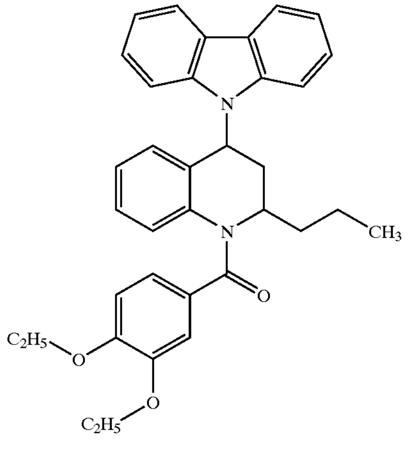

Starting with 2,4-cis-4-(9H-9-carbazolyl)-2-propyl-1,2,3,4-tetrahydroquinoline (500 mg, 1.47 mmol) prepared in Reference Example 6, the same procedure as shown in Reference Example 20 was repeated to give the titled compound (79 mg, yield: 10%) as a white crystal.

Elementary Analysis for $C_{35}H_{36}N_2O_3$ $0.1H_2O$: Calculated: C, 78.65; H, 6.83; N, 5.24. Found: C, 78.96; H, 7.20; N, 5.00.

Melting point: 220° C.

Example 148

2,4-cis-9-[2-Butyl-1-(4-ethoxy-3-methoxybenzoyl)-1,2,3,4-tetrahydro-4-quinolinyl]-9H-carbazole

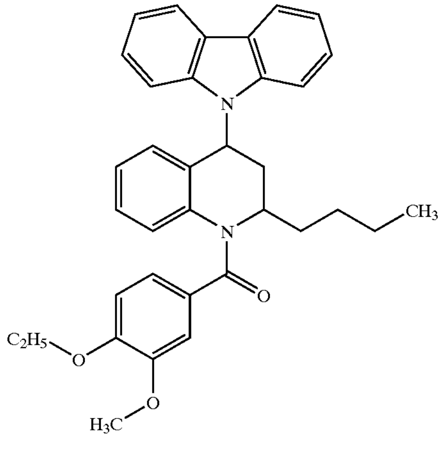

Starting with 2,4-cis-2-butyl-4-(9H-9-carbazolyl)-1,2,3,4-tetrahydroquinoline (0.67 g, 2.05 mmol) prepared in Reference Example 7 and 4-ethoxy-3-methoxybenzoyl chloride (0.48 g, 2.46 mmol), the same procedure as shown in Reference Example 19 was repeated to give the titled compound (0.37 g, 34%) as a white crystal.

Melting point: 231° C.–232° C.

Elementary Analysis for $C_{35}H_{36}N_2O_3$: Calculated: C, 78.92; H, 6.81; N, 5.26. Found: C, 78.70; H, 6.75; N, 5.25.

Example 149

2,4-cis-9-[2-Butyl-1-(3,4-diethoxybenzoyl)-1,2,3,4-tetrahydro-4-quinolinyl]-9H-carbazole

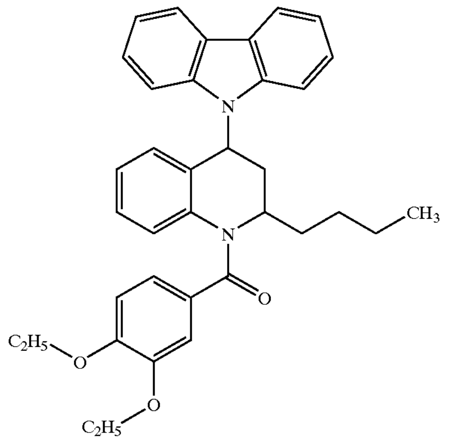

Starting with 2,4-cis-2-butyl-4-(9H-9-carbazolyl)-1,2,3,4-tetrahydroquinoline (0.50 g, 1.41 mmol) prepared in Reference Example 7 and 3,4-diethoxybenzoyl chloride (0.45 g, 2.12 mmol), the same procedure as shown in Reference Example 20 was repeated to give the titled compound (0.20 g, 26%) as a white crystal.

Melting point: 232° C.–233° C.

FABMS 547.2 [$M+H^+$]

Example 150

2,4-cis-9-[2-Ethyl-1-(3-methoxy-4-methylthiobenzoyl)-1,2,3,4-tetrahydro-4-quinolinyl]-9H-carbazole

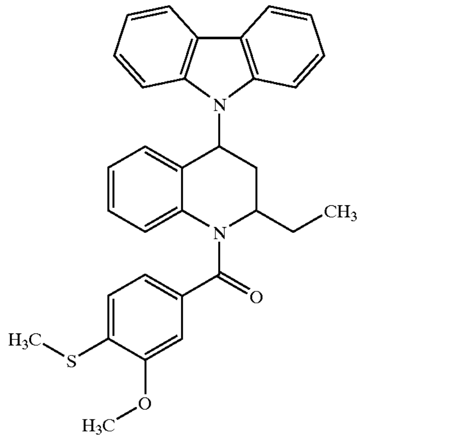

Starting with 2,4-cis-4-(9H-9-carbazolyl)-2-ethyl-1,2,3,4-tetrahydroquinoline (0.56 g, 1.71 mmol) prepared in Reference Example 5 and 3-methoxy-4-methylthiobenzoyl chloride (0.51 g, 2.57 mmol), the same procedure as shown in Example 32 was repeated to give the titled compound (0.41 g, 47%) as a white crystal.

Melting point: 210° C.–211° C.

FABMS 507.0 [$M+H^+$]

Example 151

2,4-cis-9-[2-Butyl-1-(3-methoxy-4-methylthiobenzoyl)-1,2,3,4-tetrahydro-4-quinolinyl]-9H-carbazole

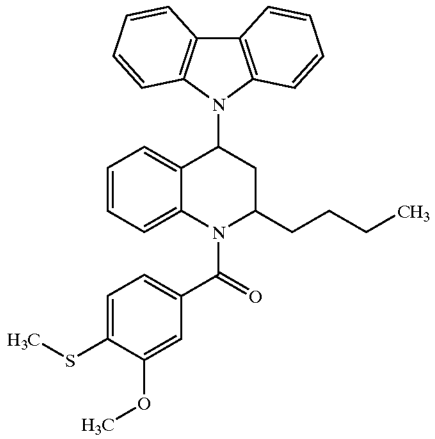

Starting with 2,4-cis-2-butyl-4-(9H-9-carbazolyl)-1,2,3,4-tetrahydroquinoline (0.47 g, 1.32 mmol) prepared in Reference Example 7 and 3-methoxy-4-methylthiobenzoyl chloride (0.34 g, 1.72 mmol), the same procedure as shown in Example 32 was repeated to give the titled compound (0.39 g, 55%) as a white crystal.

Melting point: 230° C.–231° C.

FABMS 534.2 [$M^+$]

Example 152

2,4-cis-4-(9H-9-Carbazolyl)-2-(2-cyanoethyl)-1-(3,4-diethoxybenzoyl)-1,2,3,4-tetrahydroquinoline

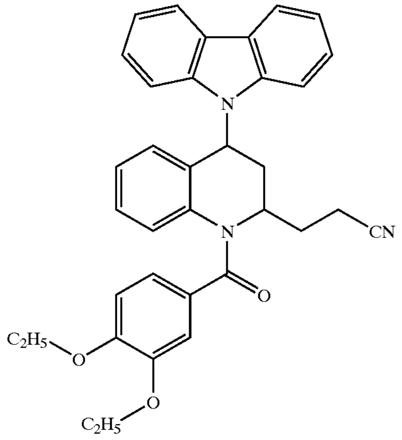

Starting with 2,4-cis-4-(9H-9-carbazolyl)-2-(2-cyanoethyl)-1,2,3,4-tetrahydroquinoline (500 mg, 1.42 mmol) prepared in Reference Example 11 and 3,4-diethoxybenzoic acid (478 mg, 2.27 mmol), the same procedure as shown in Reference Example 19 was repeated to give the titled compound (118 mg, yield: 15%) as a white crystal.

FABMS(pos) 544.2 [$M+H^+$]

Example 153

2,4-cis-4-(9H-9-Carbazolyl)-2-(2-cyanoethyl)-1-(4-methoxybenzoyl)-1,2,3,4-tetrahydroquinoline

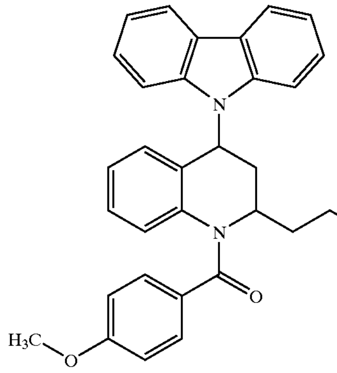

Starting with 2,4-cis-4-(9H-9-carbazolyl)-2-(2-cyanoethyl)-1,2,3,4-tetrahydroquinoline (1.0 g, 2.85 mmol) prepared in Reference Example 11 and 4-methoxybenzoyl chloride (677 mg, 4.28 mmol), the same procedure as shown in Example 32 was repeated to give the titled compound (480 mg, yield: 33%) as a white crystal.

Elementary Analysis for $C_{31}H_{27}N_3O_2$ $0.3H_2O$: Calculated: C, 77.74; H, 5.81; N, 8.77. Found: C, 77.78; H, 5.74; N, 8.50.

Example 154 tert-Butyl N-[3-[2,4-cis-4-(9H-9-carbazolyl)-1-(4-methoxybenzoyl)-1,2,3,4-tetrahydroquinolin-2-yl]propyl]carbamate

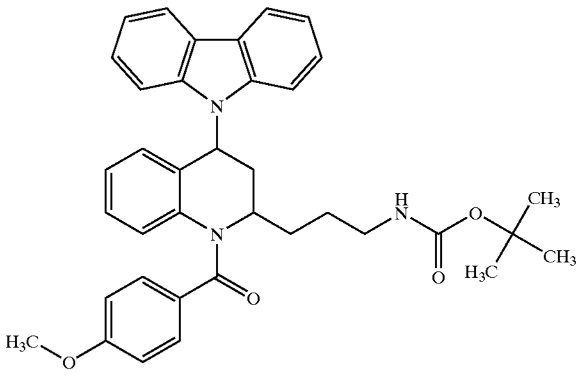

Starting with 2,4-cis-4-(9H-9-carbazolyl)-2-(2-cyanoethyl)-1-(4-methoxybenzoyl)-1,2,3,4-tetrahydroquinoline (3.6 g, 6.98 mmol) prepared in Reference Example 153, the same procedure as shown in Example 45 was repeated to give the titled compound (3.21 g, yield: 97%) as a white crystal.

$^1H$ NMR ($CDCl_3$) δ 1.42 (s, 9H), 1.50–1.70 (m, 3H), 1.80–2.00 (m, 1H), 2.50–2.63 (m, 1H), 2.71–2.81 (m, 1H), 3.17 (br s, 2H), 3.79 (s, 3H), 4.60–4.75 (m, 1H), 4.90–5.05 (m, 1H), 5.90 (dd, J=11.9, 5.9 Hz, 1H), 6.66–6.97 (m, 6H), 7.07 (d, J=7.8 Hz, 1H), 7.22–7.33 (m, 5H), 7.45–7.55 (m, 2H), 8.18 (d, J=7.7 Hz, 2H).

Example 155

3-[2,4-cis-4-(9H-9-Carbazolyl)-1-(4-methoxybenzoyl)-1,2,3,4-tetrahydroquinolin-2-yl]propylamine hydrochloride

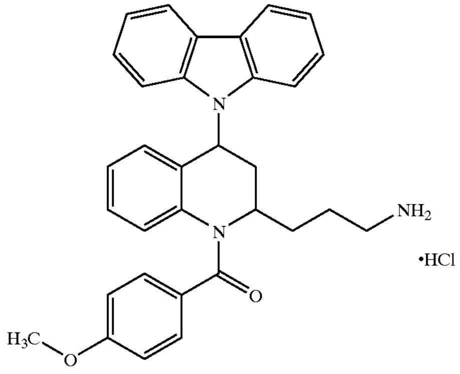

Starting with tert-butyl N-[3-[2,4-cis-4-(9H-9-carbazolyl)-1-(4-methoxybenzoyl)-1,2,3,4-tetrahydroquinolin-2-yl]propyl]carbamate (3.10 g, 6.55 mmol) prepared in Reference Example 154, the same procedure as shown in Example 46 was repeated to give the titled compound (1.65 g, yield: 48%) as a white crystal.

$^1H$ NMR ($CDCl_3$) δ 1.67 (br s, 1H), 1.90 (br s, 3H), 2.47 (br s, 1H), 2.69 (br s, 1H), 3.12 (br s, 2H), 3.66 (s, 3H), 5.00 (br s, 1H), 5.86 (br s, 1H), 6.64–6.76 (m, 4H), 6.87–6.90 (m, 2H), 7.03 (d, J=8.0, 1H), 7.18–7.33 (m, 4H), 7.46 (br s, 2H), 8.11 (d, J=7.7, 2H), 8.52 (br s, 3H).

Example 156

N-[3-[2,4-cis-4-(9H-9-Carbazolyl)-1-(4-methoxybenzoyl)-1,2,3,4-tetrahydroquinolin-2-yl]propyl]butanamide

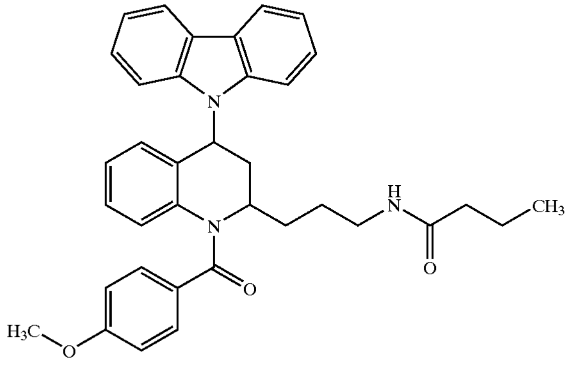

Starting with 2,4-cis-4-(9H-9-carbazolyl)-2-(2-cyanoethyl)-1-(4-methoxybenzoyl)-1,2,3,4-tetrahydroquinoline (200 mg, 0.388 mmol) prepared in Reference Example 153 and butyric anhydride (123 mg, 0.776 mmol), the same procedure as shown in Example 45 was repeated to give the titled compound (60 mg, yield: 28%) as a white crystal.

$^1H$ NMR ($CDCl_3$) δ 0.91–0.97 (m, 3H), 1.50–1.80 (m, 6H), 1.90–2.10 (m, 1H), 2.19 (t, J=7.3, 2H), 2.50–2.65 (m, 1H), 2.73–2.78 (m, 1H), 3.20–3.30 (m, 1H), 3.35–3.50 (m, 1H), 3.79 (s, 3H), 4.95–5.10 (m, 1H), 5.91 (dd, J=11.9, 6.1, 1H), 6.12 (br s, 1H), 6.65–6.80 (m, 3H), 6.80–7.10 (m, 4H), 7.20–7.35 (m, 4H), 7.40–7.55 (m, 2H), 8.17–8.20 (m, 2H).

Example 157

Ethyl 5-[4-(9H-9-carbazolyl)-1-(4-methoxybenzoyl)-1,2,3,4-tetrahydro-2-quinolinyl]pentanoate

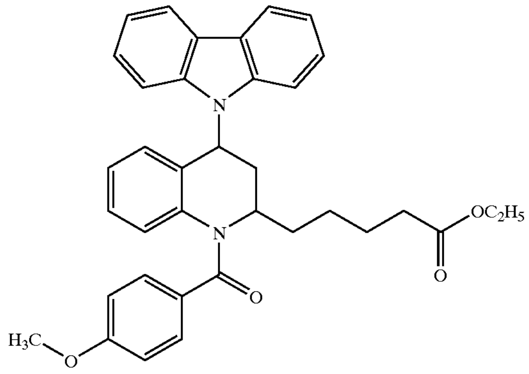

Starting with ethyl 6-formylhexanoate (4.51 g, 28.5 mmol), the same procedures as shown in Reference Example 4 and Example 32 were repeated to give the titled compound (1.70 g, overall yield: 11%) as a white crystal (cis:trans=12:1).

Melting point: 167° C.–168° C.

FABMS 561.1[M+H$^+$]

Example 158

5-[4-(9H-9-Carbazolyl)-1-(4-methoxybenzoyl)-1,2,3,4-tetrahydro-2-quinolinyl]pentanoic acid

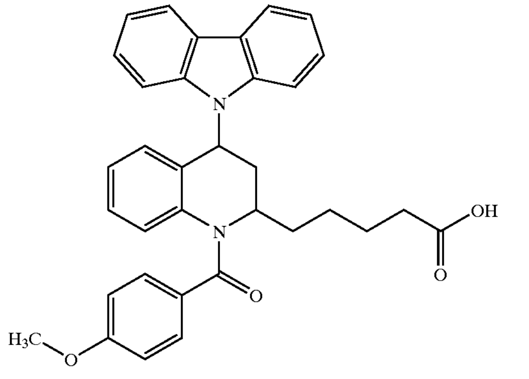

Starting with ethyl 5-[4-(9H-9-carbazolyl)-1-(4-methoxybenzoyl)-1,2,3,4-tetrahydro-2-quinolinyl]pentanoate (1.60 g, 2.85 mmol) prepared in Example 157, the same procedure as shown in Example 128 was repeated to give the titled compound (1.51 g, yield: 99%) as a white powder (cis:trans=12:1).

FABMS 533.1[M+H$^+$]

The titled compounds of Examples 143 to 158 are summarized in Table 12 below.

TABLE 12

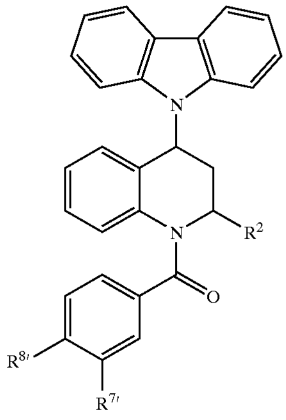

| Example No. | $R^2$ | $R^{7'}$ | $R^{8'}$ | Stereo-chemistry |
|---|---|---|---|---|
| 143 | $CH_3$ | $OC_2H_5$ | $OCH_3$ | cis |
| 144 | $CH_3$ | $OC_2H_5$ | $OC_2H_5$ | cis |
| 145 | $C_2H_5$ | $OC_2H_5$ | $OC_2H_5$ | cis |
| 146 | $C_3H_7$ | $OC_2H_5$ | $OCH_3$ | cis |
| 147 | $C_3H_7$ | $OC_2H_5$ | $OC_2H_5$ | cis |
| 148 | $C_4H_9$ | $OC_2H_5$ | $OCH_3$ | cis |
| 149 | $C_4H_9$ | $OC_2H_5$ | $OC_2H_5$ | cis |
| 150 | $C_2H_5$ | $SCH_3$ | $OCH_3$ | cis |
| 151 | $C_4H_9$ | $SCH_3$ | $OCH_3$ | cis |
| 152 | $CH_2CH_2CN$ | $OC_2H_5$ | $OC_2H_5$ | cis |
| 153 | $CH_2CH_2CN$ | $OCH_3$ | H | cis |
| 154 | $CH_2CH_2CH_2NHBoc$ | $OCH_3$ | H | cis |
| 155 | $CH_2CH_2CH_2NH_2$ | $OCH_3$ | H | cis |
| 156 | $CH_2CH_2CH_2NHCOC_3H_7$ | $OCH_3$ | H | cis |
| 157 | $CH_2CH_2CH_2CH_2COOEt$ | $OCH_3$ | H | cis/trans = 12/1 |
| 158 | $CH_2CH_2CH_2CH_2COOH$ | $OCH_3$ | H | cis/trans = 12/1 |

Example 159

3-[1-(3,4-Dimethoxybenzoyl)-2-methyl-1,2-dihydro-4-quinolinyl]-1,2,4,5-tetrahydro-3H-3-benzazepine

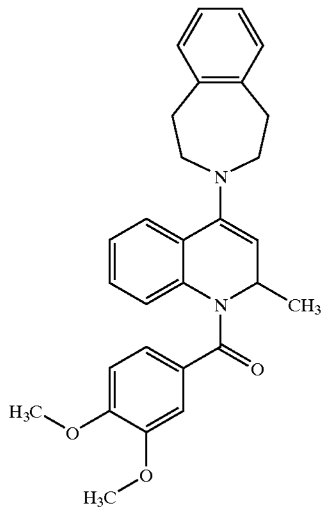

Starting with 2,3-trans-2,4-cis-1-(3,4-dimethoxybenzoyl)-3-hydroxy-2-methyl-4-(1,2,4,5-tetrahydro-3H-3-benzazepin-3-yl)-1,2,3,4-tetrahydroquinoline (560 mg, 1.18 mmol) prepared in Example 88, the same procedure as shown in Example 54 was repeated to give the titled compound (160 mg, yield: 29%) as a colorless oil.

$^1$H NMR ($CDCl_3$) δ 1.23 (d, J=6.7 Hz, 3H), 2.97–3.09 (m, 4H), 3.56–3.60 (m, 4H), 3.67 (s, 3H), 3.85 (s, 3H), 5.46 (s, 1H), 5.68 (q, J=6.7 Hz, 1H), 6.45 (d, J=7.9 Hz, 1H), 6.62 (t, J=7.3 Hz, 1H), 6.69 (d, J=8.4 Hz, 1H), 6.85 (s, 1H), 6.93–7.10 (m, 3H), 7.13 (s, 4H).

Example 160

4-(5-Chloro-1,2,3,4-tetrahydroquinolin-1-yl)-1-(3,4-dimethoxybenzoyl)-2-methyl-1,2-dihydroquinoline

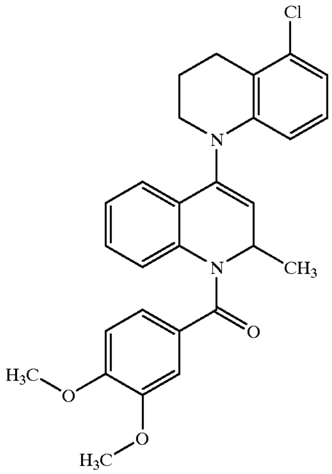

Starting with 2,3-trans-2,4-cis-4-(5-chloro-1,2,3,4-tetrahydroquinolin-1-yl)-1-(3,4-dimethoxybenzoyl)-3-hydroxy-2-methyl-1,2,3,4-tetrahydroquinoline (493 mg, 1.00 mmol) prepared in Example 86, the same procedure as shown in Example 54 was repeated to give the titled compound (95 mg, yield: 28%) as a white crystal.

Elementary Analysis for $C_{28}H_{27}ClN_2O_3$: Calculated: C, 70.80; H, 5.73; N, 5.90. Found: C, 70.54; H, 5.50; N, 5.82.

Melting point: 162° C.–163° C. (crystallization solvent: diethyl ether-hexane)

Example 161

4-(9H-9-Carbazolyl)-1-(3,4-dimethoxybenzoyl)-2-methyl-1,2-dihydroquinoline

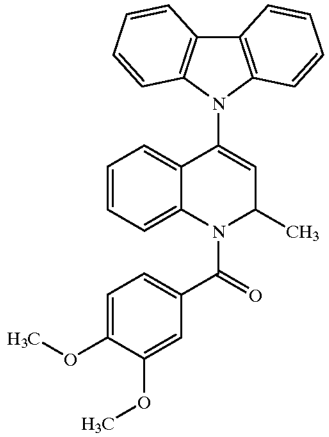

Starting with 3-(3,4-dimethoxybenzoyl)-2-methyl-1a,2,3,7b-tetrahydrooxyleno[2,3-c]quinoline (5.4 g, 16.6 mmol) synthesized in Reference Example 3, the same procedure as shown in Example 59 was repeated to give the titled compound (1.5 g, yield: 19%) as a white crystal.

Elementary Analysis for $C_{31}H_{26}N_2O_3$: Calculated: C, 78.46; H, 5.52; N, 5.90. Found: C, 78.71; H, 5.97; N, 5.86.

Melting point: 184° C.–185° C.

Example 162

4-(9H-9-Carbazolyl)-1-(3,4-dimethoxybenzoyl)-3-hydroxy-2-methyl-1,2,3,4-tetrahydroquinoline

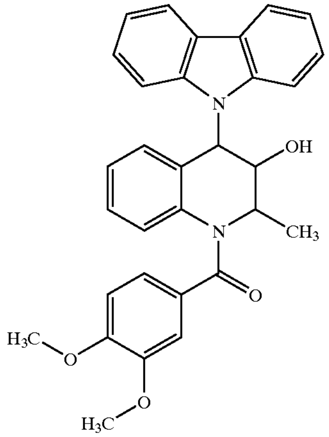

Starting with 3-(3,4-dimethoxybenzoyl)-2-methyl-1a,2,3,7b-tetrahydrooxyleno[2,3-c]quinoline (5.4 g, 16.6 mmol) synthesized in Reference Example 3, the same procedure as shown in Example 59 was repeated to give the titled compound (175 mg, yield: 2%) as a white crystal.

Elementary Analysis for $C_{31}H_{28}N_2O_4$ $H_2O$: Calculated: C, 72.92; H, 5.92; N, 5.48. Found: C, 73.22; H, 5.85; N, 5.31.

Melting point: 194° C.–195° C.

The titled compounds of Examples 159 to 162 are summarized in Table 13 below.

TABLE 13

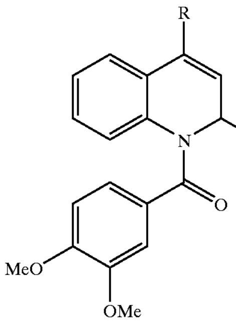

| Example No. | R |
| --- | --- |
| 159 | 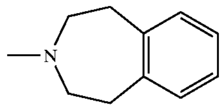 |
| 160 | 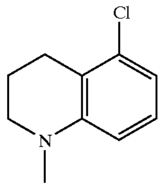 |
| 161 | 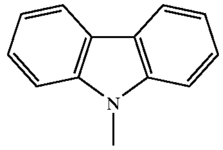 |
| 162* | 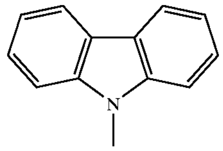 |

*

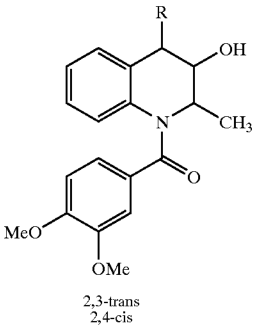

2,3-trans
2,4-cis

Example 163

Ethyl 2,3-trans-2,4-cis-5-[[1-[1-(3,4-dimethylbenzoyl)-2-methyl-1,2,3,4-tetrahydro-4-quinolinyl]-1,2,3,4-tetrahydro-6-quinolinyl]oxy] pentanoate

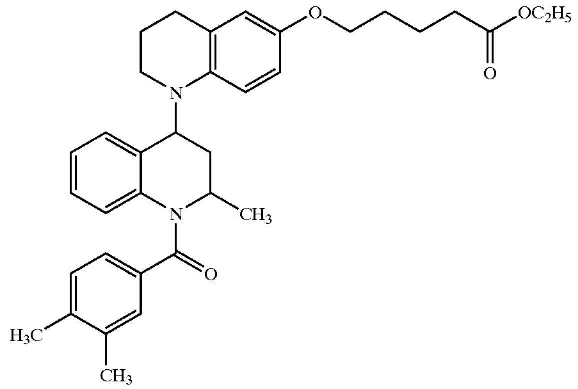

Starting with 2-methyl-1-(3,4-dimethylbenzoyl)-1,2,3,4-tetrahydro-4-quinolinol (1.1 g, 3.7 mmol) prepared in Reference Example 23 and ethyl 5-[(1,2,3,4-tetrahydro-6-quinolinyl)oxy]pentanoate (1.0 g, 3.7 mmol), the same procedure as shown in Example 1 was repeated to give the titled compound (0.31 g, yield: 15%) as a colorless oil. (cis:trans=3:2)

$^{1}H$ NMR ($CDCl_3$) δ 1.23–1.35 (m, 6H), 1.78–2.26 (m, 12H), 2.35–2.40 (m, 2H), 2.63–2.87 (m, 3H), 3.06–3.70 (m, 3H), 3.86–3.93 (m, 2H), 4.10–4.18 (m, 2H), 4.69–4.88 (m, 0.8H), 4.96–5.04 (m, 0.6H), 5.18–5.24 (m, 0.6H), 6.44–7.38 (m, 10H).

Example 164

5-[[1-[1-(3,4-Dimethylbenzoyl)-2-methyl-1,2,3,4-tetrahydro-4-quinolinyl]-1,2,3,4-tetrahydro-6-quinolinyl]oxy]pentanoic acid

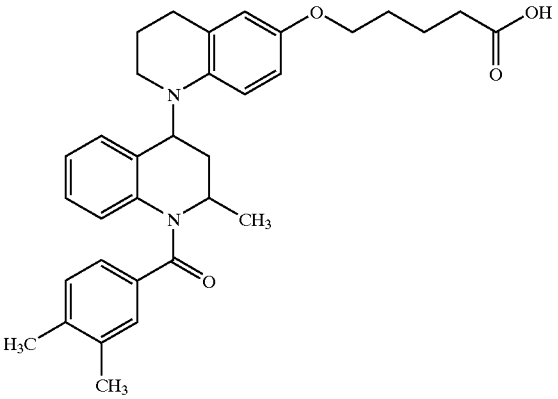

Starting with ethyl 5-[[1-[1-(3,4-dimethylbenzoyl)-2-methyl-1,2,3,4-tetrahydro-4-quinolinyl]-1,2,3,4-tetrahydro-6-quinolinyl]oxy]pentanoate (0.30 g, 0.54 mmol) prepared in Example 163, the same procedure as shown in Example 95 was repeated to give the titled compound (0.20 g, yield: 70%) as an amorphous powder. (cis:trans=3:2)

$^{1}H$ NMR ($CDCl_3$) δ 1.13–1.33 (m, 3H), 1.70–2.32 (m, 14H), 2.40–2.44 (m, 2H), 2.63–3.32 (m, 4H), 3.91 (br s, 2H), 4.72–4.88 (m, 0.8H), 5.00 (br s, 0.6H), 5.18–5.24 (m, 0.6H), 6.44–7.38 (m, 10H).

The titled compounds of Examples 163 and 164 are summarized in Table 14 below.

TABLE 14

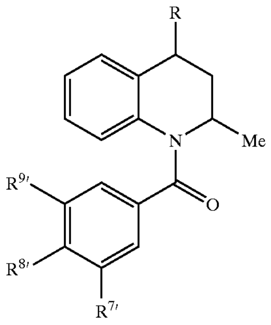

| Example No. | R | $R^{7'}$ | $R^{8'}$ | $R^{9'}$ | Stereochemistry |
|---|---|---|---|---|---|
| 163 | 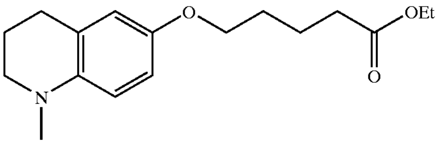 | $CH_3$ | $CH_3$ | H | cis/trans = 3/2 |
| 164 | 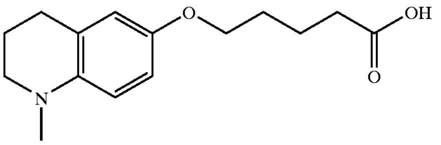 | $CH_3$ | $CH_3$ | H | cis/trans = 3/2 |

Experimental Example-1

Stimulatory Effects on sAPP Secretion and Inhibitory Effects on Cell Death in Rat-Derived Pheochromocytoma PC12h Cells 1) Experimental Materials and Methods Experimental Materials PC12h cells, a subspecies of rat-derived pheochromocytoma PC12 cells, were provided by the late Professor Hiroshi Hatanaka (Osaka University, Japan). Dulbecco's modified Eagle's medium (DMEM), phosphate buffered saline (PBS), HEPES (N-2-hydroxyethylpiperazine-N'-2-ethanesulfonic acid) buffer (pH 7.4), horse serum (HS) and a penicillin (5000 U/ml)/streptomycin (5 mg/ml) mixture were purchased from Gibco BRL. Fetal calf serum (FCS) was purchased from Bioscience PTY. Transferrin, insulin and progesterone were purchased from Sigma. The flasks used for culture were manufactured by Falcon, and the collagen-coated 96-well and 6-well multiwell plates used for assay were manufactured by Iwaki Glass Co., Ltd. (Japan). An LDH assay kit (LDH cytotoxic test Wako) and an anti-βAPP antibody 22C11 were purchased from Wako Pure Chemical Industries, Ltd. (Japan) and Chemicon, respectively. All other chemicals used were commercially available and of reagent grade.

Stimulatory Effects on sAPP Secretion

PC12h cells were grown in DMEM culture medium supplemented with 10% FCS, 5% HS and penicillin/streptomycin, and then released by pipetting. The cells were seeded in collagen-coated 6-well plates at a confluency of 50% to 70% and allowed to stand for 1 day. On the following day, the wells were washed once with 10 mM HEPES/DMEM (1 ml) and then filled with 10 mM HEPES/DMEM culture medium (0.5 ml), followed by addition of Example No. 5 or 32. After 5 hours, the culture supernatant was collected from each well. Trichloroacetic acid (final concentration: 15%) was added to the culture supernatant to precipitate proteins, which were then concentrated. After addition of SDS-PAGE sample buffer (Daiichi Pure Chemicals Co., Ltd., Japan), each sample was boiled for 5 minutes, subjected to SDS-PAGE (10/20% gel, ATTO) and then transferred to a PVDF membrane (Bio-Rad Laboratories) at 2 $mA/cm^2$ for 60 minutes. Each membrane was blocked overnight at 4° C. with 0.1% Tween 20/20 mM Tris-buffered saline (pH 7.4) supplemented with 5% skimmed milk. The anti-βAPP antibody 22C11 was added at 50-fold dilution and reacted for 1 hour. An HRP (horse-radish peroxidase)-conjugated anti-mouse antibody (Zymed) was diluted 5000-fold for use as a secondary antibody. An ECL Plus (Amersham) was used for detection and the signals were digitized by an LAS-1000 plus (Fuji film, Japan), followed by quantification with NIH-image software.

Inhibitory Effects on Glutamate-Induced Cell Death

PC12h cells were seeded in 96-well plates at a density of $2\times10^4$ $cells/cm^2$. On the following day, the culture medium was replaced by HEPES/DMEM medium supplemented with 5 mg/ml transferrin, 5 mg/ml insulin and 20 nM progesterone, followed by addition of glutamic acid (1 mM) together with Example No. 5 or 32 or a solvent. A control group received a solvent only. After 72 hours, living cells were counted. Cell counts were determined as follows: after removal of the culture medium, living cells were solubilized in 0.1% Tween 20-containing PBS and assayed for LDH activity. The results were expressed as % of control, whose LDH activity was set to 100.

2) Results a) Stimulatory Effects of Example Nos. 5 and 32 on sAPP Secretion

FIG. 1 shows stimulatory effects on sAPP secretion 5 hours after addition of Example Nos. 5 and 32 selected among the compounds according to the present invention. In the upper panels of FIGS. 1(*a*) and 1(*b*), the result of Western blotting is shown for each Example No. Both compounds of Example Nos. 5 and 32 caused a concentration-dependent increase in sAPP level in the culture medium, as compared to the control group. In the lower panels of FIGS. 1(*a*) and 1(*b*), % increase in sAPP production (quantified with NIH image software and averaged from triplicate wells for each concentration) is shown for each Example No. When compared to the control group, Example No. 5 caused an approximately 2.0-fold increase at 10 nM concentration, while Example No. 32 caused an approximately 2.2-fold increase at 1 nM concentration.

b) Inhibitory Effects of Example Nos. 5 and 32 on Cell Death

Figure 2:
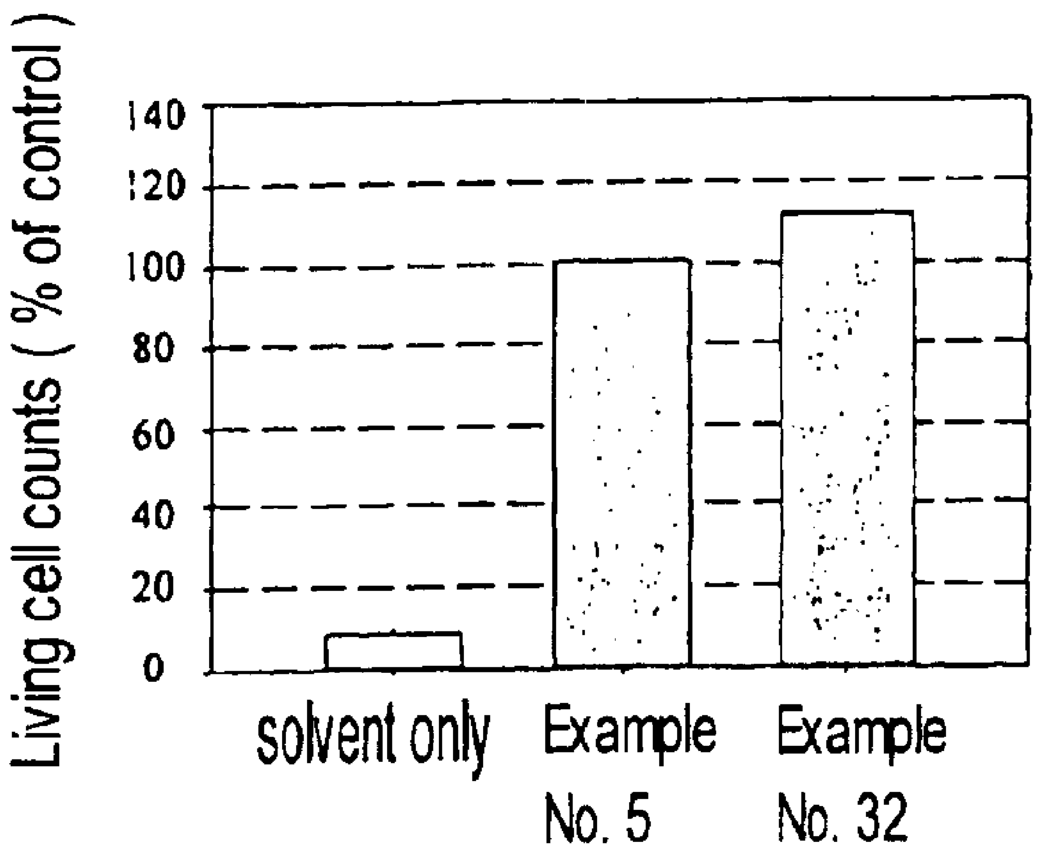
FIG. 2 is a graph showing the inhibitory effects of Example Nos. 5 and 32 on glutamate-induced cell death in PC12h cells (averaged from triplicate wells).

In PC12h cells, glutamic acid in the culture medium blocks the intracellular uptake of cystine, which is a starting material of glutathione. Thus, when cultured for 3 days or longer in the presence of 1 mM or more glutamic acid, PC12h cells are known to be killed by apoptosis due to a decrease in intracellular level of glutathione. At a concentration of 1 μM, both Example Nos. 5 and 32 completely inhibited such cell death induced by addition of 1 mM glutamic acid (FIG. 2).

INDUSTRIAL APPLICABILITY

The compounds of the present invention have a strong ability to stimulate sAPP secretion and also inhibit cellular, particularly neuronal, dysfunction and apoptosis with the aid of secreted sAPP having a neurotrophic factor-like action. Examples of possible target diseases include Alzheimer's disease, Parkinson's disease, prion disease, diabetic neuropathy, senile dementia and cerebrovascular disorder-induced neuronopathy. The compounds of the present invention can be used for prevention or treatment of these diseases.

What is claimed is:

1. A compound of the following Formula (I) or a salt or prodrug thereof:

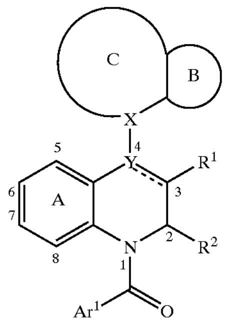

wherein $R^1$ and $R^2$, which may be the same or different, each represent a hydrogen atom, an optionally substituted lower alkyl group or an optionally substituted hydroxy group, or $R^1$ and $R^2$ may together form a 4- to 7-membered ring together with their adjacent carbon atoms, $Ar^1$ represents an optionally substituted aromatic group, the ring A represents an optionally substituted benzene ring, the ring B represents an optionally substituted aromatic ring, the ring C represents an optionally substituted 4- to 8-membered ring which may further be condensed with an optionally substituted ring, X represents CH or N, and ═ represents a single bond or a double bond, provided that Y represents CH or N when said bond is a single bond, and Y represents C when said bond is a double bond.

2. A compound of the following Formula (I') or a salt or prodrug thereof:

(I')

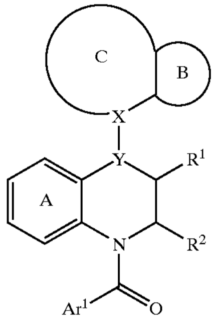

wherein $R^1$ and $R^2$, which may be the same or different, each represent a hydrogen atom or an optionally substituted lower alkyl group, or $R^1$ and $R^2$ may together form a 4- to 7-membered ring together with their adjacent carbon atoms, Ar1 represents an optionally substituted aromatic group, the ring A represents an optionally substituted benzene ring, the ring B represents an optionally substituted aromatic ring, the ring C represents an optionally substituted 4- to 8-membered ring, X represents CH or N, and Y represents CH or N.

3. The compound of claim 1 or a salt or prodrug thereof, wherein the partial structure:

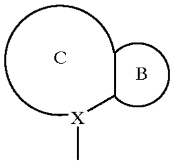

wherein the ring B, the ring C and X are as defined in claim 1, has the following formula:

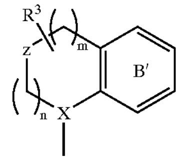

wherein $R^3$ represents a hydrogen atom, a halogen atom, an optionally substituted lower alkyl group or an optionally substituted lower alkoxy group, the ring B' represents an optionally substituted benzene ring, X represents CH or N, Z represents an oxygen atom, a sulfur atom, $CR^4R^5$, $NR^6$ or

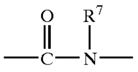 or 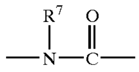

wherein $R^4$, $R^5$, $R^6$ and $R^7$, which may be the same or different, each represent a hydrogen atom or an optionally substituted lower alkyl group), m represents 0 or 1, and n represents an integer of 1 to 4.

4. The compound of claim 1 or a salt or prodrug thereof, wherein the ring C is further condensed with a monocyclic ring in addition to the ring B.

5. The compound of claim 1 or a salt or prodrug thereof, wherein $R^1$ is a hydrogen atom.

6. The compound of claim 1 or a salt or prodrug thereof, wherein $R^1$ is a hydroxy group, an optionally substituted alkoxy group or an optionally substituted acyloxy group.

7. The compound of claim 1 or a salt or prodrug thereof, wherein $R^2$ is a hydrogen atom or an optionally substituted lower alkyl group.

8. The compound of claim 1 or a salt or prodrug thereof, wherein $Ar^1$ is an optionally substituted monocyclic aromatic group.

9. The compound of claim 1 or a salt or prodrug thereof, wherein $Ar^1$ is an optionally substituted phenyl, furyl, thienyl or pyridyl group.

10. The compound of claim 1 or a salt or prodrug thereof, wherein the ring A is an unsubstituted benzene ring.

11. The compound of claim 1 or a salt or prodrug thereof, wherein at least one of X and Y is N.

12. The compound of claim 1 or a salt or prodrug thereof, wherein X is N and Y is C.

13. The compound of claim 1 or a salt or prodrug thereof, wherein $R^1$ is a hydrogen atom, an alkyloxy group or an acyloxy group, $R^2$ is a hydrogen atom or an optionally substituted lower alkyl group, $Ar^1$ is an optionally substituted phenyl group, an optionally substituted furyl group, an optionally substituted thieny group or an optionally substituted pyridyl group, the ring A is an unsubstituted benzene ring, the ring B is an optionally substituted benzene ring, the ring C is an optionally substituted nitrogen-containing 5- to 7-membered heterocyclic ring which may be condensed with an unsubstituted benzene ring, X is N, and Y is CH.

14. The compound of claim 1 or a salt or prodrug thereof, wherein $R^1$ is a hydrogen atom or an acyloxy group, $R^2$ is an unsubstituted $C_{1-6}$ alkyl group, $Ar^1$ is a phenyl group which may be substituted with an optionally halogenated $C_{1-6}$ alkoxy group, the ring A is an unsubstituted benzene ring, the ring B is an unsubstituted benzene ring, the ring C is tetrahydropyrrole, hexahydropyridine, hexahydropyrazine, tetrahydro-1,4-oxazine, tetrahydro-1,4-thiazine, perhydroazepine or pyrrole, X is N, and Y is CH.

15. The compound of claim 1, which is any one of the following compounds or salts or prodrugs thereof:

(−)-2,4-cis-1-(3,4-dimethoxybenzoyl)-2-methyl-4-(1,2,3,4-tetrahydroquinolin-1-yl)-1,2,3,4-tetrahydroquinoline;

(−)-2,4-cis-4-(3,4-dihydro-2H-1,4-benzoxazin-4-yl)-1-(3,4-dimethoxybenzoyl)-2-methyl-1,2,3,4-tetrahydroquinoline 2,4-cis-1-(3,4-dimethoxybenzoyl)-2-methyl-4-(1,2,3,4-tetrahydroquinolin-1-yl)-1,2,3,4-tetrahydroquinoline;

2,3-trans-2,4-cis-3-acetoxy-1-(3,4-dimethoxybenzoyl)-2-methyl-4-(1,2,3,4-tetrahydroquinolin-1-yl)-1,2,3,4-tetrahydroquinoline;

2,4-cis-4-(3,4-dihydro-2H-1,4-benzothiazin-4-yl)-1-(3,4-dimethoxybenzoyl)-2-methyl-1,2,3,4-tetrahydroquinoline;

2,4-cis-4-(1-benzyl-1,2,3,4-tetrahydroquinoxalin-4-yl)-1-(3,4-dimethoxybernzoyl)-2-methyl-1,2,3,4-tetrahydroquinoline;

2,4-cis-1-(3,4-dimethoxybenzoyl)-2-methyl-4-(2,3,4,5-tetrahydro-1H-1-benzazepinyl)-1,2,3,4-tetrahydroquinoline;

2,3-trans-2,4-cis-3-{[(benzylamino)carbonyl]oxy}-1-(3,4-dimethoxybenzoyl)-2-methyl-4-(2,3,4,5-tetrahydro-1H-1-benzazepinyl)-1,2,3,4-tetrahydroquinoline;

2,4-cis-4-(9H-9-carbazolyl)-1-(3,4-dimethoxybenzoyl)-2-methyl-1,2,3,4-tetrahydroquinoline;

(−)-2,4-cis-4-(9H-9-carbazolyl)-1-(3,4-dimethoxybenzoyl)-2-methyl-1,2,3,4-tetrahydroquin; and 2-butyl-4-(9H-9-carbazolyl)-1-(3,4-dimethoxybenzoyl)-1,2-dihydroquinoline.

16. The compound of claim 1 or a salt or prodrug thereof, wherein the 2- and 4-positions of the Formula (I) is formed the cis(−)-configuration.

17. A method for preparing a compound of the following formula or a salt or prodrug thereof:

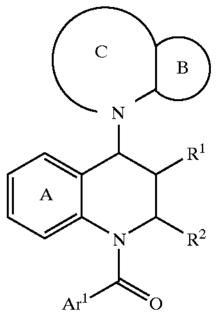

wherein $R^1$, $R^2$, $Ar^1$ and the rings A, B and C are as defined below, which comprises reacting a compound of the following formula or a salt thereof:

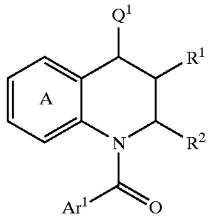

wherein $R^1$ and $R^2$, which may be the same or different, each represent a hydrogen atom, an optionally substituted lower alkyl group or an optionally substituted hydroxy group, or $R^1$ and $R^2$ may together form a 4- to 7-membered ring together with their adjacent carbon atoms, $Ar^1$ represents an optionally substituted aromatic group, the ring A represents an optionally substituted benzene ring, and $Q^1$ represents a reactive substituent, with a compound of the following formula or a salt thereof:

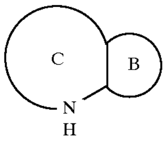

wherein the ring B represents an optionally substituted aromatic ring, and the ring C represents an optionally substituted 4- to 8-membered ring which may further be condensed with an optionally substituted ring.

18. A pharmaceutical composition comprising the compound of claim 1 or a salt or prodrug thereof.

19. The pharmaceutical composition of claim 18, which is a double β-amyloid precursor protein secretion stimulator and/or an apoptosis inhibitor.

20. The pharmaceutical composition of claim 18, which is a therapeutic agent for Alzheimer's disease, Parkinson's disease, neuropathy, senile dementia, cerebrovascular disorder-induced neuronopathy or cerebrovascular dementia.

* * * * *